US012686869B1

(12) United States Patent
Borrajo et al.

(10) Patent No.: US 12,686,869 B1
(45) Date of Patent: Jul. 21, 2026

(54) METHODS AND COMPOSITIONS FOR TRANS-SPLICING UTILIZING TRIFUNCTIONAL ELEMENTS

(71) Applicant: Amber Bio Inc., San Francisco, CA (US)

(72) Inventors: Jacob Borrajo, San Francisco, CA (US); Brigit Riley, San Francisco, CA (US); Kamyab Javanmardi, San Francisco, CA (US); Patricia Biezonski, San Francisco, CA (US); Samuel Demario, San Francisco, CA (US)

(73) Assignee: Amber Bio Inc., South San Francisco, CA (US)

( * ) Notice: Subject to any disclaimer, the term of this patent is extended or adjusted under 35 U.S.C. 154(b) by 0 days.

(21) Appl. No.: 19/457,807

(22) Filed: Jan. 23, 2026

(51) Int. Cl.
*C12N 15/113* (2010.01)

(52) U.S. Cl.
CPC ...... *C12N 15/1136* (2013.01); *C12N 2310/14* (2013.01); *C12N 2320/33* (2013.01)

(58) Field of Classification Search
CPC ............ C12N 15/1136; C12N 2310/14; C12N 2320/33
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 5,942,395 A | 8/1999 | Fournier et al. | |
| 6,258,595 B1 | 7/2001 | Gao et al. | |
| 7,399,753 B2 | 7/2008 | Mitchell et al. | |
| 8,053,232 B2 | 11/2011 | Puttaraju et al. | |
| 8,603,457 B2 | 12/2013 | Yu | |
| 8,735,366 B2 | 5/2014 | Bauer et al. | |
| 8,883,753 B2 | 11/2014 | Puttaraju et al. | |
| 9,040,491 B2 | 5/2015 | Dreyfuss et al. | |
| 9,074,207 B2 | 7/2015 | Pagani et al. | |
| 9,669,109 B1 | 6/2017 | Pagani et al. | |
| 10,987,433 B2 | 4/2021 | Bennett et al. | |
| 11,377,646 B2 | 7/2022 | Doudna et al. | |
| 11,530,398 B2 | 12/2022 | Doudna et al. | |
| 11,578,313 B2 | 2/2023 | Doudna et al. | |
| 11,685,909 B2 | 6/2023 | Doudna et al. | |
| 11,739,309 B2 | 8/2023 | Doudna et al. | |
| 11,767,528 B2 | 9/2023 | Borrajo | |
| 11,946,050 B2 | 4/2024 | Bruno Quinta De Souza Leal | |
| 11,993,776 B2 | 5/2024 | Johnson et al. | |
| 12,351,818 B2 | 7/2025 | Al-Shayeb et al. | |
| 2004/0058344 A1 | 3/2004 | Mitchell et al. | |
| 2006/0134658 A1 | 6/2006 | Garcia-Blanco | |
| 2006/0194317 A1 | 8/2006 | Puttaraju et al. | |
| 2006/0234247 A1 | 10/2006 | Puttaraju et al. | |
| 2011/0212058 A1 | 9/2011 | Lamond et al. | |

| | | | |
|---|---|---|---|
| 2013/0059901 A1 | 3/2013 | Bauer et al. | |
| 2014/0186300 A1 | 7/2014 | Yu et al. | |
| 2015/0209448 A1 | 7/2015 | de Boer et al. | |
| 2022/0062437 A1 | 3/2022 | Bennett et al. | |
| 2022/0160898 A1 | 5/2022 | Michalakis et al. | |
| 2022/0204989 A1 | 6/2022 | Fisher et al. | |
| 2022/0213469 A1 | 7/2022 | Blainey et al. | |
| 2022/0243194 A1 | 8/2022 | Wei et al. | |
| 2023/0340469 A1 | 10/2023 | Nelles | |
| 2024/0011026 A1 | 1/2024 | Nelles | |
| 2024/0209366 A1 | 6/2024 | Nelles | |
| 2024/0318186 A1 | 9/2024 | Johnson et al. | |
| 2025/0179494 A1 | 6/2025 | Abudayyeh et al. | |
| 2025/0270553 A1* | 8/2025 | Nelles ................ A61K 31/7105 |

FOREIGN PATENT DOCUMENTS

| | | |
|---|---|---|
| EP | 1521766 B1 | 11/2012 |
| EP | 2205739 B1 | 7/2014 |
| EP | 2627339 B1 | 5/2015 |
| EP | 2872632 A1 | 5/2015 |
| EP | 2320952 B1 | 5/2016 |
| EP | 3377116 A1 | 9/2018 |
| EP | 3781213 A1 | 2/2021 |
| EP | 3898996 A1 | 10/2021 |
| EP | 4217010 A1 | 8/2023 |
| EP | 4323391 A1 | 2/2024 |
| EP | 4370680 A2 | 5/2024 |
| WO | 95/13392 A1 | 5/1995 |
| WO | 96/17947 A1 | 10/1996 |
| WO | 97/06243 A1 | 2/1997 |
| WO | 97/08298 A1 | 3/1997 |
| WO | 97/09441 A2 | 3/1997 |
| WO | 97/21825 A1 | 6/1997 |
| WO | 99/11764 A2 | 3/1999 |

(Continued)

OTHER PUBLICATIONS

Berger et al., "mRNA trans-splicing in gene therapy for genetic diseases", WIRE's RNA 2016, 7:487-498. (Year: 2016).*
Akiyama, et al., "A max-margin training of RNA secondary structure prediction integrated with the thermodynamic model", Journal of Bioinformatics and Computational Biology, vol. 1, No. 6, published Dec. 19, 2018.
Andronescu, et al., "Computational approaches for RNA energy parameter estimation," Bioinformatics, vol. 16, No. 12, pp. 2304-2318 (2010).
Andronescu, et al., "Efficient parameter estimation for RNA secondary structure prediction", Bioinformatics, vol. 23, pp. i19-i28, (2007).

(Continued)

*Primary Examiner* — Abigail Vanhorn
*Assistant Examiner* — Stephanie L Sullivan
(74) *Attorney, Agent, or Firm* — Morgan, Lewis & Bockius LLP

(57) ABSTRACT

The present disclosure provides a trans-splicing molecule that has a trifunctional element suitable for targeted trans-splicing of an RNA or pre-mRNA molecule.

27 Claims, 17 Drawing Sheets

Specification includes a Sequence Listing.

(56)                References Cited

FOREIGN PATENT DOCUMENTS

| | | |
|---|---|---|
| WO | 2003104412 A2 | 12/2003 |
| WO | 2013151666 A2 | 10/2013 |
| WO | 2020181101 A1 | 9/2020 |
| WO | 2020181102 A1 | 9/2020 |
| WO | 2020214973 A1 | 10/2020 |
| WO | 2021034717 A1 | 2/2021 |
| WO | 2021076656 A1 | 4/2021 |
| WO | 2021133829 A1 | 7/2021 |
| WO | 2021172925 A1 | 9/2021 |
| WO | 2021216512 A1 | 10/2021 |
| WO | 2022019706 A1 | 1/2022 |
| WO | 2022055998 A1 | 3/2022 |
| WO | 2022067228 A1 | 3/2022 |
| WO | 2022158891 A1 | 7/2022 |
| WO | 2022191642 A1 | 9/2022 |
| WO | 2022220968 A1 | 10/2022 |
| WO | 2023014206 A1 | 2/2023 |
| WO | 2023039346 A1 | 3/2023 |
| WO | 2023039373 A2 | 3/2023 |
| WO | 2023064895 A1 | 4/2023 |
| WO | 2023128048 A1 | 7/2023 |
| WO | 2023130959 A1 | 7/2023 |
| WO | 2023201203 A2 | 10/2023 |
| WO | 2023205694 A2 | 10/2023 |
| WO | 2023215761 A1 | 11/2023 |
| WO | 2023220566 A1 | 11/2023 |
| WO | 2023220742 A2 | 11/2023 |
| WO | 2023237627 A1 | 12/2023 |
| WO | 2023237638 A1 | 12/2023 |
| WO | 2023250384 A2 | 12/2023 |
| WO | 2024019801 A1 | 1/2024 |
| WO | 2024054047 A1 | 3/2024 |
| WO | 2024054048 A1 | 3/2024 |
| WO | 2024068898 A1 | 4/2024 |
| WO | 2024102659 A1 | 5/2024 |
| WO | 2024112957 A1 | 5/2024 |
| WO | 2024118946 A1 | 6/2024 |
| WO | 2024124237 A2 | 6/2024 |
| WO | 2024124238 A1 | 6/2024 |
| WO | 2024173719 A1 | 8/2024 |
| WO | 2025038853 A1 | 2/2025 |
| WO | 2025042942 A1 | 2/2025 |
| WO | 2025085691 A1 | 4/2025 |
| WO | 2025117698 A1 | 6/2025 |
| WO | 2025147110 A1 | 7/2025 |
| WO | 2025170919 A1 | 8/2025 |
| WO | 2025198390 A1 | 9/2025 |

OTHER PUBLICATIONS

Black, et al., "U2 as well as U1 Small Nuclear Ribonucleoproteins are Involved in Premessenger RNA Splicing", (1985) Cell 42: 737-750.

Bratkovic, et al., "Functional diversity of small nucleolar RNAs", Nucleic Acids Res. Feb. 28, 2020; 48(4): 1627-1651.

Charenton, et al., "Mechanism of 5' splice site transfer for human spliceosome activation", (2019) Science 364:362-367.

Chen, et al., "RNA Secondary Structure Prediction by Learning Unrolled Algorithms", Published as a conference paper at International Conference on Learning Representations (ICLR) (2020) (arXiv:2002.05810).

Cotten, et al., "Specific contacts between mammalian U7 snRNA and histone precursor RNA are indispensable for the in vitro 3' RNA processing reaction", (1988) The EMBO Journal 7:801-808.

Dieci, et al., "Eukaryotic snoRNAs: A paradigm for gene expression flexibility", Elsevier, Genomics 94 (2009) 83-88.

Do, et al., "ONTRAfold: RNA secondary structure prediction without physics-based models", Bioinformatics, vol. 22, No. 14, 2006.

Eddy, et al., "RNA sequence analysis using convariance models", Nucleic Acids Research, 1994, vol. 22, No. 11, 2079-2088.

*Homo sapiens* small nucleolar RNA, H/ACA box 48 (SNORA48), small nucleolar RNA NCBI Reference Sequence: NR_002918.1 (Year: 2020).

Jaganathan, et al., "Predicting Splicing from Primary Sequence with Deep Learning", Cell, vol. 176, No. 3, pp. 535-548 (2019).

Kolossova, et al., "U11 snRNA interacts in vivo with the 5' splice site of U12-dependent (AU-AC) pre-mRNA introns", (1997) RNA 3: 227.

Lasda and Blumenthal, "Trans-splicing", Wiley Interdiscip Rev RNA, vol. 2, No. 3, pp. 417-434 (2011).

Laughlin, et al., "Cloning of infectious adeno-associated virus genomes in bacterial plasmids", Gene, vol. 23, No. 1, pp. 65-73 (1983).

Lebkowski, et al., "Adeno-Associated Virus: a Vector System for Efficient Introduction and Integration of DNA into a Variety of Mammalian Cell Types", Molecular and Cellular Biology. 1988, vol. 8, No. 10, p. 3988-399.

Liu, et al., "Partial correction of endogenous ΔF508 CFTR in human cystic fibrosis airway epithelia by spliceosome-mediated RNA trans-splicing", Nat Biotechnol, vol. 20, pp. 47-52 (2002).

Liu, et al., "Splicing inactivation generates hybrid mRNA-snoRNA transcripts targeted by cytoplasmic RNA decay", RNAS, Jul. 25, 2022. vol. 119, No. 31, pp. 1-9.

Lorenz, et al., "ViennaRNA Package 2.0", Algorithms for Molecular Biology 2011, 6:26.

Ma, et al., "Pol III Promoters to Express Small RNAs: Delineation of Transcription Initiation", Mol Ther Nucleic Acids, vol. 3, No. 5, e161 (2014).

Mansfield, et al., "Repair of CFTR mRNA by spliceosome-mediated RNA trans-splicing", Gene Therapy (2000) 7, 1885-1895.

Markham & Zuker, "UNAFold Software for Nucleic Acid Folding and Hybridization," Methods Mol Biol, vol. 453, pp. 3-31 (2008).

Matera, et al., "A day in the life of the spliceosome", Nat Rev Mol Cell Biol, vol. 15, pp. 108-121 (2014).

McLaughlin, et al., "Adeno-Associated Virus General Transduction Vectors: Analysis of Proviral Structures", Journal of Virology, (1988) vol. 62, No. 6, p. 1963-1973.

Miyagishi, et al., "U6 promoter-driven siRNAs with four uridine 3' overhangs efficiently suppress targeted gene expression in mammalian cells", Nature Biotechnology, vol. 19 (2022).

Mosig, et al., "To code or not to code? That is the question for RNA in timekeeping", Biochem (Lond) (2020) vol. 42, No. 2: pp. 12-15.

Muzyczka, "Use of Adeno-Associated Virus as a General Transduction Vector for Mammalian Cells", Current Topics in Microbiology and Immunology, vol. 158, 1992.

Nguyen, et al., "The architecture of the spliceosomal U4/U6. U5 tri-snRNP", (2015), Nature 523:47-52.

Ni, et al., "Small Nucleolar RNAs Direct Site-Specific Synthesis of Pseudouridine in Ribosomal RNA", Cell. May 16, 1997;89(4):565-71.

Paul, et al., "Increased Viral Titer Through Concentration of Viral Harvests from Retroviral Packaging Lines", Human Gene Therapy 4:609-615 (1993).

Reuter, et al., "RNAstructure: software for RNA secondary structure prediction and analysis", Reuter and Mathews BMC Bioinformatics 2010, 11:129.

Rindt, et al., "Replacement of huntingtin exon 1 by trans-splicing", Cell. Mol. Life Sci. (2012) 69:4191-4204.

Rivas, et al., "A range of complex probabilistic models for RNA secondary structure prediction that includes the nearest-neighbor model and more," RNA, vol. 18, No. 2: pp. 193-212 (2025).

Roithova, et al., "The Sm-core mediates the retention of partially-assembled spliceosomal snRNPs in Cajal bodies until their full maturation", Nucleic Acids Research, 2018, vol. 46, No. 7, 3774-3790.

Rossi, et al., "Involvement of U1 Small Nuclear Ribonucleoproteins (snRNP) in 5* Splice Site-U1 snRNP Interaction", vol. 271, No. 39, Issue of Sep. 27, pp. 23985-23991, 1996.

Samulski, et al., "Cloning of adeno-associated virus into pBR322: Rescue of intact virus from the recombinant plasmid in human cells", Proc. Natt Acad. Sci. USA vol. 79, pp. 2077-2081, Mar. 1982, Microbiology.

Samulski, et al., "Helper-Free Stocks of Recombinant Adeno-Associated Viruses: Normal Integration Does Not Require Viral Gene Expression", Journal of Virology, (1989) pp. 3822-3828.

(56) References Cited

OTHER PUBLICATIONS

Schroeder, et al., "Optical Melting Measurements of Nucleic Acid Thermodynamics", Methods Enzymol. (2009) 468: 371-387.

Semple, et al., "Rational design of cationic lipids for siRNA delivery", Nature Biotechnology, vol. 28, pp. 172-176 (2010).

Senapathy, et al., "Replication of Adeno-associated virus DNA", J. Mol. Kiol. (1984) 178, 179, 1-20.

Singh, et al., "RNA secondary structure prediction using an ensemble of two-dimensional deep neural networks and transfer learning", Nature Communications, vol. 10, No. 5407 (2019).

Soldati, et al., "Structural and Functional Characterization of Mouse U7 Small Nuclear RNA Active in 3' Processing of Histone Pre-mRNA", (1988), Molecular and Cellular Biology 8:1518-1524.

Strub, et al., "The cDNA sequences of the sea urchin U7 small nuclear RNA suggest specific contacts between histone mRNA precursor and U7 RNA during RNA processing", (1984) EMBO journal 3:2801-2807.

The RNAcentral Consortium "RNAcentral: a comprehensive database of non-coding RNA sequences," Nucleic Acids Research, vol. 45, No. D1, pp. D128-D134 (2016).

Tratschin, et al., "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, Oct. 1984, p. 2072-2081.

Turner, et al., "NNDB: the nearest neighbor parameter database for predicting stability of nucleic acid secondary structure", Nucleic Acids Research, 2010, vol. 38, D280-D282.

Turunen, et al., "HnRNPH1/H2, U1 snRNP, and U11 snRNP cooperate to regulate the stability of the U11-48K pre-mRNA", (2013) RNA 4:61-76.

Wilkinson, et al., "RNA Splicing by the Spliceosome", Annual Review of Biochemistry, vol. 89, pp. 359-388 (2020).

Xia, et al., "An enhanced U6 promoter for synthesis of short hairpin RNA", Nucleic Acids Research, 2003, vol. 31, No. 17 e100.

Zakov, et al., "Rich Parameterization Improves RNA Structure Prediction", Journal of Computational Biology, vol. 18, No. 11, pp. 1525-1542 (2011).

Zeng, et al., "Predicting RNA splicing from DNA sequence using Pangolin", Genome Biology, vol. 23, No. 103 (2022).

Zuker, et al., "Mfold web server for nucleic acid folding and hybridization prediction" Mfold web server for nucleic acid folding and hybridization prediction, Nucleic Acids Research, 2003, vol. 31, No. 13, 3406-3415.

Zuker, et al., "Optimal computer folding of lare RNA sequences using thermodynamics and auxiliary Information" Nucleic Acids Research, vol. 9, No. 1 (1981).

Hirose, et al., "Splicing-Dependent and -Independent Modes of Assembly for Intron-Encoded Box C/D snoRNPs in Mammalian Cells," Molecular Cell, vol. 12, pp. 113-123, Jul. 2003.

Wang, et al. "The m6A Consensus Motif Provides a Paradigm of Epitranscriptomic Studies," Biochemistry 2021, 60, 3410-3412.

Reichow et al., 2007, Nucleic Acids Research, vol. 35, No. 5, p. 1452-1464 (Year: 2007).

Bergeron, Sep. 27, 2022, Nucleic Acids Research, vol. 51, D291-D296; https://bioinfo-scottgroup.med.usherbrooke.ca/snoDB / (Year: 2022).

Coady et al., 2007, Molecular Therapy, vol. 15, No. 8, p. 1471-1478 (Year: 2007).

Dooley et al., 2018, Molecular Therapy: Nucleic Acids, vol. 12, p. 294-308 (Year: 2018).

Jorjani et al., 2016, Nucleic Acids Research, vol. 44, No. 11, p. 5068-5082 (Year: 2016).

Monjaret et al., 2014, Molecular Therapy, vol. 22, No. 6, p. 1176-1187 (Year: 2014).

Puttaraju et al., 1999, Nature Biotechnology, vol. 17, p. 246-252 (Year: 1999).

Wally et al., 2012, Journal of Investigative Dermatology, vol. 132, p. 1959-1966 (Year: 2012).

* cited by examiner

FIG. 1

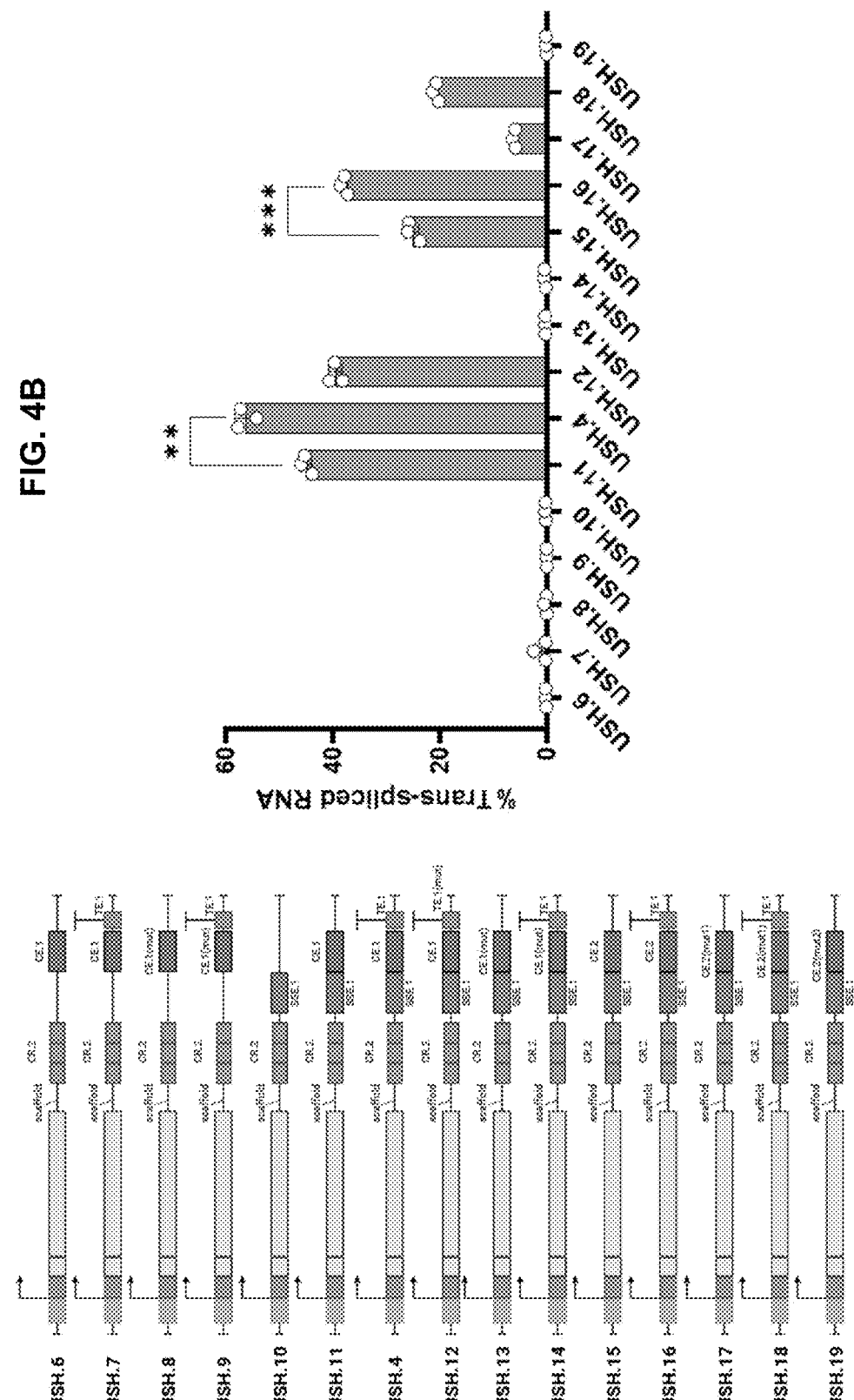

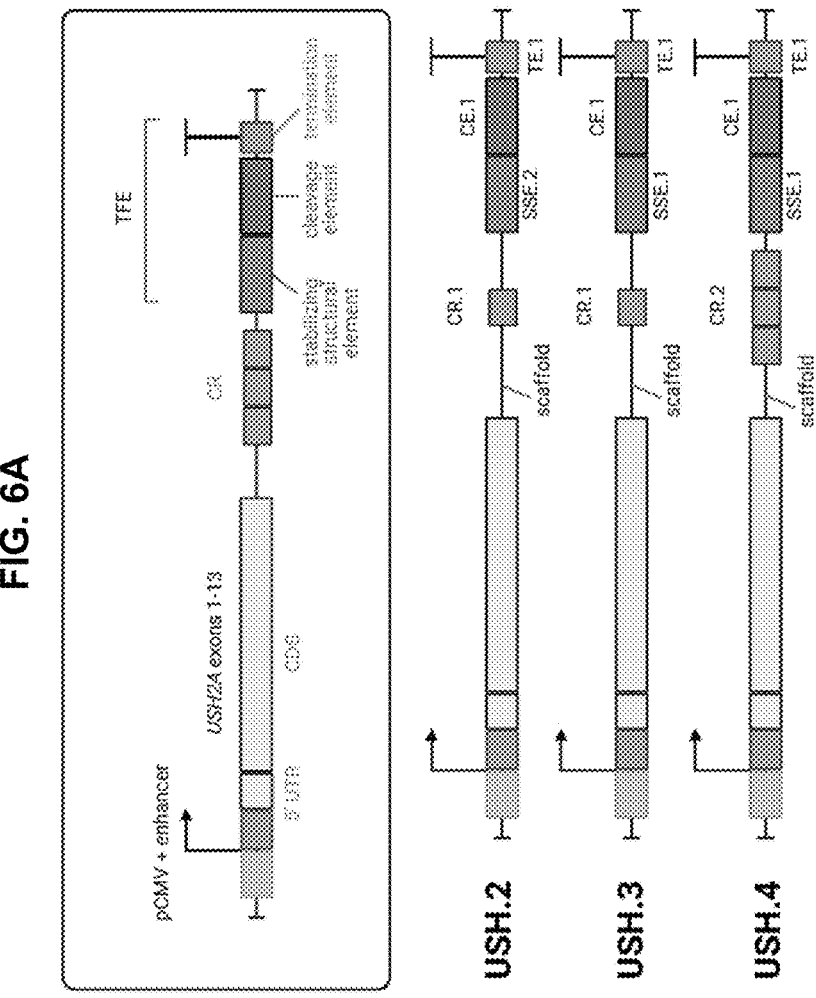

FIG. 7
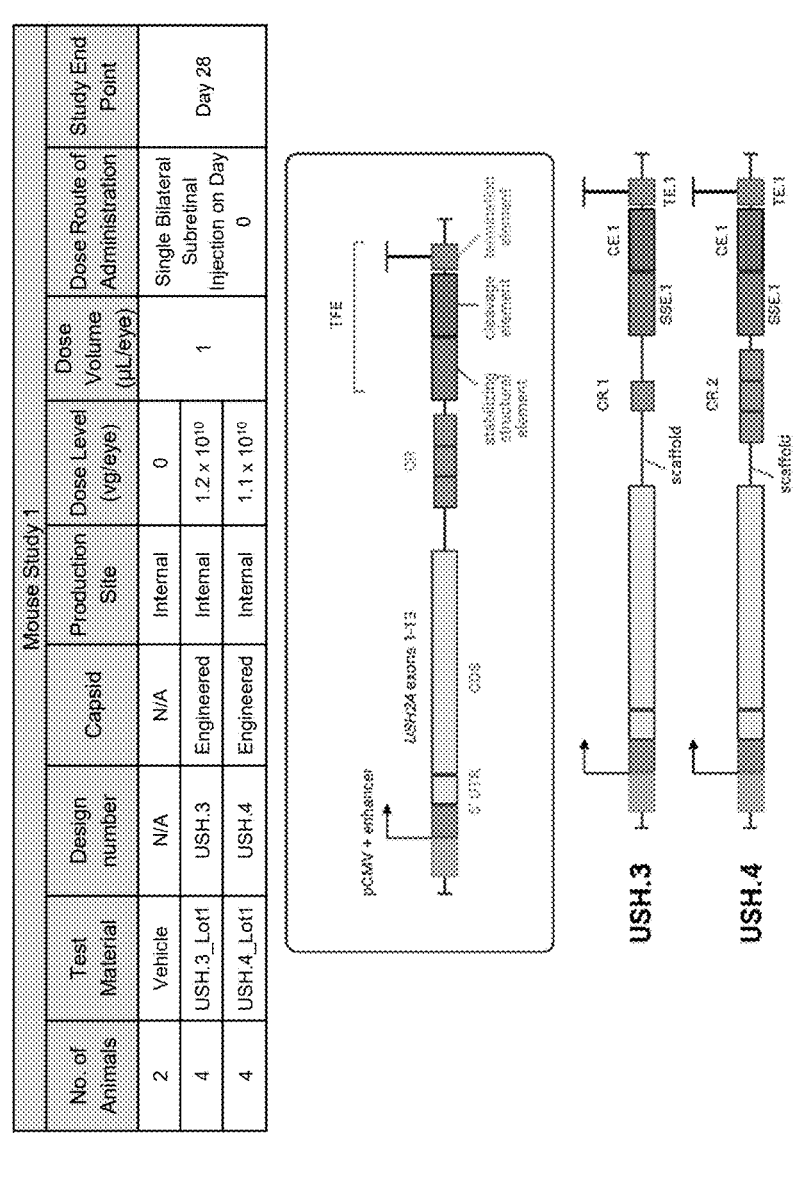
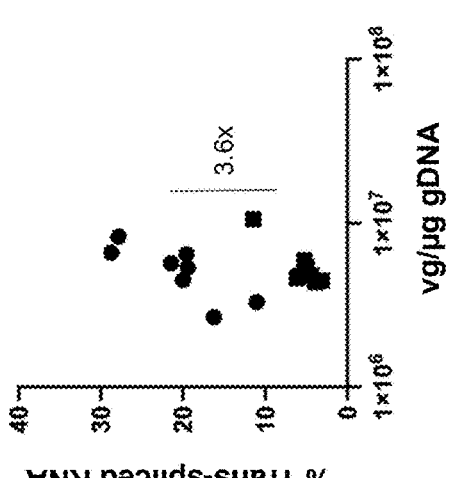

FIG. 8
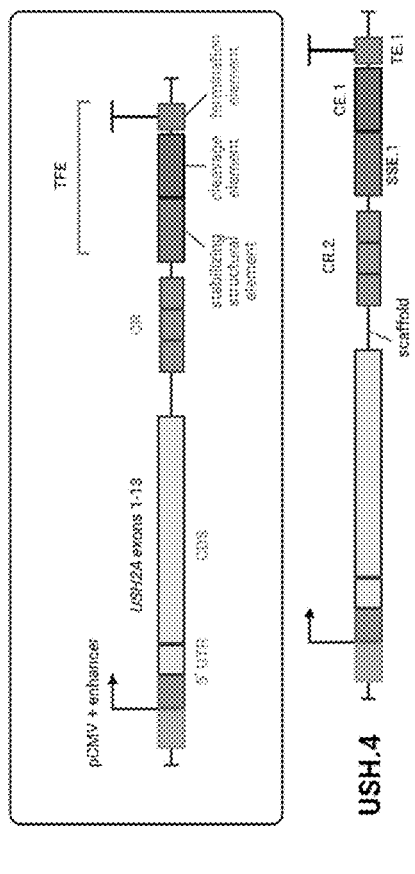
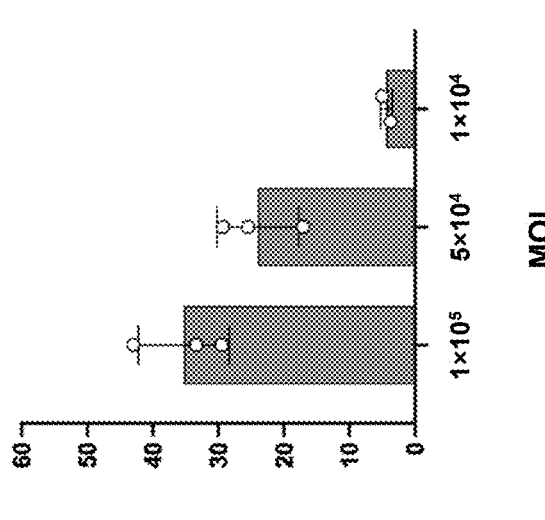

FIG. 9
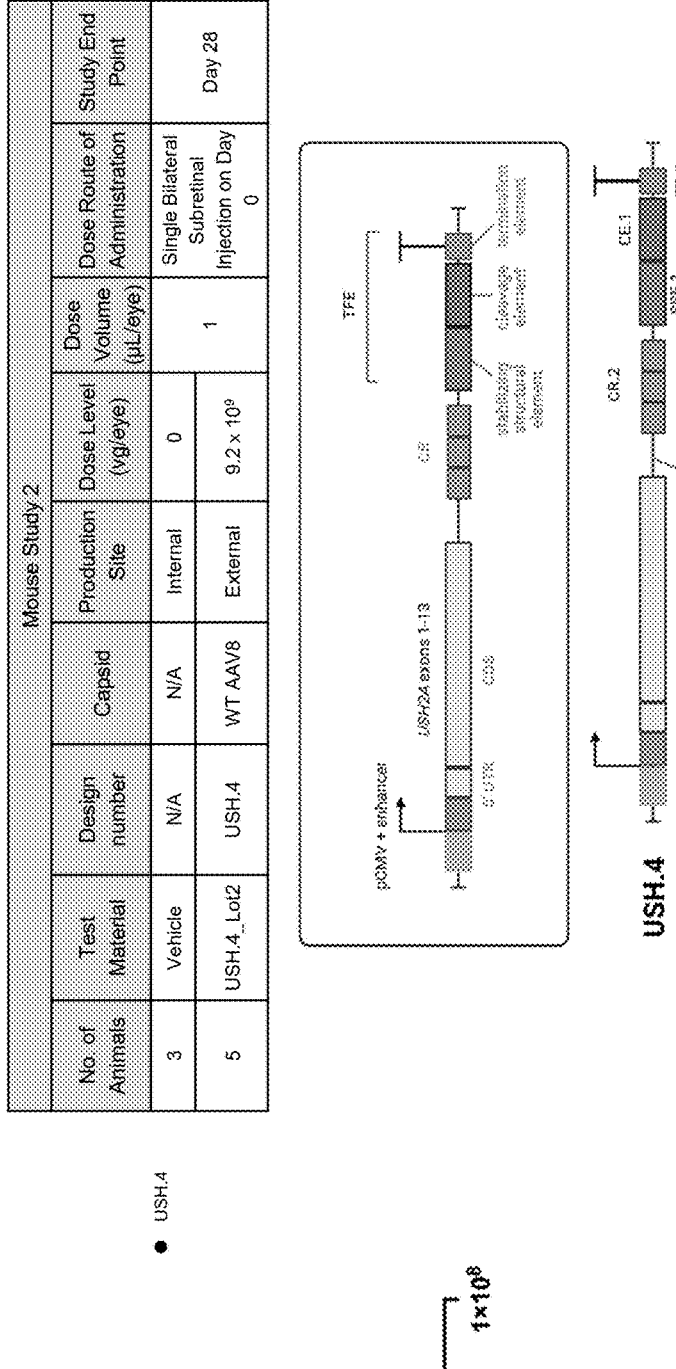
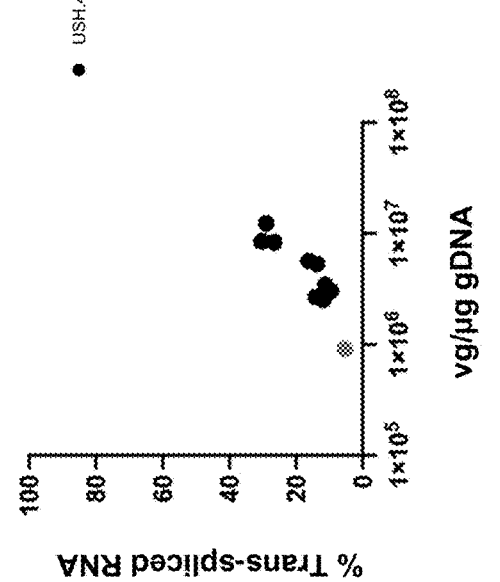

FIG. 10
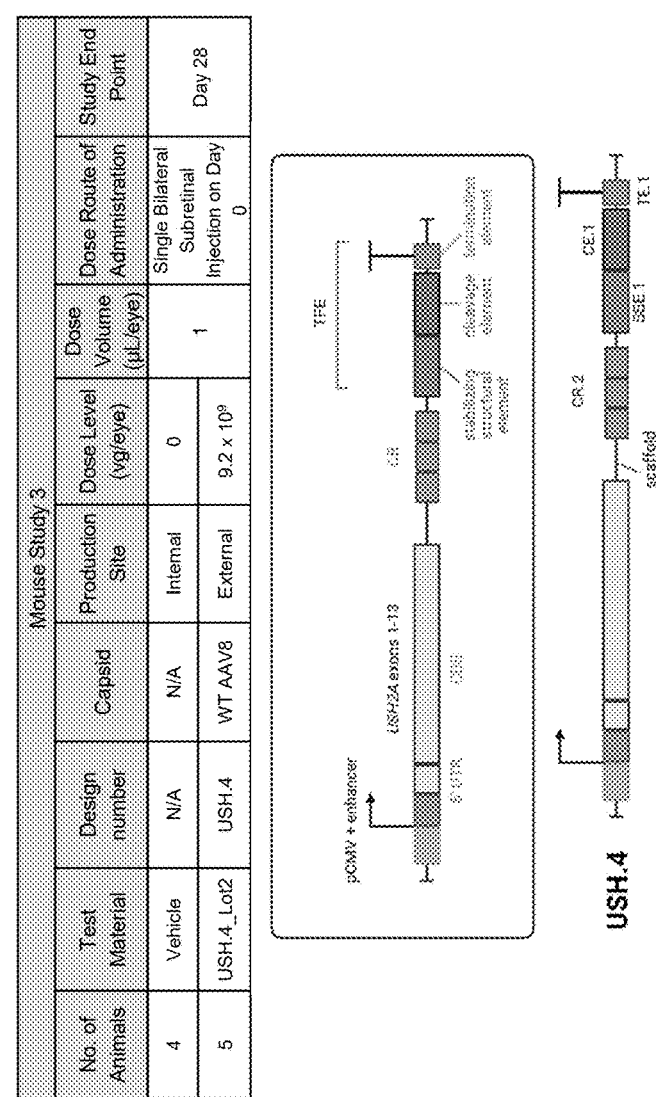
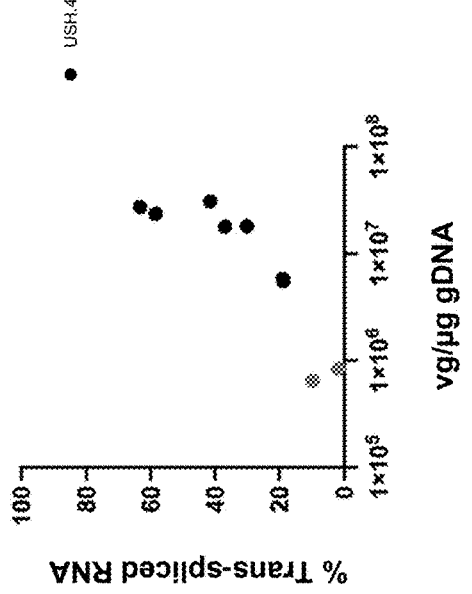

FIG. 11B

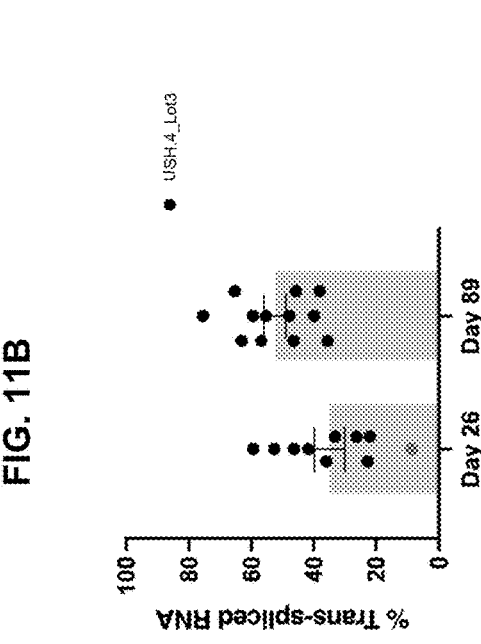

FIG. 11A

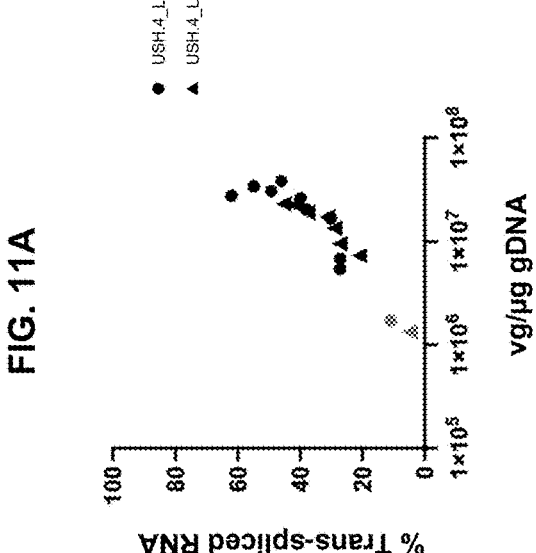

| No. of Animals | Test Material | Design number | Capsid | Production Site | Dose Level (vg/eye) | Dose Volume (µL/eye) | Dose Route of Administration | Study End Point |
|---|---|---|---|---|---|---|---|---|
| | | | | | Mouse Study 4 | | | |
| 2 | Vehicle | N/A | N/A | Internal | 0 | | | Day 26 |
| 5 | USH.4_Lot3 | USH.4 | WT AAV8 | Internal | $1.2 \times 10^{10}$ | 1 | Single Bilateral Subretinal Injection on Day 0 | |
| 4 | USH.4_Lot4 | USH.4 | WT AAV8 | External | $1.0 \times 10^{10}$ | | | |
| 3 | Vehicle | N/A | N/A | Internal | 0 | | | Day 89 |
| 6 | USH.4_Lot3 | USH.4 | WT AAV8 | Internal | $1.2 \times 10^{10}$ | | | |

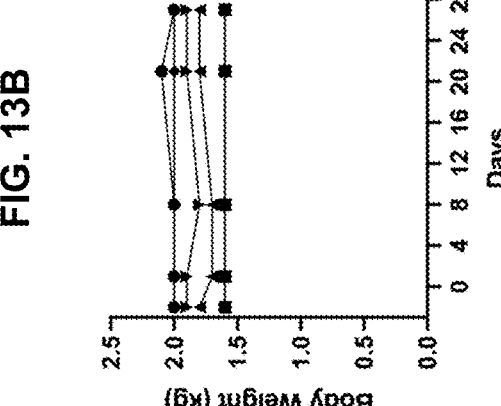
FIG. 13B
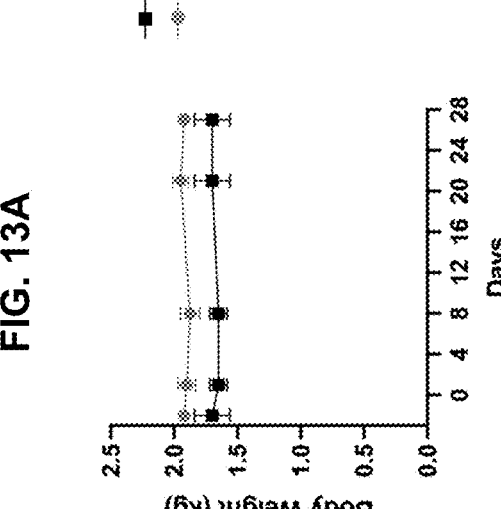
FIG. 13A

METHODS AND COMPOSITIONS FOR TRANS-SPLICING UTILIZING TRIFUNCTIONAL ELEMENTS

FIELD

The disclosure relates to, inter alia, a trifunctional element suitable for targeted trans-splicing of an RNA or pre-mRNA molecule, and related methods.

SEQUENCE LISTING

The instant application contains a sequence listing, which has been submitted in XML format via Patent Center. The contents of the XML copy named "134241-5030_Sequence-_Listing.xml," which was created on Jan. 20, 2026, and is approximately 280,488 bytes in size, are incorporated herein by reference in their entirety.

BACKGROUND

RNA-based therapeutic strategies have emerged as promising approaches for correcting genetic defects at the transcript level. For example, traditional methods, such as antisense oligonucleotides and RNA interference, primarily modulate gene expression. However, these methods do not restore functional coding sequences. Splice-switching oligonucleotides and self-splicing introns have also been investigated to repair aberrant splicing; however, these approaches often suffer from limited precision and durability. Trans-splicing ribozymes, which replace defective exons by splicing in a correct sequence, typically offer a more direct means of repairing mutant transcripts. Despite all the potential, early trans-splicing systems have demonstrated low efficiency and instability in cellular environments, limiting their therapeutic applicability.

One major challenge in the field has been achieving robust and precise trans-splicing in the presence of competing cis-splicing events. Endogenous splicing machinery typically favors cis-splicing, which can outcompete engineered trans-splicing reactions. Furthermore, RNA repair constructs can be susceptible to degradation by exonucleases, and incomplete transcript processing can lead to truncated or non-functional products. These limitations have impeded the development of clinically viable RNA repair platforms, particularly for genes implicated in diseases and inherited disorders. Thus, there is a need for improved trans-splicing constructs that enable clinically relevant RNA repair therapies.

SUMMARY

Accordingly, the present disclosure provides, in aspects, a trifunctional element suitable for targeted trans-splicing of an RNA or pre-mRNA molecule, wherein the trifunctional element comprises: (i) one or more stabilizing structural elements; (ii) one or more cleavage elements; and (iii) a termination element.

In aspects, disclosed herein is a trans-splicing molecule comprising a trifunctional element suitable for targeted trans-splicing of an RNA or pre-mRNA molecule, wherein the trifunctional element comprises: (i) one or more stabilizing structural elements; (ii) one or more cleavage elements; and (iii) a termination element.

In embodiments, the one or more cleavage elements is located adjacent to, or abuts, the one or more stabilizing structural elements. In embodiments, the one or more cleavage elements is about 5, about 10, about 15, about 20, about 25, about 50, about 100, about 200, about 500, or about 1000 nucleotides from the one or more stabilizing structural elements.

In embodiments, the one or more cleavage elements, e.g., without limitation, is a ribozyme sequence.

In embodiments, the one or more ribozyme sequences are cis-cleaving (e.g., cleaves within the ribozyme sequence, or scarlessly). In embodiments, the one or more stabilizing structural elements comprises an element having one or more AU Hoogsteen repeat sequences.

In embodiments, the one or more stabilizing structural elements is located at the 3' end of the trifunctional element. In embodiments, the one or more stabilizing structural elements is about 5, about 10, about 15, about 20, about 25, about 50, about 100, about 200, about 500, or about 1000 nucleotides from the 3' end of the trifunctional element. In embodiments, the one or more stabilizing structural elements is located at the 5' end of the trifunctional element. In embodiments, the one or more stabilizing structural elements is about 5, about 10, about 15, about 20, about 25, about 50, about 100, about 200, about 500, or about 1000 nucleotides from the 5' end of the trifunctional element.

In embodiments, the one or more stabilizing structural elements stabilizes, or is suitable for stabilizing, the 3' end of the trans-splicing molecule and/or the trifunctional element after ribozyme cleavage and/or removal of the termination sequence.

In embodiments, the termination sequence is selected from a polyadenine (polyA) sequence, a Bovine Growth Hormone polyadenylation signal (bGHpA), a SV40 polyadenylation signal (SV40 pA), or a human Growth Hormone polyA sequence (hGH polyA sequence).

In embodiments, the polyadenine (polyA) sequence enhances RNA stability prior to ribozyme-mediated cleavage in comparison to a composition lacking one or more of: (i) the stabilizing structural element; (ii) the cleavage element; or (iii) the termination sequence. In embodiments, the enhancement of RNA stability is characterized by at least one of: (i) an increase in RNA half-life; (ii) reduction of exonuclease-mediated degradation; (iii) specific nuclear localization/retention; and/or (iv) a decrease in one or more of: a) aberrant translation, b) off-target translation, c) non-specific splice editor translation, d) ectopic translation, and/ or e) unintended polypeptide synthesis.

In embodiments, and without wishing to be bound by theory, the trans-splicing molecule and/or trifunctional element results in an increase or decrease of the trans-spliced RNA molecule into a protein product in comparison to a composition lacking the trans-splicing molecule and/or trifunctional element, wherein the improvement comprises an increase or decrease synthesis of a protein product, and/or decreased synthesis of an aberrant or deleterious polypeptide (e.g., an un-spliced rep RNA), or wherein improvement comprises an increase in yield of an intended protein and/or a decrease in off-target or incomplete polypeptide synthesis.

In embodiments, the trans-splicing molecule and/or trifunctional element increases the production of trans-spliced RNA molecule in comparison to a composition lacking one or more of: (i) the stabilizing structural element; (ii) the cleavage element; or (iii) the termination element optionally a polyadenine (polyA) sequence, wherein improvement comprises an increase in yield of an intended protein and/or a decrease in off-target or incomplete polypeptide synthesis.

In embodiments, the translated protein comprises a therapeutic protein, or a functional version of a genetically mutated protein.

In embodiments, the trans-splicing molecule and/or the trifunctional element further comprises a 5' cap, and/or one or more of a 5' untranslated region (UTR).

In embodiments, the trans-splicing molecule and/or the trifunctional element comprises one or more RNA localization signals suitable for directing subcellular localization of the RNA molecule.

In embodiments, the one or more RNA localization signals comprise a localization motif selected from: (i) j-actin zipcode; (ii) ZBP1-binding motif; (iii) AU-rich element (ARE); (iv) GA-rich motif; (v) a stem-loop structure; (vi) BORG (BMP2-OP1-responsive gene) pentamers; (vii) C-rich motifs from nuclear retained long non-coding RNAs (lncRNAs); (viii) XIST motifs from lncRNAs; (viiii) U7 small nuclear RNA (smU7); or (x) SINE-derived nuclear RNA localization elements (SIRLOIN).

In embodiments, the one or more RNA localization signals facilitate co-localization with a ribonucleoprotein (RNP). In embodiments, the one or more RNA localization signals improve trans-splicing efficiency by directing the RNA molecule to a subcellular compartment enriched in target pre-mRNA in comparison to a composition one or more RNA localization signals, and/or lacking one or more of: (i) a stabilizing structural element; (ii) a cleavage element; or (iii) a termination element.

In embodiments, the one or more RNA localization signals is located either: i) between the one or more cleavage elements and the stabilizing structural element; ii) at the 3' end; (iii) or at the 5' end of the trifunctional element.

In embodiments, the one or more cleavage elements is self-cleaving.

In embodiments, the one or more cleavage elements is trans-cleaving.

In embodiments, at least one ribozyme is self-cleaving and at least one ribozyme is trans-cleaving.

In embodiments, the one or more stabilizing structural elements is suitable for stabilizing the 3' end of the trans-splicing molecule and/or the trifunctional element. In embodiments, the one or more cleavage elements facilitates subcellular localization of the RNA or pre-mRNA molecule, and the trans-splicing molecule and/or the trifunctional element further allows for termination or reduction of translation of an incomplete or toxic intermediate protein (e.g., an un-spliced repRNA).

In embodiments, the one or more cleavage elements is about or at least about 20 nucleotides to about or at least about 240 nucleotides in length. In embodiments, the one or more cleavage elements is about or at least about 20 nucleotides in length, about or at least about 30 nucleotides in length, about or at least about 40 nucleotides in length, about or at least about 50 nucleotides in length, about or at least about 60 nucleotides in length, about or at least about 70 nucleotides in length, about or at least about 80 nucleotides in length, about or at least about 90 nucleotides in length, about or at least about 100 nucleotides in length, about or at least about 120 nucleotides in length, about or at least about 140 nucleotides in length, about or at least about 160 nucleotides in length, about or at least about 180 nucleotides in length, about or at least about 200 nucleotides in length, about or at least about 220 nucleotides in length, or about or at least about 240 nucleotides in length.

In embodiments, the one or more cleavage elements is, comprises, or is derived from a ribozyme, and the ribozyme is selected from hepatitis delta virus (HDV) ribozyme, HDV-like (CPEB3) ribozyme, aminoacyltransferase ribozyme, β-globin co-transcriptional cleavage ribozyme, CotC ribozyme, GIR1 branching ribozyme, GlmS (glucosamine-6-phosphate activated) ribozyme, Hairpin ribozyme, Hammerhead ribozyme, Hatchet ribozyme, Hepatitis delta virus ribozyme, Hovlinc ribozyme, Lead-zyme, Ligase ribozyme, Mammalian CPEB3 ribozyme, Θrz (class I or II) ribozyme, Pistol ribozyme, Ribonuclease P, RNase MRP, RNR1 ribozyme, RNR2 ribozyme, RNR3 ribozyme, RNR4 ribozyme, RNR5 ribozyme, Twister ribozyme, Twister-sister ribozyme, Varkud satellite (VS), Vg1 ribozyme, VS ribozyme, or a variant thereof. In embodiments the one or more cleavage elements is a ribozyme, and the ribozyme is derived from a species selected from *Trichosurus vulpecula, Chinchilla lanigera, Galeopterus variegatus, Monodelphis domestica, Mus spicilegus*, and *Macropus eugenii*. In embodiments, the one or more ribozymes is selected from a HDV ribozyme, a *Galeopterus variegatus* (Malayan flying lemur) ribozyme, a *Chinchilla lanigera* (long-tailed *Chinchilla*) ribozyme, an Θrz (1789 theta) ribozyme, or an Θrz (1768 theta) ribozyme. In embodiments, the one or more ribozymes is or comprises a HDV ribozyme, an HDV-like ribozyme, an Θrz ribozyme, or an Θrz-like ribozyme.

In embodiments, the one or more cleavage elements comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of any one of SEQ ID NOs: 1-194. In embodiments, the one or more cleavage elements is or comprises the nucleic acid sequence of any one of SEQ ID NOs: 1-194.

In embodiments, the trans-splicing molecule further comprises one or more complementary regions (CRs) to the target RNA molecule.

In embodiments, the trans-splicing molecule further comprises one or more exons.

In embodiments, the one or more cleavage elements is downstream (3') of one or more exons and/or introns.

In embodiments, the one or more cleavage elements is a cis-cleaving ribozyme that cleaves, or is suitable for cleaving, at an internal site within the trifunctional element.

In embodiments, the one or more cleavage elements cleaves, or is suitable for cleaving, at the 3' end of the RNA or pre-mRNA molecule; and/or cleaves, or is suitable for cleaving, at a site located within about or at least about 10 nucleobases to about or at least about 1000 nucleobases from the 3' end of the RNA or pre-mRNA molecule.

In embodiments, the one or more cleavage elements removes, or is suitable for removing, the termination element, optionally the polyadenine (polyA) sequence, from the RNA or pre-mRNA molecule.

In embodiments, the trans-splicing molecule and/or the trifunctional element comprises a transcriptional termination sequence. In embodiments, transcriptional termination sequence comprises a polyadenine (polyA) sequence.

In embodiments, the trans-splicing molecule does not comprise: (i) one or more snRNA sequences, (ii) one or more small nucleolar RNA (snoRNA) sequences, and/or (iii) one or more small Cajal RNA (scaRNA) sequence.

In embodiments, the one or more stabilizing structural elements comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of SEQ ID NOs: 195-198. In embodiments, the one or more stabilizing structural elements is or comprises the nucleic acid sequence of SEQ ID NOs: 195-198.

In embodiments, the trifunctional element is oriented from 5' to 3' in order one or more stabilizing structural elements, one or more ribozyme sequences, and a termination element. In embodiments, the trifunctional element is oriented from 5' to 3' in order of a 5' cap, one or more ribozyme sequences, and one or more stabilizing structural elements.

In embodiments, the trans-splicing molecule further comprises one or more CRs, wherein the one or more CRs is about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 110 nucleotides in length, about 120 nucleotides in length, about 130 nucleotides in length, about 140 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, or about 500 nucleotides in length, or wherein the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the trans-splicing molecule further comprises one or more CRs, wherein the one or more CRs is 20 to 29 nucleotides in length, 30 to 39 nucleotides in length, 40 to 49 nucleotides in length, 50 to 59 nucleotides in length, 60 to 69 nucleotides in length, 70 to 79 nucleotides in length, 80 to 89 nucleotides in length, 90 to 99 nucleotides in length, 100 to 109 nucleotides in length, 110 to 119 nucleotides in length, 120 to 129 nucleotides in length, 130 to 139 nucleotides in length, 140 to 149 nucleotides in length, 150 to 159 nucleotides in length, 200 to 249 nucleotides in length, 250 to 299 nucleotides in length, 300 to 399 nucleotides in length, 400 to 499 nucleotides in length, or 500 to 1000 nucleotides in length, or wherein the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the one or more CRs are located outside of the one or more stabilizing structural elements. In embodiments, the one or more CRs are located within the one or more stabilizing structural elements.

In embodiments, the trans-splicing molecule comprises one CR, 2 CRs, or comprises more than 2 CRs. In embodiments, the one or more CRs is about or at least about 5 nucleotides in length to about or at least about 300 nucleotides in length. In embodiments, the one or more CRs is about or at least about 5 nucleotides in length, about or at least about 10 nucleotides in length, about or at least about 15 nucleotides in length, about or at least about 20 nucleotides in length, about or at least about 25 nucleotides in length, about or at least about 30 nucleotides in length, about or at least about 35 nucleotides in length, about or at least about 50 nucleotides in length, about or at least about 100 nucleotides in length, about or at least about 200 nucleotides in length, or about or at least about 300 nucleotides in length, at least about 400 nucleotides in length, or at least about 500 nucleotides in length.

In embodiments, the trans-splicing molecule comprises one or more CRs each having about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to one or more RNA or pre-mRNA target sequences. In embodiments, the one or more CR sequences comprises at least about 90% complementarity to one or more RNA or pre-mRNA target sequences. In embodiments, the one or more CR sequences comprises at least about 95% complementarity to one or more RNA or pre-mRNA target sequences.

In embodiments, the one or more CRs target a pre-mRNA target selected from one or more pre-mRNA intron and/or exons of USH2A.

In embodiments, the trans-splicing molecule further comprises one or more splicing signals, optionally comprising one or more exonic splicing enhancers (ESEs), one or more intronic splicing enhancers (ISEs), one or more exonic splicing silencers (ESSs), one or more intronic splicing silencers (ISSs), one or more U1 binding motifs, one or more polypyrimidine tracts, one or more branch points, and combinations thereof.

In embodiments, the trans-splicing molecule further comprises one or more splice acceptors (SAs) and/or one or more splice donors (SDs). In embodiments, each splice acceptor is positioned upstream (5') of an exon and each splice donor is positioned downstream (3') of an exon of the trans-splicing molecule.

In embodiments, the trans-splicing molecule comprises one or more SDs and is suitable for 5' editing of one or more RNA or pre-mRNA target sequences.

In embodiments, disclosed herein is a trifunctional element comprising: (i) one or more stabilizing structural elements; (ii) one or more cleavage elements; and (iii) a termination sequence.

In embodiments, disclosed herein is a trans-splicing molecule comprising: (a) a trifunctional element comprising: (i) one or more stabilizing structural elements; (ii) one or more cleavage elements; and (iii) a termination sequence; and (b) one or more exon sequences, and (c) one or more complementary regions (CR), wherein the trans-splicing molecule optionally comprises a splice acceptor (SA) or splice donor (SD).

In embodiments, disclosed herein is a nucleic acid construct encoding a trifunctional element and/or a trans-splicing molecule of any one of the embodiments disclosed herein. In embodiments, the nucleic acid construct is a DNA plasmid, viral vector, non-viral vector, in vitro transcribed RNA (IVT RNA), circular RNA (circRNA), or self-amplifying RNA (saRNA) encoding the RNA or pre-mRNA molecule, optionally wherein the nucleic acids are introduced into a cell by a viral vector, optionally wherein the viral vector is AAV. In embodiments, the nucleic acid construct is codon optimized, optionally for expression in a mammalian cell. In embodiments, the nucleic acid construct comprises one or more base modifications and/or backbone modifications.

In embodiments, disclosed herein is a lipid nanoparticle (LNP), liposome, lipoplex, or polymeric nanoparticle comprising a trans-splicing molecule and/or a trifunctional element of any one of the embodiments disclosed herein, or a nucleic acid construct of any one of the embodiments disclosed herein.

In embodiments, the LNP, liposome, lipoplex, or polymeric nanoparticle of any one of the embodiments disclosed herein, further comprises one or more of ionizable lipids, amino lipids, anionic lipids, neutral lipids, amphipathic lipids, helper lipids, structural lipids, PEG lipids, and lipids.

In embodiments, disclosed herein is a cell comprising a trans-splicing molecule and/or a trifunctional element of any one of the embodiments disclosed herein, or a nucleic acid construct of any one of the embodiments disclosed herein.

In embodiments, the cell is a eukaryotic cell.

In embodiments, the eukaryotic cell comprises a mammalian cell, human cell, immortalized cell, or a cell harvested from a subject.

In embodiments, disclosed herein is a pharmaceutical composition comprising a trans-splicing molecule and/or a trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein.

In embodiments, disclosed herein is a kit comprising one or more pharmaceutical compositions comprising a trans-splicing molecule and/or a trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein.

In embodiments, disclosed herein is a method for trans-splicing one or more RNAs or pre-mRNAs comprising: (a) contacting a cell with: (i) a trans-splicing molecule and/or a trifunctional element, of any one of the embodiments disclosed herein and one or more exons and/or introns; (ii) one or more nucleic acid constructs of any of any one of the embodiments disclosed herein; or (iii) one or more lipid nanoparticles (LNPs), liposomes, lipoplexes, or polymeric nanoparticles of any one of the embodiments disclosed herein; and (b) replacing at least a portion of the one or more RNAs or pre-mRNAs with one or more exons and/or introns via trans-splicing with the trans-splicing molecule comprising the trifunctional element.

In embodiments, the trans-splicing comprises exon/intron skipping and/or exon/intron replacement.

In embodiments, the trans-splicing comprises binding one or more CRs of the trans-splicing molecule to one or more target sequences of the one or more RNAs or pre-mRNAs.

In embodiments, the one or more target sequences is or comprises an intron.

In embodiments, the one or more cleavage elements is self-cleaving; and/or wherein one or more cleavage elements removes a 3' polyadenine (polyA) sequence.

In embodiments, the presence of the one or more cleavage elements and/or cleavage by the one or more cleavage elements results in higher trans-splicing efficiency in comparison to a trifunctional element molecule lacking one or more of: (i) a stabilizing structural element; (ii) a cleavage element; or (iii) a termination sequence.

In embodiments, the method further comprises measuring the trans-splicing efficiency, optionally by performing one or more of flow cytometry, confocal microscopy (confocal laser scanning microscopy, spinning-disk confocal microscopy), in situ fluorescence, immunohistochemistry, SDS- PAGE, western blotting, short-read sequencing, nuclear cytoplasmic fractionation, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the presence of the one or more cleavage elements and/or cleavage by the one or more cleavage elements results in reduced expression/translation of unspliced and/or undesired protein products in comparison to a trifunctional element molecule lacking one or more of: (i) a stabilizing structural element; (ii) a cleavage element; or (iii) a termination sequence.

In embodiments, the method further comprises assessing the expression/translation of unspliced and/or undesired protein products, optionally by performing one or more of flow cytometry, confocal microscopy (confocal laser scanning microscopy, spinning-disk confocal microscopy), in situ fluorescence, immunohistochemistry, mass spectrometry, SDS-PAGE, western blotting, short-read sequencing, nuclear cytoplasmic fractionation, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the presence of the one or more cleavage elements and/or cleavage by the one or more cleavage elements results in an increase of nuclear retention/localization of the trans-splicing RNA in comparison to a trifunctional element molecule lacking one or more of: (i) a stabilizing structural element; (ii) a cleavage element; or (iii) a termination sequence.

In embodiments, the method further comprises assessing the nuclear retention of the trans-splicing RNA the expression of unspliced and/or undesired protein products, optionally by performing one or more of flow cytometry, confocal microscopy (confocal laser scanning microscopy, spinning-disk confocal microscopy), in situ fluorescence, immunohistochemistry, SDS-PAGE, western blotting, short-read sequencing, nuclear cytoplasmic fractionation, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the one or more trans-splicing molecule binds a ribonucleoprotein (RNP) to form a RNP complex and directs trans-splicing of the one or more exons and/or introns with the one or more RNAs or pre-mRNAs.

In embodiments, disclosed herein is a method of treating a subject having a disease or disorder, the method comprising administering a trans-splicing molecule and/or trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein to the subject in vivo, or to a harvested cell ex vivo, under conditions suitable for trans-splicing of a target RNA, thereby restoring or modifying expression of a functional protein in the subject.

In embodiments, disclosed herein is a method of trans-splicing screening comprising: (a) providing a trans-splicing molecule comprising: (i) a trifunctional element comprising: (a) one or more stabilizing structural elements; (b) one or more cleavage elements; optionally wherein the one or more cleavage elements is located at a 5' or 3' end of the trifunctional element; and (c) a termination sequence; (ii) one or more complementary regions (CRs); and (iii) one or more exon and/or intron sequences; (b) co-expressing, in a cell, the trans-splicing molecule with one or more target RNA or pre-mRNA sequences, wherein the one or more CRs of the trans-splicing molecule is at least partially complementary to the one or more target RNA or pre-mRNA sequences and binds the one or more target RNA or pre-mRNA, and wherein trans-splicing occurs between the one or more exon and/or intron sequences of the trans-splicing molecule and the one or more target RNA or pre-mRNA sequences; and (c) measuring trans-splicing between the one or more exon and/or intron sequences of the trans-splicing RNA molecules.

In embodiments, the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the trans-splicing forms a complete/functional protein-coding mRNA sequence of a reporter molecule comprising a reporter molecule operably linked to a regulatory element that is activated by an exogenous small molecule. In embodiments, the exogenous small molecule is a kill switch that induces apoptosis, inhibits cell viability, and/or turns off the trans-splicing molecule.

In embodiments, the one or more target RNA or pre-mRNA sequences comprises an exogenous target sequence.

In embodiments, measuring the trans-splicing comprises barcode sequencing of the trans-spliced product. In embodiments, measuring the trans-splicing comprises a barcode sequence, optionally adjacent to or within a 5' UTR sequence, optionally as a biomarker in a biological fluid sample.

In embodiments, measuring the trans-splicing comprises measuring fluorescence, optionally comprising one or more of flow cytometry, confocal microscopy, confocal laser scanning microscopy, spinning-disk confocal microscopy, and in situ fluorescence.

In embodiments, the method further comprises ranking and/or selecting the one or more CRs, target RNA or pre-mRNA sequences, and/or trifunctional element as a function of measuring the trans-splicing.

In embodiments, the trifunctional element comprises, in sequential order from 5' to 3': (i) one or more stabilizing structural elements having at least about 95% sequence identity to the nucleic acid sequence of any one of SEQ ID NOs: 195-198; (ii) one or more ribozyme sequences having at least about 95% sequence identity to the nucleic acid sequence of any one of SEQ ID NOs: 1-194; and (iii) a termination sequence, optionally having at least about 95% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 97% sequence identity to the nucleic acid sequence of any one of SEQ ID NOs: 195-198; (ii) one or more ribozyme sequences having at least about 97% sequence identity to the nucleic acid sequence of any one of SEQ ID NOs: 1-194; and (iii) a termination sequence, optionally having at least about 97% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 98% sequence identity to the nucleic acid sequence of any one of SEQ ID NOs: 195-198; (ii) one or more ribozyme sequences having at least about 98% sequence identity to the nucleic acid sequence of any one of SEQ ID NOs: 1-194; and (iii) a termination sequence, optionally having at least about 98% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 100% sequence identity to the nucleic acid sequence of any one of SEQ ID NOs: 195-198; (ii) one or more ribozyme sequences having at least about 100% sequence identity to the nucleic acid sequence of any one of SEQ ID NOs: 1-194; and (iii) a termination sequence, optionally having at least about 100% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises one or more cleavage elements having at least about 80%, 85% 90%, 95%, 97%, 98%, or 100% identity to SEQ ID NOs: 1-194; one or more stabilizing structural elements having at least about 80%, 85% 90%, 95%, 97%, 98%, or 100% identity SEQ ID NOs: 195-198; and a termination sequence, optionally having at least about 80%, 85% 90%, 95%, 97%, 98%, or 100% identity SEQ ID NOs: 248-254.

In embodiments, disclosed herein is a trans-splicing molecule of any one of the embodiments disclosed herein, wherein the trans-splicing molecule comprises a CMV enhancer having at least about 80%, 85% 90%, 95%, 97%, 98%, or 100% identity SEQ ID NO: 204.

In embodiments, disclosed herein is a trans-splicing molecule of any one of the embodiments disclosed herein, wherein the trans-splicing molecule comprises a CMV promoter having at least about 80%, 85% 90%, 95%, 97%, 98%, or 100% identity SEQ ID NO: 205.

In embodiments, disclosed herein is a trans-splicing molecule of any one of the embodiments disclosed herein, wherein the trans-splicing molecule comprises an untranscribed region having at least about 80%, 85% 90%, 95%, 97%, 98%, or 100% identity SEQ ID NO: 206, optionally wherein the untranscribed region is a CMV-derived untranscribed region.

In embodiments, disclosed herein is a trans-splicing molecule of any one of the embodiments disclosed herein, wherein the trans-splicing molecule comprises an Usherin (5' UTR) sequence having at least about 80%, 85% 90%, 95%, 97%, 98%, or 100% identity SEQ ID NO: 207 or SEQ ID NO: 208.

In embodiments, disclosed herein is a trans-splicing molecule of any one of the embodiments disclosed herein, wherein the trans-splicing molecule comprises an Usherin (CDS) sequence having at least about 80%, 85% 90%, 95%, 97%, 98%, or 100% identity SEQ ID NO: 209.

In embodiments, disclosed herein is a trans-splicing molecule of any one of the embodiments disclosed herein, wherein the trans-splicing molecule comprises a splice donor (SD) sequence having at least about 80%, 85% 90%, 95%, 97%, 98%, or 100% identity to GTAAGT.

In embodiments, disclosed herein is a trans-splicing molecule of any one of the embodiments disclosed herein, wherein the trans-splicing molecule comprises a short scaffold sequence having at least about 80%, 85% 90%, 95%, 97%, 98%, or 100% SEQ ID NO: 211.

In embodiments, disclosed herein is a trans-splicing molecule of any one of the embodiments disclosed herein, wherein the trans-splicing molecule comprises a complementary region 1 sequence having at least about 80%, 85% 90%, 95%, 97%, 98%, or 100% identity SEQ ID NO: 212.

In embodiments, disclosed herein is a trans-splicing molecule of any one of the embodiments disclosed herein, wherein the trans-splicing molecule comprises a complementary region 2 sequence having at least about 80%, 85% 90%, 95%, 97%, 98%, or 100% identity SEQ ID NO: 213.

In embodiments, disclosed herein is a trans-splicing molecule of any one of the embodiments disclosed herein, wherein the trans-splicing molecule comprises a complementary region 3 sequence having at least about 80%, 85% 90%, 95%, 97%, 98%, or 100% identity SEQ ID NO: 214.

In embodiments, disclosed herein is a trans-splicing molecule of any one of the embodiments disclosed herein, wherein the trans-splicing molecule comprises an filler sequence having at least about 80%, 85% 90%, 95%, 97%, 98%, or 100% identity SEQ ID NO: 215.

In embodiments, disclosed herein is a trans-splicing molecule and/or a trifunctional element of any one of the embodiments disclosed herein, wherein the trans-splicing molecule and/or trifunctional element comprises a stabilizing structural element (SSE) SSE.1 sequence having at least about 80%, 85% 90%, 95%, 97%, 98%, or 100% identity SEQ ID NO: 216 or SEQ ID NO: 274.

In embodiments, disclosed herein is a trans-splicing molecule and/or a trifunctional element of any one of the embodiments disclosed herein, wherein the trans-splicing molecule and/or trifunctional element comprises a cleavage element (CE) CE.1 sequence having at least about 80%, 85% 90%, 95%, 97%, 98%, or 100% identity SEQ ID NO: 217.

In embodiments, disclosed herein is a trans-splicing molecule and/or a trifunctional element of any one of the embodiments disclosed herein, wherein the trans-splicing molecule and/or trifunctional element comprises a termination element (TE) sequence having at least about 80%, 85% 90%, 95%, 97%, 98%, or 100% identity SEQ ID NO: 218.

BRIEF DESCRIPTION OF THE DRAWINGS

FIG. 1 shows a non-limiting schematic of a trans-splicing molecule for 5' RNA replacement via trans-splicing. From left to right the composition comprises: CMV enhancer and promoter, 5' untranslated region (5' UTR) and coding sequence (CDS) derived from USH2A, a complementary region(s) (CR) targeting USH2A intron 13, and a trifunctional element (TFE) composed of a stabilizing structural element (SSE), a cleavage element (CE), and a termination element (TE).

FIG. 2A shows a non-limiting schematic of human USH2A target pre-mRNA with a zoomed in insert showing exons 12 through 15. A representative trans-splicing molecule for replacing exons 1-13 is shown hybridizing with intron 13 via a complementary region (CR). FIG. 2B shows a non-limiting schematic of a human USH2A minigene featuring cDNA for exons 1-12 and 14-21 from the USH2A short isoform, with chimeric introns for introns 12 and 13 flanking a mutant exon 13. The USH2A minigene can be expressed through episomal plasmids or after stable integration into a cell line's genome.

FIG. 3A shows a non-limiting schematic for USH2A trans-splicing based constructs with key design differences noted for each USH2A construct (e.g., USH.0 through USH.4). In FIG. 3A, "TFE" refers to a trifunctional element, "CR" refers to a complementary region, "SSE" refers to a stabilizing structural element, "CE" refers to a cleavage element, and "TE" refers a "termination element". USH.0 is a non-targeting control, and is based on a scaffold sequence, has CR.0, which is a non-targeting and effectively scrambled sequence and does not align to the human genome, an SSE.1 element, a cleavage element, and a termination element. USH.1 is based on a scaffold sequence, has one CR, an SSE.1 element, a cleavage element, and a termination element (SEQ ID NO: 219). USH.2 is based on a scaffold sequence, has one CR, an SSE.2 element, a cleavage element, and a termination element (SEQ ID NO: 220). USH.3 is based on a scaffold sequence, has one CR, an SSE.1 element, a cleavage element, and a termination element. USH.4 (SEQ ID NO: 255) is based on a scaffold sequence, has three CRs, an SSE.1 element, a cleavage element, and a termination element. FIG. 3B shows RNA trans-splicing results for HEK293FT cells co-transfected with SE and USH2A minigene plasmids. Y-axis results show percent of USH2A transcripts edited by SE. Fold-changes in activity for all trans-splicing based constructs shown, relative to top performing design (USH.4). Each point represents an independent biological replicate.

FIG. 4A and FIG. 4B show an in vitro trans-splicing analysis of constructs containing different trifunctional element (TFE) compositions. FIG. 4A shows a non-limiting schematic for USH2A trans-splicing based constructs with key design differences noted for each USH2A construct (e.g., USH.6 through USH.19). For example, USH.6 (SEQ ID NO: 221) is based on a scaffold sequence, has three CRs, a cleavage element, but does not include a termination element. USH.7 (SEQ ID NO: 222) is based on a scaffold sequence, has three CRs, a cleavage element, and a termination element. USH.8 (SEQ ID NO: 223) is based on a scaffold sequence, has three CRs, a mutant cleavage element, but does not include a termination element. USH.9 (SEQ ID NO: 224) is based on a scaffold sequence, has three CRs, a mutant cleavage element, and a termination element. USH.10 (SEQ ID NO: 225) is based on a scaffold sequence, has three CRs, an SSE.1 element, but does not include cleavage element and does not include a termination element. USH.11 (SEQ ID NO: 226) is based on a scaffold sequence, has three CRs, an SSE.1 element, a cleavage element, but does not include a termination element. USH.4 (SEQ ID NO: 255) is based on a scaffold sequence, has three CRs, an SSE.1 element, a cleavage element, and a termination element. USH.12 (SEQ ID NO: 227) is based on a scaffold sequence, has three CRs, an SSE.1 element, a cleavage element, and a mutant termination element. USH.13 (SEQ ID NO: 229) is based on a scaffold sequence, has three CRs, an SSE.1 element, a mutant cleavage element, does not include a termination element. USH.14 (SEQ ID NO: 230) is based on a scaffold sequence, has three CRs, an SSE.1 element, a mutant cleavage element, and a termination element. USH.15 (SEQ ID NO: 230) is based on a scaffold sequence, has three CRs, an SSE.1 element, a cleavage element, but does not include a termination element. USH.16 (SEQ ID NO: 232) is based on a scaffold sequence, has three CRs, an SSE.1 element, a cleavage element, and a termination element. USH.17 (SEQ ID NO: 233) is based on a scaffold sequence, has three CRs, an SSE.1 element, a mutant cleavage element, but does not include a termination element. USH.18 (SEQ ID NO: 234) is based on a scaffold sequence, has three CRs, an SSE.1 element, a mutant cleavage element, and a termination element. USH.19 (SEQ ID NO: 235) is based on a scaffold sequence, has three CRs, an SSE.1 element, a mutant cleavage element, but does not include a termination element. FIG. 4B shows RNA trans-splicing results for biotriplicate HEK293FT cells co-transfected with SE and CRISPRa components to upregulate USH2A. Total RNA was isolated from cells 44-hours post-transfection. The percent trans-spliced RNA was quantified by amplicon-based sequencing of trans-spliced and cis-spliced USH2A using the Illumina MiniSeq platform.

FIG. 5A shows a non-limiting schematic for USH2A trans-splicing based constructs with key design differences noted for each USH2A construct (e.g., USH.20 through USH.33). USH.20 (SEQ ID NO: 276) is based on a scaffold sequence, has three CRs, a cleavage element, but does not include a SSE element, and does not include a termination element. USH.21 (SEQ ID NO: 275) is based on a scaffold sequence, has three CRs, a cleavage element, and a termination element, but does not include a SSE element. USH.22 (SEQ ID NO: 247) is based on a scaffold sequence, has three CRs, a mutant cleavage element, but does not include a SSE element, and does not include a termination element. USH.23 (SEQ ID NO: 246) is based on a scaffold sequence, has three CRs, a mutant cleavage element, and a termination element, but does not include a SSE element. USH.24 (SEQ ID NO: 245) is based on a scaffold sequence, has three CRs, and a SSE.3 element, but does not include a cleavage element, and does not include a termination element. USH.25 (SEQ ID NO: 244) is based on a scaffold sequence, has three CRs, a SSE.3 element, a cleavage element, but does not include a termination element. USH.26 (SEQ ID NO: 243) is based on a scaffold sequence, has three CRs, a SSE.3 element, a cleavage element, and a termination element. USH.27 (SEQ ID NO: 242) is based on a scaffold sequence, has three CRs, a SSE.3 element, a cleavage element, and a mutant termination element. USH.28 (SEQ ID NO: 241) is based on a scaffold sequence, has three CRs, a SSE.3 element, a mutant cleavage element, but does not include a termination element. USH.29 (SEQ ID NO: 240) is based on a scaffold sequence, has three CRs, a SSE.3 element, a mutant cleavage element, and a termination element. USH.30 (SEQ ID NO: 239) is based on a scaffold sequence, has three CRs, a SSE.3 element, a cleavage element, but does not include a termination element. USH.31 (SEQ ID NO: 238) is based on a scaffold sequence, has three CRs, a SSE.3 element, a cleavage element, and a termination element. USH.32 (SEQ ID NO: 237) is based on a scaffold sequence, has three CRs, a SSE.3 element, a mutant cleavage element, but does not include a termination element. USH.33 (SEQ ID NO: 236) is based on a scaffold sequence, has three CRs, a SSE.3 element, a mutant cleavage element, and a termination element. FIG. 5B shows RNA trans-splicing results for biotriplicate HEK293FT cells co-transfected with SE and CRISPRa components to upregulate USH2A. Total RNA was isolated from cells 44-hours post-transfection. The percent trans-spliced RNA was quantified by amplicon-based sequencing of trans- and cis-spliced USH2A using the Illumina MiniSeq platform. Biological triplicates.  $P \leq 0.01$  $P \leq 0.0001$ FIG. 6A and FIG. 6B show an in vitro trans-splicing assay using engineered AAV capsid to deliver a trans-splicing molecule and a stably integrated (genomic) USH2A minigene. FIG. 6A shows a non-limiting schematic for USH2A trans-splicing based constructs with key design differences noted for each version. In FIG. 6A, USH.2 is based on a scaffold sequence, has one CR, an SSE.2 element, a cleavage element, and a termination element (SEQ ID NO: 220). USH.3 is based on a scaffold sequence, has one CR, an SSE.1 element, a cleavage element, and a termination element. USH.4 (SEQ ID NO: 255) is based on a scaffold sequence, has three CRs, an SSE.1 element, a cleavage element, and a termination element. FIG. 6B** shows RNA trans-splicing results for transduced engineered AAV capsid trans-splicing molecules delivered into a HEK293FT cell line with stably integrated USH2A minigene, in biotriplicate. Y-axis results show percent of USH2A transcripts edited by trans-splicing molecules. Fold-changes in activity for all trans-splicing molecules shown, relative to top performing design (USH.4).

FIG. 7 shows an in vivo mouse experiment using engineered AAV capsid to deliver a trans-splicing molecule. In FIG. 7, USH.3 is based on a scaffold sequence, has one CR, an SSE.1 element, a cleavage element, and a termination element. USH.4 (SEQ ID NO: 255) is based on a scaffold sequence, has three CRs, an SSE.1 element, a cleavage element, and a termination element. Bilateral subretinal administration of vehicle or engineered AAV capsid was performed. Retinas were collected approximately one-month post-injection. Individual values from each eye are plotted. Vector genomes (vg) were quantified by digital droplet PCR (ddPCR) and are plotted as the number of vector genomes per microgram (µg) genomic DNA (gDNA). The percent trans-spliced RNA was quantified using a multiplex ddPCR assay that simultaneously measures total USH2A mRNA and trans-spliced USH2A mRNA. vg=vector genomes, µg=microgram, gDNA=genomic DNA FIG. 8 shows an in vitro trans-splicing assay using wild-type AAV capsid to deliver a trans-splicing molecule. In FIG. 8, USH.4 (SEQ ID NO: 255) is based on a scaffold sequence, has three CRs, an SSE.1 element, a cleavage element, and a termination element. In this experiment, AAV was transduced at three different multiplicities of infection (MOIs) in a monoclonal HEK293FT cell line stably expressing a multi-serotype AAV receptor. CRISPRa components to upregulate USH2A expression were transfected 24-hours post-transduction. Total RNA was isolated from cells 44-hours post-transfection. The percent trans-spliced RNA was quantified by amplicon-based sequencing of trans- and cis-spliced USH2A using the Illumina MiniSeq platform. Data represent biological triplicates ($1 \times 10^5$; $5 \times 10^4$) or duplicates ($1 \times 10^4$). MOI=Multiplicity of infection FIG. 9 shows an in vivo mouse experiment using wild-type AAV capsid to deliver a trans-splicing molecule. In FIG. 9, USH.4 (SEQ ID NO: 255) is based on a scaffold sequence, has three CRs, an SSE.1 element, a cleavage element, and a termination element. Bilateral subretinal administration of vehicle or AAV was performed. Retinas were collected approximately one-month post-injection. Individual values from each eye are plotted. Vector genomes (vg) were quantified by digital droplet PCR (ddPCR) and are plotted as the number of vector genomes per microgram (µg)

genomic DNA (gDNA). The percent trans-spliced RNA was quantified using a multiplex ddPCR assay that simultaneously measures total USH2A mRNA and trans-spliced USH2A mRNA. Gray symbols denote failed subretinal bleb formation based on clinical dosing observation and post-dose ocular imaging. vg=vector genomes, μg=microgram, gDNA=genomic DNA FIG. 10 shows an in vivo mouse experiment using wild-type AAV capsid to deliver a trans-splicing molecule. In FIG. 10, USH.4 (SEQ ID NO: 255) is based on a scaffold sequence, has three CRs, an SSE.1 element, a cleavage element, and a termination element. Bilateral subretinal administration of vehicle or AAV was performed. Retinas were collected approximately one-month post-injection. Individual values from each eye are plotted. Vector genomes (vg) were quantified by digital droplet PCR (ddPCR) and are plotted as the number of vector genomes per microgram (μg) genomic DNA (gDNA). The percent trans-spliced RNA was quantified using a multiplex ddPCR assay that simultaneously measures total USH2A mRNA and trans-spliced USH2A mRNA. Gray symbols denote failed subretinal bleb formation based on clinical dosing observation and post-dose ocular imaging. vg=vector genomes, μg=microgram, gDNA=genomic DNA FIG. 11 shows an in vivo mouse experiment using wild-type AAV capsid to deliver a trans-splicing molecule. In FIG. 11, USH.4 (SEQ ID NO: 255) is based on a scaffold sequence, has three CRs, an SSE.1 element, a cleavage element, and a termination element. Bilateral subretinal administration of vehicle, USH.4_Lot3, or USH.4_Lot4 was performed. USH.4_Lot3 was purified by affinity chromatography followed by iodixanol gradient ultracentrifugation. USH.4_Lot4 was purified using two sequential cesium chloride density gradients. Retinas were collected approximately one-month post-injection. Individual values from each eye are plotted. Vector genomes (vg) were quantified by digital droplet PCR (ddPCR) and are plotted as the number of vector genomes per microgram (pg) genomic DNA (gDNA). The percent trans-spliced RNA was quantified by amplicon-based sequencing of trans- and cis-spliced USH2A using the Illumina MiniSeq platform. Gray symbols denote failed subretinal bleb formation based on clinical dosing observation and post-dose ocular imaging. vg=vector genomes, μg=microgram, gDNA=genomic DNA In FIG. 12, USH.4 (SEQ ID NO: 255) is based on a scaffold sequence, has three CRs, an SSE.1 element, a cleavage element, and a termination element. Bilateral sub-retinal administration of vehicle or AAV was performed. Punches from retinas were collected approximately one-month post-injection. Peak values from each eye are plotted. Vector genomes (vg) were quantified by digital droplet PCR (ddPCR) and are plotted as the number of vector genomes per microgram (μg) genomic DNA (gDNA). The percent trans-spliced RNA was quantified using a multiplex ddPCR assay that simultaneously measures total USH2A mRNA and trans-spliced USH2A mRNA. vg=vector genomes, μg=microgram, gDNA=genomic DNA.

FIG. 13A and FIG. 13B are graphs showing the body weights during the in vivo non-human primate study using AAV capsid to deliver a trans-splicing molecule. Body weights were measured on Days −2, 1, 8, 22, and 27. FIG. 13A shows the mean±SEM body weights for each treatment group. FIG. 13B shows body weights of individual animals across the same time points. Vehicle: 1001 Oculus Dexter (OD), 1002 Oculus Uterque (OU); USH.4: 1001 Oculus Sinister (OS), 2001 OU, 2002 OU, 2003 OU. Note that in A, animal 1001 appears in both groups as it received Vehicle in one eye and USH.4 in the other eye.

FIG. 14A shows the mean±SEM for each treatment group. FIG. 14B shows the intraocular pressure of individual eyes are shown. Vehicle: 1001 OD, 1002 OU; USH.4: 1001 OS, 2001 OU, 2002 OU, 2003 OU. IOP=intraocular pressure, mmHg=millimeter of mercury.

FIG. 15A shows the mean severity score ±SEM is shown for each treatment group. FIG. 15B shows the severity score of individual eyes is shown. Vehicle: 1001 OD, 1002 OU; USH.4: 1001 OS, 2001 OU, 2002 OU, 2003 OU.

FIG. 16A shows the mean severity score ±SEM is shown for each treatment group. FIG. 16A shows the severity score of individual eyes is shown. Vehicle: 1001 OD, 1002 OU; USH.4: 1001 OS, 2001 OU, 2002 OU, 2003 OU.

DETAILED DESCRIPTION

Figures 2A, 2B:
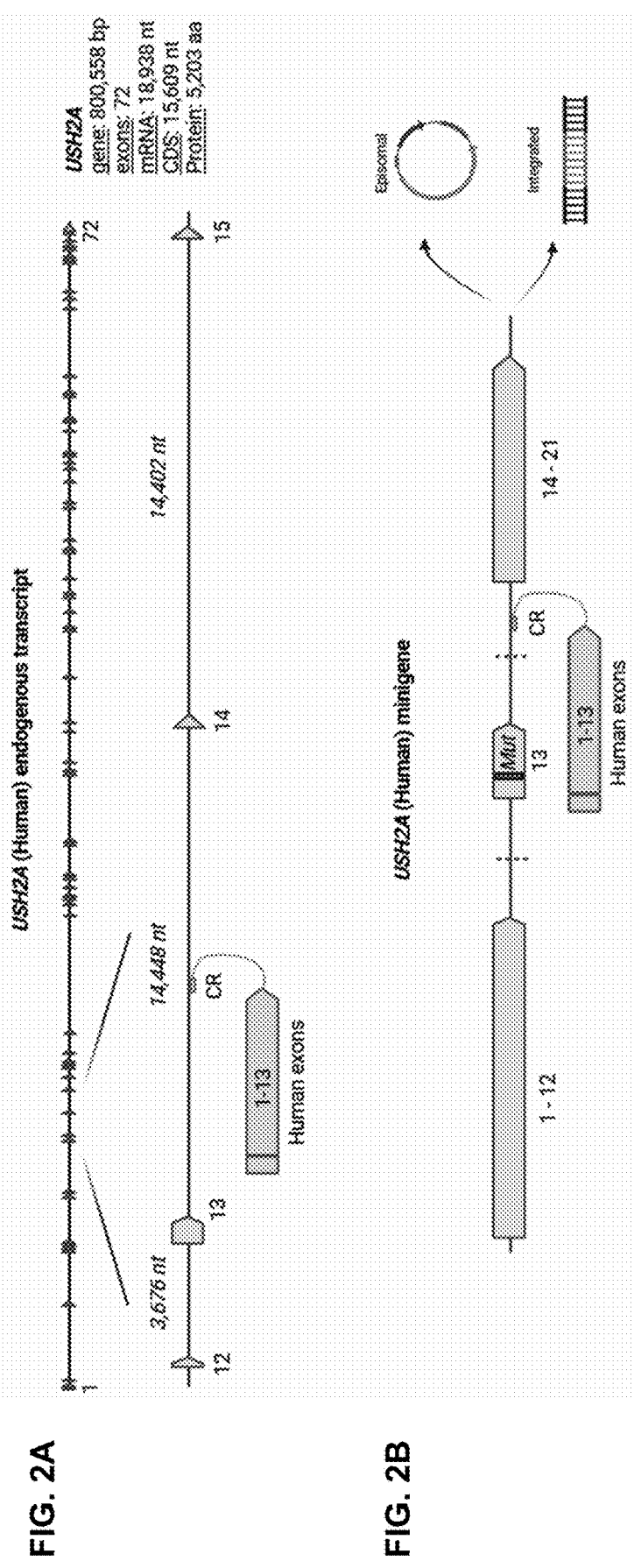
FIG. 2A and FIG. 2B each show a non-limiting schematic of USH2A pre-mRNA targets used for cis-vs trans-splicing RNA quantification, in vitro.

The present disclosure provides, inter alia, a trifunctional element suitable for targeted trans-splicing of an RNA or pre-mRNA molecule, wherein the trifunctional element comprises: (i) one or more stabilizing structural elements; (ii) one or more cleavage elements; and (iii) a termination element.

The present disclosure also provides, inter alia, a trans-splicing molecule comprising a trifunctional element, or a trifunctional element, that is suitable for targeted trans-splicing of an RNA or pre-mRNA molecule, e.g., in a cell or tissue, wherein the trifunctional element comprises: (i) one or more stabilizing structural elements (e.g., to stabilize the RNA structure and protect against exonucleolytic degradation); (ii) one or more cleavage elements (e.g., to mediate site-specific cleavage); and (iii) a termination sequence (e.g., to ensure transcript termination).

Collectively, the trifunctional element and/or trans-splicing molecule enhances trans-splicing efficiency, thereby improving the precision and durability of RNA repair, such as for therapeutic applications.

As described herein, arrangement of the components of the disclosed trans-splicing molecule and/or trifunctional element can be adjusted to optimize structural stability and catalytic activity.

In embodiments, references to "trans-splicing molecule" or "trifunctional element" refer to a nucleic acid construct that is capable of engaging in targeted trans-splicing, where the trifunctional element can be an RNA nucleic acid, or a reverse complement DNA nucleic acid that encodes the RNA-version of the trifunctional element.

Figure 1:
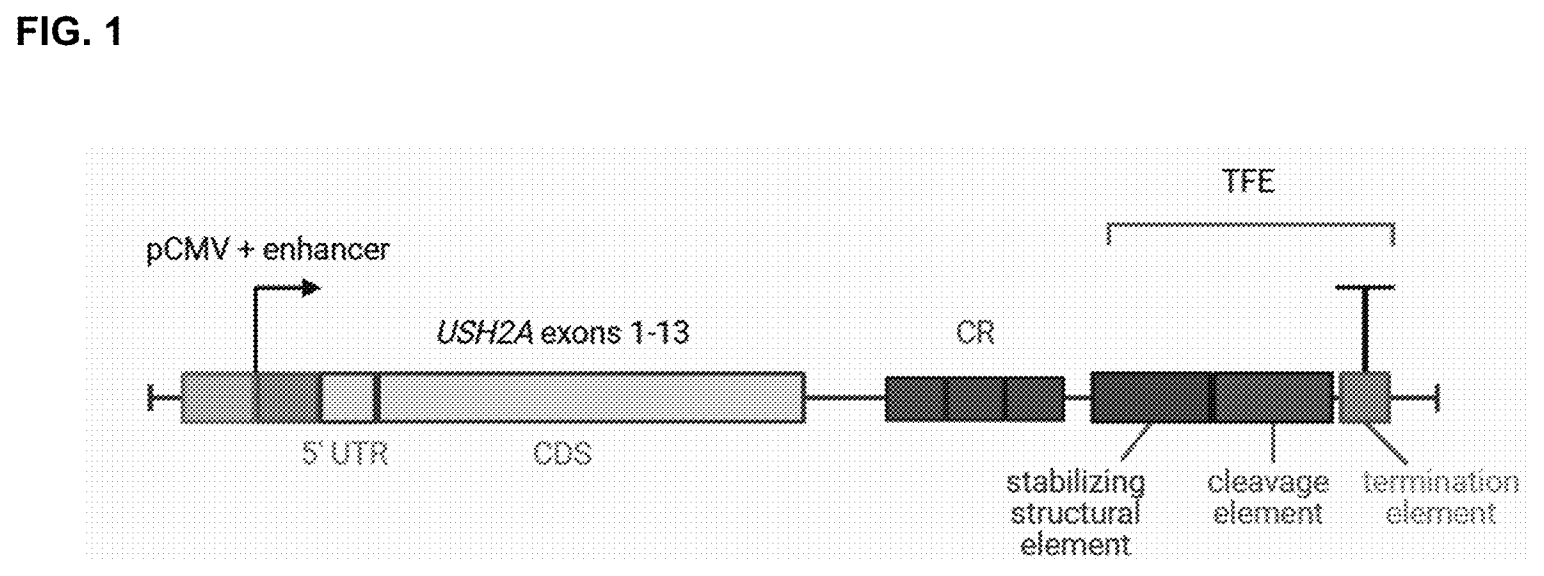

In embodiments, the trifunctional element is, without wishing to be bound by theory, substantially the same as shown in FIG. 1.

In embodiments, the trans-splicing molecule is, without wishing to be bound by theory, substantially the same as shown in FIG. 1.

In embodiments, "complementary region" and "complementary region," or "CR," are used interchangeably to refer to a nucleic acid sequence that binds to another nucleic acid molecule (e.g., also referred to as "target sequence").

In embodiments, the term "target sequence" refers to a sequence of contiguous nucleotides present in a target RNA (e.g., pre-mRNA) targeted for trans-splicing. In embodiments, the term "contiguous nucleotides" refers to a string of nucleotides that are covalently linked and immediately adjacent to one another. In embodiments, the target sequence is at least about or at least about 4 nucleotides in length to about or at least about 300 nucleotides in length (e.g., about 4, 5, 6, 7, 8, 9, 10, 11, 12, 13, 14, 15, 20, 30, 40, 50, 100, 150, 200, or 300 nucleotides in length, including lengths therebetween). In embodiments, the target sequence is less than about 300, 250, 200, 100, 150, or 50 nucleotides in length. In embodiments, the target sequence is about 5-10 nucleotides in length, about 10-20 nucleotides in length, about 20-30 nucleotides in length, about 30-40 nucleotides in length, about 40-50 nucleotides in length, about 50-100 nucleotides in length, about 100-150 nucleotides in length, about 150-200 nucleotides in length, or about 200-300 nucleotides in length, including ranges therein.

Without being bound by theory, the trans-splicing molecule and/or trifunctional element described herein is brought into proximity of a region of the target RNA (e.g., pre-mRNA) selected for trans-splicing and recruits one or more ribonuclear protein (RNP) to form an RNP complex (e.g., the spliceosome) to the target RNA such that efficient trans-splicing occurs. In embodiments, the target RNA is a pre-mRNA. In embodiments, the pre-mRNA is of a gene related to a disease or disorder.

Trifunctional Element

In embodiments, disclosed herein is a trifunctional element suitable for targeted trans-splicing of an RNA or pre-mRNA molecule, wherein the trifunctional element comprises: (i) one or more stabilizing structural elements; (ii) one or more cleavage elements; and (iii) a termination sequence.

In embodiments, disclosed herein is a trans-splicing molecule comprising a trifunctional element suitable for targeted trans-splicing of an RNA or pre-mRNA molecule, wherein the trifunctional element comprises: (i) one or more stabilizing structural elements; (ii) one or more cleavage elements; and (iii) a termination sequence.

In embodiments, the one or more cleavage elements is located adjacent to, or abuts, the one or more stabilizing structural elements. In embodiments, the one or more cleavage elements is about 5, about 10, about 15, about 20, about 25, about 50, about 100, about 200, about 500, or about 1000 nucleotides from the one or more stabilizing structural elements.

In embodiments, the one or more stabilizing structural elements, e.g., without limitation, comprises one or both sequences from Table 1. In embodiments, the sequence is selected from Table 1. In embodiments, the sequence is a sequence having 1, 2, 3, 4, 5, 6, 7, 8, 9, 10 or more nucleic acid changes relative to SEQ ID NOs: 195-198.

TABLE 1

Illustrative of one or more stabilizing structural elements, e.g., without limitation, in the trifunctional elements disclosed herein. Sequences are listed as DNA sequences. In embodiments, the RNA equivalent is used.

| SEQ ID NO | Illustrative Sequence |
|---|---|
| SEQ ID NO: 195 | TCCAATGCTCTTCAGTAGGGTCATGAAGGTTTTTCTTTTCC TGAGAAAACAACACGTATTGTTTTCTCAGGTTTTGCTTTTT GGCCTTTTTCTAGCTTAAAAAAAAAAAAAGCAAAAGA |
| SEQ ID NO: 196 | TATGAAGGTTTTTCTTTTCCTGAGAAAACAACACGTATTGT TTTCTCAGGTTTTGCTTTTTGGCCTTTTTCTAGCTTAAAAA AAAAAAAAGCAAAA |
| SEQ ID NO: 197 | TCCAATGCTCTTCAGTAGGGTCATGAAGGTTTTTCTTTTCC TGAGAAAACAACACGTATTGTTTTCTCAGGTTTTGCTTTTT GGCCTTTTTCTAGCTTAAAAAAAAAAAAAGCAAAA |
| SEQ ID NO: 198 | TATGAAGGTTTTTCTTTTCCTGAGAAAACAACACGTATTGT TTTCTCAGGTTTTGCTTTTTGGCCTTTTTCTAGCTTAAAAA AAAAAAAAGCAAAAGA |

In embodiments, the one or more stabilizing structural elements comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of SEQ ID NOs: 195-198. In embodiments, the one or more stabilizing structural elements is or comprises the nucleic acid sequence of SEQ ID NOs: 195-198.

In embodiments, one or more stabilizing structural elements are included in the trifunctional element adjacent to one or more self-cleaving ribozyme sequence to stabilize the end (5' or 3' end) of the trifunctional element after ribozyme cleavage.

In embodiments, the stabilizing structural element sequence comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of SEQ ID NOs: 195-198.

In embodiments, the stabilizing structural element sequence is based on the nucleic acid sequence of SEQ ID NOs: 195-198. In embodiments, SEQ ID NOs: 195-198 comprises 1, 2, 3, 4, 5, 6, 7, 8, 9, or 10 changes (e.g., nucleic acid mutations, substitutions, deletions, or insertions) relative to the nucleic acid sequence of SEQ ID NOs: 195-198.

In embodiments, the stabilizing structural element sequence is or comprises a nucleic acid sequence of SEQ ID NOs: 195-198. In embodiments, the stabilizing structural element is or comprises the nucleic acid sequence of SEQ ID NO: 195. In embodiments, the stabilizing structural element is or comprises the nucleic acid sequence of SEQ ID NO: 196.

In embodiments, the trifunctional element comprises one or more stabilizing structural element sequences, or a sequence that resembles a secondary structure that adopts a stable core, or is capable of adopting a substantially similar secondary structure. In embodiments, the trifunctional element comprises a stabilizing structural element sequence adjacent to one or more ribozyme sequence which functions to stabilize the trifunctional element after cleavage (e.g., cis-cleavage or trans-cleavage). In embodiments, the stabilizing structural element (or similar secondary structural element) folds at one or both ends (5' and/or 3') of the trifunctional element to maintain trans-splicing integrity, avoid trafficking outside of the nucleus, improve half-life, reduce degradation and/or exonuclease activity, etc.

In embodiments, the one or more stabilizing structural element sequences is located at the 3' end of the trifunctional element and/or adjacent to one or more ribozyme sequences. In embodiments, the one or more cleavage elements cleaves, or is suitable for cleaving, at a site adjacent to the one or more stabilizing structural elements such that a stabilizing structural element sequence becomes the 3' end of the trifunctional element after ribozyme cleavage. In embodiments, the one or more stabilizing structural elements is configured to adopt a stabilizing structural element structure and/or does not form an RNP complex.

In embodiments, the one or more cleavage elements, e.g., without limitation, is a ribozyme sequence.

In embodiments, the one or more ribozyme sequences are cis-cleaving (e.g., cleaves within the ribozyme sequence, or scarlessly). In embodiments, the one or more stabilizing structural elements comprises an element having one or more AU Hoogsteen repeat sequences.

In embodiments, the orientation and placement of the one or more stabilizing structural elements relative to the trifunctional element can be varied to optimize stability and termination efficiency. In embodiments, the one or more stabilizing structural elements is located at the 3' end of the trifunctional element. In embodiments, the one or more stabilizing structural elements is about 5, about 10, about 15, about 20, about 25, about 50, about 100, about 200, about 500, or about 1000 nucleotides from the 3' end of the trifunctional element. In embodiments, the one or more stabilizing structural elements is located at the 5' end of the trifunctional element. In embodiments, the one or more stabilizing structural elements is about 5, about 10, about 15, about 20, about 25, about 50, about 100, about 200, about 500, or about 1000 nucleotides from the 5' end of the trifunctional element.

In embodiments, the one or more stabilizing structural elements stabilizes, or is suitable for stabilizing, the 3' end of the trans-splicing molecule and/or the trifunctional element after ribozyme cleavage and/or removal of the termination sequence.

In embodiments, the termination sequence is selected from a polyadenine (polyA) sequence, a Bovine Growth Hormone polyadenylation signal (bGHpA), a SV40 polyadenylation signal (SV40 pA), or a human Growth Hormone polyA sequence (hGH polyA sequence).

In embodiments, the polyadenine (polyA) sequence enhances RNA stability prior to ribozyme-mediated cleavage in comparison to a composition lacking one or more of: (i) the cleavage element; (ii) the stabilizing structural element; or (iii) a termination sequence. In embodiments, the enhancement of RNA stability is characterized by at least one of: (i) an increase in RNA half-life; (ii) reduction of exonuclease-mediated degradation; (iii) specific nuclear localization/retention; and/or (iv) a decrease in one or more of: a) aberrant translation, b) off-target translation, c) non-specific splice editor translation, d) ectopic translation, and/or e) unintended polypeptide synthesis.

As disclosed herein, the trifunctional element also influences translation dynamics. In embodiments, and without wishing to be bound by theory, the trifunctional element results in an increase or decrease in translated trans-spliced RNA molecule into a protein product in comparison to a composition lacking the trifunctional element, wherein the improvement comprises an increase or decrease synthesis of a protein product, and/or decreased synthesis of an aberrant or deleterious polypeptide (e.g., an un-spliced rep RNA), or wherein improvement comprises an increase in yield of an intended protein and/or a decrease in off-target or incomplete polypeptide synthesis.

In embodiments, the trifunctional element improves the amount of the trans-spliced RNA molecule into a protein product in comparison to a composition lacking one or more of: (i) the stabilizing structural element; (ii) the cleavage element; or (iii) the polyadenine (polyA) sequence, wherein the improvement comprises an increase or decrease in synthesized protein product, and/or decreased synthesis of an aberrant or deleterious polypeptide (e.g., an un-spliced rep RNA), or wherein improvement comprises an increase in yield of an intended protein and/or a decrease in off-target or incomplete polypeptide synthesis.

As disclosed herein, the described improvements in trans-splicing based on the trifunctional element support the generation of functional or therapeutic proteins. In embodiments, the translated protein comprises a therapeutic protein, or a functional version of a genetically mutated protein.

In embodiments, the translated protein is used in a method of treating inherited retinal disease (IRDs).

In embodiments, the inherited retinal disease (IRD) is selected from achromatopsia, Bardet-Biedl syndrome, Batten disease, Best disease (Bestrophinopathy), choroideremia, cone dystrophy, cone-rod dystrophy (CRD), congenital stationary night blindness, conjunctival telangiectasia, crossed eye (strabismus), Leber congenital amaurosis (LCA), macular degeneration, macular dystrophy, nystagmus, ocular telangiectasias, oculomotor apraxia, optic atrophy, pattern dystrophy, photophobia, retinitis pigmentosa (RP), Stargardt macular dystrophy, type 1 Usher syndrome, type 2 Usher syndrome, vitelliform macular dystrophy, X-linked retinitis pigmentosa (XLRP), and X-linked retinoschisis (XLRS). Numerous IRDs suitable for treatment by the compositions and methods herein, and their gene-phenotype pathology as well as clinical endpoints for determining treatment, are known and/or can be determined, for example using tools such as Eye2Gene and various other art-recognized methods, including as described in Pontikos et al. "Next-generation phenotyping of inherited retinal diseases from multimodal imaging with Eye2Gene," Nat. Mach. Intell. (2025) Vol. 7, pp: 367-78; Thirunavukarasu et al., "Visualizing treatment effects in low-vision settings: proven and potential endpoints for clinical trials of inherited retinal disease therapies," Gene Ther. (2025) doieorg/0.1038/s41434-025-00552-7; and Crutchfield et al., "Inherited retinal disease in global Indigenous populations: A scoping review," Survey of Ophthalmology, (2025) doiorg/e0.1016/j.survophthal.2025.06.005.

In non-limiting embodiments, the IRD is selected from Table 2. In embodiments, the trans-splicing molecules disclosed herein comprise one or more CRs that target one or more introns of a gene listed in Table 2.

TABLE 2

| Illustrative genes involved in inherited retinal diseases (IRDs). | | |
|---|---|---|
| Gene | Illustrative IRDs/Phenotypes | Illustrative Reference(s) |
| ABCA4 | Stargardt macular dystrophy, Cone-rod dystrophy (CRD) | Pontikos et al. (2020), Lynn et al. (2024) |
| USH2A | Retinitis Pigmentosa (RP), type 2 Usher syndrome | Pontikos et al. (2020), Toms et al. (2020) |
| RPGR | X-linked Retinitis Pigmentosa (RP), Cone-rod dystrophy (CRD) | Pontikos et al. (2020), Sharon et al. (2003) |
| PRPH2 | Pattern dystrophy, Retinitis Pigmentosa (RP), Macular degeneration | Pontikos et al. (2020), Jeffery et al. (2024), Oishi et al. (2021) |
| BEST1 | Best disease (Bestrophinopathy), Retinitis Pigmentosa (RP), | Pontikos et al. (2020), Boon et al. (2021) |
| RS1 | X-linked retinoschisis (XLRS) | Pontikos et al. (2020), van der Veen et al. (2024) |
| RP1 | Retinitis Pigmentosa (RP) | Pontikos et al. (2020), Silva et al. (2020) |
| RHO | Retinitis Pigmentosa, Congenital Stationary Night Blindness | Pontikos et al. (2020), Athanasiou et al. (2018) |
| CHM | Choroideremia | Pontikos et al. (2020), Elsayed et al. (2025) |
| CRB1, LRAT, LCA5 | Leber Congenital Amaurosis (LCA), Retinitis Pigmentosa (RP), Macular dystrophy | Pontikos et al. (2020), Den Hollander et al. (2008) |
| PRPF31 | Retinitis Pigmentosa (RP) (Autosomal Dominant) | Pontikos et al. (2020), Aweidah et al. (2023) |
| MYO7A | Type 1 Usher Syndrome | Pontikos et al. (2020), Rong et al. (2014), Yoshimura et al. (2013) |
| OPA1 | Optic atrophy | Pontikos et al. (2020), Wong et al. (2023) |
| CNGB3 | Achromatopsia, Cone dystrophy | Pontikos et al. (2020), Kohl et al. (2003) |
| RPE65 | Leber Congenital Amaurosis (LCA), Retinitis Pigmentosa (RP) | Pontikos et al. (2020), Cideciyan et al. (2013) |
| EYS | Retinitis Pigmentosa (RP) | Pontikos et al. (2020), Collin et al. (2011) |
| GUCY2D | Leber Congenital Amaurosis (LCA), Retinitis Pigmentosa (RP), Cone or Cone-rod dystrophy | Pontikos et al. (2020), Boye et al. (2015) |
| PROM1 | Macular dystrophy, Cone-rod dystrophy, Retinitis Pigmentosa (RP) | Pontikos et al. (2020), Lynn et al. (2024) |
| CNGA3 | Achromatopsia, Cone dystrophy | Pontikos et al. (2020), Wissinger et al. (2001) |
| RDH12 | Leber Congenital Amaurosis (LCA), Retinitis Pigmentosa (RP) | Pontikos et al. (2020), Lynn et al. (2024) |
| KIZ | Retinitis Pigmentosa (RP) | Sundaresan et al. (2024) Ganapathi et al. (2022) |

In embodiments, the CR targets an intron of the ABCA4 gene. Mutations of the ABCA4 gene have been demonstrated to the etiological agents of Stargardt macular dystrophy and cone-rod dystrophy (CRD), for example, as described in Pontikos et al., "*Genetic Basis of Inherited Retinal Disease in a Molecularly Characterized Cohort of More Than 3000 Families from the United Kingdom,*" *Opthamology*, (2020) Vol. 127, No. 10, pp; 1384-94; and Lynn et al., "*Expanding the Mutation Spectrum for Inherited Retinal Diseases,*" Genes, (2024) Vol. 16, No. 1. In embodiments, trans-splicing molecules with CRs targeting ABCA4 pre-mRNA are useful in methods of treating Stargardt macular dystrophy and CRD. In such embodiments, the trans-splicing molecule includes one or more exons of ABCA4 and the CRs enable the trans-splicing molecule to come into proximity with the pre-mRNA to splice the one or more exons into the pre-mRNA to replace a defective portion of the ABCA4 pre-mRNA, restoring functional ABCA4 protein to the cell.

In embodiments, the CR targets an intron of the USH2A gene. Mutations of the USH2A gene are a major cause of type 2 Usher syndrome, which is the leading genetic cause of combined deaf-blindness worldwide. This disorder is characterized by progressive vision loss due to Retinitis Pigmentosa (RP) and sensorineural hearing loss resulting from cochlear hair cell dysfunction, as described in Pontikos et al., (2020) and Toms et al., "*Usher syndrome: clinical features, molecular Genetics and advancing therapeutics,*" *Ther Adv Ophthalmol.* (2020) Vol. 12, pp: 1-19. In embodiments, trans-splicing molecules with CRs targeting USH2A pre-mRNA are useful in methods of treating both retinal degeneration and auditory impairment associated with 2 Usher syndrome. In such embodiments, the trans-splicing molecule includes one or more exons of USH2A and the CRs enable the trans-splicing molecule to come into proximity with the pre-mRNA to splice the one or more exons into the pre-mRNA to replace a defective portion of the USH2A pre-mRNA, restoring functional USH2A protein to the cell.

In embodiments, the CR targets an intron of the RPGR gene. Mutations of the RPGR gene have been demonstrated to the etiological agents of RP and CRD, for example, as described in Pontikos et al., (2020) and Sharon et al., "*RP2 and RPGR mutations and clinical correlations in patients with X-linked retinitis pigmentosa,*" *Am J Hum Genet.* (2003) Vol. 73, No. 5, pp: 1131-46. In embodiments, trans-splicing molecules with CRs targeting RPGR pre-mRNA are useful in methods of treating RP and CRD. In such embodiments, the trans-splicing molecule includes one or more exons of RPGR and the CRs enable the trans-splicing molecule to come into proximity with the pre-mRNA to splice the one or more exons into the pre-mRNA to replace a defective portion of the RPGR pre-mRNA, restoring functional RPGR protein to the cell.

In embodiments, the CR targets an intron of the BEST1 gene. Mutations of the BEST1 gene have been demonstrated to the etiological agents of Best disease (Bestrophinopathy) and RP, for example, as described in Pontikos et al., (2020) and Boon et al., "*The spectrum of ocular phenotypes caused by mutations in the BEST1 gene,*" *Prog Retin Eye Res.*, (2009) Vol. 23, No. 3, pp: 187-205. In embodiments, trans-splicing molecules with CRs targeting BEST1 pre-mRNA are useful in methods of treating Bestrophinopathy and RP. In such embodiments, the trans-splicing molecule includes one or more exons of BEST1 and the CRs enable the trans-splicing molecule to come into proximity with the pre-mRNA to splice the one or more exons into the pre-mRNA to replace a defective portion of the BEST1 pre-mRNA, restoring functional BEST1 protein to the cell.

In embodiments, the CR targets an intron of the RS1 gene. Mutations of the RS1 gene have been demonstrated to the etiological agents of X-linked retinoschisis (XLRS), for example, as described in Pontikos et al., (2020) and van der Veen et al., "*The Road towards Gene Therapy for X-Linked Juvenile Retinoschisis: A Systematic Review of Preclinical Gene Therapy in Cell-Based and Rodent Models of XLRS,*" *Int J Mol Sci.* (2024) Vol. 25, No. 1267, pp: 1-37. In embodiments, trans-splicing molecules with CRs targeting RS1 pre-mRNA are useful in methods of treating SLRS. In such embodiments, the trans-splicing molecule includes one or more exons of RS1 and the CRs enable the trans-splicing molecule to come into proximity with the pre-mRNA to splice the one or more exons into the pre-mRNA to replace a defective portion of the RS1 pre-mRNA, restoring functional RS1 protein to the cell.

In embodiments, the CR targets an intron of the RP1 gene. Mutations of the RP1 gene have been demonstrated to the etiological agents of RP, for example, as described in Pontikos et al., (2020) and Silva et al., "*Retinitis Pigmentosa Due to Rp Biallelic Variants,*" *Sci Rep.* (2020) Vol. 10, No. 1603. In embodiments, trans-splicing molecules with CRs targeting RP1 pre-mRNA are useful in methods of treating RP. In such embodiments, the trans-splicing molecule includes one or more exons of RP1 and the CRs enable the trans-splicing molecule to come into proximity with the pre-mRNA to splice the one or more exons into the pre-mRNA to replace a defective portion of the RP1 pre-mRNA, restoring functional RP1 protein to the cell.

In embodiments, the CR targets an intron of the RHO gene. Mutations of the RHO gene have been demonstrated to the etiological agents of RP and congenital stationary night blindness, for example, as described in Pontikos et al., (2020) and Silva et al., "*Retinitis Pigmentosa Due to Rp Biallelic Variants,*" *Sci Rep.* (2020) Vol. 10, No. 1603. In embodiments, trans-splicing molecules with CRs targeting RHO pre-mRNA are useful in methods of treating RP and congenital stationary night blindness. In such embodiments, the trans-splicing molecule includes one or more exons of RHO and the CRs enable the trans-splicing molecule to come into proximity with the pre-mRNA to splice the one or more exons into the pre-mRNA to replace a defective portion of the RHO pre-mRNA, restoring functional RHO protein to the cell.

In embodiments, the CR targets an intron of the CHM gene. Mutations in the CHM gene have been demonstrated to the etiological agents of choroideremia, for example, as described in Pontikos et al., (2020) and Elsayed et al., "*Gene therapy for choroideremia: progress, potential and pitfalls,*" *Expert Opin Biol Ther.* (2025) Vol. 25, No. 3, pp: 257-63. In embodiments, trans-splicing molecules with CRs targeting CHM pre-mRNA are useful in methods of treating choroideremia. In such embodiments, the trans-splicing molecule includes one or more exons of CHM and the CRs enable the trans-splicing molecule to come into proximity with the pre-mRNA to splice the one or more exons into the pre-mRNA to replace a defective portion of the CHM pre-mRNA, restoring functional CHM protein to the cell.

In embodiments, the CR targets an intron of one or more of the CRB1, LRAT, or LCA5 gene. Mutations in each of the CRBa, LRAT, and LCA5 genes have been demonstrated to be the etiological agents of LCA, RP, and macular dystrophy, for example, as described in Pontikos et al., (2020), Den Hollander et al., "*Leber congenital amaurosis: genes, proteins and disease mechanisms,*" *Prog Retin Eye Res.* (2008) Vol. 27, No. 4, pp: 332-46; and Cideciyan et al., "*Human retinal gene therapy for Leber congenital amaurosis shows advancing retinal degeneration despite enduring visual improvement,*" *PNAS,* (2013) Vol. 110, No. 6, pp: E517-25. In embodiments, trans-splicing molecules with CRs targeting the CRB1, LRAT, or LCA5 pre-mRNAs are useful in methods of treating LCA, RP, and macular dystrophy. In such embodiments, the trans-splicing molecule includes one or more exons of CRB1, LRAT, or LCA5 and the CRs enable the trans-splicing molecule to come into proximity with the pre-mRNA to splice the one or more exons into the pre-mRNA to replace a defective portion of the CRB1, LRAT, or LCA5 pre-mRNA, restoring functional CRB1, LRAT, or LCA5 protein to the cell, respectively.

In embodiments, the CR targets an intron of the PRPF31 gene. Mutations in the PRPF31 gene have been demonstrated to be the etiological agents of RP, particularly autosomal dominant forms of RP, for example, as described in Pontikos et al., (2020) and Aweidah et al., "*PRPF*31-*retinitis pigmentosa: Challenges and opportunities for clinical translation,*" *Vision Research,* (2023) Vol. 213, No. 108315. In embodiments, trans-splicing molecules with CRs targeting the PRPF31 pre-mRNA are useful in methods of treating RP. In such embodiments, the trans-splicing molecule includes one or more exons of PRPF31 and the CRs enable the trans-splicing molecule to come into proximity with the pre-mRNA to splice the one or more exons into the pre-mRNA to replace a defective portion of the PRPF31 pre-mRNA, restoring functional PRPF31 protein to the cell.

In embodiments, the CR targets an intron of the MYO7A gene. Mutations in the MYO7A gene have been demonstrated to be the etiological agents of type 1 Usher syndrome, for example, as described in Pontikos et al., (2020), Rong et al., "*Novel and Recurrent MYO7A Mutations in Usher Syndrome Type 1 and Type 2,*" *PLoS One.* (2014) Vol. 9, No. 5: e97808; and Yoshimura et al., "*An Usher syndrome type 1 patient diagnosed before the appearance of visual,*" *Int J Pediatr Otorhinolaryngol.* (2013) Vol. 77, No. 2, pp: 289-302. In embodiments, trans-splicing molecules with CRs targeting the MYO7A pre-mRNA are useful in methods of treating type 1 Usher syndrome. In such embodiments, the trans-splicing molecule includes one or more exons of MYO7A and the CRs enable the trans-splicing molecule to come into proximity with the pre-mRNA to splice the one or more exons into the pre-mRNA to replace a defective portion of the MYO7A pre-mRNA, restoring functional MYO7A protein to the cell.

In embodiments, the CR targets an intron of the OPA1 gene. Mutations in the OPA1 gene have been demonstrated to be the etiological agents of optic atrophy, for example, as described in Pontikos et al., (2020) and Wong et al., "*OPA*1 Dominant Optic Atrophy: Pathogenesis and Therapeutic Targets,*" *J Neuroophthalmol.* Vol. 43, No. 4, pp: 464-74. In embodiments, trans-splicing molecules with CRs targeting the OPA1 pre-mRNA are useful in methods of treating optic atrophy. In such embodiments, the trans-splicing molecule includes one or more exons of OPA1 and the CRs enable the trans-splicing molecule to come into proximity with the pre-mRNA to splice the one or more exons into the pre-mRNA to replace a defective portion of the OPA1 pre-mRNA, restoring functional OPA1 protein to the cell.

In embodiments, the CR targets an intron of the CNGB3 gene. Mutations in the CNGB3 gene have been demonstrated to be the etiological agents of achromatopsia (particularly autosomal recessive forms, arRP) and cone dystrophy, for example, as described in Pontikos et al., (2020) and Kohl et al. "*CNGB*3 *mutations account for* 50% *of all cases with autosomal recessive achromatopsia,*" *European Journal of Human Genetics,* (2003) Vol. 13, pp: 302-8. In embodiments, trans-splicing molecules with CRs targeting the CNGB3 pre-mRNA are useful in methods of treating achromatopsia and cone dystrophy. In such embodiments, the trans-splicing molecule includes one or more exons of CNGB3 and the CRs enable the trans-splicing molecule to come into proximity with the pre-mRNA to splice the one or more exons into the pre-mRNA to replace a defective portion of the CNGB3 pre-mRNA, restoring functional CNGB3 protein to the cell.

In embodiments, the CR targets an intron of the EYS gene (the human ortholog related to the *Drosophila* gene, EGLF11). Mutations in the EYS gene have been demonstrated to be the etiological agents of RP, for example, as described in Pontikos et al., (2020) and Collin et al., "*Identification of a 2 Mb human ortholog of Drosophila eyes shut/spacemaker that is mutated in patients with retinitis*

*pigmentosa," Am J Hum Genet.* (2008) Vol. 83, No. 5, pp: 594-603. In embodiments, trans-splicing molecules with CRs targeting the EYS pre-mRNA are useful in methods of treating RP. In such embodiments, the trans-splicing molecule includes one or more exons of EYS and the CRs enable the trans-splicing molecule to come into proximity with the pre-mRNA to splice the one or more exons into the pre-mRNA to replace a defective portion of the EYS pre-mRNA, restoring functional EYS protein to the cell.

In embodiments, the CR targets an intron of the GUCY2D gene. Mutations in the GUCY2D gene have been demonstrated to be the etiological agents of LCA, RP, and cone or cone-rod dystrophy, for example as described in Pontikos et al., (2020) and Boye, *"Leber Congenital Amaurosis Caused by Mutations in GUCY2D," Cold Spring Harb Perspect Med.* (2015) Vol. 5, No. 1. In embodiments, trans-splicing molecules with CRs targeting the GUCY2D pre-mRNA are useful in methods of treating LCA, RP, and cone or cone-rod dystrophy. In such embodiments, the trans-splicing molecule includes one or more exons of GUCY2D and the CRs enable the trans-splicing molecule to come into proximity with the pre-mRNA to splice the one or more exons into the pre-mRNA to replace a defective portion of the GUCY2D pre-mRNA, restoring functional GUCY2D protein to the cell.

In embodiments, the CR targets an intron of the GUCY2D gene. Mutations in the GUCY2D gene have been demonstrated to be the etiological agents of LCA, RP, and cone or cone-rod dystrophy, for example as described in Pontikos et al., (2020) and Boye, *"Leber Congenital Amaurosis Caused by Mutations in GUCY2D," Cold Spring Harb Perspect Med.* (2015) Vol. 5, No. 1. In embodiments, trans-splicing molecules with CRs targeting the GUCY2D pre-mRNA are useful in methods of treating LCA, RP, and cone or cone-rod dystrophy. In such embodiments, the trans-splicing molecule includes one or more exons of GUCY2D and the CRs enable the trans-splicing molecule to come into proximity with the pre-mRNA to splice the one or more exons into the pre-mRNA to replace a defective portion of the GUCY2D pre-mRNA, restoring functional GUCY2D protein to the cell.

In embodiments, the CR targets an intron of the PROM1 gene. Mutations in the PROM1 gene have been demonstrated to be the etiological agents of macular dystrophy, cone-rod dystrophy, and RP, for example as described in Pontikos et al., (2020) and Lynn et al., *"Expanding the Mutation Spectrum for Inherited Retinal Diseases," Genes,* (2024) Vol. 16, No. 1. In embodiments, trans-splicing molecules with CRs targeting the PROM1 pre-mRNA are useful in methods of treating macular dystrophy, cone-rod dystrophy, and RP. In such embodiments, the trans-splicing molecule includes one or more exons of PROM1 and the CRs enable the trans-splicing molecule to come into proximity with the pre-mRNA to splice the one or more exons into the pre-mRNA to replace a defective portion of the PROM1 pre-mRNA, restoring functional PROM1 protein to the cell.

In embodiments, the CR targets an intron of the CNGA3 gene. Mutations in the CNGA3 gene have been demonstrated to be the etiological agents of achromatopsia and cone dystrophy, for example as described in Pontikos et al., (2020) and Wissinger et al. *"CNGA3 Mutations in Hereditary Cone Photoreceptor Disorders," Am J Hum Genet.,* (2001) Vol, 69, No. 9, pp: 722-37. In embodiments, trans-splicing molecules with CRs targeting the CNGA3 pre-mRNA are useful in methods of treating macular dystrophy, cone-rod dystrophy, and RP. In such embodiments, the trans-splicing molecule includes one or more exons of CNGA3 and the CRs enable the trans-splicing molecule to come into proximity with the pre-mRNA to splice the one or more exons into the pre-mRNA to replace a defective portion of the CNGA3 pre-mRNA, restoring functional CNGA3 protein to the cell.

In embodiments, the CR targets an intron of the RDH12 gene. Mutations in the RDH12 gene have been demonstrated to be the etiological agents of LCA and RP, for example as described in Pontikos et al., (2020) and Lynn et al., (2024). In embodiments, trans-splicing molecules with CRs targeting the RDH12 pre-mRNA are useful in methods of treating LCA and RP. In such embodiments, the trans-splicing molecule includes one or more exons of RDH12 and the CRs enable the trans-splicing molecule to come into proximity with the pre-mRNA to splice the one or more exons into the pre-mRNA to replace a defective portion of the RDH12 pre-mRNA, restoring functional RDH12 protein to the cell.

In embodiments, the trans-splicing molecule and/or CR targets an intron of the KIZ gene. Mutations in the KIZ gene have been demonstrated to be the etiological agents of RP, for example as described in Sundaresan et al., *"Genetic and Clinical Analyses of the KIZ-c.226C>T Variant Resulting in a Dual Mutational Mechanism," Genes,* (2024) Vol. 15, No. 6; and Ganapathi et al., *"Clinical exome sequencing for inherited retinal degenerations at a tertiary care center," Sci Rep.* (2022) Vol. 12:9358. In embodiments, the trans-splicing molecule and/or CRs targeting the KIZ pre-mRNA are useful in methods of treating RP. In such embodiments, the trans-splicing molecule includes one or more exons of KIZ and the CRs enable the trans-splicing molecule to come into proximity with the pre-mRNA to splice the one or more exons into the pre-mRNA to replace a defective portion of the KIZ pre-mRNA, restoring functional KIZ protein to the cell.

In embodiments, the trans-splicing molecule targets a gene associated with an IRD, for example, being selected from USH2A, MYO7A, PRPF31, ABCA4, RPGR, EYS, KIZ, PRPH2, BEST1, RS1, RP1, RHO, CHM, CRB1, LRAT; LCA5, OPA1, CNGB3, RPE65, GUCY2D, PROM1, CNGA3, and RDH12. In some embodiments, the trans-splicing molecule (and CR) targets a gene selected from USH2A, ATM, MYO7A, PRPF31, and ABCA4. In embodiments, the CR targets an intron of one or more of these genes.

In embodiments, structural modifications can further enhance the trans-splicing molecule. For example, in embodiments, the trans-splicing molecule and/or the trifunctional element further comprises a 5′ cap, and/or one or more of a 5′ untranslated region (UTR).

In addition, in some embodiments, localization signals provide an additional layer of control over the RNA. In embodiments, the trans-splicing molecule and/or the trifunctional element comprises one or more RNA localization signals suitable for directing subcellular localization of the RNA molecule. In embodiments, the one or more RNA localization signals comprise a localization motif selected from: (i) β-actin zipcode; (ii) ZBP1-binding motif; (iii) AU-rich element (ARE); (iv) GA-rich motif, (v) a stem-loop structure; (vi) BORG (BMP2-OP1-responsive gene) pentamers; (vii) C-rich motifs from nuclear retained long noncoding RNAs (lncRNAs); (viii) XIST motifs from lncRNAs; (viiii) U7 small nuclear RNA (smU7); or (x) SINE-derived nuclear RNA localization elements (SIRLOIN).

The localization signals describe herein not only direct RNA positioning but also improve functional outcomes by promoting efficient trans-splicing in relevant cellular compartment. For example, in embodiments, the one or more RNA localization signals facilitate co-localization with a ribonucleoprotein (RNP). In embodiments, the one or more RNA localization signals improve trans-splicing efficiency by directing the RNA molecule to a subcellular compartment enriched in target pre-mRNA in comparison to a composition one or more RNA localization signals, and/or lacking one or more of: (i) a stabilizing structural element; (ii) a cleavage element; or (iii) the termination element.

In embodiments, the one or more RNA localization signals is located either: i) between the one or more cleavage elements and the stabilizing structural element; ii) at the 3' end; (iii) or at the 5' end of the trifunctional element.

In embodiments, the one or more cleavage elements is self-cleaving.

In embodiments, the one or more cleavage elements is trans-cleaving.

In embodiments, at least one cleavage element is self-cleaving and at least one cleavage element is trans-cleaving. In embodiments, a self-cleaving ribozyme within the trifunctional element autonomously removes itself or a flanking sequence after transcription. In embodiments, the trans-splicing RNA adopts the correct structural conformation for hybridization and catalytic activity.

By eliminating unnecessary sequences scarlessly, self-cleavage promotes stability and prevents interference with the trans-splicing reaction.

In embodiments, a trans-cleaving ribozyme targets and cleaves an endogenous pre-mRNA at a specific site, creating an entry point for the trans-splicing molecule and/or trifunctional element to replace or repair the defective region. In embodiments, the cleavage facilitates the alignment of the trans-splicing molecule and/or trifunctional element with the target transcript, enabling accurate trans-splicing and incorporation of the intended coding sequence.

In embodiments, the one or more stabilizing structural elements is suitable for stabilizing the 3' end of the trans-splicing molecule and/or the trifunctional element. In embodiments, the one or more cleavage elements facilitates subcellular localization of the RNA or pre-mRNA molecule, and the trans-splicing molecule and/or the trifunctional element further allows for termination or reduction of translation of an incomplete or toxic intermediate protein (e.g., an un-spliced repRNA).

In embodiments, the one or more cleavage elements is about or at least about 20 nucleotides to about or at least about 240 nucleotides in length. In embodiments, the one or more cleavage elements is about or at least about 20 nucleotides in length, about or at least about 30 nucleotides in length, about or at least about 40 nucleotides in length, about or at least about 50 nucleotides in length, about or at least about 60 nucleotides in length, about or at least about 70 nucleotides in length, about or at least about 80 nucleotides in length, about or at least about 90 nucleotides in length, about or at least about 100 nucleotides in length, about or at least about 120 nucleotides in length, about or at least about 140 nucleotides in length, about or at least about 160 nucleotides in length, about or at least about 180 nucleotides in length, about or at least about 200 nucleotides in length, about or at least about 220 nucleotides in length, or about or at least about 240 nucleotides in length.

In embodiments, the trans-splicing molecule and/or trifunctional element disclosed herein (and methods using the same) function similarly among a variety of cell systems, including but not limited to, eukaryotic cells. In embodiments, the trans-splicing molecule and/or trifunctional element disclosed herein (and methods using the same) function similarly across multiple eukaryotic systems, including but not limited to, yeasts, mammalian cells, amphibian cells, reptilian cells, fish cells, and avian cells, as well as organisms such as higher vertebrates, for example as described in Lei et al., (2016). In embodiments, the trans-splicing molecule and/or trifunctional element disclosed herein (and methods using the same) are usable in a cell line, such as human embryonic cells (HEK). Those skilled in the art, with the benefit of this disclosure in its entirety, will understand trans-splicing molecules and/or trifunctional elements (and methods using the same) herein are expected to function similarly across cell types, organisms, and targets.

In embodiments, the trifunctional element disclosed herein comprise one or more sequences which relate to one or more cleavage elements. In embodiments, ribozymes refer to small nucleolytic ribonucleic acids which perform site-specific phosphodiester scission (as well as phosphoryl transfer, transesterification, acid-base catalysis, metal ion catalysis, and/or hydrolysis reactions) without the need for extraneous protein chaperones or enzymes.

In embodiments, ribozymes herein catalyze cleavage of RNA via a variety of mechanisms. For example, in non-limiting embodiments, ribozymes herein catalyze site-specific cleavage via nucleophilic attack of a 2'-hydroxyl group on the adjacent 3'-phosphorus to form a cyclic 2',3'-phosphate (or by the 5'-hydroxyl group in the reverse reaction). In embodiments, ribozymes herein include one or more cleavage elements that catalyze phosphoryl transfer reactions between nucleobases. In embodiments, ribozymes herein include one or more cleavage elements that use acid-base catalysis, e.g., between guanine and adenine nucleobases acting as general base and acid, which results in cleavage of a phosphodiester bond. In embodiments, ribozymes herein include one or more cleavage elements that act as metalloenzymes (e.g., using metal ion catalysis with, for example, a magnesium ion ($Mg^{2+}$). In embodiments, ribozymes used in trifunctional elements herein have functionality that overlaps with two or more different modes of catalysis.

Persons skilled in the art, with the benefit of this disclosure in its entirety, will be aware of the various programs that are available to identify putative ribozymes and ribozyme sequences, such as using a BLAST algorithm (or similar algorithm) which relies upon sequence homology (Altschul et al., (1990)), secondary structural motif searching and classification such as with RNAMotif (Macke, "*RNAMotif, an RNA secondary structure definition and search algorithm,*" *Nucleic Acids Res.* (2001) Vol. 29, pp. 4724-35), Infernal (Nawrocki, "*Infernal 1.0: inference of RNA alignments,*" *Bioinformatics.* (2009), Vol. 25, pp. 1335-37), and RNArobo (Rampášek, et al., "*RNA motif search with data-driven element ordering,*" *BMC Bioinf* (2016) Vol. 17, No. 216), RfamGen which is useful to design ribozymes by assimilating both sequence and secondary structure similarity with machine learning (Sumi et al., "*Deep generative design of RNA family sequences,*" *Nat. Methods.* (2024) Vol. 21, pp. 435-43), and the like.

There are a variety art-recognized techniques, including biochemical assays and computational modeling, that have been developed to assess the activity of ribozymes and validate true ribozyme sequences. For example, in embodiments, high-throughput activity assays to validate ribozyme sequences as having ribozyme activity have been described in Yokobayashi et al., "*High-throughput analysis and engineering of ribozymes and deoxyribozymes by sequencing,*" *Acc. Chem. Res.* (2020) Vol. 53, pp. 2903-12. In non-limiting embodiments, doped solid phase synthesis and/or error-prone PCR are useful to produce the DNA templates and next-generation sequencing (NGS) to measure cleavage have been used to identify and test ribozyme sequences, as well as mutational analysis of ribozymes (to identify ribozyme variants/derivatives), for example as described in Yokobayashi et al. 2020; Kobori et al., "*High-throughput assay and engineering of self-cleaving ribozymes by sequencing,*" *Nucleic Acids Res.* (2015) Vol. 43, No. e85; Kobori et al., "*High-throughput mutational analysis of a twister ribozyme,*" *Angew. Chem. Int. Ed.* (2016) Vol. 55, pp. 10354-57; Andreasson et al., "*Comprehensive sequence-to-function mapping of cofactor-dependent RNA catalysis in the glmS ribozyme,*" *Nat. Commun.* (2020) Vol. 11, No. 1663; Roberts et al., "RNA sequence to structure analysis from comprehensive pairwise mutagenesis of multiple self-cleaving ribozymes," eLife. (2023) Vol. 12, No. e80360; and Yamagami et al., "*High-throughput mutational analysis of a methyltransferase ribozyme,*" *Front. RNA Res.* (2024) Vol. 2, No. 1415530. In non-limiting embodiments, computational kinetic modeling has proven useful for tracking ribozyme activity with high accuracy, for example, using k-seq kinetic rate profiling for ribozyme kinetics, as described in Shen et al., "*Kinetic sequencing (k-Seq) as a massively parallel assay for ribozyme kinetics: utility and critical parameters,*" *Nucleic Acids Res.* (2021) Vol. 49, No. e67.

Robust structure-function analysis of a variety of classes of ribozymes has been elucidated, for example, as described in Roth et al., "*A widespread self-cleaving ribozyme class is revealed by bioinformatics,*" *Nat. Chem. Biol.* (2014) Vol. 10, pp. 56-60; Lai et al. "*Effects of circular permutation on the cis-cleavage reaction of a Hepatitis Delta Virus ribozyme: application to transacting ribozyme design,*" *Biochemistry.* (1996) Vol. 35, pp. 124-31; Zamel et al. "*Exceptionally fast self-cleavage by a Neurospora Varkud satellite ribozyme,*" *Proc. Natl Acad. Sci. USA.* (2004) Vol. 101, pp. 1467-72; Hammann et al., "*The ubiquitous hammerhead ribozyme,*" *RNA.* (2012) Vol. 18, pp. 871-85; Weinberg et al., "*Identification of over* 200-*fold more hairpin ribozymes than previously known in diverse circular RNAs,*" *Nucleic Acids Res.* (2021) Vol. 49, pp. 6375-88; Mustafina et al., "*Circularly-permuted pistol ribozyme: a synthetic ribozyme scaffold for mammalian riboswitches,*" *ACS Synth. Biol.* (2021) Vol. 10, pp. 2040-48; and Eckert et al., "*Discovery of natural non-circular permutations in non-coding RNAs,*" *Nucleic Acids Res.* (2023) Vol. 51, pp. 2850-61.

Persons skilled in the art, with the benefit of this disclosure in its entirety, will be aware of the ribozymes that are compatible with the trans-splicing molecule and/or trifunctional element disclosed herein, as well as how to test the ribozymes for their effect on trans-splicing.

As disclosed herein, the diversity of ribozyme sources and types enables customization for specific therapeutic contexts and target sequences. In embodiments, the one or more cleavage elements is, comprises, or is derived from a ribozyme, and the ribozyme is selected from hepatitis delta virus (HDV) ribozyme, HDV-like (CPEB3) ribozyme, aminoacyltransferase ribozyme, β-globin co-transcriptional cleavage ribozyme, CotC ribozyme, GIR1 branching ribozyme, GlmS (glucosamine-6-phosphate activated) ribozyme, Hairpin ribozyme, Hammerhead ribozyme, Hatchet ribozyme, Hepatitis delta virus ribozyme, Hovlinc ribozyme, Leadzyme, Ligase ribozyme, Mammalian CPEB3 ribozyme, Θrz (class I or II) theta ribozyme, Pistol ribozyme, Ribonuclease P, RNase MRP, RNR1 ribozyme, RNR2 ribozyme, RNR3 ribozyme, RNR4 ribozyme, RNR5 ribozyme, Twister ribozyme, Twister-sister ribozyme, Varkud satellite (VS), Vg1 ribozyme, VS ribozyme, or a variant thereof. In embodiments, the one or more cleavage elements is a ribozyme, and the ribozyme is derived from a species selected from *Trichosurus vulpecula, Chinchilla lanigera, Galeopterus variegatus, Monodelphis domestica, Mus spicilegus,* and *Macropus eugenii.*

In embodiments, the one or more ribozymes is selected from a HDV ribozyme, a *Galeopterus variegatus* (Malayan flying lemur) ribozyme, a *Chinchilla lanigera* (long-tailed *Chinchilla*) ribozyme, an Θrz (1789 theta) ribozyme, or an Θrz (1768 theta) ribozyme. In embodiments, the one or more ribozymes is or comprises a HDV ribozyme, an HDV-like ribozyme, an Θrz ribozyme, or an Θrz-like ribozyme.

In embodiments, an HDV-like ribozyme is derived from a wild-type hepatitis delta virus ribozyme through rational design or directed mutagenesis while preserving its catalytic core.

In non-limiting embodiments, the ribozyme originates from, or is derived from, a species selected from *Trichosurus vulpecula, Chinchilla langiera, Galeopterus variegatus, Monodelphins domestica, Mus spicilegus,* and *Macropus eugenii.* In embodiments, the one or more cleavage elements is selected from a HDV ribozyme, a *Galeopterus variegatus* (Malayan flying lemur) ribozyme, a *Chinchilla langiera* (long-tailed *Chinchilla*) ribozyme, an Θrz (1789 theta) ribozyme, or an Θrz (1768 theta) ribozyme.

In embodiments, the one or more cleavage elements comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of any one of SEQ ID NOs: 1-194. In embodiments, the one or more cleavage elements is or comprises the nucleic acid sequence of any one of SEQ ID NOs: 1-194.

In embodiments, the one or more ribozyme is or comprises one or more nucleic acid sequences selected from Table 3.

TABLE 3

| Illustrative ribozyme sequences for a trifunctional element | | | | |
|---|---|---|---|---|
| Ribozyme | Illustrative Designation | Illustrative Sequence | SEQ ID | Length (nt) |
| Algerian_mouse | test_set | GGGGGCCACAGCAGAAGCGTTCACGTCG CGGCCCCTGTCAGATTCTGGCGAATCTGC GAATTCTGCT | SEQ ID NO: 1 | 67 |
| alpine_marmot | test_set | GGGGGCCACAGCAGAAGCGTTCACGTCG CGGCCCCTGTCAGATTCTGATGAATCTGC GAATTCTGCT | SEQ ID NO: 2 | 67 |

TABLE 3-continued

| | | Illustrative ribozyme sequences for a trifunctional element | | |
|---|---|---|---|---|
| Ribozyme | Illustrative Designation | Illustrative Sequence | SEQ ID | Length (nt) |
| American_beaver | test_set | GGGGGCCACAGCAGAAGCGTTCACGTCG CGGCCCCTGTCAGATTCTGAAGAATCTGC GAATTCTGCT | SEQ ID NO: 3 | 67 |
| Aminoacyl-tRNA_synthetase_(aaRS) | test_set | GGAACAACTTCGACGTTTCGACGTCGATC TTACCGTGAAAATGGTTAGAAGCATCTGA GGTTATGCTTTTTGTTTTTGGTTG | SEQ ID NO: 4 | 82 |
| Arctic_ground_squirrel | test_set | GGGGGCCACAGCAGAAGCGTTCACGTCG CGGCCCCTGTCAGATTCTGATGAATCTGC GAATTCTGCT | SEQ ID NO: 5 | 67 |
| armadillo | test_set | TGGGGCCACAGCAGAAGCATTCATGTTG CAGCCCTTGTGAGATTCAAGTGAATCTGT GAATTCTGCT | SEQ ID NO: 6 | 67 |
| Beta-globin_co-transcriptional_cleavage | test_set | GCATAGTGTTACCATCAACCACCTTAACT TCATTTTTTCTTATTCAATACCTAGGTAGG TAGATGCTGATTCTGGAAATAAAATATGA GTCTCAAGTGGTCCTTGTCCTCTCTCTCCC AGTCAAATTCTGAATCTAGTTGGCAAGAT TCTGAAATCAGGGCATATAATCAGTAATA AGTGATGATAGAAGGGTA | SEQ ID NO: 7 | 194 |
| bighorn_sheep | test_set | AGGGGCCAGAGCAGAAGCATTCACGTCG TGGCCCCTGTCAGATTCTGGTGAATCTGC GAATTCTGCT | SEQ ID NO: 8 | 67 |
| bison | test_set | AGGGGCCAGAGCAGAAGCATTCACGTCG CGGCCCCTGTCAGATTCTGGTGAATCTGC GAATTCTGCT | SEQ ID NO: 9 | 67 |
| Brazilian_guinea_pig | test_set | GGGGGCCACAGCAGAAGCGTTCACGTCG CGGCCCCTGTCAGATTCTGATGAATCTGC GAATTCTGCT | SEQ ID NO: 10 | 67 |
| C30 | test_set | GGACAACCAAAAGACAAATCTGCCCTCA GAGCTTGAGAACATCTTCGGATGTAGAG GAGGCAGCCTCCGGTGGCGCAATAGCGC CAACGTTCTCAACAGATACCCAATACTCC CGCTCCGGCGGGTGGGGATAACACCTGA CGAAAAGGCGCTGTTAGACACGCCAAGG TCATAATCCCCGGAGCTTCGGCTCCGCGG CCGCAAAAAAAAAGGCTTACC | SEQ ID NO: 11 | 220 |
| C8 | test_set | GGACAACCAAAAGACAAATCTGCCCTC AGAGCTTGAGAACATCTTCGGATGCAGA GGAGGCAGCCTCCGGTGGCGCGAGAGCG CCAACGTTCTCAACAGACGCACAATACTC CCGCTTCGGCGGGTGGGGATAACACCTG ACGAAAAGGCGATGTTAGACACGCCAAG GTCATAATCCCCGGAGCTTCGGCTCCGCG GCCGCAAAAAAAAAGGCTTACC | SEQ ID NO: 12 | 221 |
| capuchin | test_set | GGGGGCCACAGCAGAAGCGTTCACGTCG TGGCCCCTGTCAGATTCTGGTGAATCTGC GAATTCTGCT | SEQ ID NO: 13 | 67 |
| cat | test_set | AGGGACCACAGCAGAAGTTTCACATCGT GGCCCCTGTCAGATGCCAGTGAATCTGTA AATTTCTGCT | SEQ ID NO: 14 | 67 |
| chinese_pangolin | test_set | CAGGTCCACAGCAGAAACATTCACGTTG CGGCCCCTGTCAGATTCTGGTGAATCTGC GAATTCTGCT | SEQ ID NO: 15 | 67 |
| common_brushtail_possum | test_set | GGGGGCCATAGCAGAAGCGTTCACGTCG CGGCCCCTGTCAGATTCATACGAATCTGC GAATTCTGCT | SEQ ID NO: 16 | 67 |
| common_wombat | test_set | GGGGGCCATAGCAGAAGCGTTCACGTCG CGGCCCCTGTCAGATTCATATGAATCTGC GAATTCTGCT | SEQ ID NO: 17 | 67 |

TABLE 3-continued

| | | Illustrative ribozyme sequences for a trifunctional element | | |
| --- | --- | --- | --- | --- |
| Ribozyme | Illustrative Designation | Illustrative Sequence | SEQ ID | Length (nt) |
| cow | test_set | AGGGGCCAGAGCAGAAGCATTCACGTCG CGGCCCCTGTCAGATTCTGGTGAATCTGC GAATTCTGCT | SEQ ID NO: 18 | 67 |
| CPEB3 | test_set | GGGGGCCACAGCAGAAGCGTTCACGTCG CGGCCCCTGTCAGATTCTGGTGAATCTGC GAATTCTGCT | SEQ ID NO: 19 | 67 |
| Damara_mole_rat | test_set | GGGGGCCACAGCACAAGCGTTCACGTCG CAGCCCCTGTCGGATTCTGAGGAATCTGC GAATTCTGCT | SEQ ID NO: 20 | 67 |
| Daurian_ground_squirrel | test_set | GGGGGCCACAGCAGAAGCGTTCACGTCG CGGCCCCTGTCAGATTCTGATGAATCTGC GAATTCTGCT | SEQ ID NO: 21 | 67 |
| degu | test_set | GGGGGCCACAGCAGAAGCGTTCACGTCG CGGCCCCTGTCAGATTCTGATGAATCTGC GAATTCTGCT | SEQ ID NO: 22 | 67 |
| dog | test_set | CGGGGCCACAGCAAAAGTGTTCACGTCA TGGCCCCTGTCAGATTCTGGTGAATCTGC AAATTCTGCT | SEQ ID NO: 23 | 67 |
| dolphin | test_set | CGGGGCTACAGCAGAAGCGTTCACATTG CAGCCCCTGTCAGATTCTGGTGAATCTGC GAATTCTGCT | SEQ ID NO: 24 | 67 |
| drz-MTgn-1 | test_set | GGTAGCACACCTATGCGTTCCCGTCGCGC TACTGATTTAGACTAAATAGGT | SEQ ID NO: 25 | 51 |
| glmS | test_set | GTGGGCGGGCGGGGTTCGACTTCTTCGGC AGCGCAGGCCCCGGCGACACGTGATGTC ACAAGCCGGGGAGACGAGGTGGAGGTCA GCGCTTTTACTGCGGATGCCTCCAGGCCC CGGTGAACGGGCCTACCCGGCGCGTGCTT TGCCGCTCTGAGTCAAAGACTCCGGCAG GCAGAACCACGCGCAAGCCCGGCGATAA GCCCCGCAGCAATGCGGGCATAAGGCCG GGCAGCTCACCACACCCCAGCAAGTGGC TG | SEQ ID NO: 26 | 257 |
| goat | test_set | AGGGGCCAGAGCAGAAGCATTCACGTTG CGGCCCCTGTCAGATTCTGGTGAATCTGC GAATTCTGCT | SEQ ID NO: 27 | 67 |
| GTR1 | test_set | CAACATCACCGCCTTGTATGCACGGGATG GTCCTTGAAGTGTGCAGCCCTGTGCGTAT GGTCCGGCCTCGCCTGTATCATACACATC CTGGCCACTTCATAGACGCTGATGTTCTG AATCTCGCCCCTAACCATCTTCGGGATTC TCCAGAACCTCGCTCGCGCATGTAAGTCT C | SEQ ID NO: 28 | 175 |
| guinea_pig | test_set | GGGGGCCACAGCAGAAGCGTTCACGTCG CGGCCCCTGTCAGATTCTGATGAATCTGC GAATTCTGCT | SEQ ID NO: 29 | 67 |
| Hatchet | test_set | AATCGTTCTTACTGCAGTGACAAACATGT GGGGCTTATATCTAATCTTCGGATTAGTA TTAGTGCAGACGTTAAAACCATGT | SEQ ID NO: 30 | 82 |
| HDV_ribozyme_(active) | positive_control | GGCCGGCATGGTCCCAGCCTCCTCGCTGG CGCCGGCTGGGCAACATGCTTCGGCATG GCGAATGGGAC | SEQ ID NO: 31 | 68 |
| HDV_ribozyme_(inactive, _excess) | negative_control | ATGGCCGGCATGGTCCCAGCCTCCTCGCT GGCGCCGGCTGGGCAACATTCCGAGGGG ACCGTCCCCTCGGTAATGGTGAATGGGAC GCACAAATCTCTCTAGCTTCCCAGAGAGA AGCGAGAGAAAAGTGGCTCTCCCTTGGC CATCCGAGTGG | SEQ ID NO: 32 | 154 |

TABLE 3-continued

| | | Illustrative ribozyme sequences for a trifunctional element | | |
|---|---|---|---|---|
| Ribozyme | Illustrative Designation | Illustrative Sequence | SEQ ID | Length (nt) |
| HDV_ribozyme_(inactive, _minimum) | negative_control | GGCCGGCATGGTCCCAGCCTCCTCGCTGG CGCCGGCTGGGCAACATTCCGAGGGGAC CGTCCCCTCGGTAATGGTGAATGGGACGC A | SEQ ID NO: 33 | 87 |
| HDV_ribozyme_(inactive, _original) | negative_control | GCCGGCATGGTCCCAGCCTCCTCGCTGGC GCCGGCTGGGCAACATGCTTCGGCATGGT GAATGGGAC | SEQ ID NO: 34 | 67 |
| hedgehog | test_set | CTCAATTCTCACAGAAGCACCCTCAAAAT GTCTTTTTTGGCCTCTGTCAGATTCTGGTG AGAAAAATCTCTCAGTCCAAACT | SEQ ID NO: 35 | 82 |
| Hovlinc | test_set | ACCTAGACTAAGCCCAGGAACATAAGAC CTCAGAGCTAATGAGCCACATACCTACCC AAGGTGAAAGCTCCTTCTCTCGCAATGTG TAACTCATGATTCTCATGACCCCTGGTTG GAGAGATCCGGACTAGGAGCCAGGGGGC CTCTGATTCTGCCAGCCACTGCTAA | SEQ ID NO: 36 | 168 |
| human | test_set | GGGGGCCACAGCAGAAGCGTTCACGTCG CAGCCCCTGTCAGATTCTGGTGAATCTGC GAATTCTGCT | SEQ ID NO: 37 | 67 |
| human-SNP | test_set | GGGGGCCACAGCAGAAGCGTTCACGTCG CAGCCCCCGTCAGATTCTGGTGAATCTGC GAATTCTGCT | SEQ ID NO: 38 | 67 |
| kangaroo_rat | test_set | CAGAGCCGTTACAGAAGTGTTCATATCAT GGTCCCTGTCAGATTCTGGTGAATCTGAA AATTCTGCT | SEQ ID NO: 39 | 67 |
| koala | test_set | GGGGGCCATAGCAGAAGCGTTCACGTCG CGGCCCCTGTCAGATTCATAGGAATCTGC GAATTCTGCT | SEQ ID NO: 40 | 67 |
| leopard | test_set | AGGGACCACAGCAGAAGT- TTCACATCGTGGCCCCTGTCAGATGCCAG TGAATCTGTAAATTTCTGCT | SEQ ID NO: 41 | 68 |
| lesser_Egyptian_jerboa | test_set | GGGGGCCACAGCAGAAGCGTTCACGTCG CGGCCCCTGTCAGATTCTGGCGAATCTGC GAATTCTGCT | SEQ ID NO: 42 | 67 |
| long- tailed_chinchilla | test_set | GGGGGCCACAGCAGAAGCGTTCACGTCG CGGCCCCTGTCAGATTCTGACGAATCTGC GAATTCTGCT | SEQ ID NO: 43 | 67 |
| Malayan_flying_lemur | test_set | GGGGGCCACAGCAGAAGCGTTCACGTCG CGGCCTCTGTCAGATTCTGGTGAATCTGC GAATTCTGCT | SEQ ID NO: 44 | 67 |
| marmoset | test_set | GGGGGGCACAGCAGAAGCATTCACTTCG TGGCCCCTGTCAGATTCTAGTGAATCTGC GAATTCTGCT | SEQ ID NO: 45 | 67 |
| Ma's_night_monkey | test_set | AGGGGCCACAGCAGAAGCGTTCACGTCG CGGCCCCTGTCAGATTCTGGTGAATCTGC GAATTCTGCT | SEQ ID NO: 46 | 67 |
| megabat | test_set | AGGGGCCACAGCAGAAGCGTTCACGTCG CGGCCCCTGTCAGATTCTGGTGAATCTGC GAATCTGCT | SEQ ID NO: 47 | 66 |
| microbat | test_set | GGGGGCCTCAGCAGACACATCACAGTCC CCATCAGATTCTGGTGAATCCGTGAATTT TGCT | SEQ ID NO: 48 | 61 |
| minke_whale | test_set | GGGGGCTACAGCAGAAGCGTTCACATTG CAGCCCCTGTCACATTCTGGTGAATCTGC GAATTCTGCT | SEQ ID NO: 49 | 67 |

TABLE 3-continued

| | Illustrative | | | Length |
|---|---|---|---|---|
| Ribozyme | Designation | Illustrative Sequence | SEQ ID | (nt) |

Illustrative ribozyme sequences for a trifunctional element

| Ribozyme | Illustrative Designation | Illustrative Sequence | SEQ ID | Length (nt) |
|---|---|---|---|---|
| mouse | test_set | GGGGGCCACAGCAGAAGCGTTCACGTCG CGGCCCCTGTCAGATTCTGGCGAATCTGC GAATTCTGCT | SEQ ID NO: 50 | 67 |
| naked_mole-rat | test_set | GGGGGCCACAGCAGAAGCGTTCACGTCG CGGCCCCTGTCAGATTCTGATGAATCTGC GAATTCTGCT | SEQ ID NO: 51 | 67 |
| opossum | test_set | GGGGGCCATAGCAGAAGCGTTCACGTCG CGGCCCCTGTCAGATTCATAGGAATCTGC GAATTCTGCT | SEQ ID NO: 52 | 67 |
| orz_theta_1754 | test_set | GGCGCGCTTTGACTTACCTCCACGCGGTG CGCGCTGGATAACGCTAACAAGTCAG | SEQ ID NO: 53 | 55 |
| orz_theta_1755 | test_set | GGTAACGAGAGAATACCTCCACGCGGTG TTACTGGATTAGACTAAATTCTTA | SEQ ID NO: 54 | 52 |
| orz_theta_1756 | test_set | GGTTGCATGTGTTTACCTCCACGTGGTGC AACTGGATTAAGACTAAAAACACA | SEQ ID NO: 55 | 53 |
| orz_theta_1757 | test_set | GGCGCCAAGAGAAGACCTCCCCGTGGTG GTGCTGGATACGACTAACTTCTCA | SEQ ID NO: 56 | 52 |
| orz_theta_1758 | test_set | GGACGACGGGCTATCAACCTCCACGCGG TGTCGTCTGGGTCATGCGAATAGATAGT | SEQ ID NO: 57 | 56 |
| orz_theta_1759 | test_set | GACTTACAATGGTAAAACCTCCGCGTGGT GTAAGTTGGGTTATGCTAATTTACCA | SEQ ID NO: 58 | 55 |
| orz_theta_1760 | test_set | GGCATCAAGTAAGAAACCTCCTCGTGGT GATGCCGGGTTGTGCTAATTCTTAC | SEQ ID NO: 59 | 53 |
| orz_theta_1761 | test_set | GGAGTTCGTATTAAACTACCTCCACGTGG TGAACTCTGGATTAAAACTAAATGTTTAA | SEQ ID NO: 60 | 58 |
| orz_theta_1762 | test_set | GGCATCAAATCAAACACCTCCACGCGGT GATGCTGGGTAAAGCTAAGTTTGAT | SEQ ID NO: 61 | 53 |
| orz_theta_1763 | test_set | GGTCCCGAGCTGCCACCTCCACGTGGTGG GACTGGATCACGCTAACGGCAGCA | SEQ ID NO: 62 | 53 |
| orz_theta_1764 | test_set | GAGATGAGAATGACTTGACCTCCGCGTG GTTCATCTTGGGTAATTCTAACAAAGTCA | SEQ ID NO: 63 | 57 |
| orz_theta_1765 | test_set | GGGGTGTTAGTAGGCAGCCTCCACGTGG CACACCCTGGTTAACGCTAATGGCCTAC | SEQ ID NO: 64 | 56 |
| orz_theta_1766 | test_set | GGATAGAATATAAGAAACCTCCACGTGG TTCTATCTGGATAATGCTAATATCTTAT | SEQ ID NO: 65 | 56 |
| orz_theta_1767 | test_set | GACTCGCAATGTACTTGCCTCCACGTGGC GCGAGTTGGATAGCTCTAAAAGTACA | SEQ ID NO: 66 | 55 |
| orz_theta_1768 | test_set | GGTCCCGAGCTGCCACCTCCACGTGGTGG GACTGGGTCACGCTAACGGCAGCA | SEQ ID NO: 67 | 53 |
| orz_theta_1769 | test_set | GGGCACATTGACTAGCCTCCACGTGGCGT GCCTGGATAACCAACCAATAGTCTA | SEQ ID NO: 68 | 54 |
| orz_theta_1770 | test_set | GGAGTCCAAGTAGTTAACCTCCTCGTGGT GGACTCTGGGTAATTCTAATAAGCTAC | SEQ ID NO: 69 | 56 |
| orz_theta_1771 | test_set | GACCGCAGAATGACAAACTTCCACGTAG TTGCGGTTGGGTAATGCTAATATGTCAT | SEQ ID NO: 70 | 56 |
| orz_theta_1772 | test_set | GGTCCCGCGCTGCCACCTCCCCGTGGTGG GACTGGATCACGCTAACGGCAGCC | SEQ ID NO: 71 | 53 |
| orz_theta_1773 | test_set | GGCACCAAGAGAAGACCTCCCCGTGGTG GTGCTGGATACGACTAACTTCTCA | SEQ ID NO: 72 | 52 |
| orz_theta_1774 | test_set | GGTCACATTGCATCGCCTCCTCGTGGCGT GACTGGATATCCAACCAAGATGCAA | SEQ ID NO: 73 | 54 |

TABLE 3-continued

Illustrative ribozyme sequences for a trifunctional element

| Ribozyme | Illustrative Designation | Illustrative Sequence | SEQ ID | Length (nt) |
|---|---|---|---|---|
| orz_theta_1775 | test_set | GGATTACATATTAGAAGCCTCCTCGTGGC GTAATCTGGGTAATGCTAATTCTAAT | SEQ ID NO: 74 | 55 |
| orz_theta_1776 | test_set | GGAGTTCATATAACTAAGCCTCCTCGTGG CGAACTCTGGGTAGCTCTAATTAGTTA | SEQ ID NO: 75 | 56 |
| orz_theta_1777 | test_set | GGACGACGGACTATCAACCTCCACGCGG TGTCGTCTGGGTCATGCGAATAGATAGT | SEQ ID NO: 76 | 56 |
| orz_theta_1778 | test_set | GAGTGGCAATATCAACAACCTCCACGTG GTGCTACTTGGGTAATGCTAATAGTTGAT | SEQ ID NO: 77 | 57 |
| orz_theta_1779 | test_set | GGGTTGTAGCTTGATGCCTCCTCGTGGCA CAACCCGGTTGGCCCTAAATCAAGC | SEQ ID NO: 78 | 54 |
| orz_theta_1780 | test_set | GAAACACTTATTACTCAACCTCCACGTGG TGTGTTTCGGGTAATGCTAATGGAGTAA | SEQ ID NO: 79 | 57 |
| orz_theta_1781 | test_set | GACTTCTAATTTCTCAGCCTCCTCGTGGC AGAAGTTGGGTAACGCTAATGAGAAA | SEQ ID NO: 80 | 55 |
| orz_theta_1782 | test_set | GAGCGCAATGCTAAAACCTTCACGTGGT GCGCTTGATTTCGACTAATTTAGCA | SEQ ID NO: 81 | 53 |
| orz_theta_1783 | test_set | GGCATCGTGAGAGAAGCCTGCTCGTGGC GATGCTGCTTTTACTAATTCTCTC | SEQ ID NO: 82 | 52 |
| orz_theta_1784 | test_set | GGATCCAAGAGAAAGCCTCCACGTGGCG GATCTGGGTAAAGCTAATTTCTCA | SEQ ID NO: 83 | 52 |
| orz_theta_1785 | test_set | GAGACACAAATCTCTATACCTCCACGTGG TGTGTCTTGGATAATACTAAATTAGAGA | SEQ ID NO: 84 | 57 |
| orz_theta_1786 | test_set | GGTAACGAGAGAAGACCTTCACGTGGTG TTACCGATTTAGACTAATTTCTCA | SEQ ID NO: 85 | 52 |
| orz_theta_1787 | test_set | GGAGTTCATATAACTAAGCCTCCTCGTGG CGAACTCTGGGTAGCTCTAATTAGTTA | SEQ ID NO: 86 | 56 |
| orz_theta_1788 | test_set | GGAGTTCAAGTAGTTAACCTCCTCGTGGT GGACTCTGGGTAATTCTAATAAACTAC | SEQ ID NO: 87 | 56 |
| orz_theta_1789 | test_set | GGGAGACAATACAGCCAACCTCCACGTG GTGTCTCCTGGGTAATTCTAATAGGCTGT | SEQ ID NO: 88 | 57 |
| orz_theta_1790 | test_set | GGGTACTATATAGAGGCCTCCCCGTGGCG TACCTGGATTAAAACTAACATCTATA | SEQ ID NO: 89 | 55 |
| orz_theta_1791 | test_set | GGACGACGGGCTATCAACCTCCACGCGG TGTCGTCTGGGTCATGCGGATAGATAGT | SEQ ID NO: 90 | 56 |
| orz_theta 1792 | test_set | GGCAACTTGTTAACAGCCTTCTCGTGGCG TTGCTGATTTCGACTAATAGTTAAC | SEQ ID NO: 91 | 54 |
| orz_theta_1793 | test_set | GATGTCAAGAACAAGCCTCCTCGTGGCG ACATCGGATAACCAACCAATTGTTCA | SEQ ID NO: 92 | 54 |
| orz_theta_1794 | test_set | GGTACCACGAGAGAAGCCTGCGCGTGGC GGTACTGCTTTAACTGATTCTCTC | SEQ ID NO: 93 | 52 |
| orz_theta_1795 | test_set | GGTATCATTAGCAAGCCTCCACGTGGCGA TACTGGATTAGAACTAATTGCTAG | SEQ ID NO: 94 | 53 |
| orz_theta_1796 | test_set | GAGGCACATTTAAGAAGCCTCCACGTGG CGTGTCTTGGGTAATGCTAATTCTTAA | SEQ ID NO: 95 | 55 |
| orz_theta_1797 | test_set | GACTGCATAACAGAGCCTCCACGTGGCG CAGTTGGGTAATGCCAATCTGTTA | SEQ ID NO: 96 | 52 |
| orz_theta_1798 | test_set | GAATGGCAAATGAGAAACCTCCACGTGG TGCTATTCGGGTAATGCTAATTCTCAT | SEQ ID NO: 97 | 55 |
| orz_theta_1799 | test_set | GAGGTGAGATGTTCTAAACCTCCACGTGG TTCACCTCGGGTAACGCTAAGATAGAAC | SEQ ID NO: 98 | 57 |

TABLE 3-continued

Illustrative ribozyme sequences for a trifunctional element

| Ribozyme | Illustrative Designation | Illustrative Sequence | SEQ ID | Length (nt) |
|---|---|---|---|---|
| orz_theta_1800 | test_set | GGCCCCAAGGTGAAGCCTTCCCGTGGCG GGGCTGGTTTCACTGATTCACCG | SEQ ID NO: 99 | 51 |
| orz_theta_1801 | test_set | GGTTCCTGTTGTGCTATACCTCCACGTGG TAGGAACTGGGTAGCTCTAAATAGTAC | SEQ ID NO: 100 | 56 |
| orz_theta_1802 | test_set | GGATAACAAATGAGAAACCTCCACGTGG TGTTATCTGGATAATGCTAATTCTCAT | SEQ ID NO: 101 | 55 |
| orz_theta_1803 | test_set | GATGTCAAGAACAAGCCTCCCCGTGGCG ACATCGGATAACCAACCAATTGTTCA | SEQ ID NO: 102 | 54 |
| orz_theta_1804 | test_set | GATTCACGTTGTATCTACCTCCACGTGGT GTGAATTGGGTAATTCTAAAAGATACA | SEQ ID NO: 103 | 56 |
| orz_theta_1805 | test_set | GGTCACATTGCATCGCCTCCTCGTGGCGT GACTGGATAACCAACCAAGATGCAA | SEQ ID NO: 104 | 54 |
| orz_theta_1806 | test_set | GGTTGCATGTGTTTACCTCCTCGTGGTGC AACTGGATTAAGACTAAAAACACA | SEQ ID NO: 105 | 53 |
| orz_theta_1807 | test_set | GGCTACGTAATAGAAACCTCCACGTGGT GTAGCTGGATAACCAACCAATTCTATT | SEQ ID NO: 106 | 55 |
| orz_theta_1808 | test_set | GGTAGCAAGAGTCAACCTCCCCGTGGTG CTACTGGATAATCAACTAATGACTCA | SEQ ID NO: 107 | 54 |
| orz_theta_1809 | test_set | GGCGCCATAAGACAGCCTCCTCGTGGCG GCGCTGGATAACCAACCAATGTCTTA | SEQ ID NO: 108 | 54 |
| orz_theta_1810 | test_set | GGCAACTTGTTAACAGCCTTCTCGCGGCG TTGCTGATTTCGACTAATAGTTAAC | SEQ ID NO: 109 | 54 |
| orz_theta_1811 | test_set | GATGTCAAGAACAAGCCTCCCCGTGGCG ACATCGGATAACCAACTAATTGTTCA | SEQ ID NO: 110 | 54 |
| orz_theta_1812 | test_set | GAGATGAGAATGACTTGACCTCCACGTG GTTCATCTTGGGTAATTCCAACAAAGTCA | SEQ ID NO: 111 | 57 |
| orz_theta_1813 | test_set | GGACGACGGACTATCAACCTCCACGCGG TGTCGTCTGGGTAGTGCAGATAGATAGT | SEQ ID NO: 112 | 56 |
| orz_theta_1814 | test_set | GAGGTACATTGTTAGATACTTCCACGTAG TGTACCTTGGGTTAAAAGCTAAATTCTAA C | SEQ ID NO: 113 | 59 |
| orz_theta_1815 | test_set | GGACGACGGGCTATCAACCTCCACGCGG TGTCGTCTGGGTAGTGCAGATAGATAGT | SEQ ID NO: 114 | 56 |
| orz_theta_1816 | test_set | GAACAGCGATGATTCTCACCTCCTCGTGG TGCTGTTCGGGTAATTCTAACGAGAGTC | SEQ ID NO: 115 | 57 |
| orz_theta_1817 | test_set | GAGAGTCGTTACTACACCTCCACGCGGTG ACTCTTGGTTAACACTAACGTAGTAA | SEQ ID NO: 116 | 55 |
| orz_theta_1818 | test_set | GAGCCACAAAGTTACAACCTCCTCGTGGT GTGGCTTGGATAACGCTAATGTAACA | SEQ ID NO: 117 | 55 |
| orz_theta_1819 | test_set | GGCAACCTGTTAACAGCCTTCTCGCGGCG TTGCTGATTTCGACTAATGGTTAAC | SEQ ID NO: 118 | 54 |
| orz_theta_1820 | test_set | GGTCACATGTAACAGCCTCCCCGTGGCGT GACTGGTTAAGACAGATGTTACA | SEQ ID NO: 119 | 52 |
| orz_theta_1821 | test_set | GGATAGCATAAGTAGAAACCTCCACGTG GTGCTATTCGGGTAATGCTAATTCTACT | SEQ ID NO: 120 | 56 |
| orz_theta_1822 | test_set | GGACCCTCGGTGACAGCCTCCTCGTGGCG GGTCTGGATTAAAGCCAATGGTCACC | SEQ ID NO: 121 | 55 |
| orz_theta_1823 | test_set | GAAGTTCAAGTAACTAACCTCCTCGTGGT GAACTTTGGGTAATTCTAATTAGTTAC | SEQ ID NO: 122 | 56 |

TABLE 3-continued

| Ribozyme | Illustrative Designation | Illustrative Sequence | SEQ ID | Length (nt) |
|---|---|---|---|---|
| orz_theta_1824 | test_set | GGTAACAAGAGTCAACCTCCCCGTGGTGT TACTGGATAACCAACTAATGACTCA | SEQ ID NO: 123 | 54 |
| orz_theta_1825 | test_set | GACTTCAATGTACTTACCTCCTCGTGGTG AAGTCGGGTAGCTCTAAATAGTACA | SEQ ID NO: 124 | 54 |
| orz_theta_1826 | test_set | GATTCACAAATTGAATACCTCCACGCGGT GTGAATCGGGTAACTCTAAATTCAAT | SEQ ID NO: 125 | 55 |
| orz_theta_1827 | test_set | GGCAACTTGTTAACAGCCTTCTCGTGGCG TTGCTGATTTCGACTAATGGTTAAC | SEQ ID NO: 126 | 54 |
| orz_theta_1828 | test_set | GAACTCACTGTATAGCCTCCTCGTGGCGA GTTTGGATAACCAACTAATATACAC | SEQ ID NO: 127 | 54 |
| orz_theta_1829 | test_set | GGGTACTATATAGAGGCCTCCCCGCGGC GTACCTGGATTAAAACTAACATCTATA | SEQ ID NO: 128 | 55 |
| orz_theta_1830 | test_set | GGGTACTATATAGAGGCCTCCCCGTGGCG TACCTGGATTAAAAACTAACATCTATA | SEQ ID NO: 129 | 56 |
| orz_theta_1831 | test_set | GGCATCTGGAGAGAAGCCTGCTCGTGGC GATGCTGCTTTTACTGATTCTCTC | SEQ ID NO: 130 | 52 |
| orz_theta_1832 | test_set | GGTAACAAGGCTTTACCTCCCCGTGGTGT TACTGGATAACCAACTAAAAAGCCA | SEQ ID NO: 131 | 54 |
| orz_theta_1833 | test_set | GGGTACTATATAGAGGCCTCCCCGCGGC GTACCTGGATTTTAACCAACATCTATA | SEQ ID NO: 132 | 55 |
| orz_theta_1834 | test_set | GGTAACGAGAGAATACCTCCACGCGGTG TTACTGGATTAGACTAAATTCTTT | SEQ ID NO: 133 | 52 |
| orz_theta_1835 | test_set | GAAGCACGTAGACTTAACCTCCTCGTGGT GTGCTTCGGGTCGCGCCGATAAGTCT | SEQ ID NO: 134 | 55 |
| orz_theta_1836 | test_set | GGTTCCGATGTATCACACCTCCTCGTGGT GGAACTGGGTAATTCTAAGTGATAC | SEQ ID NO: 135 | 54 |
| orz_theta_1837 | test_set | GAGAGAAGTTATCATTTACCTCCACGTGG TTTCTCTTGGGTAATGCTAAATAATGAT | SEQ ID NO: 136 | 57 |
| orz_theta_1838 | test_set | GAGCACAATGATAGAAGCCTCCACGTGG CTGTGCTTGGGTAATACTAATATCTATC | SEQ ID NO: 137 | 56 |
| orz_theta_1839 | test_set | GGAATCAAGCTGAAAACCTCCTCGTGGT GATTCTGGATTCGACTAATTTCAGC | SEQ ID NO: 138 | 53 |
| orz_theta_1840 | test_set | GGCAACCTGTTAACAGCCTTCTCGTGGCG TTGCTGATTTCGACTAATGGTTAAC | SEQ ID NO: 139 | 54 |
| orz_theta_1841 | test_set | GGAGAATATTAACCAAACCTCCTCGTGGT ATTCTCTGGGTAATGCTAATTGGTTA | SEQ ID NO: 140 | 55 |
| orz_theta_1842 | test_set | GGCATCAAGTGAATACCTCCCCGTGGTGA TGCTGGATAATTAACTAAATTCACA | SEQ ID NO: 141 | 54 |
| orz_theta_1843 | test_set | GGAGTTCGTATAACTAAACCTCCTCGTGG TGAACTCTGGGTAATTCTAATTAGTTA | SEQ ID NO: 142 | 56 |
| orz_theta_1844 | test_set | GGCGACAGTTTCAAAAACCTCCACGTGGT TGTCGCTGGATAACGCTAATATTTGAA | SEQ ID NO: 143 | 56 |
| orz_theta_1845 | test_set | GGTGATAAAAGCAAAAACCTCCTCGTGG TTATCACTGGGTAACTCTAATTTTTGCT | SEQ ID NO: 144 | 56 |
| orz_theta_1846 | test_set | GGCACCAAGATAGACGCCTTCTCGCGGC GGTGCTGATTTCGACTAAGTCTATC | SEQ ID NO: 145 | 53 |
| orz_theta_1847 | test_set | GGGGTGTCAGTAGGCAGCCTCCACGTGG CACACCCTGGTTAACGCTAATGGCCTAC | SEQ ID NO: 146 | 56 |
| orz_theta_1848 | test_set | GGAGTCCAAGTAGTTAACCTCCTCGTGGT GGACTCTGGGTAATTCTAATAAACTAC | SEQ ID NO: 147 | 56 |

TABLE 3-continued

Illustrative ribozyme sequences for a trifunctional element

| Ribozyme | Illustrative Designation | Illustrative Sequence | SEQ ID | Length (nt) |
|---|---|---|---|---|
| orz_theta_1849 | test_set | GAGTCACTATACAAACAACCTTCTCGTGG TGTGACTTGATTTCGACTAATAGTTTGT | SEQ ID NO: 148 | 57 |
| orz_theta_1850 | test_set | GGGGAACTTGTTGCTGACCTCCTCGTGGT GTTCCCTGGATTAAAACTAACAAGCAAC | SEQ ID NO: 149 | 57 |
| orz_theta_1851 | test_set | GGCAACTTGTTAACAGCCTTCTCGTGGCG TTGCTGATTTCGACTGATAGTTAAC | SEQ ID NO: 150 | 54 |
| orz_theta_1852 | test_set | GACTCGCATTTGTACTTGCCTCCTCGTGG CGCGAGTTGGATAGCTCTAAAAGTACA | SEQ ID NO: 151 | 56 |
| P5abc,_P5a_loop | test_set | CCGTTCAGTACCAAGTCTCAGGGGAAACT TTGAGATGGCCTTGCAAAGGTATGGTAAT AAGCTGACGG | SEQ ID NO: 152 | 68 |
| panda | test_set | CGGGGCCACAGCAGAAGCGTTCACGTCG CGGCCCCTGTCAGATTCTGGTGAATCTGC AAATTCTGCT | SEQ ID NO: 153 | 67 |
| pig | test_set | GGCAGCCACAGTAGAAGCATTCACATTG TGGTCCATGTCAGATTCTGGTGAATTTGC AAATTCTGCT | SEQ ID NO: 154 | 67 |
| pika | test_set | GGGGGCCACAGCAGAAGCGTTCACGTCG CGGCCCCTGTCAGATTCTGATGAATCTGC GAATTCTGCT | SEQ ID NO: 155 | 67 |
| Pistol_Alistipes | test_set | AGCCGTTCGGGTGGCTATAAATAGACCTT AGGCCCGAAGCGTGGCGGCACCTGCCGC CGGTGGTA | SEQ ID NO: 156 | 65 |
| Pistol_Lysini bacillus | test_set | TATAGAAAACTCGACTAAGCGAGTATAA ACAGGCATTAGGCTTAGAGCGTTCTCACG TTATCTGAATGATGATGTGAGAGGTTGCA ATAGAAAA | SEQ ID NO: 157 | 94 |
| platypus | test_set | ATGGGACACTGTCCTGTTGCTTTCCTCCC TGAGGCAGGAGTGGGTGTCAGATTCTGG TGAATAGCTGGGAGCCCAGAAA | SEQ ID NO: 158 | 79 |
| prairie_vole | test_set | GGGGGCCACAGCAGAAGCGTTCACGTCG CGGCCCCTGTCAGATTCCGGTGAATCTGC GAATTCTGCT | SEQ ID NO: 159 | 67 |
| R18 | test_set | GGACAACCAAAAAGACAAATCTGCCCTC AGAGCTTGAGAACATCTTCGGATGCAGA GGAGGCAGCCTCCGGTGGCGCGATAGCG CCAACGTTCTCAACAGGCGCCCAATACTC CCGCTTCGGCGGGTGGGGATAACACCTG ACGAAAAGGCGATGTTAGACACGCCAAG GTCATAATCCCCGGAGCTTCGGCTCC | SEQ ID NO: 160 | 195 |
| rat | test_set | AGGGGCCACAGCAGAAGCGTTCACGTCG CGGCCCCTGTCAGATTCTGGTGAATCTGC GAATTCTGCT | SEQ ID NO: 161 | 67 |
| RbZ | test_set | GGGACTTAAGCCCACTGATGAGTCGCTG AGATGCGACGAAACGCCC | SEQ ID NO: 162 | 46 |
| red_fox | test_set | CGGGGCCACAGCAGAAGCGTTCATGTTG TGGCCCCTGTCAGATTCTGGTGAATCTGC GAATTCTGCT | SEQ ID NO: 163 | 67 |
| RiboJ | test_set | AGCTGTCACCGGATGTGCTTTCCGGTCTG ATGAGTCCGTGAGGACGAAACAGCCTCT ACAAATAATTTTGTTTAA | SEQ ID NO: 164 | 75 |
| rock_hyrax | test_set | GGGGGCCACAGCAGAAGCGTTCACGTCG CGGCCCCTGTCAGATTCTTGTGAATCTGC GAATTCTGCT | SEQ ID NO: 165 | 67 |
| Ryukyu_mouse | test_set | GGGGGCCACAGCAGAAGCGTTCACGTCG CGGCCCCTGTCAGATTCTGGCGAATCTGC GAATTCTGCT | SEQ ID NO: 166 | 67 |

TABLE 3-continued

| | | Illustrative ribozyme sequences for a trifunctional element | | |
|---|---|---|---|---|
| Ribozyme | Illustrative Designation | Illustrative Sequence | SEQ ID | Length (nt) |
| Rz333_(caspase-7_targeted_) | test_set | GGGGGCCACAGCAGAAGCGUUCACGUCG CGGCCCCUGUCAGAUUCUGGCGAAUCUG CGAAUUCUGCU | SEQ ID NO: 167 | 67 |
| RzI_Caspase-3_hammerhead | test_set | TTGCTGCATCCTGATGAGTCCGAGAGGAC GAACATCTGTACCA | SEQ ID NO: 168 | 43 |
| SAMURI | test_set | TTGAAGGCATGGCTCAGGGACTTCGGTCC GCTGCAGTCAGTATGT | SEQ ID NO: 169 | 45 |
| sheep | test_set | AGGGGCCAGAGCAGAAGCATTCACGTCG TGGCCCCTGTCAGATTCTGGTGAATCTGC GAATTCTGCT | SEQ ID NO: 170 | 67 |
| SIV | test_set | GGUCGCUCUGCGGAGAGAGGCUGGCAG AUUGAGCCCUGGGAGGUUCUCUCCAGCA CUAGCAGGUAGAGCCUGGGUGUUCCCUG CUAGACUCUCCCAGCACUUGGCGGUGCU GGGCAGAGUGGCUCCACGCUUGCUUGCU UAAA | SEQ ID NO: 171 | 143 |
| sloth | test_set | CGGGGCCACAGCAGAAGCATTCATGTCG CAGCCCCTGTCAGATTCTGGTGAATCTGC GGATTCTGCT | SEQ ID NO: 172 | 67 |
| squirrel_monkey | test_set | GGGGGGGCACAGCAGAAGCGTTCACGTCG CGGCCCCTGTCAGATTCTGGTGAATCTGC GAATTCTGCT | SEQ ID NO: 173 | 67 |
| steppe_mouse | test_set | GGGGGCCACAGCAGAAGCGTTCACGTCG CGGCCCCTGTCAGATTCTGGCGAATCTGC GAATTCTGCT | SEQ ID NO: 174 | 67 |
| SunY | test_set | GATCGATCTCGCCCGCGAAATTAATACGA CTCACTATAGGGAAAATCTGCCTAAACG GGGAAACACTCACTGAGTCAATCCCGTG CTAAATCAGCAGTAGCTGTAAATGCCTAA CGACTATCCCTGATGAATGTAAGGGAGT AGGGTCAAGCGACCCGAAACGGCAGACA ACTCTAAGAGTTGAAGATATAGTCTGAAC TGCATGGTGACATGCAGGATC | SEQ ID NO: 175 | 220 |
| SunY_mutant | test_set | GGGAAAATCTGCCTAAACGGGGAAACAC TCACTGAGTCAATCCCGTGCTAAATCAGC AGTAGCTGTAAATGCCTAACGACTATCCC TGATGAATGTAAGGGAGTAGGGTCAAGC GACCCGAAACGGCAGACAACTCTAAGAG TTGAAGATATAGTCTGAACTGCATGGTGA CATGCAGGATC | SEQ ID NO: 176 | 182 |
| tasmanian_devil | test_set | GGGGGCCATAGCAGAAGCGTTCACGTCG CGGCCCCTGTCAGATTCATATGAATCTGC GAATTCTGCT | SEQ ID NO: 177 | 67 |
| tC9Y | test_set | GTCATTGAAAAAAAAAAAAAAGACAAATC TGCCCTCAGAGCTTGAGAACATCTTCGGA TGCAGAGGAGGCAGCCTTCGGTGGCGCG AGAGCGCCAACGTTCTCAACAGACGCAC AATACTCCCGCTTCGGCGGGTGGGGATA ACACCTGACGAAAGGCGATGTTAGACA CGCCAAGGTCATAATCCCCGGAGCTTCGG CTCC | SEQ ID NO: 178 | 202 |
| tenrec | test_set | CAGGGCCACCCCAAAGCGTTCACATTGTG GCCCCTGTCAGATTCTGGTAAATCTGCGA GTTCTGCT | SEQ ID NO: 179 | 66 |
| thirteen-lined_ground squirrel | test_set | GGGGGCCACAGCAGAAGCGTTCACGTCG CGGCCCCTGTCAGATTCTGATGAATCTGC GAATTCTGCT | SEQ ID NO: 180 | 67 |
| tiger | test_set | ACGGACCACAGCAGAAGTTTCACATCGT GGCCCCTGTCAGATGCCAGTGAATCTGTA AATTTCTGCT | SEQ ID NO: 181 | 67 |

TABLE 3-continued

Illustrative ribozyme sequences for a trifunctional element

| Ribozyme | Illustrative Designation | Illustrative Sequence | SEQ ID | Length (nt) |
|---|---|---|---|---|
| tRNALeu0024_0009 | test_set | GAAACACAAGATTGAAACCTCCACGTGG TGTGTTTTGGGTAAAGCTAATTCAATC | SEQ ID NO: 182 | 55 |
| tRNALeu0112_0016 | test_set | GAATAGCAAATGAGAAACCTCCACGTGG TGCTATTTGGGTAACGCTAATTCTCAT | SEQ ID NO: 183 | 55 |
| tRNASup0028_0092 | test_set | GAATAGCAATAGTAGAAACCTCCACGTG GTGCTATTTGGGTAATGCTAATTCTACT | SEQ ID NO: 184 | 56 |
| tRNAVal0025_0046 | test_set | GGTCACTAAAGTAGATACTTCCACGTAGT GTGACTGGATTAAAACTAAAATCTACT | SEQ ID NO: 185 | 56 |
| Twister | test_set | TATGTAACTCCGCCTATGTCTCTTATAAA TGATATAGGCGGTTACAACCGCAAAAG GAGGAGGTTATA | SEQ ID NO: 186 | 69 |
| Twister-sister | test_set | GCAGGGCAAGGCCCAGTCCCGTGCAAGC CGGGACCGCCCCGGGGCGCGGCGCTCAT TCCTGC | SEQ ID NO: 187 | 62 |
| Varkud_Satellite_(VS) | test_set | GCGGTAGTAAGCGGGAACTCACCTCCAA TTTCAGTACTGAAATTGTCGTAGCAGTTG ACTACTGTTATGTGATTGGTAGAGGCTAA GTGACGGTATTGGCGTAAGTCAGTATTGC AGACCAGCACAAGCCCGCTTGCGGAGAA T | SEQ ID NO: 188 | 144 |
| Vg1 | test_set | GGACTGTTACCAACACCCACACCCTGTGA TGAAACAAAA | SEQ ID NO: 189 | 39 |
| wallaby | test_set | GGGGGCCATAGCAGAAGCGTTCACGTCG CGGCCCCTGTCAGATTCATATGAATCTGC GAATTCTGCT | SEQ ID NO: 190 | 67 |
| white_rhinoceros | test_set | GGGGGCCACAGCAGAAGCGTTCCCGTCG CGGCCCCTGTCAGATTCCGGTGAATCTGC GAATTCTGCT | SEQ ID NO: 191 | 67 |
| wild_yak | test_set | AGGGGCCAGAGCAGAAGCATTCACGTCG CGGCCCCTGTCAGATTCTGGTGAATCTGC GAATTCTGCT | SEQ ID NO: 192 | 67 |
| Ribozyme_Y | test_set | GGACAACCAAAAAGACAAATCTGCCCTC AGAGCTTGAGAACATCTTCGGATGCAGA GGAGGCAGCCTTCGGTGGCGCGAGAGCG CCAACGTTCTCAACAGACGCACAATACTC CCGCTTCGGCGGGTGGGGATAACACCTG ACGAAAAGGCGATGTTAGACACGCCAAG GTCATAATCCCCGGAGCTTCGGCTCC | SEQ ID NO: 193 | 195 |
| zebu | test_set | AGGGGCCAGAGCAGAAGCATTCACGTCG CGGCCCCTGTCAGATTCTGGTGAATCTGC GAATTCTGCT | SEQ ID NO: 194 | 67 |

In embodiments, the trans-splicing molecule further comprises one or more complementary regions (CRs) to the target RNA molecule.

In embodiments, the trans-splicing molecule further comprises one or more exons.

In embodiments, the one or more cleavage elements is downstream (3') of one or more exons and/or introns.

In embodiments, the one or more cleavage elements is a cis-cleaving ribozyme that cleaves, or is suitable for cleaving, at an internal site within the trifunctional element.

In embodiments, the one or more cleavage elements cleaves, or is suitable for cleaving, at the 3' end of the RNA or pre-mRNA molecule; and/or cleaves, or is suitable for cleaving, at a site located within about or at least about 10 nucleobases to about or at least about 1000 nucleobases from the 3' end of the RNA or pre-mRNA molecule.

In embodiments, the one or more cleavage elements removes, or is suitable for removing, the polyadenine (polyA) sequence from the RNA or pre-mRNA molecule.

In embodiments, the trans-splicing molecule and/or the trifunctional element comprises a transcriptional termination sequence. In embodiments, the trans-splicing molecule and/ or the trifunctional element comprises a polyadenine (polyA) sequence.

In embodiments, the trans-splicing molecule does not comprise: (i) one or more snRNA sequences, (ii) one or more small nucleolar RNA (snoRNA) sequences, and/or (iii) one or more small Cajal RNA (scaRNA) sequence.

In embodiments, the one or more stabilizing structural elements comprises about or at least about 70%, about or at least about 75%, about or at least about 80%, about or at least about 85%, about or at least about 90%, about or at least about 95%, about or at least about 96%, about or at least about 97%, about or at least about 98%, or about or at least about 99% sequence identity to the nucleic acid sequence of SEQ ID NOs: 195-198. In embodiments, the one or more stabilizing structural elements is or comprises the nucleic acid sequence of SEQ ID NOs: 195-198.

In embodiments, the trifunctional element is oriented from 5' to 3' in order of one or more stabilizing structural elements, one or more ribozyme sequence, and a poly(A) sequence.

In embodiments, the trans-splicing molecule further comprises one or more CRs, wherein the one or more CRs is about 20 nucleotides in length, about 30 nucleotides in length, about 40 nucleotides in length, about 50 nucleotides in length, about 60 nucleotides in length, about 70 nucleotides in length, about 80 nucleotides in length, about 90 nucleotides in length, about 100 nucleotides in length, about 110 nucleotides in length, about 120 nucleotides in length, about 130 nucleotides in length, about 140 nucleotides in length, about 150 nucleotides in length, about 200 nucleotides in length, about 250 nucleotides in length, about 300 nucleotides in length, about 350 nucleotides in length, about 400 nucleotides in length, about 450 nucleotides in length, or about 500 nucleotides in length, or wherein the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the trans-splicing molecule further comprises one or more CRs, wherein the one or more CRs is 20 to 29 nucleotides in length, 30 to 39 nucleotides in length, 40 to 49 nucleotides in length, 50 to 59 nucleotides in length, 60 to 69 nucleotides in length, 70 to 79 nucleotides in length, 80 to 89 nucleotides in length, 90 to 99 nucleotides in length, 100 to 109 nucleotides in length, 110 to 119 nucleotides in length, 120 to 129 nucleotides in length, 130 to 139 nucleotides in length, 140 to 149 nucleotides in length, 150 to 159 nucleotides in length, 200 to 249 nucleotides in length, 250 to 299 nucleotides in length, 300 to 399 nucleotides in length, 400 to 499 nucleotides in length, or 500 to 1000 nucleotides in length, or wherein the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the one or more CRs are located outside of the one or more stabilizing structural elements. In embodiments, the one or more CRs are located within the one or more stabilizing structural elements.

In embodiments, the trans-splicing molecule comprises one CR, 2 CRs, or comprises more than 2 CRs. In embodiments, the one or more CRs is about or at least about 5 nucleotides in length to about or at least about 500 nucleotides in length. In embodiments, the one or more CRs is about or at least about 5 nucleotides in length, about or at least about 10 nucleotides in length, about or at least about 15 nucleotides in length, about or at least about 20 nucleotides in length, about or at least about 25 nucleotides in length, about or at least about 30 nucleotides in length, about or at least about 35 nucleotides in length, about or at least about 50 nucleotides in length, about or at least about 100 nucleotides in length, about or at least about 200 nucleotides in length, or about or at least about 300 nucleotides in length, at least about 400 nucleotides in length, or at least about 500 nucleotides in length.

In embodiments, the trans-splicing molecule comprises one or more CRs each having about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to one or more RNA or pre-mRNA target sequences. In embodiments, the one or more CR sequences comprises at least about 90% complementarity to one or more RNA or pre-mRNA target sequences. In embodiments, the one or more CR sequences comprises at least about 95% complementarity to one or more RNA or pre-mRNA target sequences.

In embodiments, the one or more CRs is about 60 nucleotides in length, about 90 nucleotides in length, or about 120 nucleotides in length.

In embodiments, CRs "targeting" an intron of a gene comprises having a degree of complementarity that enables Watson-Crick complementary base pairing to a target sequence in the intron. In embodiments, such a degree of complementarity with a target sequence is about or at least about 80% to about or at least about 99% sequence identity. In embodiments, the CR has a level of complementarity to a target sequence of about or at least about 80% about or at least about 85%, about or at least about 90%, about or at least about 95%, about or at least about 96%, about or at least about 97%, about or at least about 98%, or about or at least about 99% complementarity to the target sequence. Persons skilled in the art, with the benefit of this disclosure in its entirety, will be aware of the various methods useful to determine complementarity between nucleic acids, for example, using Basic Local Alignment Search Tool (BLAST) algorithms which relies upon sequence homology (Altschul et al., "Basic local alignment search tool," J. Mol. Biol. (1990) Vol. 215, pp. 403-10), and can design any CR sequence using standard techniques such as PCR, nucleic acid sequencing (e.g., Sanger, NGS, etc.), electrophoresis, gel extraction and purification, etc.

In embodiments, a CR is complementary to a target sequence in the target RNA (e.g., pre-mRNA) if it base-pairs to the target sequence under conditions suitable for modulating trans-splicing. In embodiments, such conditions can be stringent conditions, e.g., combination of the target RNA (e.g., pre-mRNA) and one or more trans-splicing molecules described herein in a buffer comprising, for example, 150 mM NaCl, 20 mM PIPES pH 6.4, 1 mM EDTA, 1 mM Mg$^{2+}$ at a temperature of 4° C.-20° C., or 20° C.-70° C., for 1-24 hrs., followed by washing (e.g., as described in "Molecular Cloning: A Laboratory Manual," Sambrook, et al., (1989) Cold Spring Harbor Laboratory Press). Other illustrative conditions include physiologically relevant conditions as can be encountered inside a cell, tissue, or organism. The skilled person will be able to determine the set of conditions most appropriate for a test of complementarity of two sequences in accordance with the ultimate application of the hybridized nucleotides.

Persons skilled in the art, with the benefit of this disclosure in its entirety, will understand how to engineer CRs to obtain binding to any target pre-mRNA sequence and how to test binding (and trans-splicing efficiency). For example, in embodiments, by using opposite complementary nucleic acid strands that interact by formation of specific hydrogen bonding (e.g., Watson-Crick, Hoogsteen, or reversed Hoogsteen hydrogen bonding). In embodiments, the base pair is formed by Watson-Crick base pairing. As understood by a person having ordinary skill in the art, Watson-Crick base pairing refers to the set of base pairing rules wherein a purine nucleobase binds to a pyrimidine nucleobase to form a complementary base pair. The nature of the hydrogen bonding depends upon the particular base pair. For example, a guanosine-cytosine base pair is formed by three hydrogen bonds and the adenine-thymine or adenine-uracil base pair is formed by two hydrogen bonds. It is understood that analogs or derivatives of canonical nucleobases will form base pair interactions via Watson Crick base pairing or non-canonical base pairing.

In embodiments, the one or more complementary region sequences has at least about 90% complementarity, or at least about 95% complementarity, to an intron of the pre-mRNA. In embodiments, the CR has 100% complementarity to a target sequence. Alternatively, in embodiments, 100% complementarity between the CR and the target sequence is not necessary, for example, as is shown in Puttaraju et al., "*Spliceosome-mediated RNA trans-splicing as a tool for gene therapy,*" *Nat. Biotechnol.*, (1999) Vol. 17, No. 3, pp: 246-52, which demonstrates that a complementary region for βhCG6 intron 1 has a section of mismatches, where approximately 90% complementarity was sufficient.

In embodiments, a CR target sequence is an intron. In embodiments, the section of the intron that the CR binds comprises a stretch of nucleotides of about or at least about 10 nucleotides to about or at least about 500 nucleotides. In embodiments, the one or more CRs targets non-contiguous stretches of nucleotides in an intron. For example, in non-limiting embodiments, a first CR targets a stretch of nucleotides within 500 nucleotides of a 5' splice donor sequence of an intron and a second CR that targets a stretch of nucleotides within 500 nucleotides of a 3' splice acceptor sequence of an intron. In other non-limiting embodiments, an intron that is targeted adopts a higher-order structural motif (e.g., hairpins, loops, pseudoknots, Hoogsteen base pairing, etc.) where the CR binds a first stretch of nucleotides and a second stretch of nucleotides that are not directly adjacent, separated by an intervening stretch of nucleotides that adopts a secondary RNA structural element. Pre-mRNAs are known to adopt higher-order structures, for example as described in Hiler et al., "*Pre-mRNA Secondary Structures Influence Exon Recognition,*" *PLoS Genet.* (2007) Vol. 3, No. 11: e204.

In embodiments, the one or more CRs target a pre-mRNA target selected from one or more pre-mRNA intron and/or exons of USH2A.

In embodiments, splicing in cis ("cis-splicing") occurs when the 2' OH group of the branch adenosine of the intron carries out a nucleophilic attack on the 5' splice site (splice donor). In embodiments, this results in cleavage at this site and ligation of the 5' end of the intron to the branch adenosine, forming a lariat structure. In embodiments, the 3' splice site (splice acceptor) is attacked by the 3' OH of the 5' exon, resulting in ligation of the 5' and 3' exons to form the mRNA and release of the intron lariat. By contrast, in embodiments, splicing in trans ("trans-splicing") occurs between two different RNA molecules, wherein the 3' splice site (splice acceptor) of a second RNA is attacked by the 3' OH of the 5' exon of a first RNA, resulting in ligation of the 5' exon of the first RNA and the 3' exon of the second RNA, thereby forming a chimeric RNA.

In embodiments, the trans-splicing molecule further comprises one or more splicing signals, optionally comprising one or more exonic splicing enhancers (ESEs), one or more intronic splicing enhancers (ISEs), one or more exonic splicing silencers (ESSs), one or more intronic splicing silencers (ISSs), one or more U1 binding motifs, one or more polypyrimidine tracts, one or more branch points, and combinations thereof.

In embodiments, the trans-splicing molecule further comprises one or more splice acceptors (SAs) and/or one or more splice donors (SDs). In embodiments, each splice acceptor is positioned upstream (5') of an exon and each splice donor is positioned downstream (3') of an exon of the trifunctional element.

In embodiments, sequences that make up splice acceptors (SAs) and splice donors (SDs) are known in the art. For example, in embodiments, a human splice site comprises a sequence of CAG|GTAAGT, or a sequence having 1 or more variations in nucleotides thereto, where the pipe denotes an exon|intron boundary and the nucleic acid sequence is a consensus sequence for the most dominant splice donor, for example as described in Sibley et al., "*Lessons from non-canonical splicing,*" *Nat Rev Genet.* (2016) Vol. 17, No. 7, pp: 407-21. In embodiments, the splice acceptor may be identified by an "AG" dinucleotide as the boundary.

Persons skilled in the art, with the benefit of this disclosure in its entirety, will be aware of the various sequences of SAs and SDs useful for trans-splicing described herein.

In non-limiting embodiments, the trans-splicing molecule comprises one or more SD sequences listed in Table 4, or a nucleic acid sequence having about or at least about 70%, about or at least about 70%, about or at least about 70%, about or at least about 70%, about or at least about 70%, about or at least about 70%, about or at least about 70%, about or at least about 70%, about or at least about 70%, about or at least about 70%, about or at least about 70% sequence identity to the nucleic acid sequence of any one of the sequences in Table 4 below. Persons skilled in the art will recognize that these are illustrative SD sequences and that numerous such sequences are known.

TABLE 4

| Illustrative splice donor (SD) sequences. Illustrative Sequence |
| --- |
| CAG GTAAGT |
| CAG GTAAGA |
| CAG GTGAGT |
| CAG GTAGGT |
| CAG GTAAGG |

In embodiments, the trans-splicing molecule comprises one or more SDs and is suitable for 5' editing of one or more RNA or pre-mRNA target sequences.

In embodiments, disclosed herein is a trifunctional element comprising: (i) one or more stabilizing structural elements; (ii) one or more cleavage elements; and (iii) a termination sequence.

In embodiments, disclosed herein is a trans-splicing molecule comprising: (a) a trifunctional element comprising: (i) one or more stabilizing structural elements; (ii) one or more cleavage elements; and (iii) a termination sequence; and (b) one or more exon sequences, and (c) one or more complementary regions (CR), wherein the trans-splicing molecule optionally comprises a splice acceptor (SA) or splice donor (SD).

In embodiments, described herein are nucleic acid constructs encoding the trans-splicing molecules and/or trifunctional elements described herein.

In embodiments, the nucleic acid construct is or comprises a DNA plasmid, viral vector, non-viral vector, in vitro transcribed RNA (IVT RNA), circular RNA (circRNA), or self-amplifying RNA (saRNA) encoding the trans-splicing molecules or trifunctional elements.

In embodiments, the nucleic acid construct is codon optimized, for example for expression in a mammalian cell. In embodiments, the nucleic acid construct comprises one or more base modifications and/or backbone modifications.

In embodiments, the nucleic acid construct is a vector. In embodiments, the vector is a DNA vector. In embodiments, the vector is circular. In embodiments, the vector is linear. Non-limiting exemplary vectors in embodiments herein include plasmids, phagemids, cosmids, artificial chromosomes, minichromosomes, transposons, viral vectors, and expression vectors.

In embodiments, the vector is an expression vector, wherein the expression vector is capable of directing the expression of nucleic acids to which it is operably linked. In embodiments, an "expression vector" includes a recombinant expression vector, replicon, plasmid, phage, virus, or cosmid, to which another DNA segment is inserted or attached so as to bring about the amplification of the inserted or attached nucleic acid in a cell.

In embodiments, the vector or expression vector is circular, double-stranded DNA which additional nucleic acid segments are ligated into.

In embodiments, the vector or expression vector is a recombinant viral vector. In embodiments, non-limiting exemplary viral vectors include viral vectors based on vaccinia virus, poliovirus, adenovirus, adeno-associated virus, SV40, herpes simplex virus, human immunodeficiency virus, and picornaviruses. In embodiments, non-limiting exemplary viral vectors include viral vectors based on a retrovirus such as a Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus. In embodiments, the vector is for use in eukaryotic target cells and includes, but is not limited to, pXT1, pSG5, pSVK3, pBPV, pMSG, and pSVLSV40 (Pharmacia).

In embodiments, the vector comprises one or more transcription and/or translation control elements. In embodiments, the one or more transcription and/or translation control elements used depends on the target cell population and the vector system. In embodiments, any number of suitable transcription and translation control elements, including constitutive and inducible promoters, transcription enhancer elements, transcription terminators, etc., are used in the expression vector.

In embodiments, the vector is operably linked to a control element, e.g., a transcriptional control element, such as a promoter, enhancer, or transcription factor-binding element. In embodiments, the transcriptional control element is functional in a eukaryotic cell, e.g., a mammalian cell, such as a human cell.

In embodiments, the expression vector comprises a promoter that is an inducible promoter. In embodiments, non-limiting examples of inducible promoters include T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter (e.g., Tet-ON, Tet-OFF, etc.), steroid-regulated promoter, metal-regulated promoter, estrogen receptor-regulated promoter, etc. In embodiments, an inducible promoter is regulated by molecules including, but not limited to, doxycycline; RNA polymerase (e.g., T7 RNA polymerase), an estrogen receptor, an estrogen receptor fusion protein, etc. In embodiments, the nucleic acid construct encodes one or more elements that assists in the control of expression of one or more other elements of nucleic acid construct and subgenomic transcripts thereof.

In embodiments, the promoter is a constitutive promoter (e.g., CMV promoter, UBC promoter).

In embodiments, the promoter is a spatially-restricted and/or temporally-restricted promoter (e.g., a tissue specific promoter, a cell type specific promoter, etc.). In embodiments, spatially-restricted promoters are also be referred to as enhancers, transcriptional control elements, control sequences, etc. In embodiments, spatially-restricted promoters are suitable for use in the present disclosure, and the choice of a suitable promoter (e.g., a photoreceptor cell specific promoter, a bipolar cell specific promoter, a retinal ganglion cell specific promoter, a cone cell specific promoter, a rod-cell specific promoter, a liver specific promoter, a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the cell type and/or organism for trans-splicing. For example, in embodiments, spatially-restricted promoters are known for plants, flies, worms, mammals, mice, humans, etc. In embodiments, spatially-restricted promoters are temporally-restricted such that the promoter is in the "ON" state or "OFF" state during specific stages of methods herein (e.g., to prevent liability of the trans-splicing molecules or trifunctional elements).

In embodiments, nucleic acid constructs herein comprise any promoter that drives expression by an RNA polymerase (e.g., pol I, pol II, pol III).

In embodiments, exemplary promoters include the SV40 early promoter, mouse mammary tumor virus long terminal repeat (LTR) promoter, adenovirus major late promoter (Ad MLP), a herpes simplex virus (HSV) promoter, a cytomegalovirus (CMV) promoter such as the CMV immediate early promoter region (CMVIE), elongation factor-1 promoter (EF1), chicken beta-actin promoter (CAG), a rous sarcoma virus (RSV) promoter, a human U6 small nuclear promoter (U6), an enhanced U6 promoter, a human H1 promoter (H1), murine stem cell virus promoter (MSCV), phosphoglycerate kinase-1 locus promoter (PGK), and mouse metallothionein-I, a synapsin promoter (SYN1), cone-specific promoters (PR1.7/PR2.1), rhodopsin promoter (Rho), rhodopsin kinase promoter (GRK1), rod-specific promoter (PDE6B), neurofilament heavy (NEFH), and the like.

In embodiments, nucleic acid constructs herein comprise one or more ribosome binding site (RBS) for translation initiation and/or a transcription terminator. In embodiments, the nucleic acid construct comprises appropriate sequences for amplifying expression (e.g., viral non-structural proteins for saRNA, etc.).

In embodiments, nucleic acid constructs, trans-splicing molecules, and/or trifunctional elements described herein are introduced to the cell or a cell population as RNA. In embodiments, the RNA has chemistries suitable for delivery, tolerability, and stability within cells, e.g., following in vivo or in vitro administration. In embodiments, the RNA is modified, e.g., comprising a modified sugar moiety, a modified internucleoside linkage, a modified nucleoside, a modified nucleotide, and/or combinations thereof. In embodiments, the modified RNA exhibits lessened immunostimulatory capacity (or less immunostimulatory), is more nuclease resistant, has improved cell uptake, has increased half-life (e.g., cellular half-life, plasma half-life, circulating half-life, etc.), has increased translation efficiency, and/or is less toxic to cells compared to a cognate non-modified RNA sequence.

In embodiments, the nucleic acids herein are introduced into a cell by a viral vector, such as AAV. In embodiments, the viral vector (e.g., AAV vector) encodes one or more nucleotide sequences described herein. In embodiments, the cloning capacity of the viral vector is sufficient to deliver the one or more nucleic acids comprising one or more nucleotide sequences described herein.

In embodiments, a recombinant adeno-associated virus (rAAV) vector is used for delivery. Techniques to produce rAAV particles, in which an AAV genome to be packaged that includes the polynucleotide to be delivered (e.g., nucleic acid encoding one or more gRNAs and/or a site-directed endonuclease), rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 AAV-rh.74, AAV-7m8, AAV-R100 and tropism modified AAV vectors. Production of pseudotyped rAAV is known in the art.

In non-limiting embodiments, with respect to AAVs for IRDs, several naturally-occurring serotypes have been found useful, such as AAV2, AVV5, and AAV8, as well as several genetically-engineered variants and recombinant AAVs, such as AAV2tYF, AAV2-7m8, and AAV-R100, for example as described in Ail et al., "*Adeno-Associated Virus (AAV)-Based Gene Therapies for Retinal Diseases: Where are We?*" *Appl. Clin. Genet.* (2023) Vol. 16, pp: 111-30.

In embodiments, a method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing, addition of synthetic linkers containing restriction endonuclease cleavage sites or by direct, blunt-end ligation. The packaging cell line is then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells. General principles of rAAV production are known in the art.

In embodiments, viral vectors of than adeno-associated viral vectors are used. Such viral vectors include, but are not limited to, adenovirus, lentivirus, alphavirus, enterovirus, pestivirus, baculovirus, herpesvirus, Epstein Barr virus, papovavirus, poxvirus, vaccinia virus, and herpes simplex virus.

In embodiments, disclosed herein is a nucleic acid construct encoding a trifunctional element and/or trans-splicing molecule of any one of the embodiments disclosed herein. In embodiments, the nucleic acid construct is a DNA plasmid, viral vector, non-viral vector, in vitro transcribed RNA (IVT RNA), circular RNA (circRNA), or self-amplifying RNA (saRNA) encoding the RNA or pre-mRNA molecule, optionally wherein the nucleic acids are introduced into a cell by a viral vector, optionally wherein the viral vector is AAV. In embodiments, the nucleic acid construct is codon optimized, optionally for expression in a mammalian cell. In embodiments, the nucleic acid construct comprises one or more base modifications and/or backbone modifications.

In embodiments, disclosed herein is a lipid nanoparticle (LNP), liposome, lipoplex, or polymeric nanoparticle comprising a trifunctional element and/or trans-splicing molecule of any one of the embodiments disclosed herein, or a nucleic acid construct of any one of the embodiments disclosed herein.

In embodiments, the LNP, liposome, lipoplex, or polymeric nanoparticle of any one of the embodiments disclosed herein, further comprises one or more of ionizable lipids, amino lipids, anionic lipids, neutral lipids, amphipathic lipids, helper lipids, structural lipids, PEG lipids, and lipids.

Nanoparticles are ultrafine particles typically ranging between about or at least about 1 nm to about or at least about 1000 nm in size with a surrounding interfacial layer and often exhibiting a size-related or size-dependent property. Nanoparticle compositions encompass lipid nanoparticles (LNPs), liposomes (e.g., lipid vesicles), and lipoplexes. In embodiments, a nanoparticle composition comprises a liposome having a lipid bilayer with a diameter of 1000 nm or less. In embodiments, nanoparticle compositions are vesicles including one or more lipid bilayers. In embodiments, a nanoparticle composition includes two or more concentric bilayers separated by aqueous compartments. In embodiments, lipid bilayers are functionalized and/or crosslinked to one another. In embodiments, lipid bilayers comprise one or more ligands, proteins, or channels.

Numerous excipients for LNP-based ocular delivery of nucleic acids are known in the art. For example, in embodiments, ocular delivery via LNPs encapsulating DNA/RNA encoding one or more trans-splicing molecules or one or more trifunctional elements comprises one or more of Brij® 78 (polyoxyethylene-20-stearyl ether), Capryol®, cetyl palmitate, Compritol® 888 ATO (Glyceryl dibehenate), Cremophor® EL, Dynasan®, Gelucire® 43/01, Gelucire® 44/14, Gelucire® 50/13, glyceryl monostearate, Imwitor® 900 K, Labrafac® PG, Labrasol®, Lauroglycol® 90, Lipocire® DM, Miglyol® 840, Mygliol® 812, Myrj® 52, oleic acid, palmitic acid, perhidrosqualene, Poloxamer® 188, Precifac® ATO 5 (Glyceryl distearate), Precirol ATO 5 (Glyceryl palmitostearate), sodium taurocholate, Softisan® 142, Softisan® 645, squalene, stearic acid, Tween® 40, Tween® 80, Witepsol® E85, for example as described in Baig et al., "*Lipid-based nanoparticles: innovations in ocular drug delivery,*" *Front Mol Biosci.* (2024) Vol. 11: 1421959.

In embodiments, disclosed herein is a cell comprising a trans-splicing molecule and/or a trifunctional element of any one of the embodiments disclosed herein, or a nucleic acid construct of any one of the embodiments disclosed herein.

In embodiments, the cell is a eukaryotic cell. In embodiments, the eukaryotic cell comprises a mammalian cell, human cell, immortalized cell, or a cell harvested from a subject. In embodiments, the cell is a human cell and the methods herein are for correcting one or more disease-causing mutations in the human cell, e.g., to treat a disease or disorder.

In embodiments, the host cell is suitable for recombinant protein production (e.g., of a reporter molecule). In embodiments, the host cell is a cell expressing an endogenous pre-mRNA or mRNA transcript which harbors a mutation to be corrected by trans-splicing. In embodiments, the host cells is a mammalian host cell. Non-limiting examples of host cells comprises: Chinese hamster ovary (CHO) cells, human embryonic kidney (e.g., HEK293, HEK293T) cells, K562 human lymphoblast cells, ARPE-19 retinal pigment epithelial cells, WERI-RB-1 retinal, Y79 retinal cells, U2OS human osteosarcoma cells, primary human fibroblasts (e.g., human dermal fibroblast (HDFa)), baby hamster kidney (BHK) cells, Vero cells, human cervical carcinoma cells (e.g., HELA), PERc6 cell, CAP cell, induced pluripotent stem cells (iPSCs), human embryonic stem cells (ESCs), or monkey kidney CV1 cells. In embodiments, the cell is a cell selected for experimental/research purposes.

In embodiments, the eukaryotic cell comprises a mammalian cell, human cell, immortalized cell, or a cell harvested from a subject.

Pharmaceutical Compositions

In embodiments, disclosed herein is a pharmaceutical composition comprising a trans-splicing molecule and/or trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein.

In embodiments, the pharmaceutical composition comprises an expression vector comprising one or more nucleic acids encoding one or more nucleotide sequences described herein, and a pharmaceutically acceptable carriers, diluents, or excipients. In embodiments, the pharmaceutical composition comprises one or more nucleic acids comprising one or more nucleotide sequences or recombinant expression vector (e.g., AAV) comprising the one or more nucleic acids comprising one or more nucleotide sequences formulated as a lipid composition (e.g., LNP), and one or more pharmaceutically acceptable carriers, diluents, or excipients. In embodiments, the pharmaceutical composition comprises a therapeutically effective amount of the one or more nucleic acids comprising one or more nucleotide sequences or recombinant expression vectors.

Exemplary pharmaceutically acceptable excipients such as carriers, solvents, stabilizers, adjuvants, diluents, etc., depending upon the particular mode of administration and dosage form. Contemplated pharmaceutical compositions can be generally formulated to achieve a physiologically compatible pH, depending on the formulation and route of administration. In embodiments, the compositions comprise a therapeutically effective amount of one or more nucleic acids comprising one or more nucleotide sequences or recombinant expression vectors, together with one or more pharmaceutically acceptable excipients.

Suitable excipients can include, for example, carrier molecules that include large, slowly metabolized macromolecules. Other exemplary excipients can include antioxidants, chelating agents, carbohydrates, stearic acid, liquids such as oils, water, saline, glycerol and ethanol, wetting or emulsifying agents, pH buffering substances, and the like.

Pharmaceutical compositions can be formulated into preparations in solutions, suppositories, injections. In embodiments, the pharmaceutical composition is formulated to result in systemic administration of the composition, system, and/or the one or more nucleic acids comprising one or more nucleotide sequences described herein or recombinant expression vectors, for example, following enteral or parenteral administration. In embodiments, the pharmaceutical composition is formulated to result in localized administration of the composition, system, and/or the one or more nucleic acids comprising one or more nucleotide sequences described herein, and/or the viral vectors, for example, following regional administration or implantation. In embodiments, the pharmaceutical composition is formulated for immediate activity or for sustained release of the composition, system, and/or the one or more nucleic acids comprising one or more nucleotide sequences described herein, and/or the viral vectors or recombinant expression vectors.

Typically, an effective amount the composition, system, and/or the one or more nucleic acids comprising one or more nucleotide sequences described herein, and/or viral vector described herein, can be provided, for example, for use in a method of treating a subject having a disease or disorder.

In embodiments, based on animal data, and other information available for the trans-splicing system, a clinician can determine the maximum safe dose for an individual, depending on the route of administration. For instance, an intravenously administered dose can be more than an intrathecally administered dose, given the greater body of fluid into which the therapeutic composition is being administered. Similarly, compositions which are rapidly cleared from the body can be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the composition, system, and/or the one or more nucleic acids comprising one or more nucleotide sequences described herein, including the viral vector described herein, can be obtained from a suitable commercial source. In embodiments, therapies based on the composition, system, and/or the one or more nucleic acids comprising one or more nucleotide sequences described herein, and/or the viral vector, recombinant expression vectors, or delivery system described herein to be used for therapeutic administration, must be sterile.

Therapeutic compositions can be generally placed into a container having a sterile access port, for example, an intravenous solution bag or vial having a stopper pierceable by a hypodermic injection needle. In some embodiments, the therapeutic components are stored in unit or multi-dose containers, for example, sealed ampules or vials, as an aqueous solution or as a lyophilized formulation for reconstitution.

Kits

The present disclosure provides kits for performing methods described herein. In embodiments, disclosed herein is a kit comprising one or more composition or pharmaceutical composition comprising a trans-splicing molecule and/or trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein.

In embodiments, the kit comprises a reagent for reconstitution and/or dilution of the nucleic acids, vectors, LNPs, liposome, lipoplex, or polymeric nanoparticles, etc., described herein, for use from a stock solution or master mix.

In embodiments, the kit comprises one or more additional reagents. In embodiments, such additional reagents are selected from a nuclease free water, buffer, a control reagent, a control vector, a control polynucleotide, a reagent for in vitro production, adaptors/primers for sequencing, and the like. In embodiment, the buffer is a stabilization buffer, a formulation buffer, a reconstituting buffer, a diluting buffer, or the like. In embodiments, the kit comprises one or more components that are used to facilitate or enhance the on-target binding or the trans-splicing and/or increase RNP formation, etc.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or subpackaging), etc. The instructions can be present as an electronic storage data file present on a suitable computer readable storage medium, e.g., CD-ROM, diskette, flash drive, etc. In some instances, the actual instructions are not present in the kit, but means for obtaining the instructions from a remote source (e.g., via the Internet), can be provided. An example of this case is a kit that comprises a web address where the instructions can be viewed and/or from which the instructions can be downloaded. As with the instructions, this means for obtaining instructions can be recorded on a suitable substrate.

In embodiments, the kit comprises a container comprising one or more components as (nucleic acid, vector, LNP, cell, etc.) described herein, or pharmaceutical composition described herein, and instructions, links Internet-based materials, and/or software for use in performing, measuring, etc., trans-splicing of a target RNA (e.g., pre-mRNA) in a cell or a population of cells.

Methods

In embodiments, disclosed herein is a method for trans-splicing one or more RNAs or pre-mRNAs comprising: (a) contacting a cell with: (i) a trans-splicing molecule and/or trifunctional element of any one of the embodiments disclosed herein and one or more exons and/or introns; (ii) one or more nucleic acid constructs of any of any one of the embodiments disclosed herein; or (iii) one or more lipid nanoparticles (LNPs), liposomes, lipoplexes, or polymeric nanoparticles of any one of the embodiments disclosed herein; and (b) replacing at least a portion of the one or more RNAs or pre-mRNAs with one or more exons and/or introns via trans-splicing with the trans-splicing molecule comprising the trans-splicing molecule and/or trifunctional element.

In embodiments, the trans-splicing comprises exon/intron skipping and/or exon/intron replacement.

In embodiments, the trans-splicing comprises binding one or more CRs of the trans-splicing molecule to one or more target sequences of the one or more RNAs or pre-mRNAs.

In embodiments, the one or more target sequences is or comprises an intron.

In embodiments, the one or more cleavage elements is self-cleaving; and/or wherein one or more cleavage elements removes a 3' polyadenine (polyA) sequence and/or a 5' cap from a trifunctional element.

In embodiments, the presence of the one or more cleavage elements and/or cleavage by the one or more cleavage elements results in higher trans-splicing efficiency in comparison to a trifunctional element molecule lacking one or more of: (i) the stabilizing structural element; (ii) the cleavage element; or (iii) a termination sequence.

In embodiments, the method further comprises measuring the trans-splicing efficiency, optionally by performing one or more of flow cytometry, confocal microscopy (confocal laser scanning microscopy, spinning-disk confocal microscopy), in situ fluorescence, immunohistochemistry, SDS-PAGE, western blotting, short-read sequencing, nuclear cytoplasmic fractionation, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the presence of the one or more cleavage elements and/or cleavage by the one or more cleavage elements results in reduced expression/translation of unspliced and/or undesired protein products in comparison to a trifunctional element molecule lacking one or more of: (i) the stabilizing structural element; (ii) the cleavage element; or (iii) a termination sequence.

In embodiments, the method further comprises assessing the expression/translation of unspliced and/or undesired protein products, optionally by performing one or more of flow cytometry, confocal microscopy (confocal laser scanning microscopy, spinning-disk confocal microscopy), in situ fluorescence, immunohistochemistry, mass spectrometry, SDS-PAGE, western blotting, short-read sequencing, nuclear cytoplasmic fractionation, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the presence of the one or more cleavage elements and/or cleavage by the one or more cleavage elements results in an increase of nuclear retention/localization of the trans-splicing RNA in comparison to a trifunctional element molecule lacking one or more of: (i) the stabilizing structural element; (ii) the cleavage element; or (iii) a termination sequence.

In embodiments, the method further comprises assessing the nuclear retention of the trans-splicing RNA the expression of unspliced and/or undesired protein products, optionally by performing one or more of flow cytometry, confocal microscopy (confocal laser scanning microscopy, spinning-disk confocal microscopy), in situ fluorescence, immunohistochemistry, SDS-PAGE, western blotting, nuclear cytoplasmic fractionation, short-read sequencing, long-read sequencing, droplet digital PCR (ddPCR), reverse transcriptase PCR (RT-PCR), quantitative or real-time PCR (RT-PCR), and enzyme-linked immunosorbent assay (ELISA).

In embodiments, the one or more trans-splicing molecule binds a ribonucleoprotein (RNP) to form a RNP complex and directs trans-splicing of the one or more exons and/or introns with the one or more RNAs or pre-mRNAs.

In embodiments, disclosed herein is a method of treating a subject having a disease or disorder, the method comprising administering a trans-splicing molecule and/or trifunctional element of any one of the embodiments disclosed herein, a nucleic acid construct of any one of the embodiments disclosed herein, a lipid nanoparticle (LNP), liposome, lipoplex, or polymeric nanoparticle of any one of the embodiments disclosed herein, or a cell of any one of the embodiments disclosed herein to the subject in vivo, or to a harvested cell ex vivo, under conditions suitable for trans-splicing of a target RNA, thereby restoring or modifying expression of a functional protein in the subject.

In embodiments, disclosed herein is a method of trans-splicing screening comprising: (a) providing a trans-splicing molecule comprising: (i) a trifunctional element comprising: (a) one or more stabilizing structural elements; (b) one or more cleavage elements; optionally wherein the one or more cleavage elements is located at a 5' or 3' end of the trifunctional element; and (c) a termination sequence; (ii) one or more complementary regions (CRs); and (iii) one or more exon and/or intron sequences; (b) co-expressing, in a cell, the trans-splicing molecule with one or more target RNA or pre-mRNA sequences, wherein the one or more CRs of the trans-splicing molecule is at least partially complementary to the one or more target RNA or pre-mRNA sequences and binds the one or more target RNA or pre-mRNA, and wherein trans-splicing occurs between the one or more exon and/or intron sequences of the trans-splicing molecule and the one or more target RNA or pre-mRNA sequences; and (c) measuring trans-splicing between the one or more exon and/or intron sequences of the trans-splicing RNA molecules.

In embodiments, the one or more CRs each have about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% sequence complementarity to the intron of the pre-mRNA.

In embodiments, the trans-splicing forms a complete/ functional protein-coding mRNA sequence comprising a reporter molecule operably linked to a regulatory element that is activated by an exogenous small molecule. In embodiments, the exogenous small molecule is a kill switch that induces apoptosis, inhibits cell viability, and/or turns off the trans-splicing molecule.

In embodiments, the one or more target RNA or pre-mRNA sequences comprises an exogenous target sequence.

In embodiments, measuring the trans-splicing comprises barcode sequencing of the trans-spliced product. In embodiments, measuring the trans-splicing comprises a barcode sequence, optionally adjacent to or within a 5' UTR sequence, optionally as a biomarker in a biological fluid sample.

In embodiments, measuring the trans-splicing comprises measuring fluorescence, optionally comprising one or more of flow cytometry, confocal microscopy, confocal laser scanning microscopy, spinning-disk confocal microscopy, and in situ fluorescence.

In embodiments, trans-splicing forms a complete/func-tional protein-coding mRNA sequence comprising a reporter molecule operably linked to a regulatory element that is activated by an exogenous small molecule. In embodiments, the exogenous small molecule is a kill switch that induces apoptosis, inhibits cell viability, and/or turns off the trans-splicing molecule. In embodiments, the reporter molecule is or comprises one or more fluorescent protein (e.g., BFP, GFP, YFP, RFP, etc.). In embodiments, trans-splicing is measured by measuring fluorescence, e.g., using flow cytometry to measure expression of a reporter molecule, using Western blotting to measure spliced/unspliced trans-lated protein, etc. In embodiments, the reporter molecule is or comprises a functional copy of the protein that results in the IRD phenotype, upon correction the disease state is corrected.

In embodiments, the one or more target pre-mRNA sequences comprises an exogenous target sequence. In embodiments, measuring the trans-splicing comprises bar-code sequencing of the trans-spliced product, e.g., amplicon sequencing, RT-PCT, qPCR, Sanger sequencing, and/or ddPCR to check for barcode sequences and/or indicia of trans-splicing.

In embodiments, the method further comprises ranking and/or selecting the one or more CRs, target RNA or pre-mRNA sequences, and/or trifunctional element as a function of measuring the trans-splicing. In embodiments, ranking and/or selecting includes sequence alignment and/or phylogenetic analysis.

In embodiments, the trifunctional element comprises, in sequential order from 5' to 3': (i) one or more stabilizing structural elements having at least about 95% sequence identity to the nucleic acid sequence of any one of SEQ ID NOs: 195-198; (ii) one or more ribozyme sequences having at least about 95% sequence identity to the nucleic acid sequence of any one of SEQ ID NOs: 1-194; and (iii) a termination sequence, optionally having at least about 95% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 97% sequence identity to the nucleic acid sequence of any one of SEQ ID NOs: 195-198; (ii) one or more ribozyme sequences having at least about 97% sequence identity to the nucleic acid sequence of any one of SEQ ID NOs: 1-194; and (iii) a termination sequence, optionally having at least about 97% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 98% sequence identity to the nucleic acid sequence of any one of SEQ ID NOs: 195-198; (ii) one or more ribozyme sequences having at least about 98% sequence identity to the nucleic acid sequence of any one of SEQ ID NOs: 1-194; and (iii) a termination sequence, optionally having at least about 98% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises, in sequential order from 5' to 3': (i) one or more stabilizing structural elements having at least about 100% sequence identity to the nucleic acid sequence of any one of SEQ ID NOs: 195-198; (ii) one or more ribozyme sequences having at least about 100% sequence identity to the nucleic acid sequence of any one of SEQ ID NOs: 1-194; and (iii) a termination sequence, optionally having at least about 100% sequence identity to the nucleic acid sequence of any one of SEQ ID NOs: 248-254, arranged such that at least one of the one or more ribozyme sequences is positioned adjacent to at least one stabilizing structural element, and adjacent to the termination sequence and/or polyadenine (polyA) sequence.

In embodiments, the trifunctional element comprises one or more cleavage elements having at least about 80%, 85% 90%, 95%, 97%, 98%, or 100% identity to SEQ ID NOs: 1-194; one or more stabilizing structural elements having at least about 80%, 85% 90%, 95%, 97%, 98%, or 100% identity SEQ ID NOs: 195-198; and a termination sequence, optionally having at least 90%, 95%, 97%, 98%, or 100% identity SEQ ID NOs: 248-254.

In embodiments, disclosed herein is a trans-splicing molecule of any one of the embodiments disclosed herein, wherein the trans-splicing molecule comprises a CMV enhancer having at least about 80%, 85% 90%, 95%, 97%, 98%, or 100% identity SEQ ID NO: 204.

In embodiments, disclosed herein is a trans-splicing molecule of any one of the embodiments disclosed herein, wherein the trans-splicing molecule comprises a CMV promoter having at least about 80%, 85% 90%, 95%, 97%, 98%, or 100% identity SEQ ID NO: 205.

In embodiments, disclosed herein is a trans-splicing molecule of any one of the embodiments disclosed herein, wherein the trans-splicing molecule comprises an untranscribed region having at least about 80%, 85% 90%, 95%, 97%, 98%, or 100% SEQ ID NO: 206, optionally wherein the untranscribed region is a CMV-derived untranscribed region.

In embodiments, disclosed herein is a trans-splicing molecule of any one of the embodiments disclosed herein, wherein the trans-splicing molecule comprises an Usherin (5' UTR) sequence having at least about 80%, 85% 90%, 95%, 97%, 98%, or 100% identity SEQ ID NO: 207 or SEQ ID NO: 208.

In embodiments, disclosed herein is a trans-splicing molecule of any one of the embodiments disclosed herein, wherein the trans-splicing molecule comprises an Usherin (CDS) sequence having at least about 80%, 85% 90%, 95%, 97%, 98%, or 100% identity SEQ ID NO: 209.

In embodiments, disclosed herein is a trans-splicing molecule of any one of the embodiments disclosed herein, wherein the trans-splicing molecule comprises a splice donor (SD) sequence having at least about 80%, 85% 90%, 95%, 97%, 98%, or 100% identity to GTAAGT. In embodiments, disclosed herein is a trans-splicing molecule of any one of the embodiments disclosed herein, wherein the trans-splicing molecule comprises a short scaffold sequence having at least about 80%, 85% 90%, 95%, 97%, 98%, or 100% identity SEQ ID NO: 211.

In embodiments, disclosed herein is a trans-splicing molecule of any one of the embodiments disclosed herein, wherein the trans-splicing molecule comprises a complementary region 1 sequence having at least about 80%, 85% 90%, 95%, 97%, 98%, or 100% identity SEQ ID NO: 212.

In embodiments, disclosed herein is a trans-splicing molecule of any one of the embodiments disclosed herein, wherein the trans-splicing molecule comprises a complementary region 2 sequence having at least about 80%, 85% 90%, 95%, 97%, 98%, or 100% identity SEQ ID NO: 213.

In embodiments, disclosed herein is a trans-splicing molecule of any one of the embodiments disclosed herein, wherein the trans-splicing molecule comprises a complementary region 3 sequence having at least about 80%, 85% 90%, 95%, 97%, 98%, or 100% identity SEQ ID NO: 214.

In embodiments, disclosed herein is a trans-splicing molecule of any one of the embodiments disclosed herein, wherein the trans-splicing molecule comprises an filler sequence having at least about 80%, 85% 90%, 95%, 97%, 98%, or 100% identity SEQ ID NO: 215.

In embodiments, disclosed herein is a trans-splicing molecule and/or a trifunctional element of any one of the embodiments disclosed herein, wherein the trans-splicing molecule and/or trifunctional element comprises a stabilizing structural element (SSE) SSE.1 sequence having at least about 80%, 85% 90%, 95%, 97%, 98%, or 100% identity SEQ ID NO: 216 or SEQ ID NO: 274.

In embodiments, disclosed herein is a trans-splicing molecule and/or a trifunctional element of any one of the embodiments disclosed herein, wherein the trans-splicing molecule and/or trifunctional element comprises a cleavage element (CE) CE.1 sequence having at least about 80%, 85% 90%, 95%, 97%, 98%, or 100% identity SEQ ID NO: 217.

In embodiments, disclosed herein is a trans-splicing molecule and/or a trifunctional element of any one of the embodiments disclosed herein, wherein the trans-splicing molecule and/or trifunctional element comprises a termination element (TE) sequence having at least about 80%, 85% 90%, 95%, 97%, 98%, or 100% identity SEQ ID NO: 218.

In embodiments, a "subject" herein refers to any animal (e.g., a mammal), including, but not limited to, humans, and non-human animals (including, but not limited to, non-human primates, dogs, cats, rodents, horses, cows, pigs, mice, rats, hamsters, rabbits, and the like (e.g., which is to be the recipient of a particular treatment, or from whom cells are harvested)). In embodiments, the subject is a human.

It will also be understood that, although the terms first, second, etc., may be used herein to describe various elements, these elements should not be limited by these terms. These terms are only used to distinguish one element from another. For example, a first nucleic acid could be termed a second nucleic acid, and, similarly, a second nucleic acid could be termed a first nucleic acid, without departing from the scope of the present disclosure. The first nucleic acid and the second nucleic acid are both elements, but they are not the same element. Furthermore, the terms "subject," "user," and "patient" are used interchangeably herein.

As used herein, the word "include," and its variants, is intended to be non-limiting, such that recitation of items in a list is not to the exclusion of other like items that may also be useful in the materials, compositions, devices, and methods of the technology herein. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

This disclosure is further illustrated by the following non-limiting examples.

EXAMPLES

Example 1: Design of Trans-Splicing Molecules & In Vitro Target Models

A non-limiting structure of a trans-splicing molecule is shown in FIG. 1. These constructs include a CMV enhancer/ promoter, a 5' untranslated region (UTR) and coding sequence derived from USH2A, a complementary region (CR) targeting intron 13, and a trifunctional element (TFE) which has one or more stabilizing elements (e.g., one or more stabilizing structural elements), one or more cleavage elements (e.g., one or more cleavage elements), and a termination sequence (e.g., a polyadenine (polyA) sequence). The design of the trans-splicing molecule, including the TFE, allows for precise hybridization to the target transcript and efficient trans-splicing.

To quantify SE activity, two complementary in vitro systems were established as shown in FIG. 2A and FIG. 2B. The first system utilized a full-length USH2A pre-mRNA target, while the second employed a minigene construct containing exons 1-12 and 14-21 with chimeric introns for introns 12 and 13 flanking a mutant exon 13. These systems allowed for testing of cis-versus trans-splicing events and provided a model for initial SE screening.

Example 2: Initial SE Performance and Optimization of Structural Elements

Figure 3B:
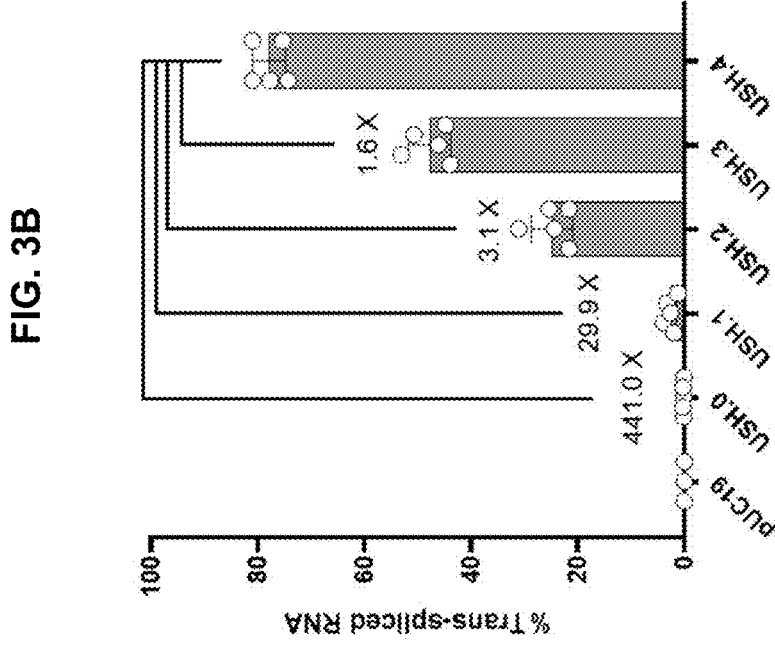
FIG. 3A and FIG. 3B show an in vitro trans-splicing assay using a transiently expressed trans-splicing based plasmid and USH2A minigene plasmid.
Figure 3A:
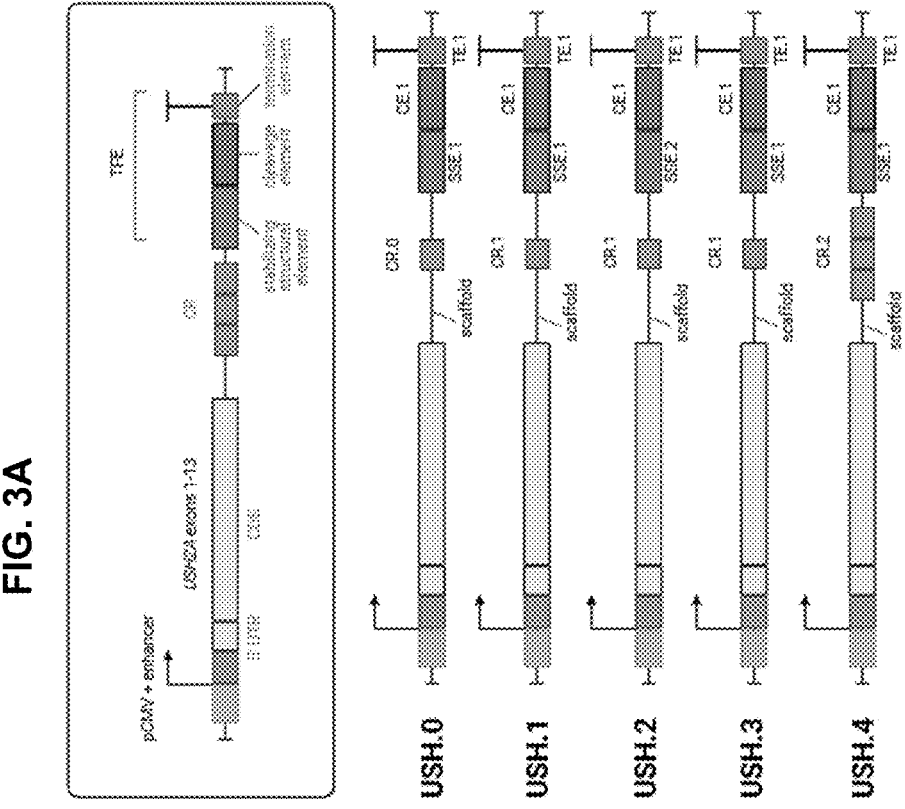

In the experiments of this example, SE designs (e.g., USH.0 through USH.4) were evaluated in HEK293FT cells co-transfected with SE and minigene plasmids, and demonstrated variable trans-splicing efficiencies, as shown in FIG. 3A and FIG. 3B. In FIG. 3A, "TFE" refers to a trifunctional element, "CR" refers to a complementary region, "SSE" refers to a stabilizing structural element, "CE" refers to a cleavage element, and "TE" refers a "termination element". USH.0 is a non-targeting control, and is based on a scaffold sequence, has CR.0, which is a non-targeting and effectively scrambled sequence and does not align to the human genome, an SSE.1 element, a cleavage element, and a termination element. USH.1 is based on a scaffold sequence, has one CR, an SSE.1 element, a cleavage element, and a termination element (SEQ ID NO: 219). USH.2 is based on a scaffold sequence, has one CR, an SSE.2 element, a cleavage element, and a termination element (SEQ ID NO: 220). USH.3 is based on a scaffold sequence, has one CR, an SSE.1 element, a cleavage element, and a termination element. USH.4 (SEQ ID NO: 255) is based on a scaffold sequence, has three CRs, an SSE.1 element, a cleavage element, and a termination element. In these experiments, USH.4 (SEQ ID NO: 15) showed the highest editing activity, confirming the optimized structural element (USH.4) and its effect for improving trans-splicing for the USH2A correction.

These experiments also examined the impact of TFE composition on SE activity. FIG. 4A and FIG. 4B and FIG. 5A and FIG. 5B show experiments in which SE variants (e.g., USH.6 through USH.33) were tested under conditions that included CRISPRa-mediated upregulation of endogenous USH2A. Trans-splicing efficiency was quantified by amplicon-based sequencing, revealing that specific TFE configurations significantly enhanced editing. Statistical analysis confirmed significant improvements for optimized designs, and therefore demonstrating the importance of optimizing structural elements in SE function.

Example 3: AAV Delivery and In Vivo Mouse Studies

To examine therapeutic application, trans-splicing molecules were delivered using AAV capsids. FIG. 6A and FIG. 6B shows experiments in HEK293FT cells that have the stably integrated USH2A minigene. FIG. 8 shows experiments with transfected CRISPRa-mediated upregulation of endogenous USH2A in a stable AAVR cell line. Trans-splicing nucleic acid constructs were introduced via AAV vectors at varying multiplicities of infection (MOIs), and trans-splicing was measured by sequencing and ddPCR. The experiments of this example demonstrated efficient AAV-mediated delivery and dose-dependent activity, thereby showing a scalable approach.

Performance of AAV-delivered trans-splicing molecules was next evaluated in mouse models. The experiments in FIG. 7, FIG. 9, and FIG. 10 show data from bilateral subretinal AAV administration, followed by retinal tissue collection one-month post-injection. Vector genomes and trans-spliced RNA were quantified by ddPCR. The results of these experiments confirmed successful delivery and editing.

Example 4: Purification Methods

The experiments in this example used an in vivo mouse model to examine two purification strategies for AAV vectors carrying the USH.4 (SEQ ID NO: 15) trans-splicing molecule (FIG. 11). Bilateral subretinal administration was performed using vectors purified either by affinity chromatography followed by iodixanol gradient ultracentrifugation, or by two sequential cesium chloride density gradients. Retinas were collected approximately one-month post-injection, and vector genomes were quantified by digital droplet PCR (ddPCR) as the number of genomes per microgram of genomic DNA (gDNA). Trans-spliced RNA was measured by amplicon-based sequencing using the Illumina MiniSeq platform.

Example 5: Non-Human Primate Evaluation & Cross-Species Comparison

Figure 12:
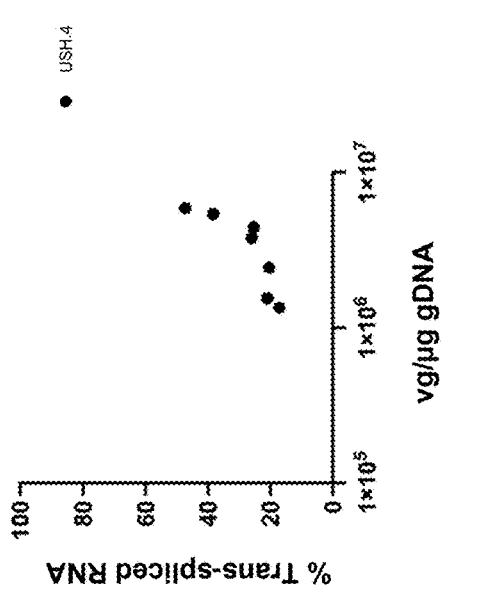
FIG. 12 shows an in vivo non-human primate experiment using wild-type AAV capsid to deliver a trans-splicing molecule.
Figures 14A, 14B:
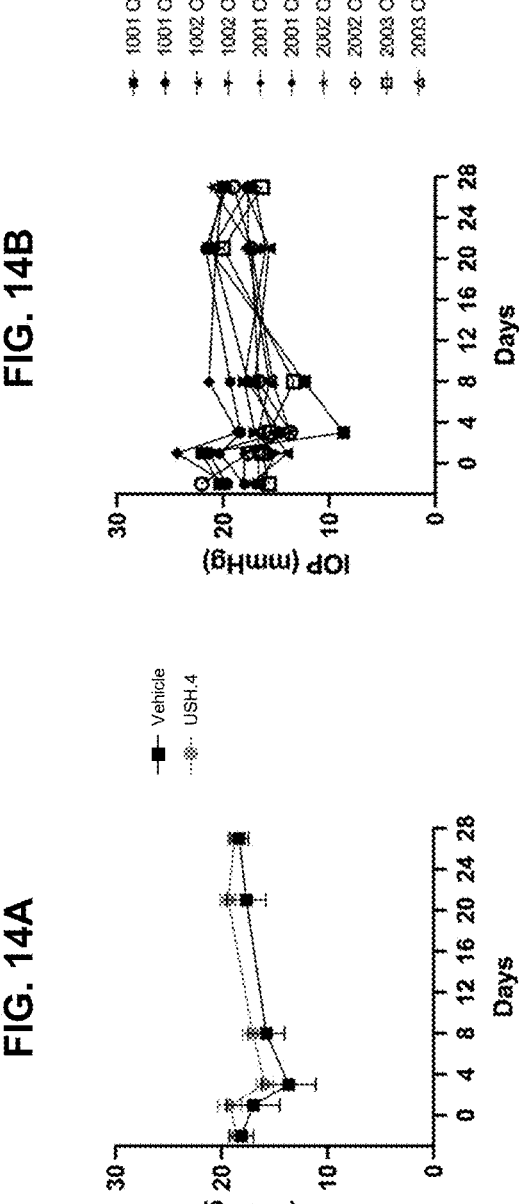
FIG. 14A and FIG. 14B are graphs showing intraocular pressure during the in vivo non-human primate study using AAV capsid to deliver a trans-splicing molecule. Intraocular pressure was measured on Days −2, 1, 3, 8, 21, and 27.
Figures 15A, 15B:
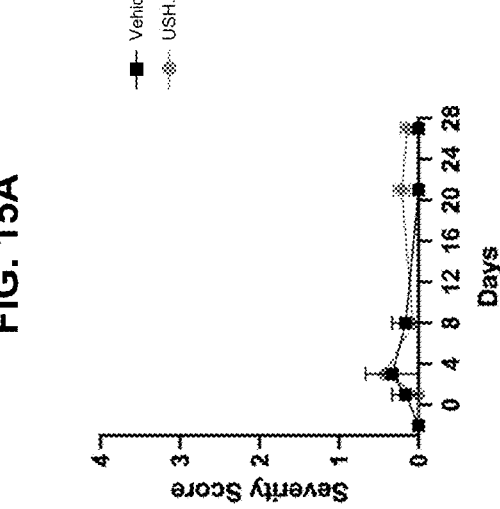
FIG. 15A and FIG. 15B are graphs showing aqueous cell severity during the in vivo non-human primate study using AAV capsid to deliver a trans-splicing molecule. Aqueous cells were measured using a modified SPOTS system on Days −2, 1, 3, 8, 21, and 27.
Figure 16B:
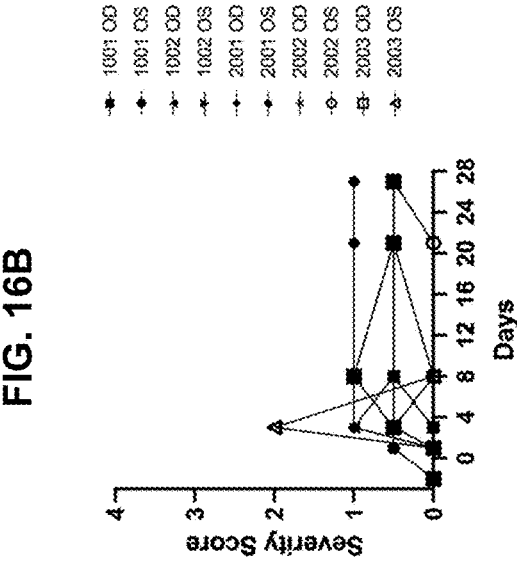
FIG. 16A and FIG. 16B are graphs showing the vitreous cell severity during the in vivo non-human primate study using AAV capsid to deliver a trans-splicing molecule. Vitreous cells were measured using a modified SPOTS system on Days −2, 1, 3, 8, 21, and 27.
Figure 16A:
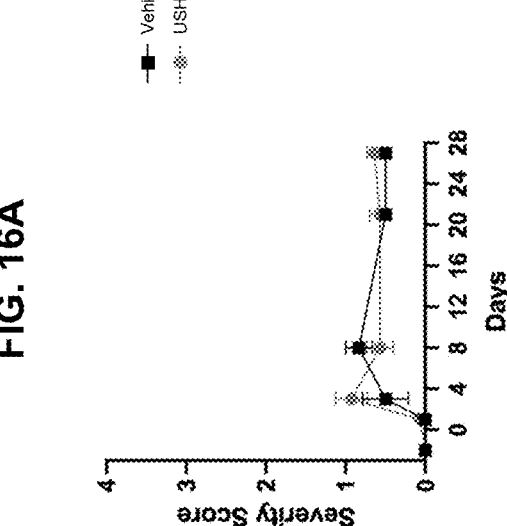
Figure 17:
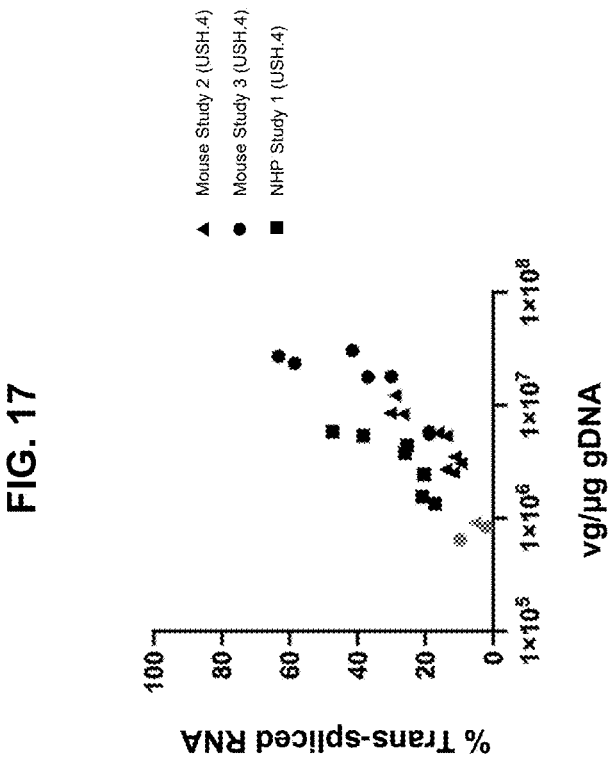
FIG. 17 is a graph showing a multi-species comparison of AAV capsid to deliver a trans-splicing molecule. Bilateral subretinal administration of vehicle or AAV (USH.4_Lot2) was performed. Retinas or retinal punches were collected approximately one-month post-injection. For mouse, individual values from each eye are plotted, while peak values from each eye are plotted for the non-human primate experiments (NHP). Vector genomes (vg) were quantified by digital droplet PCR (ddPCR) and are plotted as the number of vector genomes per microgram (μg) genomic DNA (gDNA). The percent trans-spliced RNA was quantified using a multiplex ddPCR assay that simultaneously measures total USH2A mRNA and trans-spliced USH2A mRNA. Gray symbols denote failed subretinal bleb formation based on clinical dosing observation and post-dose ocular imaging. vg=vector genomes, μg=microgram, gDNA=genomic DNA.

The experiments of this example show an in vivo study conducted in non-human primates to assess the delivery and activity of AAV capsid-delivered trans-splicing molecules in a species with ocular anatomy more closely related to humans (FIG. 12). Bilateral subretinal administration of vehicle or AAV was performed, and retinal punches were collected approximately one-month post-injection. Vector genomes were quantified by ddPCR, and trans-spliced RNA was measured using a multiplex ddPCR assay that simultaneously detects total USH2A mRNA and trans-spliced USH2A mRNA. Peak values from each eye were plotted, and the results of this experiment confirm successful delivery and editing in non-human primates.

The experiments in FIG. 13 show a comparative analysis of AAV capsid-delivered trans-splicing molecule performance across mouse and non-human primate models. Bilateral subretinal administration of vehicle or AAV (USH.4_Lot2) was performed, and tissues were collected approximately one-month post-injection. For mice, individual values from each eye were plotted, while peak values per eye were reported for non-human primates. Vector genomes were quantified by ddPCR, and trans-spliced RNA was measured using a multiplex ddPCR assay that simultaneously detects total USH2A mRNA and trans-spliced USH2A mRNA. Gray symbols indicate failed subretinal bleb formation based on clinical dosing observations and post-dose ocular imaging. This comparison demonstrates consistent trans-splicing activity across species, reinforcing the significance of the optimized delivery platform and clinically relevant doses.

Collectively, these experiments demonstrate that structural optimization enhances the delivery of the trans-splicing molecules, including the TFEs disclosed herein, and significantly enhances trans-splicing efficiency across in vitro systems, mouse models, and non-human primates. These experiments establish a robust and scalable platform for correcting gene defects, and demonstrate how the trans-splicing approach described herein is a viable therapeutic strategy.

Methods

Trans-Splicing Readout for Minigene Assays RNA was extracted using RNA QuickExtract (Biosearch Technologies; QERO90150). Briefly, media was aspirated and wells were washed with 100 µL of PBS. Then, 50 µL of cold RNA QuickExtract buffer was added directly to each well and pipetted up and down 50 times to ensure thorough lysis. Plates were incubated on ice for 10 minutes, sealed with foil, gently vortexed for 1 minute, and briefly centrifuged (1 minute at 1,000 g) before opening. cDNA was synthesized using SuperScript IV Reverse Transcriptase (Invitrogen; 18090010) according to the manufacturer's instructions. Briefly, 2 µL of undiluted QuickExtract lysate was used as input, along with an oligo(dT)$_{1-20}$ primer. Each reaction included 10 U/µL of SSIV enzyme, and extension time was increased to 90 minutes to promote full-length cDNA synthesis. Unpurified cDNA was used directly for PCR.

PCR amplification was performed using primers 1627_exon12_fwd (GAGATATTACCTGTCAC-CAAAATTC) (SEQ ID NO: 259) and 1628_exon14_rev (CAGGCTATTACAGATGTGATTAAC) (SEQ ID NO: 260) to detect both cis- and trans-spliced USH2A transcripts. Reactions were carried out using 24 cycles, with a 61° C. annealing temperature and 30-second extension time. Ten percent of the PCR reaction volume consisted of cDNA input. PCR products were purified using AMPure XP beads at a 0.8× bead ratio, then submitted to Plasmidsaurus for Sanger sequencing.

RNA Extraction by Kingfisher

Forty-four hours post transfection; media was carefully aspirated from each well and plates were sealed with an aluminum seal. Plates were immediately stored at −80° C. for a minimum of 30 minutes to freeze cells.

RNA extraction was then performed using MagMAX™-96 Total RNA Isolation Kit (AM1830, Invitrogen™) on a Kingfisher Flex equipped with a 96 deep-well head (5400630, Thermo Scientific™). Lysis buffer was added directly to frozen cells. Extraction was performed according to the manufacturer's protocol and samples were eluted in 50 µL elution buffer. After extraction, the RNA was transferred to a clean DNA low-bind plate and quantified by nanodrop and the Qubit™ RNA Broad Range assay kit (Q10211, Thermo Scientific™).

cDNA Synthesis

SuperScript IV (Invitrogen; 18090010) was used according to manufacturer's protocol for cDNA synthesis. Purified RNA 11 µL was used as input for the cDNA synthesis. A final concentration of 250 nM Oligo(dT)$_{1-20}$ (IDT) was used as the RT-primer. SuperScript IV enzyme (2 Units/µL of) was used for each RT-reaction. To facilitate full-length cDNA synthesis, the extension time was increased to 30 minutes. To increase PCR efficiency, after cDNA synthesis was complete, 7 Units of RNAseH (Takara bio; 2150B) was added. The reaction was then incubated at 37° C. for 20 minutes. The reactions were then incubated at 80° C. for 10 minutes to inactivate enzymes. Unpurified cDNA was used as the template for PCR steps.

Trans-Splicing by MiniSeq

Sequencing libraries were generated through two rounds of limited-cycle PCR amplification using Phusion Hot Start Flex DNA Polymerase (New England Biolabs; M0535L). In the first PCR (PCR1), primers specific to human USH2A exons 12 and 14 (2421_USH2a13_F (TCGTCGGCAGCGTCAGATGTGTATAAGAGACAG CACAGGTACAATTTGACCAT) (SEQ ID NO: 261) and 2423_USH2a13_R (GTCTCGTGGGCTCG-GAGATGTGTATAAGAGACAG CTATTACAGATGT-GATTAACTGC) (SEQ ID NO: 262)) were used to amplify the target regions and append adapter sequences for subsequent barcoding. Unpurified cDNA served as the template, with 10% of the PCR1 reaction volume consisting of template cDNA. PCR1 was performed with an annealing temperature of 58° C., an extension time of 30 seconds, and 18 amplification cycles.

Following PCR1, products were purified using a 0.8× AMPure XP bead cleanup (Beckman Coulter; A63882) and eluted in 12 µL of nuclease-free water. A 4 µL aliquot of the purified PCR1 product was used as a template for a 40 µL PCR2 reaction. PCR2 appended Illumina-compatible sequencing adapters and sample-specific indices to facilitate multiplexing. The PCR2 thermocycling conditions included an annealing temperature of 60° C., an extension time of 30 s, and 18 cycles.

PCR2 products were pooled and visualized on a 2% SYBR Safe E-gel (Invitrogen; A42135). A single band corresponding to the expected library size was excised and purified using the Zymoclean Gel DNA Recovery Kit (Zymo Research; D4007). A final 0.8× AMPure XP bead purification was performed prior to sequencing. Libraries were sequenced on the Illumina MiniSeq platform.

Following sequencing, amplicons were demultiplexed using Illumina's BCL2fastq (v2.20.0.422). Overall, reads were classified as originating from the splice-editor-encoded repRNA (trans-spliced) or endogenous transcript (cis-spliced) based on the presence or absence of the codon-diversified patch unique to the repRNA sequence. Percent trans-splicing was quantified by dividing the number of trans-spliced reads by the summed total of the trans- and cis-spliced reads, then multiplying by 100.

In Vivo Mouse Studies

Mouse studies two, three, and four utilized humanized USH2A male mice of approximately 6-13 weeks of age obtained from Cyagen (Product ID: C001554). Mouse study one utilized male mice of approximately 6-13 weeks of age with a variant of this humanized USH2A model that contains a two base pair deletion in exon 13. All procedures were performed in accordance with the regulations of the Association for Assessment and Accreditation of Laboratory Animal Care (AAALAC). In brief, the eyes of deeply anesthetized mice were dilated, examined for abnormalities, and then locally anesthetized and cleaned. A syringe was filled with the dosing material, ensuring no air bubbles were present. A preliminary perforation or sclerotomy hole was made, depending on whether a transcorneal or transscleral approach was used.

Mouse study 1 implemented a transcorneal approach. A preliminary perforation was made 1 mm from the corneal limbus using a 29-gauge needle. Then, a 33-gauge needle was inserted through the perforation and advanced along the internal scleral surface through the sclera and choroid. The needle was progressed until it reached the subretinal space, then 1 μL of test material was delivered by manually depressing the plunger of the syringe.

Mouse studies 2-4 implemented a transscleral approach. The bulbar conjunctiva at the superior temporal aspect of the eye was incised to reveal the sclera, and a 30-gauge needle was used to create a sclerotomy hole. In mouse study 2, a syringe was attached to an ocular injection kit that included SilFlex tubing, a gasket, a holder, and a 35-gauge beveled NanoFil needle. The needle was inserted into the sclerotomy hole, and 1 μL of test material was delivered by manually depressing the plunger of the syringe. For mouse studies 3 and 4, a simplified injection setup was used that eliminated the injection kit. Here, a syringe with a 33-35-gauge needle was inserted into the sclerotomy hole, and 1 μL of test material was delivered by manually depressing the plunger of the syringe.

Subretinal bleb formation was assessed by optical coherence tomography immediately post-dose. The approximate dose level for each eye was $1.0×10^{10}$ vector genomes (vg). Animals were monitored throughout the duration of the study. After 26-28 days, the animals were euthanized, both eyes were enucleated, and the whole retina was dissected from each eye and snap-frozen separately.

In Vivo NHP Study

Five male *Macaca fascicularis* aged one to three years old were enrolled in the study. The study protocol and any amendments or procedures involving the care or use of animals in this study were reviewed and approved by the testing facility's Institutional Animal Care and Use Committee (IACUC) before the initiation of such procedures. The testing facilities are accredited by AAALAC and registered with the United States Department of Agriculture. Prior to study start, whole blood was collected, processed to serum, and tested for neutralizing antibodies against AAV8 (VRL). Two days prior to dosing, animals were administered a Rituximab biosimilar (10 mg/kg) via intravenous infusion over ~30 minutes.

On the day of dosing (study day 1), the eyes of deeply anesthetized animals were dilated, locally anesthetized, and cleaned. Eyes were held open with a speculum and two trocars were placed in the eye to place scleral cannulas. One cannula was used for endoillumination and one was used to insert a blunt needle (WPI; NANOFIL 33-38 gauge) attached to an ocular injection kit (WPI; IO-KIT), a gas-tight microinjection system (WPI; NANOFIL-100) and a micro-injection syringe pump (WPI; UMP3). The needle was advanced behind the lens and gently touched down on the retina. Vehicle or test article ($5.7×10^{10}$ vg/mL) was infused subretinally in two separate 50 μL blebs in each eye. Triamcinolone Acetonide Injectable Suspension, USP (40 mg/mL, 0.1 mL; Amneal Biosciences; 70121-1049-05) was administered subconjunctivally in each eye. Post-dose and on Day 8, animals were administered prednisone (10 mg/kg) via intramuscular injection. Animals received oral prednisone (1 mg/kg) on Days 3, 14, and 21. Topical Bromfenac was applied to the eye post-dose and on Days 3 and 8.

Ocular exams were performed on Days −2, 1, 3, 8, 21, and 27. Ocular exams covered a number of measurements, including intraocular pressure, aqueous cells, and vitreous cells. Optical coherence tomography was performed on Days −2, 1, 8, and 27. Clinical observations were performed once pre-dose and daily throughout the duration of the study. Body weights were recorded weekly. On Day 28 of the study, animals were euthanized, eyes were dissected out fresh and retina was separated from other optic tissue. Punches were taken from each retina, collected separately, and snap frozen on dry ice.

Body weights and intraocular pressure remained within normal range for the duration of the study. Aqueous and vitreous cells were scored based on a modified SPOTS system with scores of 0 (<1 cell in field), 0.5 (trace; 1-5 cells in field), 1 (6-25 cells in field), 2 (26-50 cells in field), 3 (51-100 cells in field), 4 (>100 cells in field). The aqueous cell scores were between 0 and 0.5 for all eyes, except one vehicle-treated eye that had a score of 1 on Day 3. The vitreous cell scores were between 0 and 1 for all eyes, except one AAV-treated eye that had a score of 2 on Day 3.

Tissue Processing

For sample analysis, total DNA, RNA, and protein were isolated and purified from whole mouse retinas and NHP retinal punches (~3 mg tissue per sample) using a DNA/RNA/Protein AllPrep Mini Kit (QIAGEN; 80004) per manufacturer's instructions. Tissues were homogenized using the Precellys 24 Touch Homogenizer (Bertin Technologies). Briefly, samples were added to Hard Tissue Reinforced Tubes (Bertin Technologies; CK28-R) containing buffer and subjected to 2 cycles of 20 seconds at 6500 rpm with a cooling period of 30 seconds between each cycle. Resultant homogenate was then processed per manufacturer's kit instructions (QIAGEN; 80004). The purified DNA and RNA sample concentrations were determined using NanoDrop One.

Vector Genome Quantification by ddPCR.

To determine vector genome copy numbers, purified genomic DNA (gDNA) samples were analyzed in a digital droplet polymerase chain reaction (ddPCR) assay using the Bio-Rad QX600 system. A primer pair that amplifies a unique region of the USH2A trans-splicing molecule (forward primer: 5'-TTGGAGTTACAGGTCTTAGGTGC-3' (SEQ ID NO: 277); reverse primer: 5'-GGATCGCAGAT-TGTTCCTGG-3') (SEQ ID NO: 263) and a double quenched fluorescent probe (5'-CCACACAGGTACAAT-TTGACCA-3') (SEQ ID NO: 264) were used.

The primers and probe were combined with a ddPCR Supermix for Probes (no dUTP) (Bio-Rad; 1863025), restriction enzyme, and water in a ddPCR 96-Well Semi-Skirted Plate (Bio-Rad; 17005224). The gDNA samples were diluted in nuclease-free water and added to the ddPCR plate. The plate was then sealed and briefly vortexed and centrifuged.

The ddPCR plate was then added to the Automated Droplet Generator (Bio-Rad) and droplet generation was performed according to the manufacturer's instructions. Immediately after the droplets were generated, the new ddPCR plate containing the droplets was sealed. Following PCR cycling (10 minutes at 95° C., 40 cycles of 30 seconds at 94° C., 1 minute at 60° C., 10 minutes at 95° C.), the samples were scanned in the QX600 Droplet Reader and analyzed using the QX Manager Standard Edition software (Bio-Rad) to determine the vector genome concentration using the Poisson distribution formula:

$$\text{concentration} = -\frac{\ln(E)}{0.85} \times 1000$$

Where concentration is the number of copies of target per microliter of the reaction solution and E is the frequency of droplets that contain no nucleic acid template. Final values were normalized to input volume and gDNA concentration.

Trans-Splicing by ddPCR cDNA was synthesized from purified total RNA using a SuperScript® IV Reverse Transcriptase (RT) kit (Thermo Fisher Scientific; 18090050). RT step one master mix was prepared and added to a 96-well PCR plate where each reaction contained 1 μL of 2 mM gene-specific primer (primer for humanized USH2A mouse studies: 5'-AGGTTTCATTCAAGGCTC-3'(SEQ ID NO: 265); primer for NHP studies: 5'-GAGGGTCCAT-TCAGTTC-3'(SEQ ID NO: 266)) and 1 μL of 10 mM dNTP mix. The total RNA samples were diluted to 18.2 ng/μL in 11 μL total volume and added to a 96-well PCR plate for a total RNA input of 200 ng per reaction. The first RT step conditions were 5 minutes at 65° C. to anneal the RNA, then incubation on ice for 1 minute. RT step two master mix was then prepared and added to the annealed RNA samples in the 96-well PCR plate, where each reaction contained 4 μL of 5×SSIV Buffer, 1 μL of 100 mM DTT, 1 μL of RNase Inhibitor, and 1 μL of SuperScript® IV Reverse Transcriptase (200 U/mL). The samples were then incubated for 90 minutes at 50° C., followed by RNase treatment for 20 minutes at 37° C., and then heat-inactivation for 10 minutes at 80° C. Samples were then placed on ice while preparing the ddPCR assay.

The percent trans-spliced RNA was quantified using a multiplex ddPCR assay using two probes. Probe one spans the exon 13-14 junction of USH2A (5'-GTAATCAGTGT-CAACCAGGTTTTTATATTTC-3' (SEQ ID NO: 267); equivalent exon 14-15 junction in NHP) and detects all USH2A mRNA transcripts, regardless of whether they are trans-spliced or cis-spliced. Probe two detects a codon-diversified region that is unique to the repRNA (5'-CCAG-GAACAATCTGCGATCCT-3' (SEQ ID NO: 268)). Primers were specific for either humanized USH2A mouse studies (Forward: 5'-ACCATTGACAATTTTCAACACTG-3'(SEQ ID NO: 269); Reverse: 5'-CAGGCTATTACAGATGTGAT-TAACTG-3' (SEQ ID NO: 270)) or NHP studies (Forward: 5'-GGTACAATTTGACCATTGACAATTTTC-3' (SEQ ID NO: 271); Reverse: 5'-GTCAGGCTATTACAGATGTGAT-3" (SEQ ID NO: 272)) The primers and probe were combined with a ddPCR Multiplex Mix (Bio-Rad; 12005910), DTT (Biorad; 1201217), and water in a ddPCR 96-Well Semi-Skirted Plate (Bio-Rad; 17005224). The cDNA samples were diluted in nuclease-free water and added to the ddPCR plate. The plate was then sealed and briefly vortexed and centrifuged.

The ddPCR plate was then added to the Automated Droplet Generator (Bio-Rad) and droplet generation was performed according to the manufacturer's instructions. Immediately after the droplets were generated, the new ddPCR plate containing the droplets was sealed. Following PCR cycling (10 minutes at 95° C., 40 cycles of 30 seconds at 94° C., 1 minute at 61.6° C., 10 minutes at 98° C.) the samples were scanned in the QX600 Droplet Reader and analyzed using the QX Manager Standard Edition software (Bio-Rad) to determine the concentration of probe 1 and/or 2 positive droplets using the Poisson distribution formula:

$$concentration = -\frac{\ln(E)}{0.85} \times 1000$$

Where concentration is the number of copies of target per microliter of the reaction solution and E is the frequency of droplets that contain no nucleic acid template. Droplets that were positive for both probes represent trans-spliced RNA, while droplets positive for only probe one represent all USH2A transcripts. The percent trans-spliced RNA was calculated by dividing the copies/μl of the dual-positive population by copies/μl of the probe one single-positive population and multiplying by 100.

AAV Production

Recombinant adeno-associated viral (AAV) vectors were produced in suspension HEK293F-derived cells using a triple-plasmid transfection approach. Briefly, cells were transfected with transgene, helper, and Rep/Cap plasmids at optimized molar ratios. Cells were harvested 72 hours post-transfection, lysed in detergent-containing buffer, subjected to freeze-thaw cycles, and treated to remove residual nucleic acids. Clarified lysates were processed and then purified by either (1) affinity chromatography followed by iodixanol gradient ultracentrifugation (Lots 1 and 3) or (2) two sequential cesium chloride density gradients (Lots 2 and 4). The resulting viral fractions were buffer-exchanged and concentrated via centrifugal filtration. Final preparations were sterile-filtered, aliquoted, and stored at 4° C. for short-term use or −80° C. for long-term storage.

AAVR Stable Cell Line Generation

HEK293FT cells were transduced with lentiviral particles encoding a multi-serotype receptor for AAV (AAVR) at a multiplicity of infection (MOI) of 5 in the presence of polybrene (8 g/mL). Following transduction, cells were incubated for 72 hours at 37° C. with 5% $CO_2$. Transduced cells were subsequently passaged at a 1:3 split ratio into fresh culture vessels and subjected to antibiotic selection using puromycin at a concentration of 2 g/mL. Selection medium was replaced every two days, and cells were maintained under selection pressure for two weeks to generate a polyclonal population of stably transduced cells.

To isolate monoclonal cell lines, limiting dilution was performed to achieve single-cell clonal populations. Cells from the polyclonal population were counted, and serial dilutions were performed in selection medium containing 2 g/mL puromycin to reach a target density of 5 cells/mL. Starting from an initial cell density of $1.5 \times 10^6$ cells/mL, cells were first diluted 1:100 to achieve $1.5 \times 10^4$ cells/mL. A subsequent 1:100 dilution yielded 150 cells/mL. A final 1:30 dilution was performed to obtain the target density of 5 cells/mL. This cell suspension was dispensed at 100 μL per well into 96-well plates, providing a theoretical distribution of approximately 1 cell per 2 wells.

Individual clones were allowed to expand for 2-4 weeks in selection medium. Successfully expanded clones were subsequently evaluated for AAVR expression and functionality using the AAV transduction assays.

AAV Transduction

HEK293FT cells stably integrated with the USH2A minigene were seeded at $2 \times 10^4$ cells per well in 96-well plates. Cells were transduced the following day with AAV vectors at a multiplicity of infection (MOI) of $1 \times 10^5$ vector genomes per cell. Cells were collected 72-hours post-transduction.

AAVR-expressing monoclonal cell lines were seeded at $2 \times 10^4$ cells per well in 96-well plates and transduced on the same day with AAV vectors at multiplicities of infection (MOIs) of $1 \times 10^5$, $5 \times 10^4$, and $1 \times 10^4$ viral genomes per cell. Twenty-four hours post-transduction, cells were transfected with CRISPRa components consisting of sgRNA targeting USH2A, dCas9, and pUC19 plasmids at a mass ratio of 1:1:2 using Lipofectamine 3000 according to the manufacturer's instructions. Forty-four hours following CRISPRa transfection (68 hours post-transduction), cells were harvested, and total RNA was isolated using the King Fisher for downstream analysis.

(SEQ ID NO: 255)

USH.4 Sequence
CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGGTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCTGTTTGCTCTGCAGA

ATACTTTACCTGGGCACCCAAGTCATCCTTCCAGCATTCCTGCTGCTAC

AGCCTATTTGCTGAGTAACCAGGGGTTACAGCAGCGTTGCCAGGCAACG

AGGGACAGCGGTCCTGTTGAAGAGCCATTTGTCACACTGAGGGGACTGG

TTGAAATGCAATAAAGAAATGATACCAGCAGCTACTCATGTCATCGCCA

TTGCTAAGAACGTCGTTGGTATTACCTTACTCTGAGAACGTGTCTGCAG

TTTCCAGAAAATGGAGTATCGCAACATCACTTAAAGTACCCTGCTTCAA

AGTATTGCTGGCAAGTGGCGTGGGCCTGATTATTTATTTAGAAATGCTT

TATCAGGAGGAGAATGCTTTTTTTGTAAACATGAATTGCCCAGTTCTTTC

ATTGGGCTCTGGCTTCTTGTTTCAGGTCATTGAAATGTTGATCTTTGCC

TATTTTGCTTCAATATCCTTGACTGAGTCACGAGGTCTTTTCCCAAGGC

TGGAGAACGTGGGAGCTTTCAAGAAAGTTTCCATCGTGCCAACCCAAGC

AGTATGTGGACTCCCAGACCGAAGCACTTTTTGTCACAGCTCTGCTGCT

GCTGAAAGTATTCAGTTCTGTACCCAGCGGTTTTGTATTCAGGATTGCC

CATACAGATCTTCACACCCTACCTACACTGCCCTTTTCTCAGCAGGCCT

CAGTAGCTGCATCACACCAGACAAGAATGATCTGCATCCTAACGCCCAT

AGCAATTCTGCAAGTTTTATTTTTGGAAATCACAAGAGCTGCTTTTCTT

CTCCTCCTTCTCCAAAGCTGATGGCATCATTTACCTTAGCTGTATGGCT

GAAACCTGAGCAACAAGGTGTAATGTGTGTTATAGAAAAGACAGTAGAT

GGGCAGATTGTGTTCAAACTTACAATATCTGAGAAAGAGACAATGTTTT

ATTATCGCACAGTAAATGGTTTGCAACCTCCAATAAAAGTAATGACACT

GGGGAGAATTCTTGTGAAGAAATGGATTCATCTTAGTGTGCAGGTCCAT

CAGACAAAAATCAGCTTCTTTATCAATGGCGTGGAGAAGGATCATACAC

CTTTCAATGCAAGAACTCTAAGTGGTTCAATTACAGATTTTGCATCTGG

TACTGTGCAAATAGGACAGAGTTTAAATGGTTTAGAGCAGTTTGTCGGA

AGAATGCAAGATTTTCGATTATACCAAGTGGCACTTACAAACAGAGAGA

TTCTGGAAGTGTTCTCTGGAGATCTTCTCAGATTGCATGCCCAATCACA

TTGCCGTTGCCCTGGCAGCCACCCGCGGGTCCACCCTTTGGCACAGCGG

TACTGCATTCCTAATGATGCAGGAGACACAGCTGATAATAGAGTGTCAC

GGTTGAATCCTGAAGCCCATCCTCTCTCTTTTGTCAATGATAATGATGT

TGGTACTTCATGGGTTTCAAATGTGTTTACAAACATTACACAGCTTAAT

CAAGGAGTGACTATTTCAGTTGATTTGGAAAATGGACAGTATCAGGTGT

TTTATATTATCATTCAGTTCTTTAGTCCACAACCAACGGAAATAAGGAT

TCAAAGGAAGAAGGAAAATAGTTTAGATTGGGAGGACTGGCAATATTTT

GCCAGGAATTGTGGTGCTTTTGGAATGAAAAACAATGGAGATTTGGAAA

AACCTGATTCTGTCAACTGCCTTCAGCTTTCCAATTTTACTCCATATTC

CCGTGGCAATGTCACATTTAGCATCCTGACACCTGGACCAAATTATCGT

CCTGGATACAATAACTTCTATAATACCCCATCTCTTCAAGAGTTCGTAA

AAGCCACGCAAATAAGGTTTCATTTTCATGGGCAGTACTATACAACTGA

GACTGCTGTTAACCTCAGACACAGATATTATGCAGTGGACGAAATCACC

ATTAGTGGGAGATGTCAGTGCCATGGTCATGCCGATAACTGCGACACAA

CAAGCCAGCCATATAGATGCCTCTGCTCCCAGGAGAGCTTCACTGAAGG

ACTTCATTGTGATCGCTGCTTGCCTCTTTATAATGACAAGCCTTTCCGC

CAAGGTGATCAAGTTTACGCTTTCAATTGTAAACCTTGTCAATGCAACA

GCCATTCCAAAAGCTGCCATTACAACATCTCTGTAGACCCATTTCCTTT

TGAGCACTTCAGAGGGGGAGGAGGAGTTTGTGATGATTGTGAGCATAAC

ACTACAGGAAGGAACTGTGAGCTGTGCAAGGATTACTTTTTTCCGACAAG

TTGGTGCAGATCCTTCGGCCATAGATGTTTGCAAACCCTGTGACTGTGA

TACAGTTGGCACTAGAAATGGTAGCATTCTTTGTGATCAGATTGGAGGA

CAGTGTAATTGTAAGAGACACGTGTCTGGCAGGCAGTGCAATCAGTGCC

AGAATGGATTCTACAATCTACAAGAGTTGGATCCTGATGGCTGCAGTCC

CTGTAACTGCAATACCTCTGGGACAGTGGATGGAGATATTACCTGTCAC

CAAAATTCAGGCCAGTGCAAGTGCAAAGCAAACGTTATTGGGCTTAGGT

GTGATCATTGCAATTTTGGATTTAAATTTCTCCGAAGCTTTAATGATGT

TGGATGTGAGCCCTGCCAGTGTAACCTCCATGGCTCAGTGAACAAATTC

TGCAATCCTCACTCTGGGCAGTGTGAGTGCAAAAAAGAAGCCAAAGGAC

TTCAGTGTGATACCTGCAGAGAAAACTTTTATGGGTTAGATGTCACCAA

TTGTAAGGCCTGTGACTGTGACACAGCTGGATCCCTCCCTGGGACTGTC

TGTAATGCTAAGACAGGGCAGTGCATCTGCAAGCCCAATGTCGAGGGAA

GGCAGTGTAACAAGTGCCTTGAAGGGAACTTCTACCTACGGCAAAATAA

TTCTTTCCTCTGTCTGCCTTGCAACTGTGATAAGACTGGGACAATAAAT

GGCTCTCTGCTGTGTAACAAATCAACAGGACAATGTCCTTGCAAGCTTG

GAGTTACGGTCTTAGGTGCAACCAGTGCGAACCACACAGGTACAATTT

GACCATTGACAATTTTCAACACTGCCAGATGTGTGAGTGTGATTCCTTG

GGGACATTACCAGGAACAATCTGCGATCCTATCAGTGGCCAGTGCCTGT

GTGTGCCTAATCGTCAAGGAAGAAGGTGTAATCAGTGTCAACCAGGTAA

GTGTAGCAATTTGGATGATTACACAGAAAAACAGAATACTCTACCAAGG

CACTAATTCCCAATACAAATGTGGTTATATATGCAGATAATTTTGAATA

AGTTAAATAGTTATATATGTGTTGGATAATGATATAAATAAATTTGTAG

AAGCCACAAACCAGAAACAGGGAGAAGTTACCTAAGTTAACAAAAGGAA

-continued

TGTCATTGTGCACTGAAAATGTAATACATTTAAATGATTAAATTAAGCA

GGTCCAATGCTCTTCAGTAGGGTCATGAAGGTTTTTCTTTTCCTGAGAA

AACAACACGTATTGTTTTCTCAGGTTTTGCTTTTTGGCCTTTTTCTAGC

TTAAAAAAAAAAAAAGCAAAAGAGGCCGGCATGGTCCCAGCCTCCTCGC

TGGCGCCGGCTGGGCAACATGCTTCGGCATGGCGAATGGGACCTTGTTT

ATTGCAGCTTATAATGGTTACAAATAAAGCAATAGCATCACAAATTTCA

CAAATAAAGCATTTTTTTCACTGCATTCTAGTTGTGGTTTGTCCAAACT

CATCAATGTATCTTAT

SEQ ID NO: 256

(USH.4a)

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGGTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCTGTTTGCTCTGCAGA

ATACTTTACCTGGGCACCCAAGTCATCCTTCCAGCATTCCTGCTGCTAC

AGCCTATTTGCTGAGTAACCAGGGGTTACAGCAGCGTTGCCAGGCAACG

AGGGACAGCGGTCCTGTTGAAGAGCCATTTGTCACACTGAGGGGACTGG

TTGAAATGCAATAAAGAAATGATACCAGCAGCTACTCATGTCATCGCCA

TTGCTAAGAACGTCGTTGGTATTACCTTACTCTGAGAACGTGTCTGCAG

TTTCCAGAAAATGGAGTATCGCAACATCACTTAAAGTACCCTGCTTCAA

AGTATTGCTGGCAAGTGGCGTGGGCCTGATTATTTATTTAGAAATGCTT

TATCAGGAGGAGAATGCTTTTTTGTAAACATGAATTGCCCAGTTCTTTC

ATTGGGCTCTGGCTTCTTGTTTCAGGTCATTGAAATGTTGATCTTTGCC

TATTTTGCTTCAATATCCTTGACTGAGTCACGAGGTCTTTTCCCAAGGC

TGGAGAACGTGGGAGCTTTCAAGAAAGTTTCCATCGTGCCAACCCAAGC

AGTATGTGGACTCCCAGACCGAAGCACTTTTTTGTCACAGCTCTGCTGCT

GCTGAAAGTATTCAGTTCTGTACCCAGCGGTTTTGTATTCAGGATTGCC

CATACAGATCTTCACACCCTACCTACACTGCCCTTTTCTCAGCAGGCCT

CAGTAGCTGCATCACACCAGACAAGAATGATCTGCATCCTAACGCCCAT

AGCAATTCTGCAAGTTTTATTTTTGGAAATCACAAGAGCTGCTTTTCTT

CTCCTCCTTCTCCAAAGCTGATGGCATCATTTACCTTAGCTGTATGGCT

GAAACCTGAGCAACAAGGTGTAATGTGTGTTATAGAAAAGACAGTAGAT

GGGCAGATTGTGTTCAAACTTACAATATCTGAGAAAGAGACAATGTTTT

-continued

ATTATCGCACAGTAAATGGTTTGCAACCTCCAATAAAAGTAATGACACT

GGGGAGAATTCTTGTGAAGAAATGGATTCATCTTAGTGTGCAGGTCCAT

CAGACAAAAATCAGCTTCTTTATCAATGGCGTGGAGAAGGATCATACAC

CTTTCAATGCAAGAACTCTAAGTGGTTCAATTACAGATTTTGCATCTGG

TACTGTGCAAATAGGACAGAGTTTAAATGGTTTAGAGCAGTTTGTCGGA

AGAATGCAAGATTTTCGATTATACCAAGTGGCACTTACAAACAGAGAGA

TTCTGGAAGTGTTCTCTGGAGATCTTCTCAGATTGCATGCCCAATCACA

TTGCCGTTGCCCTGGCAGCCACCCGCGGGTCCACCCTTTGGCACAGCGG

TACTGCATTCCTAATGATGCAGGAGACACAGCTGATAATAGAGTGTCAC

GGTTGAATCCTGAAGCCCATCCTCTCTCTTTTGTCAATGATAATGATGT

TGGTACTTCATGGGTTTCAAATGTGTTTACAAACATTACACAGCTTAAT

CAAGGAGTGACTATTTCAGTTGATTTGGAAAATGGACAGTATCAGGTGT

TTTATATTATCATTCAGTTCTTTAGTCCACAACCAACGGAAATAAGGAT

TCAAAGGAAGAAGGAAAATAGTTTAGATTGGGAGGACTGGCAATATTTT

GCCAGGAATTGTGGTGCTTTTGGAATGAAAAACAATGGAGATTTGGAAA

AACCTGATTCTGTCAACTGCCTTCAGCTTTCCAATTTTACTCCATATTC

CCGTGGCAATGTCACATTTAGCATCCTGACACCTGGACCAAATTATCGT

CCTGGATACAATAACTTCTATAATACCCCATCTCTTCAAGAGTTCGTAA

AAGCCACGCAAATAAGGTTTCATTTTCATGGGCAGTACTATACAACTGA

GACTGCTGTTAACCTCAGACACAGATATTATGCAGTGGACGAAATCACC

ATTAGTGGGAGATGTCAGTGCCATGGTCATGCCGATAACTGCGACACAA

CAAGCCAGCCATATAGATGCCTCTGCTCCCAGGAGAGCTTCACTGAAGG

ACTTCATTGTGATCGCTGCTTGCCTCTTTATAATGACAAGCCTTTCCGC

CAAGGTGATCAAGTTTACGCTTTCAATTGTAAACCTTGTCAATGCAACA

GCCATTCCAAAAGCTGCCATTACAACATCTCTGTAGACCCATTTCCTTT

TGAGCACTTCAGAGGGGGAGGAGGAGTTTGTGATGATTGTGAGCATAAC

ACTACAGGAAGGAACTGTGAGCTGTGCAAGGATTACTTTTTTCCGACAAG

TTGGTGCAGATCCTTCGGCCATAGATGTTTGCAAACCCTGTGACTGTGA

TACAGTTGGCACTAGAAATGGTAGCATTCTTTGTGATCAGATTGGAGGA

CAGTGTAATTGTAAGAGACACGTGTCTGGCAGGCAGTGCAATCAGTGCC

AGAATGGATTCTACAATCTACAAGAGTTGGATCCTGATGGCTGCAGTCC

CTGTAACTGCAATACCTCTGGGACAGTGGATGGAGATATTACCTGTCAC

CAAAATTCAGGCCAGTGCAAGTGCAAAGCAAACGTTATTGGGCTTAGGT

GTGATCATTGCAATTTTGGATTTAAATTTCTCCGAAGCTTTAATGATGT

TGGATGTGAGCCCTGCCAGTGTAACCTCCATGGCTCAGTGAACAAATTC

TGCAATCCTCACTCTGGGCAGTGTGAGTGCAAAAAAGAAGCCAAAGGAC

TTCAGTGTGATACCTGCAGAGAAAACTTTTATGGGTTAGATGTCACCAA

TTGTAAGGCCTGTGACTGTGACACAGCTGGATCCCTCCCTGGGACTGTC

TGTAATGCTAAGACAGGGCAGTGCATCTGCAAGCCCAATGTCGAGGGAA

GGCAGTGTAACAAGTGCCTTGAAGGGAACTTCTACCTACGGCAAAATAA

TTCTTTCCTCTGTCTGCCTTGCAACTGTGATAAGACTGGGACAATAAAT

-continued

GGCTCTCTGCTGTGTAACAAATCAACAGGACAATGTCCTTGCAAGCTTG

GAGTTACAGGTCTTAGGTGCAACCAGTGCGAACCACACAGGTACAATTT

GACCATTGACAATTTTCAACACTGCCAGATGTGTGAGTGTGATTCCTTG

GGGACATTACCAGGAACAATCTGCGATCCTATCAGTGGCCAGTGCCTGT

GTGTGCCTAATCGTCAAGGAAGAAGGTGTAATCAGTGTCAACCAGGTAA

GTGTAGCAATTTGGATGATTACACAGAAAAACAGAATACTCTACCAAGG

CACTAATTCCCAATACAAATGTGGTTATATATGCAGATAATTTTGAATA

AGTTAAATAGTTATATATGTGTTGGATAATGATATAAATAAATTTGTAG

AAGCCACAAACCAGAAACAGGGAGAAGTTACCTAAGTTAACAAAAGGAA

TGTCATTGTGCACTGAAAATGTAATACATTTAAATGATTAAATTAAGCA

GGTCCAATGCTCTTCAGTAGGGTCATGAAGGTTTTTCTTTTCCTGAGAA

AACAACACGTATTGTTTTCTCAGGTTTTGCTTTTTGGCCTTTTTCTAGC

TTAAAAAAAAAAAAAGCAAAAGGCCGGCATGGTCCCAGCCTCCTCGCTG

GCGCCGGCTGGGCAACATGCTTCGGCATGGCGAATGGGACCTTGTTTAT

TGCAGCTTATAATGGTTACAAATAAAGCAATAGCATCACAAATTTCACA

AATAAAGCATTTTTTTCACTGCATTCTAGTTGTGGTTTGTCCAAACTCA

TCAATGTATCTTAT

SEQ ID NO: 257

(USH.4b)

CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGGTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

GTCTATATAAGCAGAGCTGGTTTAGTGAACCGTCAGTTCCAAGAGGGCC

ACCAAGCAGACCACGCTCTGAGCTTCAGGGAACCAAGTGTTTGCTCTGC

AGAATACTTTACCTGGGCACCCAAGTCATCCTTCCAGCATTCCTGCTGC

TACAGCCTATTTGCTGAGTAACCAGGGGTTACAGCAGCGTTGCCAGGCA

ACGAGGGACAGCGGTCCTGTTGAAGAGCCATTTGTCACACTGAGGGGAC

TGGTTGAAATGCAATAAAGAAATGATACCAGCAGCTACTCATGTCATCG

CCATTGCTAAGAACGTCGTTGGTATTACCTTACTCTGAGAACGTGTCTG

CAGTTTCCAGAAAATGGAGTATCGCAACATCACTTAAAGTACCCTGCTT

CAAAGTATTGCTGGCAAGTGGCGTGGGCCTGATTATTTATTTAGAAATG

CTTTATCAGGAGGAGAATGCTTTTTTGTAAACATGAATTGCCCAGTTCT

TTCATTGGGCTCTGGCTTCTTGTTTCAGGTCATTGAAATGTTGATCTTT

-continued

GCCTATTTTGCTTCAATATCCTTGACTGAGTCACGAGGTCTTTTCCCAA

GGCTGGAGAACGTGGGAGCTTTCAAGAAAGTTTCCATCGTGCCAACCCA

AGCAGTATGTGGACTCCCAGACCGAAGCACTTTTTGTCACAGCTCTGCT

GCTGCTGAAAGTATTCAGTTCTGTACCCAGCGGTTTTGTATTCAGGATT

GCCCATACAGATCTTCACACCCTACCTACACTGCCCTTTTCTCAGCAGG

CCTCAGTAGCTGCATCACACCAGACAAGAATGATCTGCATCCTAACGCC

CATAGCAATTCTGCAAGTTTTATTTTTGGAAATCACAAGAGCTGCTTTT

CTTCTCCTCCTTCTCCAAAGCTGATGGCATCATTTACCTTAGCTGTATG

GCTGAAACCTGAGCAACAAGGTGTAATGTGTGTTATAGAAAAGACAGTA

GATGGGCAGATTGTGTTCAAACTTACAATATCTGAGAAAGAGACAATGT

TTTATTATCGCACAGTAAATGGTTTGCAACCTCCAATAAAAGTAATGAC

ACTGGGGAGAATTCTTGTGAAGAAATGGATTCATCTTAGTGTGCAGGTC

CATCAGACAAAAATCAGCTTCTTTATCAATGGCGTGGAGAAGGATCATA

CACCTTTCAATGCAAGAACTCTAAGTGGTTCAATTACAGATTTTGCATC

TGGTACTGTGCAAATAGGACAGAGTTTAAATGGTTTAGAGCAGTTTGTC

GGAAGAATGCAAGATTTTCGATTATACCAAGTGGCACTTACAAACAGAG

AGATTCTGGAAGTGTTCTCTGGAGATCTTCTCAGATTGCATGCCCAATC

ACATTGCCGTTGCCCTGGCAGCCACCCGCGGGTCCACCCTTTGGCACAG

CGGTACTGCATTCCTAATGATGCAGGAGACACAGCTGATAATAGAGTGT

CACGGTTGAATCCTGAAGCCCATCCTCTCTCTTTTGTCAATGATAATGA

TGTTGGTACTTCATGGGTTTCAAATGTGTTTACAAACATTACACAGCTT

AATCAAGGAGTGACTATTTCAGTTGATTTGGAAAATGGACAGTATCAGG

TGTTTTATATTATCATTCAGTTCTTTAGTCCACAACCAACGGAAATAAG

GATTCAAAGGAAGAAGGAAAATAGTTTAGATTGGGAGGACTGGCAATAT

TTTGCCAGGAATTGTGGTGCTTTTGGAATGAAAAACAATGGAGATTTGG

AAAAACCTGATTCTGTCAACTGCCTTCAGCTTTCCAATTTTACTCCATA

TTCCCGTGGCAATGTCACATTTAGCATCCTGACACCTGGACCAAATTAT

CGTCCTGGATACAATAACTTCTATAATACCCCATCTCTTCAAGAGTTCG

TAAAAGCCACGCAAATAAGGTTTCATTTTCATGGGCAGTACTATACAAC

TGAGACTGCTGTTAACCTCAGACACAGATATTATGCAGTGGACGAAATC

ACCATTAGTGGGAGATGTCAGTGCCATGGTCATGCCGATAACTGCGACA

CAACAAGCCAGCCATATAGATGCCTCTGCTCCCAGGAGAGCTTCACTGA

AGGACTTCATTGTGATCGCTGCTTGCCTCTTTATAATGACAAGCCTTTC

CGCCAAGGTGATCAAGTTTACGCTTTCAATTGTAAACCTTGTCAATGCA

ACAGCCATTCCAAAAGCTGCCATTACAACATCTCTGTAGACCCATTTCC

TTTTGAGCACTTCAGAGGGGGAGGAGGAGTTTGTGATGATTGTGAGCAT

AACACTACAGGAAGGAACTGTGAGCTGTGCAAGGATTACTTTTTCCGAC

AAGTTGGTGCAGATCCTTCGGCCATAGATGTTTGCAAACCCTGTGACTG

TGATACAGTTGGCACTAGAAATGGTAGCATTCTTTGTGATCAGATTGGA

GGACAGTGTAATTGTAAGAGACACGTGTCTGGCAGGCAGTGCAATCAGT

-continued

GCCAGAATGGATTCTACAATCTACAAGAGTTGGATCCTGATGGCTGCAG

TCCCTGTAACTGCAATACCTCTGGGACAGTGGATGGAGATATTACCTGT

CACCAAAATTCAGGCCAGTGCAAGTGCAAAGCAAACGTTATTGGGCTTA

GGTGTGATCATTGCAATTTTGGATTTAAATTTCTCCGAAGCTTTAATGA

TGTTGGATGTGAGCCCTGCCAGTGTAACCTCCATGGCTCAGTGAACAAA

TTCTGCAATCCTCACTCTGGGCAGTGTGAGTGCAAAAAGAAGCCAAAG

GACTTCAGTGTGATACCTGCAGAGAAACTTTTATGGGTTAGATGTCAC

CAATTGTAAGGCCTGTGACTGTGACACAGCTGGATCCCTCCCTGGGACT

GTCTGTAATGCTAAGACAGGGCAGTGCATCTGCAAGCCCAATGTCGAGG

GAAGGCAGTGTAACAAGTGCCTTGAAGGGAACTTCTACCTACGGCAAAA

TAATTCTTTCCTCTGTCTGCCTTGCAACTGTGATAAGACTGGGACAATA

AATGGCTCTCTGCTGTGTAACAAATCAACAGGACAATGTCCTTGCAAGC

TTGGAGTTACAGGTCTTAGGTGCAACCAGTGCGAACCACACAGGTACAA

TTTGACCATTGACAATTTTCAACACTGCCAGATGTGTGAGTGTGATTCC

TTGGGGACATTACCAGGAACAATCTGCGATCCTATCAGTGGCCAGTGCC

TGTGTGTGCCTAATCGTCAAGGAAGAAGGTGTAATCAGTGTCAACCAGG

TAAGTGTAGCAATTTGGATGATTACACAGAAAAACAGAATACTCTACCA

AGGCACTAATTCCCAATACAAATGTGGTTATATATGCAGATAATTTTGA

ATAAGTTAAATAGTTATATATGTGTTGGATAATGATATAAATAAATTTG

TAGAAGCCACAAACCAGAAACAGGGAGAAGTTACCTAAGTTAACAAAG

GAATGTCATTGTGCACTGAAAATGTAATACATTTAAATGATTAAATTAA

GCAGGTCCAATGCTCTTCAGTAGGGTCATGAAGGTTTTTCTTTTCCTGA

GAAAACAACACGTATTGTTTTCTCAGGTTTTGCTTTTTGGCCTTTTTCT

AGCTTAAAAAAAAAAAAAAGCAAAGAGGCCGGCATGGTCCCAGCCTCCT

CGCTGGCGCCGGCTGGGCAACATGCTTCGGCATGGCGAATGGGACCTTG

TTTATTGCAGCTTATAATGGTTACAAATAAAGCAATAGCATCACAAATT

TCACAAATAAAGCATTTTTTTCACTGCATTCTAGTTGTGGTTTGTCCAA

ACTCATCAATGTATCTTAT

SEQ ID NO: 258
(USH.4c)
CGTTACATAACTTACGGTAAATGGCCCGCCTGGCTGACCGCCCAACGAC

CCCCGCCCATTGACGTCAATAATGACGTATGTTCCCATAGTAACGCCAA

TAGGGACTTTCCATTGACGTCAATGGGTGGAGTATTTACGGTAAACTGC

CCACTTGGCAGTACATCAAGTGTATCATATGCCAAGTACGCCCCCTATT

GACGTCAATGACGGTAAATGGCCCGCCTGGCATTATGCCCAGTACATGA

CCTTATGGGACTTTCCTACTTGGCAGTACATCTACGTATTAGTCATCGC

TATTACCATGGTGATGCGGTTTTGGCAGTACATCAATGGGCGTGGATAG

CGGTTTGACTCACGGGGATTTCCAAGTCTCCACCCCATTGACGTCAATG

GGAGTTTGTTTTGGCACCAAAATCAACGGGACTTTCCAAAATGTCGTAA

CAACTCCGCCCCATTGACGCAAATGGGCGGTAGGCGTGTACGGTGGGAG

-continued

GTCTATATAAGCAGAGCTGGTTTAGTGAACCGTCAGTTCCAAGAGGGCC

ACCAAGCAGACCACGCTCTGAGCTTCAGGGAACCAAGTGTTTGCTCTGC

AGAATACTTTACCTGGGCACCCAAGTCATCCTTCCAGCATTCCTGCTGC

TACAGCCTATTTGCTGAGTAACCAGGGGTTACAGCAGCGTTGCCAGGCA

ACGAGGGACAGCGGTCCTGTTGAAGAGCCATTTGTCACACTGAGGGGAC

TGGTTGAAATGCAATAAAGAAATGATACCAGCAGCTACTCATGTCATCG

CCATTGCTAAGAACGTCGTTGGTATTACCTTACTCTGAGAACGTGTCTG

CAGTTTCCAGAAAATGGAGTATCGCAACATCACTTAAAGTACCCTGCTT

CAAAGTATTGCTGGCAAGTGGCGTGGGCCTGATTATTTATTTAGAAATG

CTTTATCAGGAGGAGAATGCTTTTTTTGTAAACATGAATTGCCCAGTTCT

TTCATTGGGCTCTGGCTTCTTGTTTCAGGTCATTGAAATGTTGATCTTT

GCCTATTTTGCTTCAATATCCTTGACTGAGTCACGAGGTCTTTTCCCAA

GGCTGGAGAACGTGGGAGCTTTCAAGAAAGTTTCCATCGTGCCAACCCA

AGCAGTATGTGGACTCCCAGACCGAAGCACTTTTTGTCACAGCTCTGCT

GCTGCTGAAAGTATTCAGTTCTGTACCCAGCGGTTTTGTATTCAGGATT

GCCCATACAGATCTTCACACCCTACCTACACTGCCCTTTTCTCAGCAGG

CCTCAGTAGCTGCATCACACCAGACAAGAATGATCTGCATCCTAACGCC

CATAGCAATTCTGCAAGTTTTATTTTTGGAAATCACAAGAGCTGCTTTT

CTTCTCCTCCTTCTCCAAAGCTGATGGCATCATTTACCTTAGCTGTATG

GCTGAAACCTGAGCAACAAGGTGTAATGTGTGTTATAGAAAAGACAGTA

GATGGGCAGATTGTGTTCAAACTTACAATATCTGAGAAAGAGACAATGT

TTTATTATCGCACAGTAAATGGTTTGCAACCTCCAATAAAAGTAATGAC

ACTGGGGAGAATTCTTGTGAAGAAATGGATTCATCTTAGTGTGCAGGTC

CATCAGACAAAAATCAGCTTCTTTATCAATGGCGTGGAGAAGGATCATA

CACCTTTCAATGCAAGAACTCTAAGTGGTTCAATTACAGATTTTGCATC

TGGTACTGTGCAAATAGGACAGAGTTTAAATGGTTTAGAGCAGTTTGTC

GGAAGAATGCAAGATTTTCGATTATACCAAGTGGCACTTACAAACAGAG

AGATTCTGGAAGTGTTCTCTGGAGATCTTCTCAGATTGCATGCCCAATC

ACATTGCCGTTGCCCTGGCAGCCACCCGCGGGTCCACCCTTTGGCACAG

CGGTACTGCATTCCTAATGATGCAGGAGACACAGCTGATAATAGAGTGT

CACGGTTGAATCCTGAAGCCCATCCTCTCTCTTTTGTCAATGATAATGA

TGTTGGTACTTCATGGGTTTCAAATGTGTTTACAAACATTACACAGCTT

AATCAAGGAGTGACTATTTCAGTTGATTTGGAAAATGGACAGTATCAGG

TGTTTTATATTATCATTCAGTTCTTTAGTCCACAACCAACGGAAATAAG

GATTCAAAGGAAGAAGGAAAATAGTTTAGATTGGGAGGACTGGCAATAT

TTTGCCAGGAATTGTGGTGCTTTTGGAATGAAAAACAATGGAGATTTGG

AAAAACCTGATTCTGTCAACTGCCTTCAGCTTTCCAATTTTACTCCATA

TTCCCGTGGCAATGTCACATTTAGCATCCTGACACCTGGACCAAATTAT

CGTCCTGGATACAATAACTTCTATAATACCCCATCTCTTCAAGAGTTCG

TAAAAGCCACGCAAATAAGGTTTCATTTTCATGGGCAGTACTATACAAC

TGAGACTGCTGTTAACCTCAGACACAGATATTATGCAGTGGACGAAATC

-continued

ACCATTAGTGGGAGATGTCAGTGCCATGGTCATGCCGATAACTGCGACA

CAACAAGCCAGCCATATAGATGCCTCTGCTCCCAGGAGAGCTTCACTGA

AGGACTTCATTGTGATCGCTGCTTGCCTCTTTATAATGACAAGCCTTTC

CGCCAAGGTGATCAAGTTTACGCTTTCAATTGTAAACCTTGTCAATGCA

ACAGCCATTCCAAAAGCTGCCATTACAACATCTCTGTAGACCCATTTCC

TTTTGAGCACTTCAGAGGGGGAGGAGGAGTTTGTGATGATTGTGAGCAT

AACACTACAGGAAGGAACTGTGAGCTGTGCAAGGATTACTTTTTCCGAC

AAGTTGGTGCAGATCCTTCGGCCATAGATGTTTGCAAACCCTGTGACTG

TGATACAGTTGGCACTAGAAATGGTAGCATTCTTTGTGATCAGATTGGA

GGACAGTGTAATTGTAAGAGACACGTGTCTGGCAGGCAGTGCAATCAGT

GCCAGAATGGATTCTACAATCTACAAGAGTTGGATCCTGATGGCTGCAG

TCCCTGTAACTGCAATACCTCTGGGACAGTGGATGGAGATATTACCTGT

CACCAAAATTCAGGCCAGTGCAAGTGCAAAGCAAACGTTATTGGGCTTA

GGTGTGATCATTGCAATTTTGGATTTAAATTTCTCCGAAGCTTTAATGA

TGTTGGATGTGAGCCCTGCCAGTGTAACCTCCATGGCTCAGTGAACAAA

TTCTGCAATCCTCACTCTGGGCAGTGTGAGTGCAAAAAAGAAGCCAAAG

GACTTCAGTGTGATACCTGCAGAGAAAACTTTTATGGGTTAGATGTCAC

CAATTGTAAGGCCTGTGACTGTGACACAGCTGGATCCCTCCCTGGGACT

GTCTGTAATGCTAAGACAGGGCAGTGCATCTGCAAGCCCAATGTCGAGG

GAAGGCAGTGTAACAAGTGCCTTGAAGGGAACTTCTACCTACGGCAAAA

TAATTCTTTCCTCTGTCTGCCTTGCAACTGTGATAAGACTGGGACAATA

AATGGCTCTCTGCTGTGTAACAAATCAACAGGACAATGTCCTTGCAAGC

TTGGAGTTACAGGTCTTAGGTGCAACCAGTGCGAACCACACAGGTACAA

TTTGACCATTGACAATTTTCAACACTGCCAGATGTGTGAGTGTGATTCC

TTGGGGACATTACCAGGAACAATCTGCGATCCTATCAGTGGCCAGTGCC

TGTGTGTGCCTAATCGTCAAGGAAGAAGGTGTAATCAGTGTCAACCAGG

TAAGTGTAGCAATTTGGATGATTACACAGAAAAACAGAATACTCTACCA

AGGCACTAATTCCCAATACAAATGTGGTTATATATGCAGATAATTTTGA

ATAAGTTAAATAGTTATATATGTGTTGGATAATGATATAAATAAATTTG

TAGAAGCCACAAACCAGAAACAGGGAGAAGTTACCTAAGTTAACAAAG

GAATGTCATTGTGCACTGAAAATGTAATACATTTAAATGATTAAATTAA

GCAGGTCCAATGCTCTTCAGTAGGGTCATGAAGGTTTTTCTTTTCCTGA

GAAAACAACACGTATTGTTTTCTCAGGTTTTGCTTTTTGGCCTTTTTCT

AGCTTAAAAAAAAAAAAAGCAAAAGGCCGGCATGGTCCCAGCCTCCTCG

CTGGCGCCGGCTGGGCAACATGCTTCGGCATGGCGAATGGGACCTTGTT

TATTGCAGCTTATAATGGTTACAAATAAAGCAATAGCATCACAAATTTC

ACAAATAAAGCATTTTTTTCACTGCATTCTAGTTGTGGTTTGTCCAAAC

TCATCAATGTATCTTAT

TABLE 5

Illustrative Trans-Splicing Molecule Elements

| SEQ ID | Name | Sequence |
|---|---|---|
| 204 | CMV Enhancer | CGTTACATAACTTACGGTAAATGGCCCGCCTGGCTGACCGCCCAACGACCCCCGCCCATT GACGTCAATAATGACGTATGTTCCCATAGTAACGCCAATAGGGACTTTCCATTGACGTCA ATGGGTGGAGTATTTACGGTAAACTGCCCACTTGGCAGTACATCAAGTGTATCATATGCC AAGTACGCCCCCTATTGACGTCAATGACGGTAAATGGCCCGCCTGGCATTATGCCCAGTA CATGACCTTATGGGACTTTCCTACTTGGCAGTACATCTACGTATTAGTCATCGCTATTACC ATG |
| 205 | CMV Promoter | GTGATGCGGTTTTGGCAGTACATCAATGGGCGTGGATAGCGGTTTGACTCACGGGGATTT CCAAGTCTCCACCCCATTGACGTCAATGGGAGTTTGTTTTGGCACCAAAATCAACGGGAC TTTCCAAAATGTCGTAACAACTCCGCCCCATTGACGCAAATGGGCGGTAGGCGTGTACGG TGGGAGGTCTATATAAGCAGAGCT |
| 206 | CMV-derived Untranscribed Region | GGTTTAGTGAACCGTC |
| 207 | Usherin (5' UTR) | TGTTTGCTCTGCAGAATACTTTACCTGGGCACCCAAGTCATCCTTCCAGCATTCCTGCTGC TACAGCCTATTTGCTGAGTAACCAGGGGTTACAGCAGCGTTGCCAGGCAACGAGGGACAG CGGTCCTGTTGAAGAGCCATTTGTCACACTGAGGGGACTGGTTGAAATGCAATAAAGAAA TGATACCAGCAGCTACTCATGTCATCGCCATTGCTAAGAACGTCGTTGGTATTACCTTACT CTGAGAACGTGTCTGCAGTTTCCAGAAAATGGAGTATCGCAACATCACTTAAAGTACCCT GCTTCAAAGTATTGCTGGCAAGTGGCGTGGGCCTGATTATTTATTTAGAAATGCTTTATCA GGAGGAGAATGCTTTTTTGTAAAC |
| | | -OR- |
| 208 | | AGTTCCAAGAGGGCCACCAAGCAGACCACGCTCTGAGCTTCAGGGAACCAAG TGTTTGCTCTGCAGAATACTTTACCTGGGCACCCAAGTCATCCTTCCAGCATTCCTGCTGC TACAGCCTATTTGCTGAGTAACCAGGGGTTACAGCAGCGTTGCCAGGCAACGAGGGACAG CGGTCCTGTTGAAGAGCCATTTGTCACACTGAGGGGACTGGTTGAAATGCAATAAAGAAA TGATACCAGCAGCTACTCATGTCATCGCCATTGCTAAGAACGTCGTTGGTATTACCTTACT CTGAGAACGTGTCTGCAGTTTCCAGAAAATGGAGTATCGCAACATCACTTAAAGTACCCT GCTTCAAAGTATTGCTGGCAAGTGGCGTGGGCCTGATTATTTATTTAGAAATGCTTTATCA GGAGGAGAATGCTTTTTTGTAAAC |

TABLE 5-continued

| Illustrative Trans-Splicing Molecule Elements | | |
|---|---|---|
| SEQ ID | Name | Sequence |

| 209 | Usherin (CDS) | ATGAATTGCCCAGTTCTTTCATTGGGCTCTGGCTTCTTGTTTCAGGTCATTGAAATGTTGAT |
| | | CTTTGCCTATTTTGCTTCAATATCCTTGACTGAGTCACGAGGTCTTTTCCCAAGGCTGGAG |
| | | AACGTGGGAGCTTTCAAGAAAGTTTCCATCGTGCCAACCCAAGCAGTATGTGGACTCCCA |
| | | GACCGAAGCACTTTTTGTCACAGCTCTGCTGCTGCTGAAAGTATTCAGTTCTGTACCCAGC |
| | | GGTTTTGTATTCAGGATTGCCCATACAGATCTTCACACCCTACCTACACTGCCCTTTTCTCA |
| | | GCAGGCCTCAGTAGCTGCATCACACCAGACAAGAATGATCTGCATCCTAACGCCCATAGC |
| | | AATTCTGCAAGTTTTATTTTTGGAAATCACAAGAGCTGCTTTTCTTCTCCTCCTTCTCCAAA |
| | | GCTGATGGCATCATTTACCTTAGCTGTATGGCTGAAACCTGAGCAACAAGGTGTAATGTG |
| | | TGTTATAGAAAAGACAGTAGATGGGCAGATTGTGTTCAAACTTACAATATCTGAGAAAGA |
| | | GACAATGTTTTATTATCGCACAGTAAATGGTTTGCAACCTCCAATAAAAGTAATGACACT |
| | | GGGGAGAATTCTTGTGAAGAAATGGATTCATCTTAGTGTGCAGGTCCATCAGACAAAAAT |
| | | CAGCTTCTTTATCAATGGCGTGGAGAAGGATCATACACCTTTCAATGCAAGAACTCTAAG |
| | | TGGTTCAATTACAGATTTTGCATCTGGTACTGTGCAAATAGGACAGAGTTTAAATGGTTTA |
| | | GAGCAGTTTGTCGGAAGAATGCAAGATTTTCGATTATACCAAGTGGCACTTACAAACAGA |
| | | GAGATTCTGGAAGTGTTCTCTGGAGATCTTCTCAGATTGCATGCCCAATCACATTGCCGTT |
| | | GCCCTGGCAGCCACCCGCGGGTCCACCCTTTGGCACAGCGGTACTGCATTCCTAATGATG |
| | | CAGGAGACACAGCTGATAATAGAGTGTCACGGTTGAATCCTGAAGCCCATCCTCTCTCTTT |
| | | TGTCAATGATAATGATGTTGGTACTTCATGGGTTTCAAATGTGTTTACAAACATTACACAG |
| | | CTTAATCAAGGAGTGACTATTTCAGTTGATTTGGAAAATGGACAGTATCAGGTGTTTTATA |
| | | TTATCATTCAGTTCTTTAGTCCACAACCAACGGAAATAAGGATTCAAAGGAAGAAGGAAA |
| | | ATAGTTTAGATTGGGAGGACTGGCAATATTTTGCCAGGAATTGTGGTGCTTTTGGAATGA |
| | | AAAACAATGGAGATTTGGAAAAACCTGATTCTGTCAACTGCCTTCAGCTTTCCAATTTTAC |
| | | TCCATATTCCCGTGGCAATGTCACATTTAGCATCCTGACACCTGGACCAAATTATCGTCCT |
| | | GGATACAATAACTTCTATAATACCCCATCTCTTCAAGAGTTCGTAAAAGCCACGCAAATA |
| | | AGGTTTCATTTTCATGGGCAGTACTATACAACTGAGACTGCTGTTAACCTCAGACACAGAT |
| | | ATTATGCAGTGGACGAAATCACCATTAGTGGGAGATGTCAGTGCCATGGTCATGCCGATA |
| | | ACTGCGACACAACAAGCCAGCCATATAGATGCCTCTGCTCCCAGGAGAGCTTCACTGAAG |
| | | GACTTCATTGTGATCGCTGCTTGCCTCTTTATAATGACAAGCCTTTCCGCCAAGGTGATCA |
| | | AGTTTACGCTTTCAATTGTAAACCTTGTCAATGCAACAGCCATTCCAAAAGCTGCCATTAC |
| | | AACATCTCTGTAGACCCATTTCCTTTTGAGCACTTCAGAGGGGGAGGAGGAGTTTGTGAT |
| | | GATTGTGAGCATAACACTACAGGAAGGAACTGTGAGCTGTGCAAGGATTACTTTTTCCGA |
| | | CAAGTTGGTGCAGATCCTTCGGCCATAGATGTTTGCAAACCCTGTGACTGTGATACAGTTG |
| | | GCACTAGAAATGGTAGCATTCTTTGTGATCAGATTGGAGGACAGTGTAATTGTAAGAGAC |
| | | ACGTGTCTGGCAGGCAGTGCAATCAGTGCCAGAATGGATTCTACAATCTACAAGAGTTGG |
| | | ATCCTGATGGCTGCAGTCCCTGTAACTGCAATACCTCTGGGACAGTGGATGGAGATATTA |
| | | CCTGTCACCAAAATTCAGGCCAGTGCAAGTGCAAAGCAAACGTTATTGGGCTTAGGTGTG |
| | | ATCATTGCAATTTTGGATTTAAATTTCTCCGAAGCTTTAATGATGTTGGATGTGAGCCCTG |
| | | CCAGTGTAACCTCCATGGCTCAGTGAACAAATTCTGCAATCCTCACTCTGGGCAGTGTGA |
| | | GTGCAAAAAGAAGCCAAAGGACTTCAGTGTGATACCTGCAGAGAAAACTTTTATGGGTT |
| | | AGATGTCACCAATTGTAAGGCCTGTGACTGTGACACAGCTGGATCCCTCCCTGGGACTGT |
| | | CTGTAATGCTAAGACAGGGCAGTGCATCTGCAAGCCCAATGTCGAGGGAAGGCAGTGTA |
| | | ACAAGTGCCTTGAAGGGAACTTCTACCTACGGCAAAATAATTCTTTCCTCTGTCTGCCTTG |
| | | CAACTGTGATAAGACTGGGACAATAAATGGCTCTCTGCTGTGTAACAAATCAACAGGACA |
| | | ATGTCCTTGCAAGCTTGGAGTTACAGGTCTTAGGTGCAACCAGTGCGAACCACACAGGTA |
| | | CAATTTGACCATTGACAATTTTCAACACTGCCAGATGTGTGAGTGTGATTCCTTGGGGACA |
| | | TTACCAGGAACAATCTGCGATCCTATCAGTGGCCAGTGCCTGTGTGTGCCTAATCGTCAAG |
| | | GAAGAAGGTGTAATCAGTGTCAACCAG |

| | Splice Donor (SD) | GTAAGT |

| 211 | Short Scaffold | GTAGCAATTTGGATG |

| 212 | CR.2a | ATTACACAGAAAAACAGAATACTCTACCAAGGCACTAATTCCCAATACAAATGTGGTTAT |

| 213 | CR.2b | ATATGCAGATAATTTTGAATAAGTTAAATAGTTATATATGTGTTGGATAATGATATAAAT |

| 214 | CR.2c | AAATTTGTAGAAGCCACAAACCAGAAACAGGGAGAAGTTACCTAAGTTAACAAAAGGAA |
| | | TGTCATTGTGCACTGAAAATGTAATACATTT |

| 215 | Filler | AAATGATTAAATTAAGCAGG |

| 216 | SSE.1 | TCCAATGCTCTTCAGTAGGGTCATGAAGGTTTTTCTTTTCCTGAGAAAACAACACGTATTG |
| | | TTTTCTCAGGTTTTGCTTTTTGGCCTTTTTCTAGCTTAAAAAAAAAAAAAAGCAAAAGA |

| 274 | SSE.1 | TCCAATGCTCTTCAGTAGGGTCATGAAGGTTTTTCTTTTCCTGAGAAAACAACACGTATTG |
| | | TTTTCTCAGGTTTTGCTTTTTGGCCTTTTTCTAGCTTAAAAAAAAAAAAAAGCAAAA |

| 217 | CE.1 | GGCCGGCATGGTCCCAGCCTCCTCGCTGGCGCCGGCTGGGCAACATGCTTCGGCATGGCG |
| | | AATGGGAC |

| 218 | TE.1 | CTTGTTTATTGCAGCTTATAATGGTTACAAATAAAGCAATAGCATCACAAATTTCACAAAT |
| | | AAAGCATTTTTTTCACTGCATTCTAGTTGTGGTTTGTCCAAACTCATCAATGTATCTTAT |

TABLE 6

| | | | Associated | |
|---|---|---|---|---|
| SEQ ID. | Description | Part(s) | FIG. | Sequence |
| 219 | USH.1, USH.3 | SSE.1, CE.1, TE.1 | FIG. 3A and FIG. 3B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT TAAAAAAAAAAAAAGCAAAAGA GGCCGGCATGGTCCCAGCCTCCTC GCTGGCGCCGGCTGGGCAACATG CTTCGGCATGGCGAATGGGACTG GCTTGTTTATTGCAGCTTATAATG GTTACAAATAAAGCAATAGCATC ACAAATTTCACAAATAAAGCATTT TTTTCACTGCATTCTAGTTGTGGTT TGTCCAAACTCATCAATGTATCTT AT |
| 220 | USH.2 | SSE.2, CE.1, TE.1 | FIG. 3A and FIG. 3B | GGAGCACTGTTCGTAACCCGTTAG CCTGGCTGTAGCTAATGGGTTCCA TTCCGGTGCAATAGCATTTCCAGC GACACATGACTGACTGACTGGTG GCTTTCAGTTTCAGGTCTTGGAGA CAAATGGCCGGCATGGTCCCAGC CTCCTCGCTGGCGCCGGCTGGGCA ACATGCTTCGGCATGGCGAATGG GACTGGCTTGTTTATTGCAGCTTA TAATGGTTACAAATAAAGCAATA GCATCACAAATTTCACAAATAAA GCATTTTTTTCACTGCATTCTAGTT GTGGTTTGTCCAAACTCATCAATG TATCTTAT |
| 221 | USH.6 | CE.1 | FIG. 4A and FIG. 4B | GGCCGGCATGGTCCCAGCCTCCTC GCTGGCGCCGGCTGGGCAACATG CTTCGGCATGGCGAATGGGAC |
| 222 | USH.7 | CE.1, TE.1 | FIG. 4A and FIG. 4B | GGCCGGCATGGTCCCAGCCTCCTC GCTGGCGCCGGCTGGGCAACATG CTTCGGCATGGCGAATGGGACTT GTTTATTGCAGCTTATAATGGTTA CAAATAAAGCAATAGCATCACAA ATTTCACAAATAAAGCATTTTTTT CACTGCATTCTAGTTGTGGTTTGT CCAAACTCATCAATGTATCTTAT |
| 223 | USH.8 | CE.1mut | FIG. 4A and FIG. 4B | GGCCGGCATGGTCCCAGCCTCCTC GCTGGCGCCGGCTGGGCAACATG CTTCGGCATGGTGAATGGGAC |
| 224 | USH.9 | CE.1mut, TE.1 | FIG. 4A and FIG. 4B | GGCCGGCATGGTCCCAGCCTCCTC GCTGGCGCCGGCTGGGCAACATG CTTCGGCATGGTGAATGGGACTT GTTTATTGCAGCTTATAATGGTTA CAAATAAAGCAATAGCATCACAA ATTTCACAAATAAAGCATTTTTTT CACTGCATTCTAGTTGTGGTTTGT CCAAACTCATCAATGTATCTTAT |
| 225 | USH.10 | SSE.1 | FIG. 4A and FIG. 4B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT TAAAAAAAAAAAAAGCAAAAGA |
| 226 | USH.11 | SSE.1, CE.1 | FIG. 4A and FIG. 4B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT TAAAAAAAAAAAAAGCAAAAGA GGCCGGCATGGTCCCAGCCTCCTC GCTGGCGCCGGCTGGGCAACATG CTTCGGCATGGCGAATGGGAC |
| 227 | USH.12 | SSE.1, CE.1, TE.1mut | FIG. 4A and FIG. 4B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT |

TABLE 6-continued

Illustrative Trifunctional Elements

| SEQ ID. | Description | Part(s) | Associated FIG. | Sequence |
|---|---|---|---|---|
| | | | | TAAAAAAAAAAAAAGCAAAAGA |
| | | | | GGCCGGCATGGTCCCAGCCTCCTC |
| | | | | GCTGGCGCCGGCTGGGCAACATG |
| | | | | CTTCGGCATGGCGAATGGGACGC |
| | | | | AGCTTATAATGGTTACAAATAAA |
| | | | | GCAATAGCATCACAAATTTCACA |
| | | | | AATAAAGCATTTTTTTCACTGCAT |
| | | | | TCTAGTTGTGGTTTGTCCAAACTC |
| | | | | ATCAATGTATCTTAT |
| 228 | USH.0, USH.4 | SSE.1, CE.1, TE.1 | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |
| | | | | GGCCGGCATGGTCCCAGCCTCCTC |
| | | | | GCTGGCGCCGGCTGGGCAACATG |
| | | | | CTTCGGCATGGCGAATGGGACCTT |
| | | | | GTTTATTGCAGCTTATAATGGTTA |
| | | | | CAAATAAAGCAATAGCATCACAA |
| | | | | ATTTCACAAATAAAGCATTTTTTT |
| | | | | CACTGCATTCTAGTTGTGGTTTGT |
| | | | | CCAAACTCATCAATGTATCTTAT |
| 229 | USH.13 | SSE.1, CE.1mut | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |
| | | | | GGCCGGCATGGTCCCAGCCTCCTC |
| | | | | GCTGGCGCCGGCTGGGCAACATG |
| | | | | CTTCGGCATGGTGAATGGGAC |
| 230 | USH.14 | SSE.1, CE.1mut, TE.1 | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |
| | | | | GGCCGGCATGGTCCCAGCCTCCTC |
| | | | | GCTGGCGCCGGCTGGGCAACATG |
| | | | | CTTCGGCATGGTGAATGGGACCTT |
| | | | | GTTTATTGCAGCTTATAATGGTTA |
| | | | | CAAATAAAGCAATAGCATCACAA |
| | | | | ATTTCACAAATAAAGCATTTTTTT |
| | | | | CACTGCATTCTAGTTGTGGTTTGT |
| | | | | CCAAACTCATCAATGTATCTTAT |
| 231 | USH.15 | SSE.1, CE.2 | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |
| | | | | GATGCTGGTGGTTGGCACTCCTGG |
| | | | | TTTCCAGGACGGGGTTCAAATCCC |
| | | | | TGCGGCGTCT |
| 232 | USH.16 | SSE.1, CE.2, TE.1 | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |
| | | | | GATGCTGGTGGTTGGCACTCCTGG |
| | | | | TTTCCAGGACGGGGTTCAAATCCC |
| | | | | TGCGGCGTCTCTTGTTTATTGCAG |
| | | | | CTTATAATGGTTACAAATAAAGCA |
| | | | | ATAGCATCACAAATTTCACAAATA |
| | | | | AAGCATTTTTTTCACTGCATTCTA |
| | | | | GTTGTGGTTTGTCCAAACTCATCA |
| | | | | ATGTATCTTAT |
| 233 | USH.17 | SSE.1, CE.2mut1 | FIG. 4A and FIG. 4B | TCCAATGCTCTTCAGTAGGGTCAT |
| | | | | GAAGGTTTTTCTTTTCCTGAGAAA |
| | | | | ACAACACGTATTGTTTTCTCAGGT |
| | | | | TTTGCTTTTTGGCCTTTTTCTAGCT |
| | | | | TAAAAAAAAAAAAAGCAAAAGA |

TABLE 6-continued

| | | | Associated | |
|---|---|---|---|---|
| SEQ ID. | Description | Part(s) | FIG. | Sequence |

Illustrative Trifunctional Elements

Figure 5B:
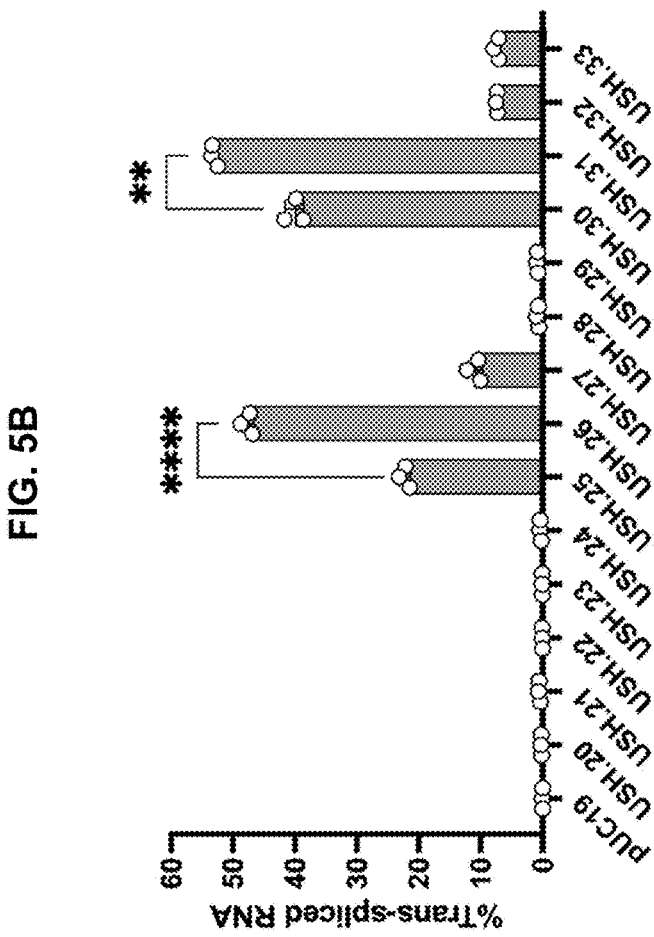
FIG. 5A and FIG. 5B show an in vitro trans-splicing analysis of constructs containing different trifunctional element (TFE) compositions in an alternative context.
Figure 5A:
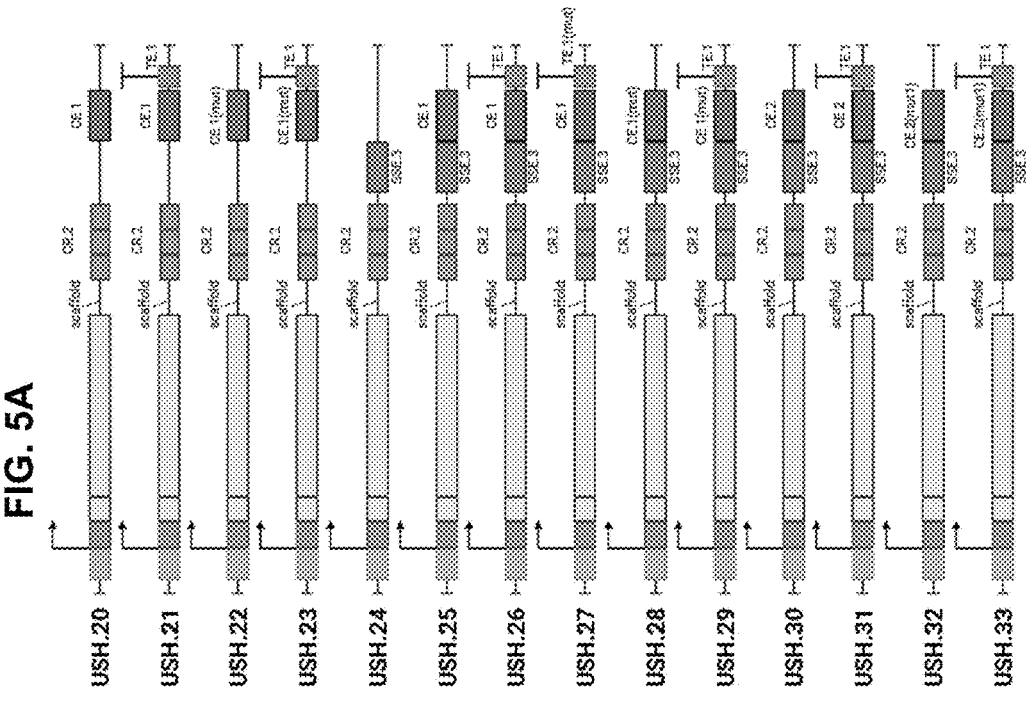

| SEQ ID. | Description | Part(s) | Associated FIG. | Sequence |
|---|---|---|---|---|
| | | | | AATGCTGGTGGTTGGCACTCCTGG TTTCCAGGACGGGGTTCAAATCCC TGCGGCGTCT |
| 234 | USH.18 | SSE.1, CE.2mut1, TE.1 | FIG. 4A and FIG. 4B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT TAAAAAAAAAAAAAGCAAAAGA AATGCTGGTGGTTGGCACTCCTGG TTTCCAGGACGGGGTTCAAATCCC TGCGGCGTCTCTTGTTTATTGCAG CTTATAATGGTTACAAATAAAGCA ATAGCATCACAAATTTCACAAATA AAGCATTTTTTTCACTGCATTCTA GTTGTGGTTTGTCCAAACTCATCA ATGTATCTTAT |
| 235 | USH.19 | SSE.1, CE.2mut2, TE.1 | FIG. 4A and FIG. 4B | TCCAATGCTCTTCAGTAGGGTCAT GAAGGTTTTTCTTTTCCTGAGAAA ACAACACGTATTGTTTTCTCAGGT TTTGCTTTTTGGCCTTTTTCTAGCT TAAAAAAAAAAAAAGCAAAGA GATGCTGGTGGTTGGCACTCCTGG TTTCCAGGACGGGGCCTAAATCCC TGCGGCGTCT |
| 236 | USH.33 | SSE.3, CE.2mut1, TE.1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAAGCAAAA AATGCTGGTGGTTGGCACTCCTGG TTTCCAGGACGGGGTTCAAATCCC TGCGGCGTCTCTTGTTTATTGCAG CTTATAATGGTTACAAATAAAGCA ATAGCATCACAAATTTCACAAATA AAGCATTTTTTTCACTGCATTCTA GTTGTGGTTTGTCCAAACTCATCA ATGTATCTTAT |
| 237 | USH.32 | SSE.3, CE.2mut1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAAGCAAAA AATGCTGGTGGTTGGCACTCCTGG TTTCCAGGACGGGGTTCAAATCCC TGCGGCGTCT |
| 238 | USH.31 | SSE.3, CE.2, TE.1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAAGCAAAA GATGCTGGTGGTTGGCACTCCTGG TTTCCAGGACGGGGTTCAAATCCC TGCGGCGTCTCTTGTTTATTGCAG CTTATAATGGTTACAAATAAAGCA ATAGCATCACAAATTTCACAAATA AAGCATTTTTTTCACTGCATTCTA GTTGTGGTTTGTCCAAACTCATCA ATGTATCTTAT |
| 239 | USH.30 | SSE.3, CE.2 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAAGCAAAA GATGCTGGTGGTTGGCACTCCTGG TTTCCAGGACGGGGTTCAAATCCC TGCGGCGTCT |
| 240 | USH.29 | SSE.3, CE.1mut, TE.1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAAGCAAAA GGCCGGCATGGTCCCAGCCTCCTC GCTGGCGCCGGCTGGGCAACATG |

TABLE 6-continued

Illustrative Trifunctional Elements

| SEQ ID. | Description | Part(s) | Associated FIG. | Sequence |
|---|---|---|---|---|
| | | | | CTTCGGCATGGTGAATGGGACCTT GTTTATTGCAGCTTATAATGGTTA CAAATAAAGCAATAGCATCACAA ATTTCACAAATAAAGCATTTTTTT CACTGCATTCTAGTTGTGGTTTGT CCAAACTCATCAATGTATCTTAT |
| 241 | USH.28 | SSE.3, CE.1mut | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAGCAAAA GGCCGGCATGGTCCCAGCCTCCTC GCTGGCGCCGGCTGGGCAACATG CTTCGGCATGGTGAATGGGAC |
| 242 | USH.27 | SSE.3, CE.1, TE.1mut | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAGCAAAA GGCCGGCATGGTCCCAGCCTCCTC GCTGGCGCCGGCTGGGCAACATG CTTCGGCATGGCGAATGGGACGC AGCTTATAATGGTTACAAATAAA GCAATAGCATCACAAATTTCACA AATAAAGCATTTTTTTCACTGCAT TCTAGTTGTGGTTTGTCCAAACTC ATCAATGTATCTTAT |
| 243 | USH.26 | SSE.3, CE.1, TE.1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAGCAAAA GGCCGGCATGGTCCCAGCCTCCTC GCTGGCGCCGGCTGGGCAACATG CTTCGGCATGGCGAATGGGACCTT GTTTATTGCAGCTTATAATGGTTA CAAATAAAGCAATAGCATCACAA ATTTCACAAATAAAGCATTTTTTT CACTGCATTCTAGTTGTGGTTTGT CCAAACTCATCAATGTATCTTAT |
| 244 | USH.25 | SSE.3, CE.1 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAGCAAAA GGCCGGCATGGTCCCAGCCTCCTC GCTGGCGCCGGCTGGGCAACATG CTTCGGCATGGCGAATGGGAC |
| 245 | USH.24 | SSE.3 | FIG. 5A and FIG. 5B | TATGAAGGTTTTTCTTTTCCTGAG AAAACAACACGTATTGTTTTCTCA GGTTTTGCTTTTTGGCCTTTTTCTA GCTTAAAAAAAAAAAAAGCAAAA |
| 246 | USH.23 | linker, CE.1mut, TE.1 | FIG. 5A and FIG. 5B | GCAGGGGCCGGCATGGTCCCAGC CTCCTCGCTGGCGCCGGCTGGGCA ACATGCTTCGGCATGGTGAATGG GACCTTGTTTATTGCAGCTTATAA TGGTTACAAATAAAGCAATAGCA TCACAAATTTCACAAATAAAGCAT TTTTTTCACTGCATTCTAGTTGTGG TTTGTCCAAACTCATCAATGTATC TTAT |
| 247 | USH.22 | linker, CE.1mut | FIG. 5A and FIG. 5B | GCAGGGGCCGGCATGGTCCCAGC CTCCTCGCTGGCGCCGGCTGGGCA ACATGCTTCGGCATGGTGAATGG GAC |
| 275 | USH.21 | linker, CE.1, TE.1 | FIG. 5A and FIG. 5B | GCAGGGGCCGGCATGGTCCCAGC CTCCTCGCTGGCGCCGGCTGGGCA ACATGCTTCGGCATGGCGAATGG GACCTTGTTTATTGCAGCTTATAA TGGTTACAAATAAAGCAATAGCA TCACAAATTTCACAAATAAAGCAT |

TABLE 6-continued

| | | | Associated | |
|---|---|---|---|---|
| SEQ ID. | Description | Part(s) | FIG. | Sequence |
| | | | | TTTTTTCACTGCATTCTAGTTGTGG TTTGTCCAAACTCATCAATGTATC TTAT |
| 276 | USH.20 | linker, CE.1 | FIG. 5A and FIG. 5B | GCAGGGGCCGGCATGGTCCCAGC CTCCTCGCTGGCGCCGGCTGGGCA ACATGCTTCGGCATGGCGAATGG GAC |

TABLE 7

Illustrative transcription terminator/polyA signal sequences for trifunctional element

| Terminator/polyA signal | Illustrative Sequence | SEQ ID |
|---|---|---|
| WPRE-bGHpA | TCGAGATAATCAACCTCTGGATTACAAAATTTGTGAAAGATTGACTGGT ATTCTTAACTATGTTGCTCCTTTTACGCTATGTGGATACGCTGCTTTAAT GCCTTTGTATCATGCTATTGCTTCCCGTATGGCTTTCATTTTCTCCTCCTT GTATAAATCCTGGTTAGTTCTTGCCACGGCGGAACTCATCGCCGCCTGCC TTGCCCGCTGCTGGACAGGGGCTCGGCTGTTGGGCACTGACAATTCCGT GGTGTGCCTTCTAGTTGCCAGCCATCTGTTGTTTGCCCCTCCCCCGTGCC TTCCTTGACCCTGGAAGGTGCCACTCCCACTGTCCTTTCCTAATAAAATG AGGAAATTGCATCGCATTGTCTGAGTAGGTGTCATTCTATTCTGGGGGG TGGGGTGGGGCAGGACAGCAAGGGGGAGGATTGGGAAGACAATAGCA GGCATGCTGGGGATGCGGTGGGCTCTATG | 248 |
| WPRE.v2-bGHpA | CTGCAGCCCCGATAATCAACCTCTGGATTACAAAATTTGTGAAAGATTG ACTGGTATTCTTAACTATGTTGCTCCTTTTACGCTATGTGGATACGCTGC TTTAATGCCTTTGTATCATGCTATTGCTTCCCGTATGGCTTTCATTTTCTC CTCCTTGTATAAATCCTGGTTGCTGTCTCTTTATGAGGAGTTGTGGCCCG TTGTCAGGCAACGTGGCGTGGTGTGCACTGTGTTTGCTGACGCAACCCC CACTGGTTGGGGCATTGCCACCACCTGTCAGCTCCTTTCCGGGACTTTCG CTTTCCCCCTCCCTATTGCCACGGCGGAACTCATCGCCGCCTGCCTTGCC CGCTGCTGGACAGGGGCTCGGCTGTTGGGCACTGACAATTCCGTGGTGT TGTCGGGGAAATCATCGTCCTTTCCTTGGCTGCTCGCCTGTGTTGCCACC TGGATTCTGCGCGGGACGTCCTTCTGCTACGTCCCTTCGGCCCTCAATCC AGCGGACCTTCCTTCCCGCGGCCTGCTGCCGGCTCTGCGGCCTCTTCCGC GTCTTCGCCTTCGCCCTCAGACGAGTCGGATCTCCCTTTGGGCCGCCTCC CCGCATCGGGGGGATCCTGTGCCTTCTAGTTGCCAGCCATCTGTTGTTTG CCCCTCCCCCGTGCCTTCCTTGACCCTGGAAGGTGCCACTCCCACTGTCC TTTCCTAATAAAATGAGGAAATTGCATCGCATTGTCTGAGTAGGTGTCA TTCTATTCTGGGGGGTGGGGTGGGGCAGGACAGCAAGGGGGAGGATTG GGAAGACAATAGCAGGCATGCTGGGGATGCGGTGGGCTCTATG | 249 |
| bGHpA | GTGCCTTCTAGTTGCCAGCCATCTGTTGTTTGCCCCTCCCCCGTGCCTTCC TTGACCCTGGAAGGTGCCACTCCCACTGTCCTTTCCTAATAAAATGAGG AAATTGCATCGCATTGTCTGAGTAGGTGTCATTCTATTCTGGGGGGTGG GGTGGGGCAGGACAGCAAGGGGGAGGATTGGGAAGACAATAGCAGGC ATGCTGGGGATGCGGTGGGCTCTATG | 250 |
| SV40pA | CTTGTTTATTGCAGCTTATAATGGTTACAAATAAAGCAATAGCATCACA AATTTCACAAATAAAGCATTTTTTTCACTGCATTCTAGTTGTGGTTTGTC CAAACTCATCAATGTATCTTAT | 251 |
| SV40pA.v2 | TCTAGCTTTATTTGTGAAATTTGTGATGCTATTGCTTTATTTGTAACCATT ATAAGCTGCAATAAACAAGTTAACAACAACAATTGCATTCATTTTATGT TTCAGGTTCAGGGGGAGATGTGGGAGGTTTTTTAAA | 252 |
| Synthetic PolyA (Choi et al. 2014) | TGTTAATAAAAGATCTTTATTTTCATTAGATCTGTGTGTTGGTTTTTTGTG TGATCGA | 253 |
| Synthetic polyA with upstream element (Choi et al. 2014) | TCTAGCTTTATTTGTGAAATTTGTGATGCTATTGCTTTATTTGTAACCATT ATAAGCTGCAATAAACAAGATCTTTATTTTCATTAGATCTGTGTGTTGGTTT TTTGTGTGATCGA | 254 |
| hGH polyA sequence (human) | GGGTGGCATCCCTGTGACCCCTCCCCAGTGCCTCTCCTGGCCCTGGAAGT TGCCACTCCAGTGCCCACCAGCCTTGTCCTAATAAAATTAAGTTGCATCA TTTTGTCTGACTAGGTGTCCTTCTATAATATTATGGGGTGGAGGGGGGTG GTATGGAGCAAGGGGCAAGTTGGGAAGACAACCTGTAGGGCCTGCGGG GTCTATTGGGAACCAAGCTGGAGTGCAGTGGCACAATCTTGGCTCACTG | 273 |

TABLE 7-continued

Illustrative transcription terminator/polyA signal sequences for trifunctional element

| Terminator/polyA signal | Illustrative Sequence | SEQ ID |
|---|---|---|
| | CAATCTCCGCCTCCTGGGTTCAAGCGATTCTCCTGCCTCAGCCTCCCGAG TTGTTGGGATTCCAGGCATGCATGACCAGGCTCAGCTAATTTTTGTTTTT TTGGTAGAGACGGGGTTTCACCATATTGGCCAGGCTGGTCTCCAACTCC TAATCTCAGGTGATCTACCCACCTTGGCCTCCCAAATTGCTGGGATTACA GGCGTGAACCACTGCTCCCTTCCCTGTCCTT | |

What is claimed is:

1. A trans-splicing molecule comprising a trifunctional element suitable for targeted trans-splicing of an RNA or pre-mRNA molecule, comprising:
(i) one or more stabilizing structural elements having at least 95% sequence identity to SEQ ID NO: 216 or 274;
(ii) one or more cleavage elements having at least 95% sequence identity to SEQ ID NO: 217; and
(iii) a termination sequence having at least 95% sequence identity to SEQ ID NO: 218.

2. The trans-splicing molecule of claim 1, comprising:
(i) one or more stabilizing structural elements having at least 95% sequence identity to SEQ ID NO: 216;
(ii) one or more cleavage elements having at least 95% sequence identity to SEQ ID NO: 217; and
(iii) a termination sequence having at least 95% sequence identity to SEQ ID NO: 218.

3. The trans-splicing molecule of claim 1, comprising:
(i) one or more stabilizing structural elements having at least 98% sequence identity to SEQ ID NO: 216 or 274;
(ii) one or more cleavage elements having at least 98% sequence identity to SEQ ID NO: 217; and
(iii) a termination sequence having at least 98% sequence identity to SEQ ID NO: 218.

4. The trans-splicing molecule of claim 1, comprising:
(i) one or more stabilizing structural elements having at least 99% sequence identity to SEQ ID NO: 216 or 274;
(ii) one or more cleavage elements having at least 99% sequence identity to SEQ ID NO: 217; and
(iii) a termination sequence having at least 99% sequence identity to SEQ ID NO: 218.

5. The trans-splicing molecule of claim 1, further comprising one or more complementary regions (CR) having at least 98% sequence identity to one of SEQ ID NOs: 212-214.

6. The trans-splicing molecule of claim 5, wherein the one or more CRs are located outside of the one or more stabilizing structural elements.

7. The trans-splicing molecule of claim 5, wherein the one or more CRs are located inside the one or more stabilizing structural elements.

8. The trans-splicing molecule of claim 1, further comprising a splice acceptor (SA) or splice donor (SD) of one of:
   i. CAGGTAAGT;
   ii. CAGGTAAGA;
   iii. CAGGTGAGT;
   iv. CAGGTAGGT; and
   v. CAGGTAAGG.

9. The trans-splicing molecule of claim 1, wherein the trans-splicing molecule further comprises a CMV enhancer having at least 98% sequence identity to SEQ ID NO: 204.

10. The trans-splicing molecule of claim 1, wherein the trans-splicing molecule further comprises a CMV promoter having at least 98% sequence identity to SEQ ID NO: 205.

11. The trans-splicing molecule of claim 1, wherein the trans-splicing molecule further comprises an untranscribed region having at least 98% sequence identity to SEQ ID NO: 206.

12. The trans-splicing molecule of claim 1, wherein the trans-splicing molecule further comprises an Usherin 5' UTR sequence having at least 98% sequence identity to SEQ ID NO: 207 or SEQ ID NO: 208.

13. The trans-splicing molecule of claim 1, wherein the trans-splicing molecule further comprises an Usherin coding sequence having at least 98% sequence identity to SEQ ID NO: 209.

14. The trans-splicing molecule of claim 1, wherein the trans-splicing molecule further comprises a splice donor (SD) sequence of: GTAAGT.

15. The trans-splicing molecule of claim 1, wherein the trans-splicing molecule further comprises a scaffold sequence having at least 98% sequence identity to SEQ ID NO: 211.

16. The trans-splicing molecule of claim 1, wherein the trans-splicing molecule further comprises a filler sequence having at least 98% sequence identity to SEQ ID NO: 215.

17. The trans-splicing molecule of claim 1, wherein the trans-splicing molecule further comprises a stabilizing structural element sequence having at least 98% sequence identity to SEQ ID NO: 216 or SEQ ID NO: 274.

18. The trans-splicing molecule of claim 1, wherein the trans-splicing molecule further comprises a cleavage element sequence having at least 98% sequence identity to SEQ ID NO: 217.

19. The trans-splicing molecule of claim 1, wherein the trans-splicing molecule further comprises a termination sequence having at least 98% sequence identity to SEQ ID NO: 218.

20. The trans-splicing molecule of claim 1, wherein the trans-splicing molecule has at least 95% identity to one of SEQ ID NOs: 255-258.

21. The trans-splicing molecule of claim 1, wherein the trans-splicing molecule has at least 98% identity to one of SEQ ID NOs: 255-258.

22. The trans-splicing molecule of claim 1, wherein the trans-splicing molecule has at least 99% identity to one of SEQ ID NOs: 255-258.

23. A trans-splicing molecule comprising a trifunctional element suitable for targeted trans-splicing of an RNA or pre-mRNA molecule, comprising:

(i) one or more stabilizing structural elements, (ii) one or more cleavage elements, and (iii) a termination sequence, wherein the trans-splicing molecule has at least 99% identity to one of SEQ ID NOs: 255-258.

24. The trans-splicing molecule of claim 23, wherein the trans-splicing molecule has at least 99% identity to SEQ ID NO: 255.

25. The trans-splicing molecule of claim 23, wherein the trans-splicing molecule has at least 99% identity to SEQ ID NO: 256.

26. The trans-splicing molecule of claim 23, wherein the trans-splicing molecule has at least 99% identity to SEQ ID NO: 257.

27. The trans-splicing molecule of claim 23, wherein the trans-splicing molecule has at least 99% identity to SEQ ID NO: 258.

\* \* \* \* \*

SEQUENCE LISTING

Sequence total quantity: 277

SEQ ID NO: 1　　　　　　　moltype = DNA　length = 67
FEATURE　　　　　　　　　　Location/Qualifiers
source　　　　　　　　　　1..67
　　　　　　　　　　　　　　mol_type = other DNA
　　　　　　　　　　　　　　organism = synthetic construct
SEQUENCE: 1
gggggccaca gcagaagcgt tcacgtcgcg gccctgtca gattctggcg aatctgcgaa　60
ttctgct　　　　　　　　　　　　　　　　　　　　　　　　　　　　　　　　67

SEQ ID NO: 2　　　　　　　moltype = DNA　length = 67
FEATURE　　　　　　　　　　Location/Qualifiers
source　　　　　　　　　　1..67
　　　　　　　　　　　　　　mol_type = other DNA
　　　　　　　　　　　　　　organism = synthetic construct
SEQUENCE: 2
gggggccaca gcagaagcgt tcacgtcgcg gccctgtca gattctgatg aatctgcgaa　60
ttctgct　　　　　　　　　　　　　　　　　　　　　　　　　　　　　　　　67

SEQ ID NO: 3　　　　　　　moltype = DNA　length = 67
FEATURE　　　　　　　　　　Location/Qualifiers
source　　　　　　　　　　1..67
　　　　　　　　　　　　　　mol_type = other DNA
　　　　　　　　　　　　　　organism = synthetic construct
SEQUENCE: 3
gggggccaca gcagaagcgt tcacgtcgcg gccctgtca gattctgaag aatctgcgaa　60
ttctgct　　　　　　　　　　　　　　　　　　　　　　　　　　　　　　　　67

SEQ ID NO: 4　　　　　　　moltype = DNA　length = 82
FEATURE　　　　　　　　　　Location/Qualifiers
source　　　　　　　　　　1..82
　　　　　　　　　　　　　　mol_type = other DNA
　　　　　　　　　　　　　　organism = synthetic construct
SEQUENCE: 4
ggaacaactt cgacgtttcg acgtcgatct taccgtgaaa atggttagaa gcatctgagg　60
ttatgctttt tgtttttggt tg　　　　　　　　　　　　　　　　　　　　　82

SEQ ID NO: 5　　　　　　　moltype = DNA　length = 67
FEATURE　　　　　　　　　　Location/Qualifiers
source　　　　　　　　　　1..67
　　　　　　　　　　　　　　mol_type = other DNA
　　　　　　　　　　　　　　organism = synthetic construct
SEQUENCE: 5
gggggccaca gcagaagcgt tcacgtcgcg gccctgtca gattctgatg aatctgcgaa　60
ttctgct　　　　　　　　　　　　　　　　　　　　　　　　　　　　　　　　67

SEQ ID NO: 6　　　　　　　moltype = DNA　length = 67
FEATURE　　　　　　　　　　Location/Qualifiers
source　　　　　　　　　　1..67
　　　　　　　　　　　　　　mol_type = other DNA
　　　　　　　　　　　　　　organism = synthetic construct
SEQUENCE: 6
tggggccaca gcagaagcat tcatgttgca gcccttgtga gattcaagtg aatctgtgaa　60
ttctgct　　　　　　　　　　　　　　　　　　　　　　　　　　　　　　　　67

SEQ ID NO: 7　　　　　　　moltype = DNA　length = 194
FEATURE　　　　　　　　　　Location/Qualifiers
source　　　　　　　　　　1..194
　　　　　　　　　　　　　　mol_type = other DNA
　　　　　　　　　　　　　　organism = synthetic construct
SEQUENCE: 7
gcatagtgtt accatcaacc accttaactt catttttct tattcaatac ctaggtaggt　60

```
agatgctgat tctggaaata aaatatgagt ctcaagtggt ccttgtcctc tctctcccag   120
tcaaattctg aatctagttg gcaagattct gaaatcaggg catataatca gtaataagtg   180
atgatagaag ggta                                                      194

SEQ ID NO: 8               moltype = DNA   length = 67
FEATURE                    Location/Qualifiers
source                     1..67
                           mol_type = other DNA
                           organism = synthetic construct
SEQUENCE: 8
aggggccaga gcagaagcat tcacgtcgtg gccctgtca gattctggtg aatctgcgaa    60
ttctgct                                                              67

SEQ ID NO: 9               moltype = DNA   length = 67
FEATURE                    Location/Qualifiers
source                     1..67
                           mol_type = other DNA
                           organism = synthetic construct
SEQUENCE: 9
aggggccaga gcagaagcat tcacgtcgcg gccctgtca gattctggtg aatctgcgaa    60
ttctgct                                                              67

SEQ ID NO: 10              moltype = DNA   length = 67
FEATURE                    Location/Qualifiers
source                     1..67
                           mol_type = other DNA
                           organism = synthetic construct
SEQUENCE: 10
ggggccaca gcagaagcgt tcacgtcgcg gccctgtca gattctgatg aatctgcgaa    60
ttctgct                                                              67

SEQ ID NO: 11              moltype = DNA   length = 220
FEATURE                    Location/Qualifiers
source                     1..220
                           mol_type = other DNA
                           organism = synthetic construct
SEQUENCE: 11
ggacaaccaa aagacaaatc tgccctcaga gcttgagaac atcttcggat gtagaggagg    60
cagcctccgg tggcgcaata gcgccaacgt tctcaacaga tacccaatac tcccgctccg   120
gcgggtgggg ataacacctg acgaaaaggc gctgttagac acgccaaggt cataatcccc   180
ggagcttcgg ctccgcggcc gcaaaaaaaa aaggcttacc                         220

SEQ ID NO: 12              moltype = DNA   length = 221
FEATURE                    Location/Qualifiers
source                     1..221
                           mol_type = other DNA
                           organism = synthetic construct
SEQUENCE: 12
ggacaaccaa aaagacaaat ctgccctcag agcttgagaa catcttcgga tgcagaggag    60
gcagcctccg gtggcgcgag agcgccaacg ttctcaacag acgcacaata ctcccgcttc   120
ggcgggtggg gataacacct gacgaaaagg cgatgttaga cacgccaagg tcataatccc   180
cggagcttcg gctccgcggc gcaaaaaaaa aaaggcttac c                       221

SEQ ID NO: 13              moltype = DNA   length = 67
FEATURE                    Location/Qualifiers
source                     1..67
                           mol_type = other DNA
                           organism = synthetic construct
SEQUENCE: 13
ggggccaca gcagaagcgt tcacgtcgtg gccctgtca gattctggtg aatctgcgaa    60
ttctgct                                                              67

SEQ ID NO: 14              moltype = DNA   length = 67
FEATURE                    Location/Qualifiers
source                     1..67
                           mol_type = other DNA
                           organism = synthetic construct
SEQUENCE: 14
agggaccaca gcagaagttt cacatcgtgg ccctgtcag atgccagtga atctgtaaat    60
ttctgct                                                              67

SEQ ID NO: 15              moltype = DNA   length = 67
FEATURE                    Location/Qualifiers
source                     1..67
                           mol_type = other DNA
                           organism = synthetic construct
SEQUENCE: 15
caggtccaca gcagaaacat tcacgttgcg gccctgtca gattctggtg aatctgcgaa    60
ttctgct                                                              67
```

-continued

```
SEQ ID NO: 16              moltype = DNA  length = 67
FEATURE                    Location/Qualifiers
source                     1..67
                           mol_type = other DNA
                           organism = synthetic construct
SEQUENCE: 16
ggggccata gcagaagcgt tcacgtcgcg gccctgtca gattcatacg aatctgcgaa      60
ttctgct                                                             67

SEQ ID NO: 17              moltype = DNA  length = 67
FEATURE                    Location/Qualifiers
source                     1..67
                           mol_type = other DNA
                           organism = synthetic construct
SEQUENCE: 17
ggggccata gcagaagcgt tcacgtcgcg gccctgtca gattcatatg aatctgcgaa      60
ttctgct                                                             67

SEQ ID NO: 18              moltype = DNA  length = 67
FEATURE                    Location/Qualifiers
source                     1..67
                           mol_type = other DNA
                           organism = synthetic construct
SEQUENCE: 18
aggggccaga gcagaagcat tcacgtcgcg gccctgtca gattctggtg aatctgcgaa     60
ttctgct                                                             67

SEQ ID NO: 19              moltype = DNA  length = 67
FEATURE                    Location/Qualifiers
source                     1..67
                           mol_type = other DNA
                           organism = synthetic construct
SEQUENCE: 19
ggggccaca gcagaagcgt tcacgtcgcg gccctgtca gattctggtg aatctgcgaa      60
ttctgct                                                             67

SEQ ID NO: 20              moltype = DNA  length = 67
FEATURE                    Location/Qualifiers
source                     1..67
                           mol_type = other DNA
                           organism = synthetic construct
SEQUENCE: 20
ggggccaca gcacaagcgt tcacgtcgca gccctgtcg gattctgagg aatctgcgaa      60
ttctgct                                                             67

SEQ ID NO: 21              moltype = DNA  length = 67
FEATURE                    Location/Qualifiers
source                     1..67
                           mol_type = other DNA
                           organism = synthetic construct
SEQUENCE: 21
ggggccaca gcagaagcgt tcacgtcgcg gccctgtca gattctgatg aatctgcgaa      60
ttctgct                                                             67

SEQ ID NO: 22              moltype = DNA  length = 67
FEATURE                    Location/Qualifiers
source                     1..67
                           mol_type = other DNA
                           organism = synthetic construct
SEQUENCE: 22
ggggccaca gcagaagcgt tcacgtcgcg gccctgtca gattctgatg aatctgcgaa      60
ttctgct                                                             67

SEQ ID NO: 23              moltype = DNA  length = 67
FEATURE                    Location/Qualifiers
source                     1..67
                           mol_type = other DNA
                           organism = synthetic construct
SEQUENCE: 23
cggggccaca gcaaaagtgt tcacgtcatg gccctgtca gattctggtg aatctgcaaa     60
ttctgct                                                             67

SEQ ID NO: 24              moltype = DNA  length = 67
FEATURE                    Location/Qualifiers
source                     1..67
                           mol_type = other DNA
                           organism = synthetic construct
SEQUENCE: 24
```

```
cggggctaca gcagaagcgt tcacattgca gcccctgtca gattctggtg aatctgcgaa   60
ttctgct                                                              67

SEQ ID NO: 25          moltype = DNA   length = 51
FEATURE                Location/Qualifiers
source                 1..51
                       mol_type = other DNA
                       organism = synthetic construct
SEQUENCE: 25
ggtagcacac ctatgcgttc ccgtcgcgct actgatttag actaaatagg t            51

SEQ ID NO: 26          moltype = DNA   length = 257
FEATURE                Location/Qualifiers
source                 1..257
                       mol_type = other DNA
                       organism = synthetic construct
SEQUENCE: 26
gtgggcgggc ggggttcgac ttcttcggca gcgcaggccc cggcgacacg tgatgtcaca   60
agccgggggag acgaggtgga ggtcagcgct tttactgcgg atgcctccag gccccggtga  120
acgggcctac ccggcgcgtg ctttgccgct ctgagtcaaa gactccggca ggcagaacca  180
cgcgcaagcc cggcgataag ccccgcagca atgcgggcat aaggccgggc agctcaccac  240
accccagcaa gtggctg                                                  257

SEQ ID NO: 27          moltype = DNA   length = 67
FEATURE                Location/Qualifiers
source                 1..67
                       mol_type = other DNA
                       organism = synthetic construct
SEQUENCE: 27
aggggccaga gcagaagcat tcacgttgcg gcccctgtca gattctggtg aatctgcgaa   60
ttctgct                                                              67

SEQ ID NO: 28          moltype = DNA   length = 175
FEATURE                Location/Qualifiers
source                 1..175
                       mol_type = other DNA
                       organism = synthetic construct
SEQUENCE: 28
caacatcacc gccttgtatg cacgggatgg tccttgaagt gtgcagccct gtgcgtatgg   60
tccggcctcg cctgtatcat acacatcctg gccacttcat agacgctgat gttctgaatc  120
tcgcccctaa ccatcttcgg gattctccag aacctcgctc gcgcatgtaa gtctc        175

SEQ ID NO: 29          moltype = DNA   length = 67
FEATURE                Location/Qualifiers
source                 1..67
                       mol_type = other DNA
                       organism = synthetic construct
SEQUENCE: 29
ggggggccaca gcagaagcgt tcacgtcgcg gcccctgtca gattctgatg aatctgcgaa   60
ttctgct                                                              67

SEQ ID NO: 30          moltype = DNA   length = 82
FEATURE                Location/Qualifiers
source                 1..82
                       mol_type = other DNA
                       organism = synthetic construct
SEQUENCE: 30
aatcgttctt actgcagtga caaacatgtg gggcttatat ctaatcttcg gattagtatt   60
agtgcagacg ttaaaaccat gt                                             82

SEQ ID NO: 31          moltype = DNA   length = 68
FEATURE                Location/Qualifiers
source                 1..68
                       mol_type = other DNA
                       organism = synthetic construct
SEQUENCE: 31
ggccggcatg gtcccagcct cctcgctggc gccggctggg caacatgctt cggcatggcg   60
aatgggac                                                             68

SEQ ID NO: 32          moltype = DNA   length = 154
FEATURE                Location/Qualifiers
source                 1..154
                       mol_type = other DNA
                       organism = synthetic construct
SEQUENCE: 32
atggccggca tggtcccagc ctcctcgctg gcgccggctg gcaacattc cgaggggacc     60
gtcccctcgg taatggtgaa tgggacgcac aaatctctct agcttcccag agagaagcga  120
gagaaaagtg gctctcccctt ggccatccga gtgg                              154
```

```
SEQ ID NO: 33           moltype = DNA   length = 87
FEATURE                 Location/Qualifiers
source                  1..87
                        mol_type = other DNA
                        organism = synthetic construct
SEQUENCE: 33
ggccggcatg gtcccagcct cctcgctggc gccggctggg caacattccg aggggaccgt   60
cccctcggta atggtgaatg ggacgca                                       87

SEQ ID NO: 34           moltype = DNA   length = 67
FEATURE                 Location/Qualifiers
source                  1..67
                        mol_type = other DNA
                        organism = synthetic construct
SEQUENCE: 34
gccggcatgg tcccagcctc ctcgctggcg ccggctgggc aacatgcttc ggcatggtga   60
atgggac                                                             67

SEQ ID NO: 35           moltype = DNA   length = 82
FEATURE                 Location/Qualifiers
source                  1..82
                        mol_type = other DNA
                        organism = synthetic construct
SEQUENCE: 35
ctcaattctc acagaagcac cctcaaaatg tctttttttgg cctctgtcag attctggtga   60
gaaaaatctc tcagtccaaa ct                                            82

SEQ ID NO: 36           moltype = DNA   length = 168
FEATURE                 Location/Qualifiers
source                  1..168
                        mol_type = other DNA
                        organism = synthetic construct
SEQUENCE: 36
acctagacta agcccaggaa cataagacct cagagctaat gagccacata cctacccaag   60
gtgaaagctc cttctctcgc aatgtgtaac tcatgattct catgacccct ggttggagag  120
atccggacta ggagccaggg ggcctctgat tctgccagcc actgctaa               168

SEQ ID NO: 37           moltype = DNA   length = 67
FEATURE                 Location/Qualifiers
source                  1..67
                        mol_type = other DNA
                        organism = synthetic construct
SEQUENCE: 37
gggggccaca gcagaagcgt tcacgtcgca gccctgtca gattctggtg aatctgcgaa    60
ttctgct                                                             67

SEQ ID NO: 38           moltype = DNA   length = 67
FEATURE                 Location/Qualifiers
source                  1..67
                        mol_type = other DNA
                        organism = synthetic construct
SEQUENCE: 38
gggggccaca gcagaagcgt tcacgtcgca gcccccgtca gattctggtg aatctgcgaa   60
ttctgct                                                             67

SEQ ID NO: 39           moltype = DNA   length = 67
FEATURE                 Location/Qualifiers
source                  1..67
                        mol_type = other DNA
                        organism = synthetic construct
SEQUENCE: 39
cagagccgtt acagaagtgt tcatatcatg gtccctgtca gattctggtg aatctgaaaa   60
ttctgct                                                             67

SEQ ID NO: 40           moltype = DNA   length = 67
FEATURE                 Location/Qualifiers
source                  1..67
                        mol_type = other DNA
                        organism = synthetic construct
SEQUENCE: 40
gggggccata gcagaagcgt tcacgtcgcg gccctgtca gattcatagg aatctgcgaa    60
ttctgct                                                             67

SEQ ID NO: 41           moltype = DNA   length = 67
FEATURE                 Location/Qualifiers
source                  1..67
                        mol_type = other DNA
                        organism = synthetic construct
SEQUENCE: 41
```

-continued

```
agggaccaca gcagaagttt cacatcgtgg cccctgtcag atgccagtga atctgtaaat   60
ttctgct                                                            67

SEQ ID NO: 42          moltype = DNA   length = 67
FEATURE                Location/Qualifiers
source                 1..67
                       mol_type = other DNA
                       organism = synthetic construct
SEQUENCE: 42
ggggccaca gcagaagcgt tcacgtcgcg cccctgtca gattctggcg aatctgcgaa     60
ttctgct                                                            67

SEQ ID NO: 43          moltype = DNA   length = 67
FEATURE                Location/Qualifiers
source                 1..67
                       mol_type = other DNA
                       organism = synthetic construct
SEQUENCE: 43
ggggccaca gcagaagcgt tcacgtcgcg cccctgtca gattctgacg aatctgcgaa     60
ttctgct                                                            67

SEQ ID NO: 44          moltype = DNA   length = 67
FEATURE                Location/Qualifiers
source                 1..67
                       mol_type = other DNA
                       organism = synthetic construct
SEQUENCE: 44
ggggccaca gcagaagcgt tcacgtcgcg gcctctgtca gattctggtg aatctgcgaa    60
ttctgct                                                            67

SEQ ID NO: 45          moltype = DNA   length = 67
FEATURE                Location/Qualifiers
source                 1..67
                       mol_type = other DNA
                       organism = synthetic construct
SEQUENCE: 45
ggggggcaca gcagaagcat tcacttcgtg cccctgtca gattctagtg aatctgcgaa    60
ttctgct                                                            67

SEQ ID NO: 46          moltype = DNA   length = 67
FEATURE                Location/Qualifiers
source                 1..67
                       mol_type = other DNA
                       organism = synthetic construct
SEQUENCE: 46
agggccaca gcagaagcgt tcacgtcgcg cccctgtca gattctggtg aatctgcgaa     60
ttctgct                                                            67

SEQ ID NO: 47          moltype = DNA   length = 66
FEATURE                Location/Qualifiers
source                 1..66
                       mol_type = other DNA
                       organism = synthetic construct
SEQUENCE: 47
agggccaca gcagaagcgt tcacgtcgcg cccctgtca gattctggtg aatctgcgaa     60
tctgct                                                             66

SEQ ID NO: 48          moltype = DNA   length = 61
FEATURE                Location/Qualifiers
source                 1..61
                       mol_type = other DNA
                       organism = synthetic construct
SEQUENCE: 48
ggggcctca gcagacacat cacagtcccc atcagattct ggtgaatccg tgaattttgc    60
t                                                                  61

SEQ ID NO: 49          moltype = DNA   length = 67
FEATURE                Location/Qualifiers
source                 1..67
                       mol_type = other DNA
                       organism = synthetic construct
SEQUENCE: 49
ggggctaca gcagaagcgt tcacattgca ccccctgtca cattctggtg aatctgcgaa    60
ttctgct                                                            67

SEQ ID NO: 50          moltype = DNA   length = 67
FEATURE                Location/Qualifiers
source                 1..67
                       mol_type = other DNA
```

-continued

```
                        organism = synthetic construct
SEQUENCE: 50
gggggccaca gcagaagcgt tcacgtcgcg gccctgtca gattctggcg aatctgcgaa    60
ttctgct                                                            67

SEQ ID NO: 51           moltype = DNA   length = 67
FEATURE                 Location/Qualifiers
source                  1..67
                        mol_type = other DNA
                        organism = synthetic construct
SEQUENCE: 51
gggggccaca gcagaagcgt tcacgtcgcg gccctgtca gattctgatg aatctgcgaa    60
ttctgct                                                            67

SEQ ID NO: 52           moltype = DNA   length = 67
FEATURE                 Location/Qualifiers
source                  1..67
                        mol_type = other DNA
                        organism = synthetic construct
SEQUENCE: 52
gggggccata gcagaagcgt tcacgtcgcg gccctgtca gattcatagg aatctgcgaa    60
ttctgct                                                            67

SEQ ID NO: 53           moltype = DNA   length = 55
FEATURE                 Location/Qualifiers
source                  1..55
                        mol_type = other DNA
                        organism = synthetic construct
SEQUENCE: 53
ggcgcgcttt gacttacctc cacgcggtgc gcgctggata acgctaacaa gtcag         55

SEQ ID NO: 54           moltype = DNA   length = 52
FEATURE                 Location/Qualifiers
source                  1..52
                        mol_type = other DNA
                        organism = synthetic construct
SEQUENCE: 54
ggtaacgaga gaatacctcc acgcggtgtt actggattag actaaattct ta            52

SEQ ID NO: 55           moltype = DNA   length = 53
FEATURE                 Location/Qualifiers
source                  1..53
                        mol_type = other DNA
                        organism = synthetic construct
SEQUENCE: 55
ggttgcatgt gtttacctcc acgtggtgca actggattaa gactaaaaac aca           53

SEQ ID NO: 56           moltype = DNA   length = 52
FEATURE                 Location/Qualifiers
source                  1..52
                        mol_type = other DNA
                        organism = synthetic construct
SEQUENCE: 56
ggcgccaaga gaagacctcc ccgtggtggt gctggatacg actaacttct ca            52

SEQ ID NO: 57           moltype = DNA   length = 56
FEATURE                 Location/Qualifiers
source                  1..56
                        mol_type = other DNA
                        organism = synthetic construct
SEQUENCE: 57
ggacgacggg ctatcaacct ccacgcggtg tcgtctgggt catgcgaata gatagt        56

SEQ ID NO: 58           moltype = DNA   length = 55
FEATURE                 Location/Qualifiers
source                  1..55
                        mol_type = other DNA
                        organism = synthetic construct
SEQUENCE: 58
gacttacaat ggtaaaacct ccgcgtggtg taagttgggt tatgctaatt tacca         55

SEQ ID NO: 59           moltype = DNA   length = 53
FEATURE                 Location/Qualifiers
source                  1..53
                        mol_type = other DNA
                        organism = synthetic construct
SEQUENCE: 59
ggcatcaagt aagaaacctc ctcgtggtga tgccgggttg tgctaattct tac           53
```

```
SEQ ID NO: 60          moltype = DNA   length = 58
FEATURE                Location/Qualifiers
source                 1..58
                       mol_type = other DNA
                       organism = synthetic construct
SEQUENCE: 60
ggagttcgta ttaaactacc tccacgtggt gaactctgga ttaaaactaa atgtttaa          58

SEQ ID NO: 61          moltype = DNA   length = 53
FEATURE                Location/Qualifiers
source                 1..53
                       mol_type = other DNA
                       organism = synthetic construct
SEQUENCE: 61
ggcatcaaat caaacacctc cacgcggtga tgctgggtaa agctaagttt gat              53

SEQ ID NO: 62          moltype = DNA   length = 53
FEATURE                Location/Qualifiers
source                 1..53
                       mol_type = other DNA
                       organism = synthetic construct
SEQUENCE: 62
ggtcccgagc tgccacctcc acgtggtggg actggatcac gctaacggca gca              53

SEQ ID NO: 63          moltype = DNA   length = 57
FEATURE                Location/Qualifiers
source                 1..57
                       mol_type = other DNA
                       organism = synthetic construct
SEQUENCE: 63
gagatgagaa tgacttgacc tccgcgtggt tcatcttggg taattctaac aaagtca          57

SEQ ID NO: 64          moltype = DNA   length = 56
FEATURE                Location/Qualifiers
source                 1..56
                       mol_type = other DNA
                       organism = synthetic construct
SEQUENCE: 64
ggggtgttag taggcagcct ccacgtggca caccctggtt aacgctaatg gcctac           56

SEQ ID NO: 65          moltype = DNA   length = 56
FEATURE                Location/Qualifiers
source                 1..56
                       mol_type = other DNA
                       organism = synthetic construct
SEQUENCE: 65
ggatagaata taagaaacct ccacgtggtt ctatctggat aatgctaata tcttat           56

SEQ ID NO: 66          moltype = DNA   length = 55
FEATURE                Location/Qualifiers
source                 1..55
                       mol_type = other DNA
                       organism = synthetic construct
SEQUENCE: 66
gactcgcaat gtacttgcct ccacgtggcg cgagttggat agctctaaaa gtaca            55

SEQ ID NO: 67          moltype = DNA   length = 53
FEATURE                Location/Qualifiers
source                 1..53
                       mol_type = other DNA
                       organism = synthetic construct
SEQUENCE: 67
ggtcccgagc tgccacctcc acgtggtggg actgggtcac gctaacggca gca              53

SEQ ID NO: 68          moltype = DNA   length = 54
FEATURE                Location/Qualifiers
source                 1..54
                       mol_type = other DNA
                       organism = synthetic construct
SEQUENCE: 68
gggcacattg actagcctcc acgtggcgtg cctggataac caaccaatag tcta             54

SEQ ID NO: 69          moltype = DNA   length = 56
FEATURE                Location/Qualifiers
source                 1..56
                       mol_type = other DNA
                       organism = synthetic construct
SEQUENCE: 69
ggagtccaag tagttaacct cctcgtggtg gactctgggt aattctaata agctac           56
```

-continued

```
SEQ ID NO: 70            moltype = DNA   length = 56
FEATURE                  Location/Qualifiers
source                   1..56
                         mol_type = other DNA
                         organism = synthetic construct
SEQUENCE: 70
gaccgcagaa tgacaaactt ccacgtagtt gcggttgggt aatgctaata tgtcat          56

SEQ ID NO: 71            moltype = DNA   length = 53
FEATURE                  Location/Qualifiers
source                   1..53
                         mol_type = other DNA
                         organism = synthetic construct
SEQUENCE: 71
ggtcccgcgc tgccacctcc ccgtggtggg actggatcac gctaacggca gcc             53

SEQ ID NO: 72            moltype = DNA   length = 52
FEATURE                  Location/Qualifiers
source                   1..52
                         mol_type = other DNA
                         organism = synthetic construct
SEQUENCE: 72
ggcaccaaga gaagacctcc ccgtggtggt gctggatacg actaacttct ca              52

SEQ ID NO: 73            moltype = DNA   length = 54
FEATURE                  Location/Qualifiers
source                   1..54
                         mol_type = other DNA
                         organism = synthetic construct
SEQUENCE: 73
ggtcacattg catcgcctcc tcgtggcgtg actggatatc caaccaagat gcaa            54

SEQ ID NO: 74            moltype = DNA   length = 55
FEATURE                  Location/Qualifiers
source                   1..55
                         mol_type = other DNA
                         organism = synthetic construct
SEQUENCE: 74
ggattacata ttagaagcct cctcgtggcg taatctgggt aatgctaatt ctaat           55

SEQ ID NO: 75            moltype = DNA   length = 56
FEATURE                  Location/Qualifiers
source                   1..56
                         mol_type = other DNA
                         organism = synthetic construct
SEQUENCE: 75
ggagttcata taactaagcc tcctcgtggc gaactctggg tagctctaat tagtta          56

SEQ ID NO: 76            moltype = DNA   length = 56
FEATURE                  Location/Qualifiers
source                   1..56
                         mol_type = other DNA
                         organism = synthetic construct
SEQUENCE: 76
ggacgacgga ctatcaacct ccacgcggtg tcgtctgggt catgcgaata gatagt          56

SEQ ID NO: 77            moltype = DNA   length = 57
FEATURE                  Location/Qualifiers
source                   1..57
                         mol_type = other DNA
                         organism = synthetic construct
SEQUENCE: 77
gagtggcaat atcaacaacc tccacgtggt gctacttggg taatgctaat agttgat         57

SEQ ID NO: 78            moltype = DNA   length = 54
FEATURE                  Location/Qualifiers
source                   1..54
                         mol_type = other DNA
                         organism = synthetic construct
SEQUENCE: 78
gggttgtagc ttgatgcctc ctcgtggcac aacccggttg gccctaaatc aagc            54

SEQ ID NO: 79            moltype = DNA   length = 57
FEATURE                  Location/Qualifiers
source                   1..57
                         mol_type = other DNA
                         organism = synthetic construct
SEQUENCE: 79
```

-continued

```
gaaacactta ttactcaacc tccacgtggt gtgtttcggg taatgctaat ggagtaa      57

SEQ ID NO: 80            moltype = DNA   length = 55
FEATURE                  Location/Qualifiers
source                   1..55
                         mol_type = other DNA
                         organism = synthetic construct
SEQUENCE: 80
gacttctaat ttctcagcct cctcgtggca gaagttgggt aacgctaatg agaaa        55

SEQ ID NO: 81            moltype = DNA   length = 53
FEATURE                  Location/Qualifiers
source                   1..53
                         mol_type = other DNA
                         organism = synthetic construct
SEQUENCE: 81
gagcgcaatg ctaaaacctt cacgtggtgc gcttgatttc gactaattta gca          53

SEQ ID NO: 82            moltype = DNA   length = 52
FEATURE                  Location/Qualifiers
source                   1..52
                         mol_type = other DNA
                         organism = synthetic construct
SEQUENCE: 82
ggcatcgtga gagaagcctg ctcgtggcga tgctgctttt actaattctc tc           52

SEQ ID NO: 83            moltype = DNA   length = 52
FEATURE                  Location/Qualifiers
source                   1..52
                         mol_type = other DNA
                         organism = synthetic construct
SEQUENCE: 83
ggatccaaga gaaagcctcc acgtggcgga tctgggtaaa gctaatttct ca           52

SEQ ID NO: 84            moltype = DNA   length = 57
FEATURE                  Location/Qualifiers
source                   1..57
                         mol_type = other DNA
                         organism = synthetic construct
SEQUENCE: 84
gagacacaaa tctctatacc tccacgtggt gtgtcttgga taatactaaa ttagaga      57

SEQ ID NO: 85            moltype = DNA   length = 52
FEATURE                  Location/Qualifiers
source                   1..52
                         mol_type = other DNA
                         organism = synthetic construct
SEQUENCE: 85
ggtaacgaga gaagaccttc acgtggtgtt accgatttag actaatttct ca           52

SEQ ID NO: 86            moltype = DNA   length = 56
FEATURE                  Location/Qualifiers
source                   1..56
                         mol_type = other DNA
                         organism = synthetic construct
SEQUENCE: 86
ggagttcata taactaagcc tcctcgtggc gaactctgga tagctctaat tagtta       56

SEQ ID NO: 87            moltype = DNA   length = 56
FEATURE                  Location/Qualifiers
source                   1..56
                         mol_type = other DNA
                         organism = synthetic construct
SEQUENCE: 87
ggagttcaag tagttaacct cctcgtggtg gactctgggt aattctaata aactac       56

SEQ ID NO: 88            moltype = DNA   length = 57
FEATURE                  Location/Qualifiers
source                   1..57
                         mol_type = other DNA
                         organism = synthetic construct
SEQUENCE: 88
gggagacaat acagccaacc tccacgtggt gtctcctggg taattctaat aggctgt      57

SEQ ID NO: 89            moltype = DNA   length = 55
FEATURE                  Location/Qualifiers
source                   1..55
                         mol_type = other DNA
                         organism = synthetic construct
```

-continued

```
SEQUENCE: 89
gggtactata tagaggcctc cccgtggcgt acctggatta aaactaacat ctata          55

SEQ ID NO: 90              moltype = DNA   length = 56
FEATURE                   Location/Qualifiers
source                    1..56
                          mol_type = other DNA
                          organism = synthetic construct
SEQUENCE: 90
ggacgacggg ctatcaacct ccacgcggtg tcgtctgggt catgcggata gatagt         56

SEQ ID NO: 91              moltype = DNA   length = 54
FEATURE                   Location/Qualifiers
source                    1..54
                          mol_type = other DNA
                          organism = synthetic construct
SEQUENCE: 91
ggcaacttgt taacagcctt ctcgtggcgt tgctgatttc gactaatagt taac           54

SEQ ID NO: 92              moltype = DNA   length = 54
FEATURE                   Location/Qualifiers
source                    1..54
                          mol_type = other DNA
                          organism = synthetic construct
SEQUENCE: 92
gatgtcaaga acaagcctcc tcgtggcgac atcggataac caaccaattg ttca           54

SEQ ID NO: 93              moltype = DNA   length = 52
FEATURE                   Location/Qualifiers
source                    1..52
                          mol_type = other DNA
                          organism = synthetic construct
SEQUENCE: 93
ggtaccacga gagaagcctg cgcgtggcgg tactgcttta actgattctc tc             52

SEQ ID NO: 94              moltype = DNA   length = 53
FEATURE                   Location/Qualifiers
source                    1..53
                          mol_type = other DNA
                          organism = synthetic construct
SEQUENCE: 94
ggtatcatta gcaagcctcc acgtggcgat actggattag aactaattgc tag            53

SEQ ID NO: 95              moltype = DNA   length = 55
FEATURE                   Location/Qualifiers
source                    1..55
                          mol_type = other DNA
                          organism = synthetic construct
SEQUENCE: 95
gaggcacatt taagaagcct ccacgtggcg tgtcttgggt aatgctaatt cttaa          55

SEQ ID NO: 96              moltype = DNA   length = 52
FEATURE                   Location/Qualifiers
source                    1..52
                          mol_type = other DNA
                          organism = synthetic construct
SEQUENCE: 96
gactgcataa cagagcctcc acgtggcgca gttgggtaat gccaatctgt ta             52

SEQ ID NO: 97              moltype = DNA   length = 55
FEATURE                   Location/Qualifiers
source                    1..55
                          mol_type = other DNA
                          organism = synthetic construct
SEQUENCE: 97
gaatggcaaa tgagaaacct ccacgtggtg ctattcgggt aatgctaatt ctcat          55

SEQ ID NO: 98              moltype = DNA   length = 57
FEATURE                   Location/Qualifiers
source                    1..57
                          mol_type = other DNA
                          organism = synthetic construct
SEQUENCE: 98
gaggtgagat gttctaaacc tccacgtggt tcacctcggg taacgctaag atagaac        57

SEQ ID NO: 99              moltype = DNA   length = 51
FEATURE                   Location/Qualifiers
source                    1..51
                          mol_type = other DNA
```

```
                        organism = synthetic construct
SEQUENCE: 99
ggccccaagg tgaagccttc ccgtggcggg gctggtttca ctgattcacc g       51

SEQ ID NO: 100          moltype = DNA   length = 56
FEATURE                 Location/Qualifiers
source                  1..56
                        mol_type = other DNA
                        organism = synthetic construct
SEQUENCE: 100
ggttcctgtt gtgctatacc tccacgtggt aggaactggg tagctctaaa tagtac    56

SEQ ID NO: 101          moltype = DNA   length = 55
FEATURE                 Location/Qualifiers
source                  1..55
                        mol_type = other DNA
                        organism = synthetic construct
SEQUENCE: 101
ggataacaaa tgagaaacct ccacgtggtg ttatctggat aatgctaatt ctcat     55

SEQ ID NO: 102          moltype = DNA   length = 54
FEATURE                 Location/Qualifiers
source                  1..54
                        mol_type = other DNA
                        organism = synthetic construct
SEQUENCE: 102
gatgtcaaga acaagcctcc ccgtggcgac atcggataac caaccaattg ttca       54

SEQ ID NO: 103          moltype = DNA   length = 56
FEATURE                 Location/Qualifiers
source                  1..56
                        mol_type = other DNA
                        organism = synthetic construct
SEQUENCE: 103
gattcacgtt gtatctacct ccacgtggtg tgaattgggt aattctaaaa gataca    56

SEQ ID NO: 104          moltype = DNA   length = 54
FEATURE                 Location/Qualifiers
source                  1..54
                        mol_type = other DNA
                        organism = synthetic construct
SEQUENCE: 104
ggtcacattg catcgcctcc tcgtggcgtg actggataac caaccaagat gcaa       54

SEQ ID NO: 105          moltype = DNA   length = 53
FEATURE                 Location/Qualifiers
source                  1..53
                        mol_type = other DNA
                        organism = synthetic construct
SEQUENCE: 105
ggttgcatgt gtttacctcc tcgtggtgca actggattaa gactaaaaac aca         53

SEQ ID NO: 106          moltype = DNA   length = 55
FEATURE                 Location/Qualifiers
source                  1..55
                        mol_type = other DNA
                        organism = synthetic construct
SEQUENCE: 106
ggctacgtaa tagaaacctc cacgtggtgt agctggataa ccaaccaatt ctatt     55

SEQ ID NO: 107          moltype = DNA   length = 54
FEATURE                 Location/Qualifiers
source                  1..54
                        mol_type = other DNA
                        organism = synthetic construct
SEQUENCE: 107
ggtagcaaga gtcaacctcc ccgtggtgct actggataat caactaatga ctca       54

SEQ ID NO: 108          moltype = DNA   length = 54
FEATURE                 Location/Qualifiers
source                  1..54
                        mol_type = other DNA
                        organism = synthetic construct
SEQUENCE: 108
ggcgccataa gacagcctcc tcgtggcggc gctggataac caaccaatgt ctta       54

SEQ ID NO: 109          moltype = DNA   length = 54
FEATURE                 Location/Qualifiers
source                  1..54
```

-continued

```
                         mol_type = other DNA
                         organism = synthetic construct
SEQUENCE: 109
ggcaacttgt taacagcctt ctcgcggcgt tgctgatttc gactaatagt taac          54

SEQ ID NO: 110          moltype = DNA   length = 54
FEATURE                 Location/Qualifiers
source                  1..54
                         mol_type = other DNA
                         organism = synthetic construct
SEQUENCE: 110
gatgtcaaga acaagcctcc ccgtggcgac atcggataac caactaattg ttca          54

SEQ ID NO: 111          moltype = DNA   length = 57
FEATURE                 Location/Qualifiers
source                  1..57
                         mol_type = other DNA
                         organism = synthetic construct
SEQUENCE: 111
gagatgagaa tgacttgacc tccacgtggt tcatcttggg taattccaac aaagtca       57

SEQ ID NO: 112          moltype = DNA   length = 56
FEATURE                 Location/Qualifiers
source                  1..56
                         mol_type = other DNA
                         organism = synthetic construct
SEQUENCE: 112
ggacgacgga ctatcaacct ccacgcggtg tcgtctgggt agtgcagata gatagt        56

SEQ ID NO: 113          moltype = DNA   length = 59
FEATURE                 Location/Qualifiers
source                  1..59
                         mol_type = other DNA
                         organism = synthetic construct
SEQUENCE: 113
gaggtacatt gttagatact tccacgtagt gtaccttggg ttaaaagcta aattctaac     59

SEQ ID NO: 114          moltype = DNA   length = 56
FEATURE                 Location/Qualifiers
source                  1..56
                         mol_type = other DNA
                         organism = synthetic construct
SEQUENCE: 114
ggacgacggg ctatcaacct ccacgcggtg tcgtctgggt agtgcagata gatagt        56

SEQ ID NO: 115          moltype = DNA   length = 57
FEATURE                 Location/Qualifiers
source                  1..57
                         mol_type = other DNA
                         organism = synthetic construct
SEQUENCE: 115
gaacagcgat gattctcacc tcctcgtggt gctgttcggg taattctaac gagagtc       57

SEQ ID NO: 116          moltype = DNA   length = 55
FEATURE                 Location/Qualifiers
source                  1..55
                         mol_type = other DNA
                         organism = synthetic construct
SEQUENCE: 116
gagagtcgtt actacacctc cacgcggtga ctcttggtta acactaacgt agtaa         55

SEQ ID NO: 117          moltype = DNA   length = 55
FEATURE                 Location/Qualifiers
source                  1..55
                         mol_type = other DNA
                         organism = synthetic construct
SEQUENCE: 117
gagccacaaa gttacaacct cctcgtggtg tggcttggat aacgctaatg taaca         55

SEQ ID NO: 118          moltype = DNA   length = 54
FEATURE                 Location/Qualifiers
source                  1..54
                         mol_type = other DNA
                         organism = synthetic construct
SEQUENCE: 118
ggcaacctgt taacagcctt ctcgcggcgt tgctgatttc gactaatggt taac          54

SEQ ID NO: 119          moltype = DNA   length = 52
FEATURE                 Location/Qualifiers
```

-continued

```
source                  1..52
                        mol_type = other DNA
                        organism = synthetic construct
SEQUENCE: 119
ggtcacatgt aacagcctcc ccgtggcgtg actggttaag acagatgtta ca          52

SEQ ID NO: 120          moltype = DNA   length = 56
FEATURE                 Location/Qualifiers
source                  1..56
                        mol_type = other DNA
                        organism = synthetic construct
SEQUENCE: 120
ggatagcata agtagaaacc tccacgtggt gctattcggg taatgctaat tctact       56

SEQ ID NO: 121          moltype = DNA   length = 55
FEATURE                 Location/Qualifiers
source                  1..55
                        mol_type = other DNA
                        organism = synthetic construct
SEQUENCE: 121
ggaccctcgg tgacagcctc ctcgtggcgg gtctggatta aagccaatgg tcacc        55

SEQ ID NO: 122          moltype = DNA   length = 56
FEATURE                 Location/Qualifiers
source                  1..56
                        mol_type = other DNA
                        organism = synthetic construct
SEQUENCE: 122
gaagttcaag taactaacct cctcgtggtg aactttgggt aattctaatt agttac       56

SEQ ID NO: 123          moltype = DNA   length = 54
FEATURE                 Location/Qualifiers
source                  1..54
                        mol_type = other DNA
                        organism = synthetic construct
SEQUENCE: 123
ggtaacaaga gtcaacctcc ccgtggtgtt actggataac caactaatga ctca         54

SEQ ID NO: 124          moltype = DNA   length = 54
FEATURE                 Location/Qualifiers
source                  1..54
                        mol_type = other DNA
                        organism = synthetic construct
SEQUENCE: 124
gacttcaatg tacttacctc ctcgtggtga agtcgggtag ctctaaatag taca         54

SEQ ID NO: 125          moltype = DNA   length = 55
FEATURE                 Location/Qualifiers
source                  1..55
                        mol_type = other DNA
                        organism = synthetic construct
SEQUENCE: 125
gattcacaaa ttgaatacct ccacgcggtg tgaatcgggt aactctaaat tcaat        55

SEQ ID NO: 126          moltype = DNA   length = 54
FEATURE                 Location/Qualifiers
source                  1..54
                        mol_type = other DNA
                        organism = synthetic construct
SEQUENCE: 126
ggcaacttgt taacagcctt ctcgtggcgt tgctgatttc gactaatggt taac         54

SEQ ID NO: 127          moltype = DNA   length = 54
FEATURE                 Location/Qualifiers
source                  1..54
                        mol_type = other DNA
                        organism = synthetic construct
SEQUENCE: 127
gaactcactg tatagcctcc tcgtggcgag tttggataac caactaatat acac         54

SEQ ID NO: 128          moltype = DNA   length = 55
FEATURE                 Location/Qualifiers
source                  1..55
                        mol_type = other DNA
                        organism = synthetic construct
SEQUENCE: 128
gggtactata tagaggcctc cccgcggcgt acctggatta aaactaacat ctata        55

SEQ ID NO: 129          moltype = DNA   length = 56
```

-continued

```
FEATURE                Location/Qualifiers
source                 1..56
                       mol_type = other DNA
                       organism = synthetic construct
SEQUENCE: 129
gggtactata tagaggcctc cccgtggcgt acctggatta aaaactaaca tctata         56

SEQ ID NO: 130         moltype = DNA   length = 52
FEATURE                Location/Qualifiers
source                 1..52
                       mol_type = other DNA
                       organism = synthetic construct
SEQUENCE: 130
ggcatctgga gagaagcctg ctcgtggcga tgctgctttt actgattctc tc             52

SEQ ID NO: 131         moltype = DNA   length = 54
FEATURE                Location/Qualifiers
source                 1..54
                       mol_type = other DNA
                       organism = synthetic construct
SEQUENCE: 131
ggtaacaagg ctttacctcc ccgtggtgtt actggataac caactaaaaa gcca           54

SEQ ID NO: 132         moltype = DNA   length = 55
FEATURE                Location/Qualifiers
source                 1..55
                       mol_type = other DNA
                       organism = synthetic construct
SEQUENCE: 132
gggtactata tagaggcctc cccgcggcgt acctggattt taaccaacat ctata          55

SEQ ID NO: 133         moltype = DNA   length = 52
FEATURE                Location/Qualifiers
source                 1..52
                       mol_type = other DNA
                       organism = synthetic construct
SEQUENCE: 133
ggtaacgaga gaatacctcc acgcggtgtt actggattag actaaattct tt             52

SEQ ID NO: 134         moltype = DNA   length = 55
FEATURE                Location/Qualifiers
source                 1..55
                       mol_type = other DNA
                       organism = synthetic construct
SEQUENCE: 134
gaagcacgta gacttaacct cctcgtggtg tgcttcgggt cgcgccgata agtct          55

SEQ ID NO: 135         moltype = DNA   length = 54
FEATURE                Location/Qualifiers
source                 1..54
                       mol_type = other DNA
                       organism = synthetic construct
SEQUENCE: 135
ggttccgatg tatcacacct cctcgtggtg gaactgggta attctaagtg atac           54

SEQ ID NO: 136         moltype = DNA   length = 57
FEATURE                Location/Qualifiers
source                 1..57
                       mol_type = other DNA
                       organism = synthetic construct
SEQUENCE: 136
gagagaagtt atcatttacc tccacgtggt ttctcttggg taatgctaaa taatgat        57

SEQ ID NO: 137         moltype = DNA   length = 56
FEATURE                Location/Qualifiers
source                 1..56
                       mol_type = other DNA
                       organism = synthetic construct
SEQUENCE: 137
gagcacaatg atagaagcct ccacgtggct gtgcttgggt aatactaata tctatc         56

SEQ ID NO: 138         moltype = DNA   length = 53
FEATURE                Location/Qualifiers
source                 1..53
                       mol_type = other DNA
                       organism = synthetic construct
SEQUENCE: 138
ggaatcaagc tgaaaacctc ctcgtggtga ttctggattc gactaatttc agc            53
```

```
SEQ ID NO: 139           moltype = DNA   length = 54
FEATURE                  Location/Qualifiers
source                   1..54
                         mol_type = other DNA
                         organism = synthetic construct
SEQUENCE: 139
ggcaacctgt taacagcctt ctcgtggcgt tgctgatttc gactaatggt taac          54

SEQ ID NO: 140           moltype = DNA   length = 55
FEATURE                  Location/Qualifiers
source                   1..55
                         mol_type = other DNA
                         organism = synthetic construct
SEQUENCE: 140
ggagaatatt aaccaaacct cctcgtggta ttctctgggt aatgctaatt ggtta          55

SEQ ID NO: 141           moltype = DNA   length = 54
FEATURE                  Location/Qualifiers
source                   1..54
                         mol_type = other DNA
                         organism = synthetic construct
SEQUENCE: 141
ggcatcaagt gaatacctcc ccgtggtgat gctggataat taactaaatt caca          54

SEQ ID NO: 142           moltype = DNA   length = 56
FEATURE                  Location/Qualifiers
source                   1..56
                         mol_type = other DNA
                         organism = synthetic construct
SEQUENCE: 142
ggagttcgta taactaaacc tcctcgtggt gaactctggg taattctaat agtta          56

SEQ ID NO: 143           moltype = DNA   length = 56
FEATURE                  Location/Qualifiers
source                   1..56
                         mol_type = other DNA
                         organism = synthetic construct
SEQUENCE: 143
ggcgacagtt tcaaaaacct ccacgtggtt gtcgctggat aacgctaata tttgaa          56

SEQ ID NO: 144           moltype = DNA   length = 56
FEATURE                  Location/Qualifiers
source                   1..56
                         mol_type = other DNA
                         organism = synthetic construct
SEQUENCE: 144
ggtgataaaa gcaaaaacct cctcgtggtt atcactgggt aactctaatt tttgct          56

SEQ ID NO: 145           moltype = DNA   length = 53
FEATURE                  Location/Qualifiers
source                   1..53
                         mol_type = other DNA
                         organism = synthetic construct
SEQUENCE: 145
ggcaccaaga tagacgcctt ctcgcggcgg tgctgatttc gactaagtct atc          53

SEQ ID NO: 146           moltype = DNA   length = 56
FEATURE                  Location/Qualifiers
source                   1..56
                         mol_type = other DNA
                         organism = synthetic construct
SEQUENCE: 146
ggggtgtcag taggcagcct ccacgtggca caccctggtt aacgctaatg gcctac          56

SEQ ID NO: 147           moltype = DNA   length = 56
FEATURE                  Location/Qualifiers
source                   1..56
                         mol_type = other DNA
                         organism = synthetic construct
SEQUENCE: 147
ggagtccaag tagttaacct cctcgtggtg gactctgggt aattctaata aactac          56

SEQ ID NO: 148           moltype = DNA   length = 57
FEATURE                  Location/Qualifiers
source                   1..57
                         mol_type = other DNA
                         organism = synthetic construct
SEQUENCE: 148
gagtcactat acaaacaacc ttctcgtggt gtgacttgat ttcgactaat agtttgt       57
```

-continued

```
SEQ ID NO: 149              moltype = DNA   length = 57
FEATURE                     Location/Qualifiers
source                      1..57
                            mol_type = other DNA
                            organism = synthetic construct
SEQUENCE: 149
ggggaacttg ttgctgacct cctcgtggtg ttccctggat taaaactaac aagcaac        57

SEQ ID NO: 150              moltype = DNA   length = 54
FEATURE                     Location/Qualifiers
source                      1..54
                            mol_type = other DNA
                            organism = synthetic construct
SEQUENCE: 150
ggcaacttgt taacagcctt ctcgtggcgt tgctgatttc gactgatagt taac           54

SEQ ID NO: 151              moltype = DNA   length = 56
FEATURE                     Location/Qualifiers
source                      1..56
                            mol_type = other DNA
                            organism = synthetic construct
SEQUENCE: 151
gactcgcatt tgtacttgcc tcctcgtggc gcgagttgga tagctctaaa agtaca         56

SEQ ID NO: 152              moltype = DNA   length = 68
FEATURE                     Location/Qualifiers
source                      1..68
                            mol_type = other DNA
                            organism = synthetic construct
SEQUENCE: 152
ccgttcagta ccaagtctca ggggaaactt tgagatggcc ttgcaaaggt atggtaataa     60
gctgacgg                                                              68

SEQ ID NO: 153              moltype = DNA   length = 67
FEATURE                     Location/Qualifiers
source                      1..67
                            mol_type = other DNA
                            organism = synthetic construct
SEQUENCE: 153
cggggccaca gcagaagcgt tcacgtcgcg gccctgtca gattctggtg aatctgcaaa      60
ttctgct                                                               67

SEQ ID NO: 154              moltype = DNA   length = 67
FEATURE                     Location/Qualifiers
source                      1..67
                            mol_type = other DNA
                            organism = synthetic construct
SEQUENCE: 154
ggcagccaca gtagaagcat tcacattgtg gtccatgtca gattctggtg aatttgcaaa     60
ttctgct                                                               67

SEQ ID NO: 155              moltype = DNA   length = 67
FEATURE                     Location/Qualifiers
source                      1..67
                            mol_type = other DNA
                            organism = synthetic construct
SEQUENCE: 155
gggggccaca gcagaagcgt tcacgtcgcg gccctgtca gattctgatg aatctgcgaa      60
ttctgct                                                               67

SEQ ID NO: 156              moltype = DNA   length = 65
FEATURE                     Location/Qualifiers
source                      1..65
                            mol_type = other DNA
                            organism = synthetic construct
SEQUENCE: 156
agccgttcgg gtggctataa atagacctta ggcccgaagc gtggcggcac ctgccgccgg     60
tggta                                                                 65

SEQ ID NO: 157              moltype = DNA   length = 94
FEATURE                     Location/Qualifiers
source                      1..94
                            mol_type = other DNA
                            organism = synthetic construct
SEQUENCE: 157
tatagaaaac tcgactaagc gagtataaac aggcattagg cttagagcgt tctcacgtta     60
tctgaatgat gatgtgagag gttgcaatag aaaa                                 94
```

-continued

```
SEQ ID NO: 158            moltype = DNA   length = 79
FEATURE                   Location/Qualifiers
source                    1..79
                          mol_type = other DNA
                          organism = synthetic construct
SEQUENCE: 158
atgggacact gtcctgttgc tttcctccct gaggcaggag tgggtgtcag attctggtga    60
atagctggga gcccagaaa                                                 79

SEQ ID NO: 159            moltype = DNA   length = 67
FEATURE                   Location/Qualifiers
source                    1..67
                          mol_type = other DNA
                          organism = synthetic construct
SEQUENCE: 159
ggggggccaca gcagaagcgt tcacgtcgcg gcccctgtca gattccggtg aatctgcgaa   60
ttctgct                                                              67

SEQ ID NO: 160            moltype = DNA   length = 195
FEATURE                   Location/Qualifiers
source                    1..195
                          mol_type = other DNA
                          organism = synthetic construct
SEQUENCE: 160
ggacaaccaa aaagacaaat ctgccctcag agcttgagaa catcttcgga tgcagaggag    60
gcagcctccg gtggcgcgat agcgccaacg ttctcaacag gcgccaata ctcccgcttc    120
ggcgggtggg gataacacct gacgaaaagg cgatgttaga cacgccaagg tcataatccc   180
cggagcttcg gctcc                                                    195

SEQ ID NO: 161            moltype = DNA   length = 67
FEATURE                   Location/Qualifiers
source                    1..67
                          mol_type = other DNA
                          organism = synthetic construct
SEQUENCE: 161
aggggccaca gcagaagcgt tcacgtcgcg gcccctgtca gattctggtg aatctgcgaa    60
ttctgct                                                              67

SEQ ID NO: 162            moltype = DNA   length = 46
FEATURE                   Location/Qualifiers
source                    1..46
                          mol_type = other DNA
                          organism = synthetic construct
SEQUENCE: 162
gggacttaag cccactgatg agtcgctgag atgcgacgaa acgccc                   46

SEQ ID NO: 163            moltype = DNA   length = 67
FEATURE                   Location/Qualifiers
source                    1..67
                          mol_type = other DNA
                          organism = synthetic construct
SEQUENCE: 163
cggggccaca gcagaagcgt tcatgttgtg gccctgtca gattctggtg aatctgcgaa     60
ttctgct                                                              67

SEQ ID NO: 164            moltype = DNA   length = 75
FEATURE                   Location/Qualifiers
source                    1..75
                          mol_type = other DNA
                          organism = synthetic construct
SEQUENCE: 164
agctgtcacc ggatgtgctt tccggtctga tgagtccgtg aggacgaaac agcctctaca    60
aataattttg tttaa                                                     75

SEQ ID NO: 165            moltype = DNA   length = 67
FEATURE                   Location/Qualifiers
source                    1..67
                          mol_type = other DNA
                          organism = synthetic construct
SEQUENCE: 165
ggggggccaca gcagaagcgt tcacgtcgcg gccctgtca gattcttgtg aatctgcgaa    60
ttctgct                                                              67

SEQ ID NO: 166            moltype = DNA   length = 67
FEATURE                   Location/Qualifiers
source                    1..67
                          mol_type = other DNA
                          organism = synthetic construct
SEQUENCE: 166
```

-continued

```
ggggggccaca gcagaagcgt tcacgtcgcg gcccctgtca gattctggcg aatctgcgaa   60
ttctgct                                                              67

SEQ ID NO: 167       moltype = DNA   length = 53
FEATURE              Location/Qualifiers
source               1..53
                     mol_type = other DNA
                     organism = synthetic construct
SEQUENCE: 167
ggggggccaca gcagaagcgc acgcgcggcc ccgcagacgg cgaacgcgaa cgc           53

SEQ ID NO: 168       moltype = DNA   length = 43
FEATURE              Location/Qualifiers
source               1..43
                     mol_type = other DNA
                     organism = synthetic construct
SEQUENCE: 168
ttgctgcatc ctgatgagtc cgagaggacg aacatctgta cca                       43

SEQ ID NO: 169       moltype = DNA   length = 45
FEATURE              Location/Qualifiers
source               1..45
                     mol_type = other DNA
                     organism = synthetic construct
SEQUENCE: 169
ttgaaggcat ggctcaggga cttcggtccg ctgcagtcag tatgt                     45

SEQ ID NO: 170       moltype = DNA   length = 67
FEATURE              Location/Qualifiers
source               1..67
                     mol_type = other DNA
                     organism = synthetic construct
SEQUENCE: 170
aggggccaga gcagaagcat tcacgtcgtg gcccctgtca gattctggtg aatctgcgaa   60
ttctgct                                                              67

SEQ ID NO: 171       moltype = DNA   length = 110
FEATURE              Location/Qualifiers
source               1..110
                     mol_type = other DNA
                     organism = synthetic construct
SEQUENCE: 171
ggcgccgcgg agagaggcgg cagagagccc gggaggcccc agcacagcag gagagccggg   60
gcccgcagac ccccagcacg gcgggcgggc agagggccca cgcgcgcaaa              110

SEQ ID NO: 172       moltype = DNA   length = 67
FEATURE              Location/Qualifiers
source               1..67
                     mol_type = other DNA
                     organism = synthetic construct
SEQUENCE: 172
cggggccaca gcagaagcat tcatgtcgca gcccctgtca gattctggtg aatctgcgga   60
ttctgct                                                              67

SEQ ID NO: 173       moltype = DNA   length = 67
FEATURE              Location/Qualifiers
source               1..67
                     mol_type = other DNA
                     organism = synthetic construct
SEQUENCE: 173
ggggggcaca gcagaagcgt tcacgtcgcg gcccctgtca gattctggtg aatctgcgaa   60
ttctgct                                                              67

SEQ ID NO: 174       moltype = DNA   length = 67
FEATURE              Location/Qualifiers
source               1..67
                     mol_type = other DNA
                     organism = synthetic construct
SEQUENCE: 174
ggggggccaca gcagaagcgt tcacgtcgcg gcccctgtca gattctggcg aatctgcgaa  60
ttctgct                                                              67

SEQ ID NO: 175       moltype = DNA   length = 220
FEATURE              Location/Qualifiers
source               1..220
                     mol_type = other DNA
                     organism = synthetic construct
SEQUENCE: 175
gatcgatctc gcccgcgaaa ttaatacgac tcactatagg gaaaatctgc ctaaacgggg   60
```

-continued

```
aaacactcac tgagtcaatc ccgtgctaaa tcagcagtag ctgtaaatgc ctaacgacta    120
tccctgatga atgtaaggga gtagggtcaa gcgacccgaa acggcagaca actctaagag    180
ttgaagatat agtctgaact gcatggtgac atgcaggatc                          220

SEQ ID NO: 176          moltype = DNA   length = 182
FEATURE                 Location/Qualifiers
source                  1..182
                        mol_type = other DNA
                        organism = synthetic construct
SEQUENCE: 176
gggaaaatct gcctaaacgg ggaaacactc actgagtcaa tcccgtgcta aatcagcagt    60
agctgtaaat gcctaacgac tatccctgat gaatgtaagg gagtagggtc aagcgacccg    120
aaacggcaga caactctaag agttgaagat atagtctgaa ctgcatggtg acatgcagga    180
tc                                                                   182

SEQ ID NO: 177          moltype = DNA   length = 67
FEATURE                 Location/Qualifiers
source                  1..67
                        mol_type = other DNA
                        organism = synthetic construct
SEQUENCE: 177
gggggccata gcagaagcgt tcacgtcgcg gccctgtca gattcatatg aatctgcgaa     60
ttctgct                                                              67

SEQ ID NO: 178          moltype = DNA   length = 202
FEATURE                 Location/Qualifiers
source                  1..202
                        mol_type = other DNA
                        organism = synthetic construct
SEQUENCE: 178
gtcattgaaa aaaaaaaaaa gacaaatctg ccctcagagc ttgagaacat cttcggatgc    60
agaggaggca gccttcggtg gcgcgagagc gccaacgttc tcaacagacg cacaatactc    120
ccgcttcggc gggtgggggat aacacctgac gaaaaggcga tgttagacac gccaaggtca    180
taatccccgg agcttcggct cc                                             202

SEQ ID NO: 179          moltype = DNA   length = 66
FEATURE                 Location/Qualifiers
source                  1..66
                        mol_type = other DNA
                        organism = synthetic construct
SEQUENCE: 179
cagggccacc ccaaagcgtt cacattgtgg ccctgtcag attctggtaa atctgcgagt     60
tctgct                                                               66

SEQ ID NO: 180          moltype = DNA   length = 67
FEATURE                 Location/Qualifiers
source                  1..67
                        mol_type = other DNA
                        organism = synthetic construct
SEQUENCE: 180
gggggccaca gcagaagcgt tcacgtcgcg gccctgtca gattctgatg aatctgcgaa     60
ttctgct                                                              67

SEQ ID NO: 181          moltype = DNA   length = 67
FEATURE                 Location/Qualifiers
source                  1..67
                        mol_type = other DNA
                        organism = synthetic construct
SEQUENCE: 181
acggaccaca gcagaagttt cacatcgtgg ccctgtcag atgccagtga atctgtaaat     60
ttctgct                                                              67

SEQ ID NO: 182          moltype = DNA   length = 55
FEATURE                 Location/Qualifiers
source                  1..55
                        mol_type = other DNA
                        organism = synthetic construct
SEQUENCE: 182
gaaacacaag attgaaacct ccacgtggtg tgttttgggt aaagctaatt caatc         55

SEQ ID NO: 183          moltype = DNA   length = 55
FEATURE                 Location/Qualifiers
source                  1..55
                        mol_type = other DNA
                        organism = synthetic construct
SEQUENCE: 183
gaatagcaaa tgagaaacct ccacgtggtg ctatttgggt aacgctaatt ctcat         55

SEQ ID NO: 184          moltype = DNA   length = 56
```

```
FEATURE                 Location/Qualifiers
source                  1..56
                        mol_type = other DNA
                        organism = synthetic construct
SEQUENCE: 184
gaatagcaat agtagaaacc tccacgtggt gctatttggg taatgctaat tctact          56

SEQ ID NO: 185          moltype = DNA   length = 56
FEATURE                 Location/Qualifiers
source                  1..56
                        mol_type = other DNA
                        organism = synthetic construct
SEQUENCE: 185
ggtcactaaa gtagatactt ccacgtagtg tgactggatt aaaactaaaa tctact          56

SEQ ID NO: 186          moltype = DNA   length = 69
FEATURE                 Location/Qualifiers
source                  1..69
                        mol_type = other DNA
                        organism = synthetic construct
SEQUENCE: 186
tatgtaactc cgcctatgtc tcttataaat gatataggcg gttacaaccg caaaaaggag       60
gaggttata                                                               69

SEQ ID NO: 187          moltype = DNA   length = 62
FEATURE                 Location/Qualifiers
source                  1..62
                        mol_type = other DNA
                        organism = synthetic construct
SEQUENCE: 187
gcagggcaag gcccagtccc gtgcaagccg ggaccgcccc ggggcgcggc gctcattcct       60
gc                                                                      62

SEQ ID NO: 188          moltype = DNA   length = 144
FEATURE                 Location/Qualifiers
source                  1..144
                        mol_type = other DNA
                        organism = synthetic construct
SEQUENCE: 188
gcggtagtaa gcgggaactc acctccaatt tcagtactga aattgtcgta gcagttgact       60
actgttatgt gattggtaga ggctaagtga cggtattggc gtaagtcagt attgcagacc      120
agcacaagcc cgcttgcgga gaat                                             144

SEQ ID NO: 189          moltype = DNA   length = 39
FEATURE                 Location/Qualifiers
source                  1..39
                        mol_type = other DNA
                        organism = synthetic construct
SEQUENCE: 189
ggactgttac caacacccac accctgtgat gaaacaaaa                              39

SEQ ID NO: 190          moltype = DNA   length = 67
FEATURE                 Location/Qualifiers
source                  1..67
                        mol_type = other DNA
                        organism = synthetic construct
SEQUENCE: 190
gggggccata gcagaagcgt tcacgtcgcg gcccctgtca gattcatatg aatctgcgaa       60
ttctgct                                                                 67

SEQ ID NO: 191          moltype = DNA   length = 67
FEATURE                 Location/Qualifiers
source                  1..67
                        mol_type = other DNA
                        organism = synthetic construct
SEQUENCE: 191
gggggccaca gcagaagcgt tcccgtcgcg gcccctgtca gattccggtg aatctgcgaa       60
ttctgct                                                                 67

SEQ ID NO: 192          moltype = DNA   length = 67
FEATURE                 Location/Qualifiers
source                  1..67
                        mol_type = other DNA
                        organism = synthetic construct
SEQUENCE: 192
aggggccaga gcagaagcat tcacgtcgcg gcccctgtca gattctggtg aatctgcgaa       60
ttctgct                                                                 67

SEQ ID NO: 193          moltype = DNA   length = 195
```

```
FEATURE                 Location/Qualifiers
source                  1..195
                        mol_type = other DNA
                        organism = synthetic construct
SEQUENCE: 193
ggacaaccaa aaagacaaat ctgccctcag agcttgagaa catcttcgga tgcagaggag    60
gcagccttcg gtggcgcgag agcgccaacg ttctcaacag acgcacaata ctcccgcttc   120
ggcgggtggg gataacacct gacgaaaagg cgatgttaga cacgccaagg tcataatccc   180
cggagcttcg gctcc                                                     195

SEQ ID NO: 194          moltype = DNA   length = 67
FEATURE                 Location/Qualifiers
source                  1..67
                        mol_type = other DNA
                        organism = synthetic construct
SEQUENCE: 194
aggggccaga gcagaagcat tcacgtcgcg gcccctgtca gattctggtg aatctgcgaa    60
ttctgct                                                              67

SEQ ID NO: 195          moltype = DNA   length = 119
FEATURE                 Location/Qualifiers
source                  1..119
                        mol_type = other DNA
                        organism = synthetic construct
SEQUENCE: 195
tccaatgctc ttcagtaggg tcatgaaggt ttttcttttc ctgagaaaac aacacgtatt    60
gttttctcag gttttgcttt ttggcctttt tctagcttaa aaaaaaaaaa agcaaaaga    119

SEQ ID NO: 196          moltype = DNA   length = 96
FEATURE                 Location/Qualifiers
source                  1..96
                        mol_type = other DNA
                        organism = synthetic construct
SEQUENCE: 196
tatgaaggtt tttcttttcc tgagaaaaca acacgtattg ttttctcagg ttttgctttt    60
tggccttttt ctagcttaaa aaaaaaaaa gcaaaa                               96

SEQ ID NO: 197          moltype = DNA   length = 117
FEATURE                 Location/Qualifiers
source                  1..117
                        mol_type = other DNA
                        organism = synthetic construct
SEQUENCE: 197
tccaatgctc ttcagtaggg tcatgaaggt ttttcttttc ctgagaaaac aacacgtatt    60
gttttctcag gttttgcttt ttggcctttt tctagcttaa aaaaaaaaaa agcaaaa      117

SEQ ID NO: 198          moltype = DNA   length = 98
FEATURE                 Location/Qualifiers
source                  1..98
                        mol_type = other DNA
                        organism = synthetic construct
SEQUENCE: 198
tatgaaggtt tttcttttcc tgagaaaaca acacgtattg ttttctcagg ttttgctttt    60
tggccttttt ctagcttaaa aaaaaaaaa gcaaaaga                             98

SEQ ID NO: 199          moltype =     length =
SEQUENCE: 199
000

SEQ ID NO: 200          moltype =     length =
SEQUENCE: 200
000

SEQ ID NO: 201          moltype =     length =
SEQUENCE: 201
000

SEQ ID NO: 202          moltype =     length =
SEQUENCE: 202
000

SEQ ID NO: 203          moltype =     length =
SEQUENCE: 203
000

SEQ ID NO: 204          moltype = DNA   length = 304
FEATURE                 Location/Qualifiers
source                  1..304
                        mol_type = other DNA
```

```
                        organism = synthetic construct
SEQUENCE: 204
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catg                                                               304

SEQ ID NO: 205          moltype = DNA   length = 204
FEATURE                 Location/Qualifiers
source                  1..204
                        mol_type = other DNA
                        organism = synthetic construct
SEQUENCE: 205
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag gcgtgtacgg   180
tgggaggtct atataagcag agct                                         204

SEQ ID NO: 206          moltype = DNA   length = 16
FEATURE                 Location/Qualifiers
source                  1..16
                        mol_type = other DNA
                        organism = synthetic construct
SEQUENCE: 206
ggtttagtga accgtc                                                   16

SEQ ID NO: 207          moltype = DNA   length = 387
FEATURE                 Location/Qualifiers
source                  1..387
                        mol_type = other DNA
                        organism = synthetic construct
SEQUENCE: 207
tgtttgctct gcagaatact ttacctgggc acccaagtca tccttccagc attcctgctg    60
ctacagccta tttgctgagt aaccaggggt tacagcagcg ttgccaggca acgagggaca   120
gcggtcctgt tgaagagcca tttgtcacac tgaggggact ggttgaaatg caataaagaa   180
atgataccag cagctactca tgtcatcgcc attgctaaga acgtcgttgg tattacctta   240
ctctgagaac gtgtctgcag tttccagaaa atggagtatc gcaacatcac ttaaagtacc   300
ctgcttcaaa gtattgctgg caagtggcgt gggcctgatt atttatttag aaatgcttta   360
tcaggaggag aatgcttttt tgtaaac                                       387

SEQ ID NO: 208          moltype = DNA   length = 439
FEATURE                 Location/Qualifiers
source                  1..439
                        mol_type = other DNA
                        organism = synthetic construct
SEQUENCE: 208
agttccaaga gggccaccaa gcagaccacg ctctgagctt cagggaacca agtgtttgct    60
ctgcagaata ctttacctgg gcacccaagt catccttcca gcattcctgc tgctacagcc   120
tatttgctga gtaaccaggg gttacagcag cgttgccagg caacgaggga cagcggtcct   180
gttgaagagc catttgtcac actgagggga ctggttgaaa tgcaataaag aaatgatacc   240
agcagctact catgtcatcg ccattgctaa gaacgtcgtt ggtattacct tactctgaga   300
acgtgtctgc agtttccaga aaatggagta tcgcaacatc acttaaagta ccctgcttca   360
aagtattgct ggcaagtggc gtgggcctga ttatttattt agaaatgctt tatcaggagg   420
agaatgcttt tttgtaaac                                                439

SEQ ID NO: 209          moltype = DNA   length = 2809
FEATURE                 Location/Qualifiers
source                  1..2809
                        mol_type = other DNA
                        organism = synthetic construct
SEQUENCE: 209
atgaattgcc cagttctttc attgggctct ggcttcttgt ttcaggtcat tgaaatgttg    60
atctttgcct attttgcttc aatatccttg actgagtcac gaggtctttt cccaaggctg   120
gagaacgtgg gagctttcaa gaaagtttcc atcgtgccaa cccaagcagt atgtggactc   180
ccagaccgaa gcactttttg tcacagctct gctgctgctg aaagtattca gttctgtacc   240
cagcggtttt gtattcagga ttgcccatac agatcttcac accctaccta cactgccctt   300
ttctcagcag gcctcagtag ctgcatcaca ccagacaaga atgatctgca tcctaacgcc   360
catagcaatt ctgcaagttt tatttttgga aatcacaaga gctgcttttc ttctcctcct   420
tctccaaagc tgatggcatc atttacctta gctgtatggc tgaaacctga gcaacaaggt   480
gtaatgtgtg ttatagaaaa gacagtagat gggcagattg tgttcaaact tacaatatct   540
gagaaagaga caatgtttta ttatcgcaca gtaaatggtt gcaacctcc aataaaagta   600
atgacactgg ggagaattct tgtgaagaaa tggattcatc ttagtgtgca ggtcatccag   660
acaaaaatca gcttctttat caatggcgtg gagaaggatc atacaccttt caatgtcaaga   720
actctaagtg gttcaattac agattttgca tctggtactg tgcaaatagg acagagttta   780
aatggtttag agcagtttgt cggaagaatg caagattttc gattataca agtggcactt   840
acaaacagag agattctgga agtgttctct ggagatcttc tcagattgca tgcccaatca   900
cattgccgtt gccctggcag ccaccgcgg gtccacccctt tggcacagcg gtactgcatt   960
```

```
cctaatgatg caggagacac agctgataat agagtgtcac ggttgaatcc tgaagcccat   1020
cctctctctt ttgtcaatga taatgatgtt ggtacttcat gggtttcaaa tgtgtttaca   1080
aacattacac agcttaatca aggagtgact atttcagttg atttggaaaa tggacagtat   1140
caggtgtttt atattatcat tcagttcttt agtccacaac caacggaaat aaggattcaa   1200
aggaagaagg aaaatagttt agattgggag gactggcaat attttgccag gaattgtggt   1260
gcttttggaa tgaaaaacaa tggagatttg gaaaaacctg attctgtcaa ctgccttcag   1320
ctttccaatt ttactccata ttcccgtggc aatgtcacat ttagcatcct gacacctgga   1380
ccaaattatc gtcctggata caataacttc tataataccc catctcttca agagttcgta   1440
aaagccacgc aaataaggtt tcattttcat gggcagtact atacaactga gactgctgtt   1500
aacctcagac acagatatta tgcagtggac gaaatcacca ttagtgggag atgtcagtgc   1560
catggtcatg ccgataactg cgacacaaca agccagccat atagatgcct ctgctcccag   1620
gagagcttca ctgaaggact tcattgtgat cgctgcttgc ctctttataa tgacaagcct   1680
ttccgccaag gtgatcaagt ttacgctttc aattgtaaac cttgtcaatg caacagccat   1740
tccaaaagct gccattacaa catctctgta gacccatttc cttttgagca cttcagaggg   1800
ggaggaggag tttgtgatga ttgtgagcat aacactacag gaaggaactg tgagctgtgc   1860
aaggattact ttttccgaca agttggtgca gatccttcgg ccatagatgt ttgcaaaccc   1920
tgtgactgtg atacagttgg cactagaaat ggtagcattc tttgtgatca gattggagga   1980
cagtgtaatt gtaagagaca cgtgtctggc aggcagtgca atgtgcagtg gaatggattc   2040
tacaatctac aagagttgga tcctgatggc tgcagtccct gtaactgcaa tacctctggg   2100
acagtggatg gagatattac ctgtcaccaa aattcaggcc agtgcaagtg caaagcaaac   2160
gttattgggc ttaggtgtga tcattgcaat tttggattta aatttctccg aagctttaat   2220
gatgttggat gtgagccctg ccagtgtaac ctccatggct cagtgaacaa attctgcaat   2280
cctcactctg ggcagtgtga gtgcaaaaaa gaagccaaag gacttcagtg tgatacctgc   2340
agagaaaact tttatgggtt agatgtcacc aattgtaagg cctgtgactg tgacacagct   2400
ggatccctcc ctgggactgt ctgtaatgct aagacagggc agtgcatctg caagcccaat   2460
gtcgagggaa ggcagtgtaa caagtgcctt gaagggaact tctacctacg gcaaaataat   2520
tctttcctct gtctgccttg caactgtgat aagactggga caataaatgg ctctctgctg   2580
tgtaacaaat caacaggaca atgtccttgc aagcttggag ttacaggtct taggtgcaac   2640
cagtgcgaac cacacaggta caatttgacc attgacaatt ttcaacactg ccagatgtgt   2700
gagtgtgatt cctgggggac attaccagga acaatctgcg atcctatcag tggccagtgc   2760
ctgtgtgtgc ctaatcgtca aggaagaagg tgtaatcagt gtcaaccag                2809
```

SEQ ID NO: 210       moltype =   length =
SEQUENCE: 210
000

SEQ ID NO: 211       moltype = DNA   length = 15
FEATURE              Location/Qualifiers
source               1..15
                     mol_type = other DNA
                     organism = synthetic construct
SEQUENCE: 211
gtagcaattt ggatg                                                       15

SEQ ID NO: 212       moltype = DNA   length = 60
FEATURE              Location/Qualifiers
source               1..60
                     mol_type = other DNA
                     organism = synthetic construct
SEQUENCE: 212
attacacaga aaaacagaat actctaccaa ggcactaatt cccaatacaa atgtggttat      60

SEQ ID NO: 213       moltype = DNA   length = 60
FEATURE              Location/Qualifiers
source               1..60
                     mol_type = other DNA
                     organism = synthetic construct
SEQUENCE: 213
atatgcagat aattttgaat aagttaaata gttatatatg tgttggataa tgatataaat      60

SEQ ID NO: 214       moltype = DNA   length = 90
FEATURE              Location/Qualifiers
source               1..90
                     mol_type = other DNA
                     organism = synthetic construct
SEQUENCE: 214
aaatttgtag aagccacaaa ccagaaacag ggagaagtta cctaagttaa caaaaggaat      60
gtcattgtgc actgaaaatg taatacattt                                       90

SEQ ID NO: 215       moltype = DNA   length = 20
FEATURE              Location/Qualifiers
source               1..20
                     mol_type = other DNA
                     organism = synthetic construct
SEQUENCE: 215
aaatgattaa attaagcagg                                                  20

SEQ ID NO: 216       moltype = DNA   length = 119
FEATURE              Location/Qualifiers -continued

```
source                  1..119
                        mol_type = other DNA
                        organism = synthetic construct
SEQUENCE: 216
tccaatgctc ttcagtaggg tcatgaaggt ttttctttc ctgagaaaac aacacgtatt    60
gttttctcag gttttgcttt ttggcctttt tctagcttaa aaaaaaaaa agcaaaaga    119

SEQ ID NO: 217         moltype = DNA   length = 68
FEATURE                Location/Qualifiers
source                 1..68
                       mol_type = other DNA
                       organism = synthetic construct
SEQUENCE: 217
ggccggcatg gtcccagcct cctcgctggc gccggctggg caacatgctt cggcatggcg    60
aatgggac                                                              68

SEQ ID NO: 218         moltype = DNA   length = 121
FEATURE                Location/Qualifiers
source                 1..121
                       mol_type = other DNA
                       organism = synthetic construct
SEQUENCE: 218
cttgtttatt gcagcttata atggttacaa ataaagcaat agcatcacaa atttcacaaa    60
taaagcattt ttttcactgc attctagttg tggtttgtcc aaactcatca atgtatctta   120
t                                                                    121

SEQ ID NO: 219         moltype = DNA   length = 311
FEATURE                Location/Qualifiers
source                 1..311
                       mol_type = other DNA
                       organism = synthetic construct
SEQUENCE: 219
tccaatgctc ttcagtaggg tcatgaaggt ttttctttc ctgagaaaac aacacgtatt    60
gttttctcag gttttgcttt ttggcctttt tctagcttaa aaaaaaaaa agcaaaagag   120
gccggcatgg tcccagcctc ctcgctggcg ccggctgggc aacatgcttc ggcatggcg    180
atgggactgg cttgtttatt gcagcttata atggttacaa ataaagcaat agcatcacaa   240
atttcacaaa taaagcattt ttttcactgc attctagttg tggtttgtcc aaactcatca   300
atgtatctta t                                                        311

SEQ ID NO: 220         moltype = DNA   length = 316
FEATURE                Location/Qualifiers
source                 1..316
                       mol_type = other DNA
                       organism = synthetic construct
SEQUENCE: 220
ggagcactgt tcgtaacccg ttagcctggc tgtagctaat gggttccatt ccggtgcaat    60
agcatttcca gcgacacatg actgactgac tggtggcttt cagtttcagg tcttggagac   120
aaatggccgg catggtccca gcctcctcgc tggcgccggc tgggcaacat gcttcggcat   180
ggcgaatggg actggcttgt ttattgcagc ttataatggt tacaaataaa gcaatagcat   240
cacaaatttc acaaataaag catttttttc actgcattct agttgtggtt tgtccaaact   300
catcaatgta tcttat                                                   316

SEQ ID NO: 221         moltype = DNA   length = 68
FEATURE                Location/Qualifiers
source                 1..68
                       mol_type = other DNA
                       organism = synthetic construct
SEQUENCE: 221
ggccggcatg gtcccagcct cctcgctggc gccggctggg caacatgctt cggcatggcg    60
aatgggac                                                              68

SEQ ID NO: 222         moltype = DNA   length = 189
FEATURE                Location/Qualifiers
source                 1..189
                       mol_type = other DNA
                       organism = synthetic construct
SEQUENCE: 222
ggccggcatg gtcccagcct cctcgctggc gccggctggg caacatgctt cggcatggcg    60
aatgggacct tgtttattgc agcttataat ggttacaaat aaagcaatag catcacaaat   120
ttcacaaata aagcattttt ttcactgcat tctagttgtg gtttgtccaa actcatcaat   180
gtatcttat                                                           189

SEQ ID NO: 223         moltype = DNA   length = 68
FEATURE                Location/Qualifiers
source                 1..68
                       mol_type = other DNA
                       organism = synthetic construct
SEQUENCE: 223
ggccggcatg gtcccagcct cctcgctggc gccggctggg caacatgctt cggcatggtg    60
```

```
aatgggac                                                                             68

SEQ ID NO: 224          moltype = DNA   length = 189
FEATURE                 Location/Qualifiers
source                  1..189
                        mol_type = other DNA
                        organism = synthetic construct
SEQUENCE: 224
ggccggcatg gtcccagcct cctcgctggc gccggctggg caacatgctt cggcatggtg     60
aatgggacct tgtttattgc agcttataat ggttacaaat aaagcaatag catcacaaat    120
ttcacaaata aagcattttt ttcactgcat tctagttgtg gtttgtccaa actcatcaat    180
gtatcttat                                                            189

SEQ ID NO: 225          moltype = DNA   length = 119
FEATURE                 Location/Qualifiers
source                  1..119
                        mol_type = other DNA
                        organism = synthetic construct
SEQUENCE: 225
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaaga     119

SEQ ID NO: 226          moltype = DNA   length = 187
FEATURE                 Location/Qualifiers
source                  1..187
                        mol_type = other DNA
                        organism = synthetic construct
SEQUENCE: 226
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaagag    120
gccggcatgg tcccagcctc ctcgctggcg ccggctgggc aacatgcttc ggcatggcga    180
atgggac                                                              187

SEQ ID NO: 227          moltype = DNA   length = 298
FEATURE                 Location/Qualifiers
source                  1..298
                        mol_type = other DNA
                        organism = synthetic construct
SEQUENCE: 227
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaagag    120
gccggcatgg tcccagcctc ctcgctggcg ccggctgggc aacatgcttc ggcatggcga    180
atgggacgca gcttataatg gttacaaata aagcaatagc atcacaaatt cacaaataa     240
agcatttttt tcactgcatt ctagttgtgg tttgtccaaa ctcatcaatg tatcttat     298

SEQ ID NO: 228          moltype = DNA   length = 308
FEATURE                 Location/Qualifiers
source                  1..308
                        mol_type = other DNA
                        organism = synthetic construct
SEQUENCE: 228
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaagag    120
gccggcatgg tcccagcctc ctcgctggcg ccggctgggc aacatgcttc ggcatggcga    180
atgggacctt gtttattgca gcttataatg gttacaaata aagcaatagc atcacaaatt    240
tcacaaataa agcatttttt tcactgcatt ctagttgtgg tttgtccaaa ctcatcaatg    300
tatcttat                                                             308

SEQ ID NO: 229          moltype = DNA   length = 187
FEATURE                 Location/Qualifiers
source                  1..187
                        mol_type = other DNA
                        organism = synthetic construct
SEQUENCE: 229
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaagag    120
gccggcatgg tcccagcctc ctcgctggcg ccggctgggc aacatgcttc ggcatggtga    180
atgggac                                                              187

SEQ ID NO: 230          moltype = DNA   length = 308
FEATURE                 Location/Qualifiers
source                  1..308
                        mol_type = other DNA
                        organism = synthetic construct
SEQUENCE: 230
tccaatgctc ttcagtaggg tcatgaaggt ttttcttttc ctgagaaaac aacacgtatt     60
gttttctcag gttttgcttt ttggcctttt tctagcttaa aaaaaaaaaa agcaaaagag    120
gccggcatgg tcccagcctc ctcgctggcg ccggctgggc aacatgcttc ggcatggtga    180
atgggacctt gtttattgca gcttataatg gttacaaata aagcaatagc atcacaaatt    240
```

```
tcacaaataa agcatttttt tcactgcatt ctagttgtgg tttgtccaaa ctcatcaatg   300
tatcttat                                                           308
```

```
SEQ ID NO: 231              moltype = DNA   length = 177
FEATURE                     Location/Qualifiers
source                      1..177
                            mol_type = other DNA
                            organism = synthetic construct
SEQUENCE: 231
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaagag   120
atgctggtgg ttggcactcc tggtttccag gacggggttc aaatccctgc ggcgtct       177
```

```
SEQ ID NO: 232              moltype = DNA   length = 298
FEATURE                     Location/Qualifiers
source                      1..298
                            mol_type = other DNA
                            organism = synthetic construct
SEQUENCE: 232
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaagag   120
atgctggtgg ttggcactcc tggtttccag gacggggttc aaatccctgc ggcgtctctt   180
gtttattgca gcttataatg gttacaaata aagcaatagc atcacaaatt tcacaaataa   240
agcatttttt tcactgcatt ctagttgtgg tttgtccaaa ctcatcaatg tatcttat      298
```

```
SEQ ID NO: 233              moltype = DNA   length = 177
FEATURE                     Location/Qualifiers
source                      1..177
                            mol_type = other DNA
                            organism = synthetic construct
SEQUENCE: 233
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaagaa   120
atgctggtgg ttggcactcc tggtttccag gacggggttc aaatccctgc ggcgtct       177
```

```
SEQ ID NO: 234              moltype = DNA   length = 298
FEATURE                     Location/Qualifiers
source                      1..298
                            mol_type = other DNA
                            organism = synthetic construct
SEQUENCE: 234
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaagaa   120
atgctggtgg ttggcactcc tggtttccag gacggggttc aaatccctgc ggcgtctctt   180
gtttattgca gcttataatg gttacaaata aagcaatagc atcacaaatt tcacaaataa   240
agcatttttt tcactgcatt ctagttgtgg tttgtccaaa ctcatcaatg tatcttat      298
```

```
SEQ ID NO: 235              moltype = DNA   length = 177
FEATURE                     Location/Qualifiers
source                      1..177
                            mol_type = other DNA
                            organism = synthetic construct
SEQUENCE: 235
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaagag   120
atgctggtgg ttggcactcc tggtttccag gacggggcct aaatccctgc ggcgtct       177
```

```
SEQ ID NO: 236              moltype = DNA   length = 275
FEATURE                     Location/Qualifiers
source                      1..275
                            mol_type = other DNA
                            organism = synthetic construct
SEQUENCE: 236
tatgaaggtt tttcttttcc tgagaaaaca acacgtattg ttttctcagg ttttgctttt   60
tggccttttt ctagcttaaa aaaaaaaaaa gcaaaaaatg ctggtggttg gcactcctgg   120
tttccaggac ggggttcaaa tccctgcggc gtctcttgtt tattgcagct tataatggtt   180
acaaataaag caatagcatc acaaatttca caaataaagc attttttca ctgcattcta     240
gttgtggttt gtccaaactc atcaatgtat cttat                              275
```

```
SEQ ID NO: 237              moltype = DNA   length = 154
FEATURE                     Location/Qualifiers
source                      1..154
                            mol_type = other DNA
                            organism = synthetic construct
SEQUENCE: 237
tatgaaggtt tttcttttcc tgagaaaaca acacgtattg ttttctcagg ttttgctttt   60
tggccttttt ctagcttaaa aaaaaaaaaa gcaaaaaatg ctggtggttg gcactcctgg   120
tttccaggac ggggttcaaa tccctgcggc gtct                                154
```

-continued

```
SEQ ID NO: 238            moltype = DNA   length = 275
FEATURE                   Location/Qualifiers
source                    1..275
                          mol_type = other DNA
                          organism = synthetic construct
SEQUENCE: 238
tatgaaggtt tttcttttcc tgagaaaaca acacgtattg ttttctcagg ttttgctttt   60
tggccttttt ctagcttaaa aaaaaaaaaa gcaaaagatg ctggtggttg gcactcctgg  120
tttccaggac ggggttcaaa tccctgcggc gtctcttgtt tattgcagct tataatggtt  180
acaaataaag caatagcatc acaaatttca caaataaagc attttttttca ctgcattcta  240
gttgtggttt gtccaaactc atcaatgtat cttat                            275

SEQ ID NO: 239            moltype = DNA   length = 154
FEATURE                   Location/Qualifiers
source                    1..154
                          mol_type = other DNA
                          organism = synthetic construct
SEQUENCE: 239
tatgaaggtt tttcttttcc tgagaaaaca acacgtattg ttttctcagg ttttgctttt   60
tggccttttt ctagcttaaa aaaaaaaaaa gcaaaagatg ctggtggttg gcactcctgg  120
tttccaggac ggggttcaaa tccctgcggc gtct                             154

SEQ ID NO: 240            moltype = DNA   length = 285
FEATURE                   Location/Qualifiers
source                    1..285
                          mol_type = other DNA
                          organism = synthetic construct
SEQUENCE: 240
tatgaaggtt tttcttttcc tgagaaaaca acacgtattg ttttctcagg ttttgctttt   60
tggccttttt ctagcttaaa aaaaaaaaaa gcaaaaggcc ggcatggtcc cagcctcctc  120
gctggcgccg gctgggcaac atgcttcggc atggtgaatg ggaccttgtt tattgcagct  180
tataatggtt acaaataaag caatagcatc acaaatttca caaataaagc attttttttca  240
ctgcattcta gttgtggttt gtccaaactc atcaatgtat cttat                285

SEQ ID NO: 241            moltype = DNA   length = 164
FEATURE                   Location/Qualifiers
source                    1..164
                          mol_type = other DNA
                          organism = synthetic construct
SEQUENCE: 241
tatgaaggtt tttcttttcc tgagaaaaca acacgtattg ttttctcagg ttttgctttt   60
tggccttttt ctagcttaaa aaaaaaaaaa gcaaaaggcc ggcatggtcc cagcctcctc  120
gctggcgccg gctgggcaac atgcttcggc atggtgaatg ggac                 164

SEQ ID NO: 242            moltype = DNA   length = 275
FEATURE                   Location/Qualifiers
source                    1..275
                          mol_type = other DNA
                          organism = synthetic construct
SEQUENCE: 242
tatgaaggtt tttcttttcc tgagaaaaca acacgtattg ttttctcagg ttttgctttt   60
tggccttttt ctagcttaaa aaaaaaaaaa gcaaaaggcc ggcatggtcc cagcctcctc  120
gctggcgccg gctgggcaac atgcttcggc atggcgaatg ggacgcagct tataatggtt  180
acaaataaag caatagcatc acaaatttca caaataaagc attttttttca ctgcattcta  240
gttgtggttt gtccaaactc atcaatgtat cttat                            275

SEQ ID NO: 243            moltype = DNA   length = 285
FEATURE                   Location/Qualifiers
source                    1..285
                          mol_type = other DNA
                          organism = synthetic construct
SEQUENCE: 243
tatgaaggtt tttcttttcc tgagaaaaca acacgtattg ttttctcagg ttttgctttt   60
tggccttttt ctagcttaaa aaaaaaaaaa gcaaaaggcc ggcatggtcc cagcctcctc  120
gctggcgccg gctgggcaac atgcttcggc atggcgaatg ggaccttgtt tattgcagct  180
tataatggtt acaaataaag caatagcatc acaaatttca caaataaagc attttttttca  240
ctgcattcta gttgtggttt gtccaaactc atcaatgtat cttat                285

SEQ ID NO: 244            moltype = DNA   length = 164
FEATURE                   Location/Qualifiers
source                    1..164
                          mol_type = other DNA
                          organism = synthetic construct
SEQUENCE: 244
tatgaaggtt tttcttttcc tgagaaaaca acacgtattg ttttctcagg ttttgctttt   60
tggccttttt ctagcttaaa aaaaaaaaaa gcaaaaggcc ggcatggtcc cagcctcctc  120
gctggcgccg gctgggcaac atgcttcggc atggcgaatg ggac                 164

SEQ ID NO: 245            moltype = DNA   length = 96
```

```
FEATURE              Location/Qualifiers
source               1..96
                     mol_type = other DNA
                     organism = synthetic construct
SEQUENCE: 245
tatgaaggtt tttctttttcc tgagaaaaca acacgtattg ttttctcagg ttttgctttt   60
tggcctttt ctagcttaaa aaaaaaaaaa gcaaaa                               96

SEQ ID NO: 246       moltype = DNA   length = 194
FEATURE              Location/Qualifiers
source               1..194
                     mol_type = other DNA
                     organism = synthetic construct
SEQUENCE: 246
gcagggccg gcatggtccc agcctcctcg ctggcgccgg ctgggcaaca tgcttcggca   60
tggtgaatgg gaccttgttt attgcagctt ataatggtta caaataaagc aatagcatca  120
caaatttcac aaataaagca ttttttttcac tgcattctag ttgtggtttg tccaaactca  180
tcaatgtatc ttat                                                    194

SEQ ID NO: 247       moltype = DNA   length = 73
FEATURE              Location/Qualifiers
source               1..73
                     mol_type = other DNA
                     organism = synthetic construct
SEQUENCE: 247
gcagggccg gcatggtccc agcctcctcg ctggcgccgg ctgggcaaca tgcttcggca   60
tggtgaatgg gac                                                      73

SEQ ID NO: 248       moltype = DNA   length = 474
FEATURE              Location/Qualifiers
source               1..474
                     mol_type = other DNA
                     organism = synthetic construct
SEQUENCE: 248
tcgagataat caacctctgg attacaaaat ttgtgaaaga ttgactggta ttcttaacta   60
tgttgctcct tttacgctat gtggatacgc tgctttaatg cctttgtatc atgctattgc  120
ttcccgtatg gctttcattt tctcctcctt gtataaatcc tggttagttc ttgccacggc  180
ggaactcatc gccgcctgcc ttgcccgctg ctggacaggg gctcggctgt tgggcactga  240
caattccgtg gtgtgccttc tagttgccag ccatctgttg tttgccctc ccccgtgcct   300
tccttgaccc tggaaggtgc cactcccact gtcctttcct aataaaatga ggaaattgca  360
tcgcattgtc tgagtaggtg tcattctatt ctggggggtg gggtggggca ggacagcaag  420
ggggaggatt gggaagacaa tagcaggcat gctggggatg cggtgggctc tatg         474

SEQ ID NO: 249       moltype = DNA   length = 838
FEATURE              Location/Qualifiers
source               1..838
                     mol_type = other DNA
                     organism = synthetic construct
SEQUENCE: 249
ctgcagcccc gataatcaac ctctggatta caaaatttgt gaaagattga ctggtattct   60
taactatgtt gctcctttta cgctatgtgg atacgctgct ttaatgcctt tgtatcatgc  120
tattgcttcc cgtatggctt tcattttctc ctccttgtat aaatcctggt tgctgtctct  180
ttatgaggag ttgtgtgccg ttgtcaggca acgtggcgtg gtgtgcactg tgtttgctga  240
cgcaacccc actggttggg gcattgccac cacctgtcag ctcctttccg ggactttcgc   300
tttccccctc cctattgcca cggcggaact catcgccgcc tgccttgccc gctgctggac  360
aggggctcgg ctgttgggca ctgacaattc cgtggtgttg tcgggggaaat catcgtcctt  420
tccttggctg ctcgcctgtg ttgccacctg gattctgcgc gggacgtcct tctgctacgt  480
cccttcggcc ctcaatccag cggaccttcc ttcccgcggc ctgctgccgg ctctgcggcc  540
tcttccgcgt cttcgccttc gccctcagac gagtcggatc tcccttttggg ccgcctcccc  600
gcatcggggg gatcctgtgc cttctagttg ccagccatct gttgtttgcc cctcccccgt  660
gccttccttg accctggaag gtgccactcc cactgtcctt tcctaataaa atgaggaaat  720
tgcatcgcat tgtctgagta ggtgtcattc tattctgggg ggtggggtgg ggcaggacag  780
caagggggag gattgggaag acaatagcag gcatgctggg gatgcggtgg gctctatg     838

SEQ ID NO: 250       moltype = DNA   length = 222
FEATURE              Location/Qualifiers
source               1..222
                     mol_type = other DNA
                     organism = synthetic construct
SEQUENCE: 250
gtgccttcta gttgccagcc atctgttgtt tgccctccc ccgtgccttc cttgaccctg    60
gaaggtgcca ctcccactgt cctttcctaa taaaatgagg aaattgcatc gcattgtctg  120
agtaggtgtc attctattct gggggtggg gtggggcagg acagcaaggg ggaggattgg   180
gaagacaata gcaggcatgc tggggatgcg gtgggctcta tg                     222

SEQ ID NO: 251       moltype = DNA   length = 121
FEATURE              Location/Qualifiers
source               1..121
                     mol_type = other DNA
```

```
                        organism = synthetic construct
SEQUENCE: 251
cttgtttatt gcagcttata atggttacaa ataaagcaat agcatcacaa atttcacaaa   60
taaagcattt ttttcactgc attctagttg tggtttgtcc aaactcatca atgtatctta   120
t                                                                  121

SEQ ID NO: 252          moltype = DNA   length = 136
FEATURE                 Location/Qualifiers
source                  1..136
                        mol_type = other DNA
                        organism = synthetic construct
SEQUENCE: 252
tctagcttta tttgtgaaat ttgtgatgct attgctttat ttgtaaccat tataagctgc   60
aataaacaag ttaacaacaa caattgcatt cattttatgt ttcaggttca gggggagatg   120
tgggaggttt tttaaa                                                   136

SEQ ID NO: 253          moltype = DNA   length = 58
FEATURE                 Location/Qualifiers
source                  1..58
                        mol_type = other DNA
                        organism = synthetic construct
SEQUENCE: 253
tgttaataaa agatctttat tttcattaga tctgtgtgtt ggttttttgt gtgatcga     58

SEQ ID NO: 254          moltype = DNA   length = 114
FEATURE                 Location/Qualifiers
source                  1..114
                        mol_type = other DNA
                        organism = synthetic construct
SEQUENCE: 254
tctagcttta tttgtgaaat ttgtgatgct attgctttat ttgtaaccat tataagctgc   60
aataaaagat ctttattttc attagatctg tgtgttggtt ttttgtgtga tcga         114

SEQ ID NO: 255          moltype = DNA   length = 4279
FEATURE                 Location/Qualifiers
source                  1..4279
                        mol_type = other DNA
                        organism = synthetic construct
SEQUENCE: 255
cgttacataa cttacggtaa atggcccgcc tggctgaccg cccaacgacc cccgcccatt   60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta acaactccgc cccattgacg caaatgggcg gtaggcgtgt   480
acggtgggag gtctatataa gcagagctgg tttagtgaac cgtctgtttg ctctgcagaa   540
tactttacct gggcacccaa gtcatccttc cagcattcct gctgctacag cctatttgct   600
gagtaaccag gggttacagc agcgttgcca ggcaacgagg acagcggtc ctgttgaaga   660
gccatttgtc acactgaggg gactggttga aatgcaataa agaaatgata ccagcagcta   720
ctcatgtcat cgccattgct aagaacgtcg ttggtattac cttactctga gaacgtgtct   780
gcagtttcca gaaaatggag tatcgcaaca tcacttaaag taccctgctt caaagtattg   840
ctggcaagtg gcgtgggcct gattatttat ttagaaatgc tttatcagga ggagaatgct   900
tttttgtaaa catgaattgc ccagttcttt cattgggctc tggcttcttg tttcaggtca   960
ttgaaatgtt gatctttgcc tattttgctt caatatcctt gactgagtca cgaggtcttt   1020
tcccaaggct ggagaacgtg ggagctttca agaaagtttc catcgtgcca acccaagcag   1080
tatgtggact cccagaccga agcactttt gtcacagctc tgctgctgct gaaagtattc   1140
agttctgtac ccagcggttt tgtattcagg attgcccata cagatcttca caccctacct   1200
acactgccct tttctcagca ggcctcagta gctgcatcac accagacaag aatgatctgc   1260
atcctaacgc ccatagcaat tctgcaagtt ttatttttgg aaatcacaag agctgctttt   1320
cttctcctcc ttctccaaag ctgatggcat catttacctt agctgtatgg ctgaaacctg   1380
agcaacaagg tgtaatgtgt gttatagaaa agacagtaga tgggcagatt gtgttcaaac   1440
ttacaatatc tgagaaagag acaatgtttt attatcgcat agtaaatggt ttgcaacctc   1500
caataaaagt aatgacactg gggagaattc ttgtgaagaa atggattcat cttagtgtgc   1560
aggtccatca gacaaaaatc agcttcttta tcaatggcgt ggagaaggat catacacctt   1620
tcaatgcaag aactctaagt ggttcaatta cagattttgc atctggtact gtgcaaatag   1680
gacagagttt aaatggttta gagcagtttg tcggaagaat gcaagatttt cgattatacc   1740
aagtggcact tacaaacaga gagattctgg aagtgttctc tggagatctt ctcagattgc   1800
atgcccaatc acattgccgt tgccctggca gccacccgcg ggtccaccct ttggcacagc   1860
ggtactgcat tcctaatgat gcaggagaca cagctgataa tagagtgtca cggttgaatc   1920
ctgaagccca tcctctctct tttgtcaatg ataatgatgt tggtacttca tgggtttcaa   1980
atgtgtttac aaacattaca cagcttaatc aaggagtgac tatttcagtt gatttggaaa   2040
atggacagta tcaggtgttt tatattatca ttcagtttct tagtccacaa ccaacggaaa   2100
taaggattca aaggaagaag gaaaatagtt tagattggga ggactggcaa tattttgcca   2160
ggaattgtgg tgcttttgga atgaaaaaca atggagattt ggaaaaacct gattctgtca   2220
actgccttca gctttccaat tttactccat attcccgtgg caatgtcaca tttagcatcc   2280
tgacacctga accaaattat cgtcctggat acaataactt ctataatacc ccatctcttc   2340
aagagttcgt aaaagccacg caaataaggt ttcattttca tgggcagtac tatacaactg   2400
```

-continued

```
agactgctgt taacctcaga cacagatatt atgcagtgga cgaaatcacc attagtggga 2460
gatgtcagtg ccatggtcat gccgataact gcgacacaac aagccagcca tatagatgcc 2520
tctgctccca ggagagcttc actgaaggac ttcattgtga tcgctgcttg cctctttata 2580
atgacaagcc tttccgccaa ggtgatcaag tttacgcttt caattgtaaa ccttgtcaat 2640
gcaacagcca ttccaaaagc tgccattaca acatctctgt agacccattt ccttttgagc 2700
acttcagagg gggaggagga gtttgtgatg attgtgagca taacactaca ggaaggaact 2760
gtgagctgtg caaggattac tttttccgac aagttggtgc agatccttcg gccatagatg 2820
tttgcaaacc ctgtgactgt gatacagttg gcactagaaa tggtagcatt ctttgtgatc 2880
agattggagg acagtgtaat tgtaagacga acgtgtctgg caggcagtgc aatcagtgcc 2940
agaatggatt ctacaatcta caagagttgg atcctgatgg ctgcagtccc tgtaactgca 3000
atacctctgg gacagtggat ggagatatta cctgtcacca aaattcaggc cagtgcaagt 3060
gcaaagcaaa cgttattggg cttaggtgtg atcattgcaa ttttggattt aaatttctcc 3120
gaagctttaa tgatgttgga tgtgagccct gccagtgtaa cctccatggc tcagtgaaca 3180
aattctgcaa tcctcactct gggcagtgtg agtgcaaaaa agaagccaaa ggacttcagt 3240
gtgatacctg cagagaaaac ttttatgggt tagatgtcac caattgtaag gcctgtgact 3300
gtgacacagc tggatccctc cctgggactg tctgtaatgc taagacaggg cagtgcatct 3360
gcaagcccaa tgtcgaggga aggcagtgta acaagtgcct tgaagggaac ttctacctac 3420
ggcaaaataa ttctttcctc tgtctgcctt gcaactgtga taagactggg acaataaatg 3480
gctctctgct gtgtaacaaa tcaacaggac aatgtccttg caagcttgga gttacaggtc 3540
ttaggtgcaa ccagtgcgaa ccacacaggt acaatttgac cattgacaat tttcaacact 3600
gccagatgtg tgagtgtgat tccttgggga cattaccagg aacaatctgc gatcctatca 3660
gtggccagtg cctgtgtgtg cctaatcgtc aaggaagaag gtgtaatcag tgtcaaccag 3720
gtaagtgtag caatttggat gattacacag aaaaacagaa tactctacca aggcactaat 3780
tcccaataca aatgtggtta tatatgcaga taattttgaa taagttaaat agttatatat 3840
gtgttggata atgatataaa taaatttgta gaagccacaa accagaaaca gggagaagtt 3900
acctaagtta acaaaaggaa tgtcattgtg cactgaaaat gtaatacatt taaatgatta 3960
aattaagcag gtccaatgct cttcagtagg gtcatgaagg ttttttctttt cctgagaaaa 4020
caacacgtat tgttttctca ggttttgctt tttggccttt ttctagctta aaaaaaaaaa 4080
aagcaaaaga ggccggcatg gtcccagcct cctcgctggc gccggctggg caacatgctt 4140
cggcatggcg aatgggacct tgtttattgc agcttataat ggttacaaat aaagcaatag 4200
catcacaaat ttcacaaata aagcattttt ttcactgcat tctagttgtg gtttgtccaa 4260
actcatcaat gtatcttat                                               4279
```

SEQ ID NO: 256          moltype = DNA  length = 4277
FEATURE                 Location/Qualifiers
source                  1..4277
                        mol_type = other DNA
                        organism = synthetic construct SEQUENCE: 256
```
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatggggc gtaggcgtgt 480
acggtgggag gtctatataa gcagagctgg tttagtgaac cgtctgtttg ctctgcagaa 540
tactttacct gggcacccaa gtcatccttc cagcattcct gctgctacag cctatttgct 600
gagtaaccag gggttacagc agcgttgcca ggcaacgagg gacagcggtc ctgttgaaga 660
gccatttgtc acactgaggg gactggttga aatgcaataa agaaatgata ccagcagtca 720
ctcatgtcat cgccattgct aagaacgtcg ttggtattac cttactctga gaacgtgtct 780
gcagtttcca gaaaatggag tatcgcaaca tcacttaaag taccctgctt caaagtattg 840
ctggcaagtg gcgtgggcct gattatttat ttagaaatgc tttatcagga ggagaatgct 900
tttttgtaaa catgaattgc ccagttcttt cattgggctc tggcttcttg tttcaggtca 960
ttgaaatgtt gatctttgcc tattttgctt caatatcctt gactgagtca cgaggtcttt 1020
tcccaaggct ggagaacgtg ggagcttca agaaagtttc catcgtgcca acccaagcag 1080
tatgtggact cccagaccga agcacttttt gtcacagctc tgctgctgct gaaagtattc 1140
agttctgtac ccagcggttt tgtattcagg attgcccata cagatcttca caccctacct 1200
acactgccct tttctcagca ggcctcagta gctgcatcac accagacaag aatgatctgc 1260
atcctaacgc ccatagcaat tctgcaagtt ttatttttgg aaatcacaag agctgctttt 1320
cttctcctcc ttctccaaag ctgatggcat catttacctt agctgtatgg ctgaaacctg 1380
agcaacaagg tgtaatgtgt gttatagaaa agacagtaga tgggcagatt gtgttcaaac 1440
ttacaatatc tgagaaagag acaatgtttt attatcgaac agtaaatggt ttgcaacctc 1500
caataaaagt aatgacactg gggagaattc ttgtgaagaa atggattcat cttagtgtgc 1560
aggtccatca gacaaaaatc agcttcttta tcaatggcgt ggagaaggat catacacctt 1620
tcaatgcaag aactctaagt ggttcaatta cagattttgc atctggtact gtgcaaatag 1680
gacagagttt aaatggttta gagcagtttg tcggaagaat gcaagatttt cgattatacc 1740
aagtggcact tacaaacaga gagattctgg aagtgttctc tggagatctt ctcagattgc 1800
atgcccaatc acattgccgt tgccctggca gccacccgcg ggtccaccct ttggcacagc 1860
ggtactgcat tcctaatgat gcaggagaca cagctgataa tagagtgtca cggttgaatc 1920
ctgaagccca tcctctctct tttgtcaatg ataatgatgt tggtacttca tgggtttcaa 1980
atgtgtttac aaacattaca cagcttaatc aaggagtgac tatttcagtt gatttggaaa 2040
atggacagta tcaggtgttt tatattatca ttcagttctt tagtccacaa ccaacggaaa 2100
taaggattca aaggaagaag gaaaatagtt tagattggga ggactggcaa tattttgcca 2160
ggaattgtgg tgcttttgga atgaaaaaca atggagattt ggaaaaacct gattctgtca 2220
actgccttca gctttccaat tttactccat attcccgtgg caatgtcaca tttagcatcc 2280
tgacacctgg accaaattat cgtcctggat acaataactt ctataatacc ccatctcttc 2340
aagagttcgt aaaagccacg caaataaggt ttcattttca tgggcagtac tatacaactg 2400
```

```
agactgctgt taacctcaga cacagatatt atgcagtgga cgaaatcacc attagtggga  2460
gatgtcagtg ccatggtcat gccgataact gcgacacaac aagccagcca tatagatgcc  2520
tctgctccca ggagagcttc actgaaggac ttcattgtga tcgctgcttg cctctttata  2580
atgacaagcc tttccgccaa ggtgatcaag tttacgcttt caattgtaaa ccttgtcaat  2640
gcaacagcca ttccaaaagc tgccattaca acatctctgt agacccattt ccttttgagc  2700
acttcagagg gggaggagga gtttgtgatg attgtgagca taacactaca ggaaggaact  2760
gtgagctgtg caaggattac ttttttccgac aagttggtgc agatccttcg gccatagatg  2820
tttgcaaacc ctgtgactgt gatacagttg gcactagaaa tggtagcatt ctttgtgatc  2880
agattggagg acagtgtaat tgtaagacga acgtgtctgg caggcagtgc aatcagtgca  2940
agaatggatt ctacaatcta caagagttgg atcctgatgg ctgcagtccc tgtaactgca  3000
atacctctgg gacagtggat ggagatatta cctgtcacca aaattcaggc cagtgcaagt  3060
gcaaagcaaa cgttattggg cttaggtgtg atcattgcaa ttttggattt aaatttctcc  3120
gaagctttaa tgatgttgga tgtgagccct gccagtgtaa cctccatggc tcagtgaaca  3180
aattctgcaa tcctcactct gggcagtgtg agtgcaaaaa agaagccaaa ggacttcagt  3240
gtgatacctg cagagaaaac ttttatgggt tagatgtcac caattgtaag gcctgtgact  3300
gtgacacagc tggatccctc cctgggactg tctgtaatgc taagacaggg cagtgcatct  3360
gcaagcccaa tgtcgaggga aggcagtgta acaagtgcct tgaagggaac ttctacctac  3420
ggcaaaataa ttctttcctc tgtctgcctt gcaactgtga taagactgtg acaataaatg  3480
gctctctgct gtgtaacaaa tcaacaggac aatgtccttg caagcttgga gttacaggtc  3540
ttaggtgcaa ccagtgcgaa ccacacaggt acaatttgac cattgacaat tttcaacact  3600
gccagatgtg tgagtgtgat tccttgggga cattaccagg aacaatctgc gatcctatca  3660
gtggccagtg cctgtgtgtg cctaatcgtc aaggaagaag gtgtaatcag tgtcaaccag  3720
gtaagtgtag caatttggat gattacacag aaaaacagaa tactctacca aggcactaat  3780
tcccaataca aatgtggtta tatatgcaga taattttgaa taagttaaat agttatatat  3840
gtgttggata atgatataaa taaatttgta gaagccacaa accagaaaca gggagaagtt  3900
acctaagtta acaaaaggaa tgtcattgtg cactgaaaat gtaatacatt taaatgatta  3960
aattaagcag gtccaatgct cttcagtagg gtcatgaagg ttttttctttt cctgagaaaa  4020
caacacgtat tgtttctca ggttttgctt tttggccttt ttctagctta aaaaaaaaaa  4080
aagcaaaagg ccggcatggt cccagcctcc tcgctggcgc cggctgggca acatgcttcg  4140
gcatggcgaa tgggaccttg tttattgcag cttataatgg ttacaaataa agcaatagca  4200
tcacaaattt cacaaataaa gcattttttt cactgcattc tagttgtggt ttgtccaaac  4260
tcatcaatgt atcttat                                                  4277
```

SEQ ID NO: 257          moltype = DNA   length = 4331
FEATURE                 Location/Qualifiers
source                  1..4331
                        mol_type = other DNA
                        organism = synthetic construct
SEQUENCE: 257

```
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta acaactccgc cccattgacg caaatgggcg gtaggcgtgt   480
acggtgggag gtctatataa gcagagctgg tttagtgaac cgtcagtcc aagagggcca    540
ccaagcagac cacgctctga gcttcaggga ccaagtgtt tgctctgcag aatactttac    600
ctgggcaccc aagtcatcct tccagcattc ctgctgctac agcctatttg ctgagtaacc   660
aggggttaca gcagcgttgc caggcaacga gggacagtgg tcctgttgaa gagccatttg   720
tcacactgag gggactggtt gaaatgcaat aaagaaatga taccagcagc tactcatgtc   780
atcgccattg ctaagaacgt cgttggtatt accttactct gagaacgtgt ctgcagtttc   840
cagaaaatgg agtatcgcaa catcacttaa agtaccctgc ttcaaagtat tgctggcaag   900
tggcgtgggc ctgattattt atttagaaat gctttatcag gaggagaatg cttttttgta   960
aacatgaatt gcccagttct ttcattgggc tctggcttct tgtttcaggt cattgaaatg  1020
ttgatctttg cctattttgc ttcaaatatcc ttgactgagt cacgaggtct tttcccaagg  1080
ctggagaacg tgggagcttt caagaaagtt tccatcgtgc caacccaagc agtatgtgga  1140
ctcccagacc gaagcacttt ttgtcacagc tctgctgctg ctgaaagtat tcagttctgt  1200
acccagcggt tttgtattca ggattgccca tacagatctt cacaccctac ctacactgcc  1260
cttttctcag caggcctcag tagctgcatc acaccagaca agaatgatct gcatcctaac  1320
gcccatagca attctgcaag ttttattttt ggaaatcaca agagctgctt ttcttctcct  1380
ccttctccaa agctgatggc atcatttacc ttagctgtat ggctgaaacc tgagcaacaa  1440
ggtgtaatgt gtgttataga aaagacagta gatgggcaga ttgtgttcaa acttacaata  1500
tctgagaaag agacaatgtt ttattatcgc acagtaaatg gtttgcaacc tccaataaaa  1560
gtaatgacac tggggagaat tcttgtgaag aaatggattc atcttagtgt gcaggtccat  1620
cagacaaaaa tcagcttctt tatcaatggc gtggagaagg atcatacacc tttcaatgca  1680
agaactctaa gtggttcaat tacagatttt gcatctggta ctgtgcaaat aggacagagt  1740
ttaaatggtt tagagcagtt tgtcggaaga atgcaagatt ttcgattata ccaagtggca  1800
cttacaaaca gagagattct ggaagtgttc tctggagatc ttctcagatt gcatgcccaa  1860
tcacattgcc gttgccctgg cagccacccg cgggtccacc cttggcaca gcggtactgc    1920
attcctaatg atgcaggaga cacagctgat aatagagtgt cacggttgaa tcctgaagcc  1980
catcctctct cttttgtcaa tgataatgat gttggtactt catgggtttc aaatgtgttt  2040
acaaacatta cacagcttaa tcaaggagtg actatttcag ttgatttgga aaatggacag  2100
tatcaggtgt tttatattat cattcagttc tttagtccac aaccaacgga aataaggatt  2160
caaaggaaga aggaaaatag tttagattgg gaggactggc aatatttttgc caggaattgt  2220
ggtgcttttg gaatgaaaaa caatggagat ttggaaaaac ctgattctgt caactgcctt  2280
cagctttcca atttttactcc atattcccgt ggcaatgtca catttagcat cctgacacct  2340
ggaccaaatt atcgtcctgg atacaataac ttctataata ccccatctct tcaagagttc  2400
```

-continued

```
gtaaaagcca cgcaaataag gtttcatttt catgggcagt actatacaac tgagactgct  2460
gttaacctca gacacagata ttatgcagtg gacgaaatca ccattagtgg gagatgtcag  2520
tgccatggtc atgccgataa ctgcgacaca acaagccagc catatagatg cctctgctcc  2580
caggagagct tcactgaagg acttcattgt gatcgctgct tgcctcttta taatgacaag  2640
cctttccgcc aaggtgatca agtttacgct ttcaattgta aaccttgtca atgcaacagc  2700
cattccaaaa gctgccatta caacatctct gtagacccat ttccttttga gcacttcaga  2760
gggggaggag gagtttgtga tgattgtgag cataacacta caggaaggaa ctgtgagctg  2820
tgcaaggatt acttttttccg acaagttggt gcagatcctt cggccataga tgtttgcaaa  2880
ccctgtgact gtgatacagt tggcactaga aatggtagca ttctttgtga tcagattgga  2940
ggacagtgta attgtaagag acacgtgtct ggcaggcagt gcaatcagtg ccagaatgga  3000
ttctacaatc tacaagagtt ggatcctgat ggctgcagtc cctgtaactg caatacctct  3060
gggacagtgg atggagatat tacctgtcac caaaattcag gccagtgcaa gtgcaaagca  3120
aacgttattg ggcttaggtg tgatcattgc aattttggat ttaaatttct ccgaagcttt  3180
aatgatgttg gatgtgagcc ctgccagtgt aacctccatg gctcagtgaa caaattctgc  3240
aatcctcact ctgggcagtg tgagtgcaaa aaagaagcca aaggacttca gtgtgatacc  3300
tgcagagaaa acttttatgg gttagatgtc accaattgta aggcctgtga ctgtgacaca  3360
gctggatccc tccctgggac tgtctgtaat gctaagacag ggcagtgcat ctgcaagccc  3420
aatgtcgagg gaaggcagtg taacaagtgc cttgaaggga acttctacct acggcaaaat  3480
aattcttttcc tctgtctgcc ttgcaactgt gataagactg ggacaataaa tggctctctg  3540
ctgtgtaaca aatcaacagg acaatgtcct tgcaagcttg gagttacagg tcttaggtgc  3600
aaccagtgcg aaccacacag gtacaatttg accattgaca attttcaaca ctgccagatg  3660
tgtgagtgta attccttggg gacattacca ggaacaatct gcgatcctat cagtggccag  3720
tgcctgtgtg tgcctaatcg tcaaggaaga aggtgtaatc agtgtcaacc aggtaagtgt  3780
agcaatttgg atgattacac agaaaaacag aatactctac caaggcacta attcccaata  3840
caaatgtggt tatatatgca gataattttg aataagttaa atagttatat atgtgttgga  3900
taatgatata aataaatttg tagaagccac aaaccagaaa cagggagaag ttacctaagt  3960
taacaaaagg aatgtcattg tgcactgaaa atgtaataca tttaaatgat taaattaagc  4020
aggtccaatg ctcttcagta gggtcatgaa ggttttttctt ttcctgagaa aacaacacgt  4080
attgtttttct caggtttttgc tttttggcct ttttctagct taaaaaaaaa aaaagcaaaa  4140
gaggccggca tggtcccagc ctcctcgctg gcgccggctg ggcaacatgc ttcggcatgg  4200
cgaatgggac cttgtttatt gcagcttata atggttacaa ataaagcaat agcatcacaa  4260
atttcacaaa taaagcattt ttttcactgc attctagttg tggtttgtcc aaactcatca  4320
atgtatctta t                                                        4331
```

```
SEQ ID NO: 258          moltype = DNA   length = 4329
FEATURE                 Location/Qualifiers
source                  1..4329
                        mol_type = other DNA
                        organism = synthetic construct
SEQUENCE: 258
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccaccccca ttgacgtcaa tgggagtttg ttttggcacc aaaatcaacg   420
ggactttcca aaatgtcgta acaactccgc cccattgacg caaatgggcg gtaggcgtgt   480
acggtgggag gtctatataa gcagagctgg tttagtgaac cgtcagttcc aagagggcca   540
ccaagcagac cacgctctga gcttcaggga accaagtgtt tgctctgcag aatacttttac   600
ctgggcaccc aagtcatcct tccagcattc ctgctgctac agcctatttg ctgagtaacc   660
aggggttaca gcagcgttgc caggcaacga gggacagcgg tcctgttgaa gagccatttg   720
tcacactgag gggactggtt gaaatgcaat aaagaaatga taccagcagc tactcatgtc   780
atcgccattg ctaagaacgt cgttggtatt accttactct gagaacgtgt ctgcagtttc   840
cagaaaatgg agtatcgcaa catcacttaa agtaccctgc ttcaaagtat tgctggcaag   900
tggcgtgggc ctgattattt atttagaaat gctttatcag gaggagaatg ctttttttgta   960
aacatgaatt gcccagttct ttcattgggc tctggcttct tgtttcaggt cattgaaatg  1020
ttgatctttg cctattttgc ttcaatatcc ttgactgagt cacgaggtct tttcccaagg  1080
ctggagaacg tgggagcttt caagaaagtt tccatcgtgc caacccaagc agtatgtgga  1140
ctcccagacc gaagcacttt ttgtcacagc tctgctgctg ctgaaagtat tcagttctgt  1200
acccagcggt tttgtattca ggattgccca tacagatctt cacaccctac ctacactgcc  1260
cttttctcag caggcctcag tagctgcatc acaccagaca agaatgatct gcatcctaac  1320
gcccatagca attctgcaag ttttattttt ggaaatcaca agagctgctt ttcttctcct  1380
ccttctccaa agctgatggc atcatttacc ttagctgtat ggctgaacca tgagcaacaa  1440
ggtgtaatgt gtgttataga aaagacagta gatgggcaga ttgtgttcaa acttacaata  1500
tctgagaaag agacaatgtt ttattatcgc acagtaaatg gtttgcaacc tccaataaaa  1560
gtaatgacac tggggagaat tcttgtgaag aaatggattc atcttagtgt gcaggtccat  1620
cagacaaaaa tcagcttctt tatcaatggc gtgggagaag atcatacacc tttcaatgca  1680
agaactctaa gtggttcaat tacagatttt gcatctggta ctgtgcaaat aggacagagt  1740
ttaaatggtt tagagcagtt tgtcggaaga atgcaagatt ttcgattata ccaagtggca  1800
cttacaaaca gagagattct ggaagtgttc tctggagatc ttctcagatt gcatgcccaa  1860
tcacattgcc gttgccctgg cagccacccg cgggtccacc ctttggcaca gcggtactgc  1920
attcctaatg atgcaggaga cacagctgat aatagagtgt cacggttgaa tcctgaagcc  1980
catcctctct ctttttgtcaa tgtataatgat gttggtactt catgggtttc aaatgtgttt  2040
acaaacatta cacagcttaa tcaaggagtg actatttcag ttgatttgga aaatggacag  2100
tatcaggtgt tttatattat cattcagttc tttagtccac aaccaacgga aataaggatt  2160
caaaggaaga aggaaaatag tttagattgg gaggactggc aatattttgc caggaattgt  2220
ggtgcttttg gaatgaaaaa caatggagat ttggaaaaac ctgattctgt caactgcctt  2280
cagctttcca atttttactcc atattcccgt ggcaatgtca catttagcat cctgacacct  2340
```

```
ggaccaaatt atcgtcctgg atacaataac ttctataata ccccatctct tcaagagttc   2400
gtaaaagcca cgcaaataag gtttcatttt catgggcagt actatacaac tgagactgct   2460
gttaacctca gacacagata ttatgcagtg gacgaaatca ccattagtgg gagatgtcag   2520
tgccatggtc atgccgataa ctgcgacaca acaagccagc catatagatg cctctgctcc   2580
caggagagct tcactgaagg acttcattgt gatcgctgct tgcctcttta taatgacaag   2640
cctttccgcc aaggtgatca agtttacgct ttcaattgta aaccttgtca atgcaacagc   2700
cattccaaaa gctgccatta caacatctct gtagacccat ttccttttga gcacttcaga   2760
gggggaggag gagtttgtga tgattgtgag cataacacta caggaaggaa ctgtgagctg   2820
tgcaaggatt acttttttccg acaagttggt gcagatcctt cggccataga tgtttgcaaa   2880
ccctgtgact gtgatacagt tggcactaga aatggtagca ttctttgtga tcagattgga   2940
ggacagtgta attgtaagag acacgtgtct ggcaggcagt gcaatcagtg ccagaatgga   3000
ttctacaatc tacaagagtt ggatcctgat ggctgcagtc cctgtaactg caatacctct   3060
gggacagtgg atggagatat tacctgtcac caaaattcag gccagtgcaa gtgcaaagca   3120
aacgttattg ggcttaggtg tgatcattgc aattttgatt ttaaatttct ccgaagcttt   3180
aatgatgttg gatgtgagcc ctgccagtgt aacctccatg gctcagtgaa caaattctgc   3240
aatcctcact ctgggcagtg tgagtgcaaa aaagaagcca aaggacttca gtgtgatacc   3300
tgcagagaaa acttttatgg gttagatgtc accaattgta aggcctgtga ctgtgacaca   3360
gctggatccc tccctgggac tgtctgtaat gctaagacag ggcagtgcat ctgcaagccc   3420
aatgtcgagg gaaggcagtg taacaagtgc cttgaaggga acttctacct acggcaaaat   3480
aattctttcc tctgtctgcc ttgcaactgt gataagactg ggacaataaa tggctctctg   3540
ctgtgtaaca aatcaacagg acaatgtcct tgcaagcttg gagttacagg tcttaggtgc   3600
aaccagtgcg aaccacacag gtacaatttg accattgaca ntttcaaca ctgccagatg   3660
tgtgagtgtg attccttggg gacattacca ggaacaatct gcgatcctat cagtggccag   3720
tgcctgtgtg tgcctaatcg tcaaggaaga aggtgtaatc agtgtcaacc aggtaagtgt   3780
agcaatttgg atgattacac agaaaaacag aatactctac caaggcacta attcccaata   3840
caaatgtggt tatatatgca gataattttg aataagttaa atagttatat atgtgttgga   3900
taatgatata aataaatttg tagaagccac aaaccagaaa cagggagaag ttacctaagt   3960
taacaaaagg aatgtcattg tgcactgaaa atgtaataca tttaaatgat taaattaagc   4020
aggtccaatg ctcttcagta gggtcatgaa ggttttttctt ttcctgagaa aacaacacgt   4080
attgttttct caggttttgc ttttttggcct ttttctagct taaaaaaaaa aaaagcaaaa   4140
ggccggcatg gtcccagcct cctcgctggc gccggctggg caacatgctt cggcatggcg   4200
aatgggacct tgtttattgc agcttataat ggttacaaat aaagcaatag catcacaaat   4260
ttcacaaata aagcattttt ttcactgcat tctagttgtg gtttgtccaa actcatcaat   4320
gtatcttat                                                           4329
```

```
SEQ ID NO: 259              moltype = DNA   length = 25
FEATURE                     Location/Qualifiers
source                      1..25
                            mol_type = other DNA
                            organism = synthetic construct
SEQUENCE: 259
gagatattac ctgtcaccaa aattc                                          25

SEQ ID NO: 260              moltype = DNA   length = 24
FEATURE                     Location/Qualifiers
source                      1..24
                            mol_type = other DNA
                            organism = synthetic construct
SEQUENCE: 260
caggctatta cagatgtgat taac                                           24

SEQ ID NO: 261              moltype = DNA   length = 53
FEATURE                     Location/Qualifiers
source                      1..53
                            mol_type = other DNA
                            organism = synthetic construct
SEQUENCE: 261
tcgtcggcag cgtcagatgt gtataagaga cagcacaggg acaatttgac cat           53

SEQ ID NO: 262              moltype = DNA   length = 57
FEATURE                     Location/Qualifiers
source                      1..57
                            mol_type = other DNA
                            organism = synthetic construct
SEQUENCE: 262
gtctcgtggg ctcggagatg tgtataagag acagctatta cagatgtgat taactgc       57

SEQ ID NO: 263              moltype = DNA   length = 20
FEATURE                     Location/Qualifiers
source                      1..20
                            mol_type = other DNA
                            organism = synthetic construct
SEQUENCE: 263
ggatcgcaga ttgttcctgg                                                20

SEQ ID NO: 264              moltype = DNA   length = 22
FEATURE                     Location/Qualifiers
source                      1..22
                            mol_type = other DNA
```

-continued

```
                               organism = synthetic construct
SEQUENCE: 264
ccacacaggt acaatttgac ca                                              22

SEQ ID NO: 265          moltype = DNA  length = 18
FEATURE                 Location/Qualifiers
source                  1..18
                        mol_type = other DNA
                        organism = synthetic construct
SEQUENCE: 265
aggtttcatt caaggctc                                                   18

SEQ ID NO: 266          moltype = DNA  length = 17
FEATURE                 Location/Qualifiers
source                  1..17
                        mol_type = other DNA
                        organism = synthetic construct
SEQUENCE: 266
gagggtccat tcagttc                                                    17

SEQ ID NO: 267          moltype = DNA  length = 31
FEATURE                 Location/Qualifiers
source                  1..31
                        mol_type = other DNA
                        organism = synthetic construct
SEQUENCE: 267
gtaatcagtg tcaaccaggt ttttatattt c                                    31

SEQ ID NO: 268          moltype = DNA  length = 21
FEATURE                 Location/Qualifiers
source                  1..21
                        mol_type = other DNA
                        organism = synthetic construct
SEQUENCE: 268
ccaggaacaa tctgcgatcc t                                               21

SEQ ID NO: 269          moltype = DNA  length = 23
FEATURE                 Location/Qualifiers
source                  1..23
                        mol_type = other DNA
                        organism = synthetic construct
SEQUENCE: 269
accattgaca attttcaaca ctg                                             23

SEQ ID NO: 270          moltype = DNA  length = 26
FEATURE                 Location/Qualifiers
source                  1..26
                        mol_type = other DNA
                        organism = synthetic construct
SEQUENCE: 270
caggctatta cagatgtgat taactg                                          26

SEQ ID NO: 271          moltype = DNA  length = 27
FEATURE                 Location/Qualifiers
source                  1..27
                        mol_type = other DNA
                        organism = synthetic construct
SEQUENCE: 271
ggtacaattt gaccattgac aattttc                                         27

SEQ ID NO: 272          moltype = DNA  length = 22
FEATURE                 Location/Qualifiers
source                  1..22
                        mol_type = other DNA
                        organism = synthetic construct
SEQUENCE: 272
gtcaggctat tacagatgtg at                                              22

SEQ ID NO: 273          moltype = DNA  length = 477
FEATURE                 Location/Qualifiers
source                  1..477
                        mol_type = other DNA
                        organism = synthetic construct
SEQUENCE: 273
gggtggcatc cctgtgaccc ctccccagtg cctctcctgg ccctggaagt tgccactcca      60
gtgcccacca gccttgtcct aataaaatta agttgcatca ttttgtctga ctaggtgtcc     120
ttctataata ttatggggtg gaggggggtg gtatggagca aggggcaagt tgggaagaca     180
acctgtaggg cctgcggggt ctattgggaa ccaagctgga gtgcagtggc acaatcttgg     240
ctcactgcaa tctccgcctc ctgggttcaa gcgattctcc tgcctcagcc tcccgagttg     300
```

```
ttgggattcc aggcatgcat gaccaggctc agctaatttt tgtttttttg gtagagacgg   360
ggtttcacca tattggccag gctggtctcc aactcctaat ctcaggtgat ctacccacct   420
tggcctccca aattgctggg attacaggcg tgaaccactg ctcccttccc tgtcctt      477

SEQ ID NO: 274          moltype = DNA  length = 117
FEATURE                 Location/Qualifiers
source                  1..117
                        mol_type = other DNA
                        organism = synthetic construct
SEQUENCE: 274
tccaatgctc ttcagtaggg tcatgaaggt ttttcttttc ctgagaaaac aacacgtatt   60
gttttctcag gttttgcttt ttggcctttt tctagcttaa aaaaaaaaaa agcaaaa      117

SEQ ID NO: 275          moltype = DNA  length = 194
FEATURE                 Location/Qualifiers
source                  1..194
                        mol_type = other DNA
                        organism = synthetic construct
SEQUENCE: 275
gcaggggccg gcatggtccc agcctcctcg ctggcgccgg ctgggcaaca tgcttcggca   60
tggcgaatgg gaccttgttt attgcagctt ataatggtta caaataaagc aatagcatca   120
caaatttcac aaataaagca ttttttttcac tgcattctag ttgtggtttg tccaaactca   180
tcaatgtatc ttat                                                      194

SEQ ID NO: 276          moltype = DNA  length = 73
FEATURE                 Location/Qualifiers
source                  1..73
                        mol_type = other DNA
                        organism = synthetic construct
SEQUENCE: 276
gcaggggccg gcatggtccc agcctcctcg ctggcgccgg ctgggcaaca tgcttcggca   60
tggcgaatgg gac                                                       73

SEQ ID NO: 277          moltype = DNA  length = 23
FEATURE                 Location/Qualifiers
source                  1..23
                        mol_type = other DNA
                        organism = synthetic construct
SEQUENCE: 277
ttggagttac aggtcttagg tgc                                             23
```